United States Patent
Patil et al.

(10) Patent No.: US 10,954,229 B2
(45) Date of Patent: *Mar. 23, 2021

(54) GPR119 AGONIST COMPOUNDS

(71) Applicant: Mankind Pharma Ltd., New Delhi (IN)

(72) Inventors: Rakesh Ishwar Patil, IMT Manesar (IN); Jeevan Verma, IMT Manesar (IN); Puneet Kumar, IMT Manesar (IN); Amol Pandurang Gunjal, IMT Manesar (IN); Himanshu Rai, IMT Manesar (IN); Santosh Kumar Rai, IMT Manesar (IN); Anil Kumar, IMT Manesar (IN)

(73) Assignee: MANKIND PHARMA LTD., New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/909,543

(22) Filed: Jun. 23, 2020

(65) Prior Publication Data

US 2020/0317661 A1  Oct. 8, 2020

Related U.S. Application Data

(63) Continuation-in-part of application No. 16/231,791, filed on Dec. 24, 2018, and a continuation of application No. 15/478,930, filed on Apr. 4, 2017, now Pat. No. 10,208,030.

(30) Foreign Application Priority Data

Apr. 8, 2016   (IN) .............................. 201611012426

(51) Int. Cl.
*C07D 417/14* (2006.01)
*C07D 513/04* (2006.01)

(52) U.S. Cl.
CPC .......... *C07D 417/14* (2013.01); *C07D 513/04* (2013.01)

(58) Field of Classification Search
CPC ............................ C07D 417/14; C07D 513/04
USPC ...................................................... 514/233.2
See application file for complete search history.

(56) References Cited

U.S. PATENT DOCUMENTS

| | | | |
|---|---|---|---|
| 10,208,030 B2 * | 2/2019 | Patil ...................... | C07D 417/14 |
| 2009/0270404 A1 | 10/2009 | Wilson et al. | |
| 2011/0160222 A1 | 6/2011 | Chen et al. | |
| 2012/0322784 A1 | 12/2012 | Himmelsbach et al. | |
| 2013/0018030 A1 | 1/2013 | Himmelsbach et al. | |
| 2013/0045986 A1 | 2/2013 | Nagarathnam et al. | |
| 2013/0053345 A1 | 2/2013 | Ye et al. | |
| 2015/0166480 A1 | 6/2015 | Lee et al. | |

FOREIGN PATENT DOCUMENTS

| | | |
|---|---|---|
| CN | 102898400 A | 1/2013 |
| JP | 64-71876 A | 3/1989 |
| WO | 1996/019467 A1 | 6/1996 |
| WO | 2009/123992 A1 | 10/2009 |
| WO | 2012/098217 A1 | 7/2012 |
| WO | 2012116145 A1 | 8/2012 |
| WO | 2012/170867 A1 | 12/2012 |

OTHER PUBLICATIONS

International Search Report dated Jun. 30, 2017, for corresponding International Patent Application No. PCT/IB2017/000466.
Written Opinion dated Jun. 30, 2017, for corresponding International Patent Application No. PCT/IB2017/000466.
Non-Final Office Action mailed by the USPTO dated Aug. 21, 2017, for corresponding U.S. Appl. No. 15/478,930.
Non-Final Office Action mailed by the USPTO dated Mar. 21, 2018, for corresponding U.S. Appl. No. 15/478,930.
Office Action mailed by the Taiwanese Intellectual Property Office dated Nov. 8, 2017, for corresponding Taiwanese Patent Application No. 106111800. (With English Translation).
International Search Report dated Jun. 30, 2017, for related International Patent Application No. PCT/IB2017/000471.
Written Opinion dated Jun. 30, 2017, for related International Patent Application No. PCT/IB2017/000471.
Non-Final Office Action mailed by the USPTO dated Aug. 18, 2017, for related U.S. Appl. No. 15/478,883.
Final Office Action mailed by the USPTO dated Apr. 19, 2018, for related U.S. Appl. No. 15/478,883.
Non-Final Office Action mailed by the USPTO dated Oct. 4, 2018, for related U.S. Appl. No. 15/478,883.
Non-Final Office Action mailed by the USPTO dated Mar. 7, 2019, for related U.S. Appl. No. 15/478,883.
Examination report No. 1 issued by IP Australia dated Feb. 27, 2019, for corresponding Australian Patent Application No. 2017247691.
Non-Final Office Action mailed by the USPTO dated Feb. 8, 2019, for corresponding U.S. Appl. No. 16/231,791.
Non-Final Office Action mailed by the USPTO dated Sep. 10, 2019, for corresponding U.S. Appl. No. 16/231,791.
STN Registry database entry for CAS RN 1340697-49-5, STN Entry Date Nov. 4, 2011, Accessed Mar. 1, 2019, cited in the Non-Final Office Action mailed by the USPTO dated Mar. 7, 2019, for related U.S. Appl. No. 15/478,883.
Office Action issued by the Canadian Patent Office dated Dec. 23, 2019 for Canadian Application 3,020,478, related to PCT/IB2017/000471.

(Continued)

*Primary Examiner* — Kristin A Vajda
(74) *Attorney, Agent, or Firm* — Pergament & Cepeda LLP; Milagros A. Cepeda; Edward D. Pergament

(57) ABSTRACT

The present invention relates to novel compounds of formula (I), process for preparation of the same and composition comprising these compounds.

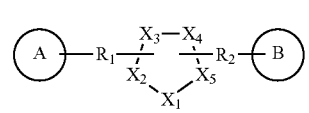

Formula (I)

7 Claims, No Drawings

(56) References Cited

OTHER PUBLICATIONS

Notice of Rejection issued by the Japanese Patent Office dated Sep. 17, 2019 for Japanese Application 2019-503800, retated to PCT/IB2017/000471.
English Translation of Notice of Rejection issued by the Japanese Patent Office dated Sep. 17, 2019, for Japanese Application 2019-503800, related to PCT/IB2017/000471.
Examination Report dated Apr. 17, 2019 issued by the New Zealand Intellectual Property Office, New Zealand Application 746954, related to PCT/IB2017/000471.
Office Action issued by the Taiwan Patent Office dated May 30, 2018, for Taiwan Application 106111799, related to PCT/IB2017/000471.
English Translation of Office Action issued by the Taiwan Patent Office dated May 30, 2018, for Taiwan Application 106111799, related to PCT/IB2017/000471.
International Preliminary Report on Patentability dated Oct. 9, 2018, related to International Patent Application No. PCT/IB2017/000471.
International Preliminary Report on Patentability dated Oct. 9, 2018, for corresponding International Patent Application No. PCT/IB2017/000466.
Office Action issued by the Patent office of Canada dated May 7, 2019, for Canadian Patent Application No. 3,020,381 corresponding to PCT/IB2017/000466.
Examination Report mailed by the Patent office of India dated Nov. 7, 2019, for Indian Patent Application No. 201817037880 corresponding to PCT/IB2017/000466.
Notice of Rejection mailed by the Japanese Patent office dated Oct. 29, 2019, for Japanese Patent Application No. JP 2019-503799 corresponding to PCT/IB2017/000466.
English translation of Notice of Rejection mailed by the Japanese Patent office dated Oct. 29, 2019, for Japanese Patent Application No. JP 2019-503799 corresponding to PCT/IB2017/000466.
Kentaro Futatsugi, et al; From partial to full agonism: Identification of a novel 2,4,5,6-tetrahydropyrrolo[3,4-c] pyrazole as a full agonist of the human GPR119 receptor; Bioorganic & Medicinal Chemistry Letters 23 (2013) pp. 194-197.
Office Action issued by the Mexican Patent Office dated Nov. 5, 2019, for Mexican Patent application No. MX/a/2018/012085 corresponding to PCT/IB2017/000466.
First Examination Report issued by New Zealand Patent Office dated Apr. 10, 2019, for New Zealand Patent Application No. 746950 corresponding to PCT/IB2017/000466.
Further Examination Report issued by New Zealand Patent Office dated Dec. 4, 2019, for New Zealand Patent Application No. 746950 corresponding to PCT/IB2017/000466.
Office Action issued by the Taiwan Patent Office dated Apr. 18, 2019, for Taiwan Patent Application No. 106111800 corresponding to PCT/IB2017/000466.
English translation to the Office Action issued by the Taiwan Patent Office dated Apr. 18, 2019, for Taiwan Patent Application No. 106111800 corresponding to PCT/IB2017/000466.
Office Action issued by the Argentina Patent Office dated Apr. 27, 2020, for Argentinian Application P170100901, related to PCT/IB2017/000471.
Office Action issued by the Canadian Patent Office dated Sep. 15, 2020 for Canadian Application 3,020,478, related to PCT/IB2017/000471.

Office Action issued by the European Patent Office dated May 26, 2020 for European Application 17 726 352.2, related to PCT/IB2017/000471.
First Examination Report issued by the Indian Patent Office dated Jul. 1, 2020 for Indian Application 201817038088, related to PCT/IB2017/000471.
Notice of Rejection issued by the Japanese Patent Office dated May 8, 2020 for Japanese Application 2019-503800, related to PCT/IB2017/000471.
English Translation of Notice of Rejection issued by the Japanese Patent Office dated May 8, 2020 for Japanese Application 2019-503800, related to PCT/IB2017/000471.
Office Action issued by the Russian Patent Office dated Feb. 21, 2020 for Russian Application 2018138050, related to PCT/IB2017/000471.
English Translation of Office Action issued by the Russian Patent Office dated Feb. 21, 2020 for Russian Application 2018138050, related to PCT/IB2017/000471.
Office Action issued by the Russian Patent Office dated Jul. 31, 2020 for Russian Application 2018138050, related to PCT/IB2017/000471.
English Translation of Office Action issued by the Russian Patent Office dated Jul. 31, 2020 for Russian Application 2018138050, related to PCT/IB2017/000471.
Office Action issued by the Patent office of Argentina dated Dec. 5, 2019, for Argentinian Patent Application No. P 17 01 00902 corresponding to PCT/IB2017/000466.
Office Action mailed by the Patent office of Argentina dated Apr. 23, 2020, for Argentinian Patent Application No. P 17 01 00902 corresponding to PCT/IB2017/000466.
First Examination Report issued by the Patent office of Australia dated Jul. 27, 2020, for Australian Patent Application No. 2020203450, corresponding to PCT/IB2017/000466.
Office Action issued by the Patent office of Canada dated Dec. 9, 2019, for Canadian Patent Application No. 3,020,381, corresponding to PCT/IB2017/000466.
Office Action issued by the Patent office of Europe dated May 28, 2020, for European Patent Application No. 17 726 029.6, corresponding to PCT/IB2017/000466.
Notice of Rejection issued by the Patent office of Japan dated Apr. 30, 2020, for Japanese Patent Application No. 2019-503799, corresponding to PCT/IB2017/000466.
English Translation of Notice of Rejection issued by the Patent office of Japan dated Apr. 30, 2020, for Japanese Patent Application No. 2019-503799, corresponding to PCT/IB2017/000466.
English translation of Office Action issued by the Patent office of Russia dated Apr. 5, 2020, for Russian Patent Application No. 2018138047, corresponding to PCT/IB2017/000466.
Office Action mailed by the Patent office of Taiwan dated Mar. 12, 2020, for Taiwanese Patent Application No. 108132646, corresponding to PCT/IB2017/000466.
English Translation of Office Action mailed by the Patent office of Taiwan dated Mar. 12, 2020, for Taiwanese Patent Application No. 108132646, corresponding to PCT/IB2017/000466.
Non-Final Office Action mailed by the USPTO dated May 14, 2020, for related U.S. Appl. No. 16/601,109.
Office Action issued by the Patent office of Russia dated Apr. 5, 2020, for Russian Patent Application No. 2018138047, corresponding to PCT/IB2017/000466.

* cited by examiner

GPR119 AGONIST COMPOUNDS

This application is a continuation-in-part of U.S. patent application Ser. No. 16/231,791, filed Dec. 24, 2018, which is a continuation of U.S. patent application Ser. No. 15/478,930, filed Apr. 4, 2017, now U.S. Pat. No. 10,208,030 issued on Feb. 19, 2019 under 35 U.S.C § 120, and claims priority under 35 U.S.C. § 119(b) to Indian Provisional Application Number 201611012426, filed on Apr. 8, 2016, which is hereby incorporated by reference in their entireties.

FIELD OF INVENTION

The present invention relates to novel compounds that are useful in the treatment and prevention of metabolic disorders, including diabetes mellitus (type I and type II), and related disorders and also includes methods for making, pharmaceutical compositions containing, and therapeutic uses for such compounds.

BACKGROUND OF THE INVENTION

Diabetes is a life-style related disease derived from multiple causative factors. It is characterized by elevated levels of plasma glucose (hyperglycemia) in the fasting state or after administration of glucose during an oral glucose tolerance test. There are two generally recognized forms of diabetes: type 1 and type 2 diabetes mellitus. In type 1 diabetes, or insulin-dependent diabetes mellitus (IDDM), patients produce little or no insulin, the hormone which regulates glucose utilization. In type 2 diabetes, or noninsulin-dependent diabetes mellitus (T2DM), insulin is still produced in the body, and patients demonstrate resistance to the effects of insulin in stimulating glucose and lipid metabolism in the main insulin-sensitive tissues, namely, muscle, liver and adipose tissue. These patients often have normal levels of insulin, and may have hyperinsulinemia (elevated plasma insulin levels), as they compensate for the reduced effectiveness of insulin by secreting increased amounts of insulin.

The treatment of T2DM generally begins weight loss, healthy diet and exercise program. Although these factors are important especially to dissolve the increased risk of cardiovascular disorders related to diabetes mellitus, they are not effective generally for the control of diabetes mellitus itself. There are many drugs useful for the treatment of diabetes mellitus, including insulin, metformin, sulfonylureas, acarbose, thiazolidinedione, GLP-1 analogue and DPP IV inhibitor. There are, however deficiencies associated with currently available treatment, including hypoglycemic episodes, weight gain, loss in responsiveness to therapy over time, gastrointestinal problems, and edema.

Although a number of receptor classes exist in humans, by far the most abundant and therapeutically relevant is represented by the G protein-coupled receptor (GPCR) class, it is estimated that approximately 4% of the protein-coding genome encodes GPCRs. GPCRs are also known as seven-transmembrane domain receptors as they share a common structural motif, having seven sequences of between 22 to 24 hydrophobic amino acids that form seven alpha helices, each of which spans the membrane. Further, there has been renewed focus on pancreatic islet-based insulin secretion that is controlled by glucose-dependent insulin secretion (GDIS). In this regard, several orphan G-protein coupled receptors (GPCR's) have recently been identified that are preferentially expressed in the 3-cell and are implicated in GDIS.

GPR119 is a cell-surface GPCR that is highly expressed in human (and rodent) islets as well as in insulin-secreting cell lines. Activation of GPR119 has been demonstrated to stimulate intracellular cAMP and lead to glucose dependent GLP-1 and insulin secretion (T. Soga et al Biochem. Biophys. Res. Commun. 2005, 326). Synthetic GPR119 agonists augment the release of insulin from isolated static mouse islets only under conditions of elevated glucose, and improve glucose tolerance in diabetic mice and diet-induced obese (DIO) C57/B6 mice without causing hypoglycemia.

There still remains a need for alternative novel synthetic compounds which acts as GPR119 agonists and are useful in the treatment and prevention of metabolic disorders, including diabetes mellitus (type I and type II), and related disorders.

OBJECT OF THE INVENTION

An object of the present invention is to provide novel compounds which acts as GPR119 agonist, composition containing such compounds and process for the preparation thereof.

SUMMARY OF THE INVENTION

In one aspect, the present invention provides compounds of formula (I):

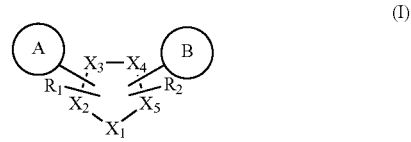

(I)

wherein, $X_1$, $X_2$, $X_3$, $X_4$ and $X_5$ are each indepedently N, O, S or CH; and $X_4$ and $X_5$ may optionally combine to form a five membered ring comprising one or more of heteroatoms each independently selected from N, O and S and the additional five membered ring may be further optionally substituted with one or more of group selected from F, Cl, Br, I, $CF_3$ and $C_{1-6}$ alkyl;

$R_1$ and $R_2$ is independently selected from the group comprising —H, —O, $C_{1-6}$ alkyl, $C_{1-6}$alkoxy, —$(CH_2)$n, amino, —CO, —CONH, —NH(Alkyl), —N(Alkyl)$_2$, —NH-aralkyl, —$CH_2$O, —OCH($CH_3$), halogenCOOR$_3$, —CONR$_3$R$_4$, NR$_3$COR$_4$;

$R_3$ and $R_4$ is independently selected from the group comprising hydrogen, or $C_{1-6}$ straight chain or branched chain alkyl which may be further substituted with halogen or $C_{1-6}$ alkyl;

n is 0, 1, 2 or 3.

A is selected from

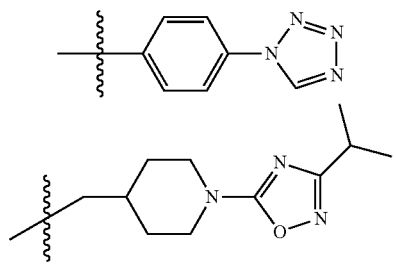

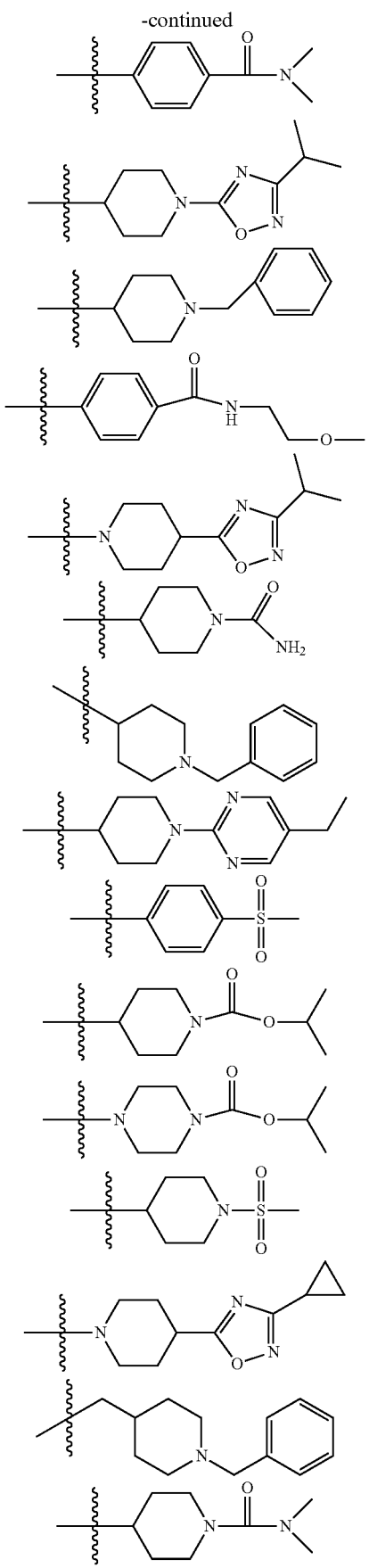
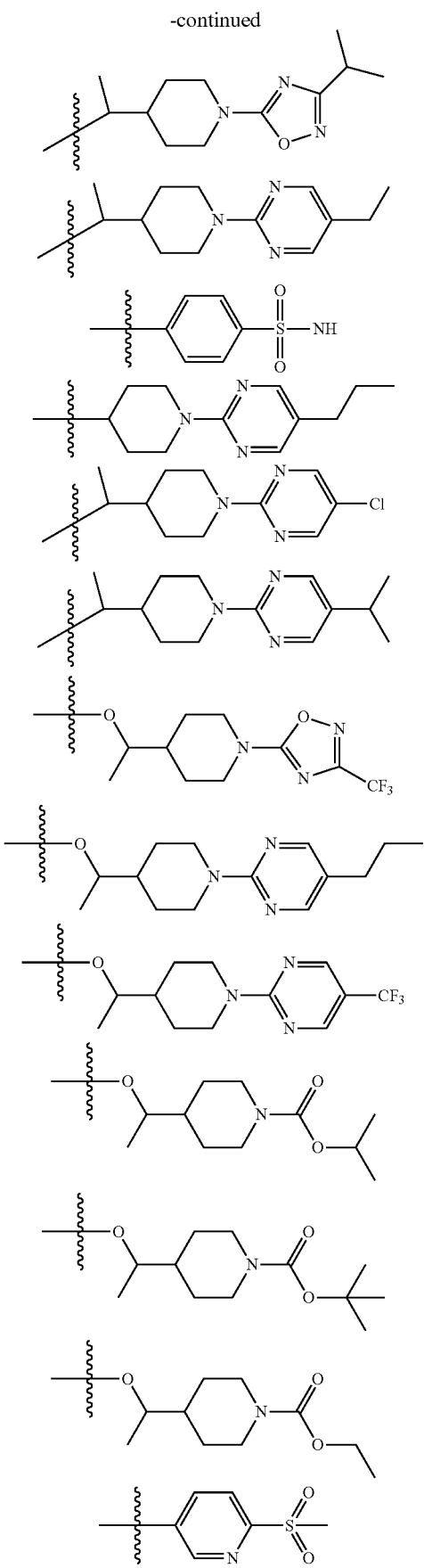

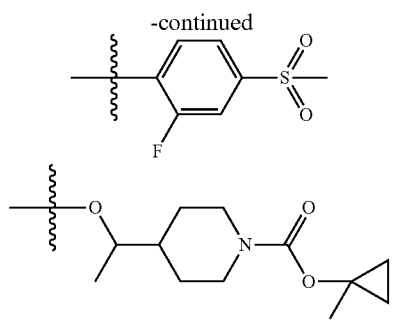
B is be selected from
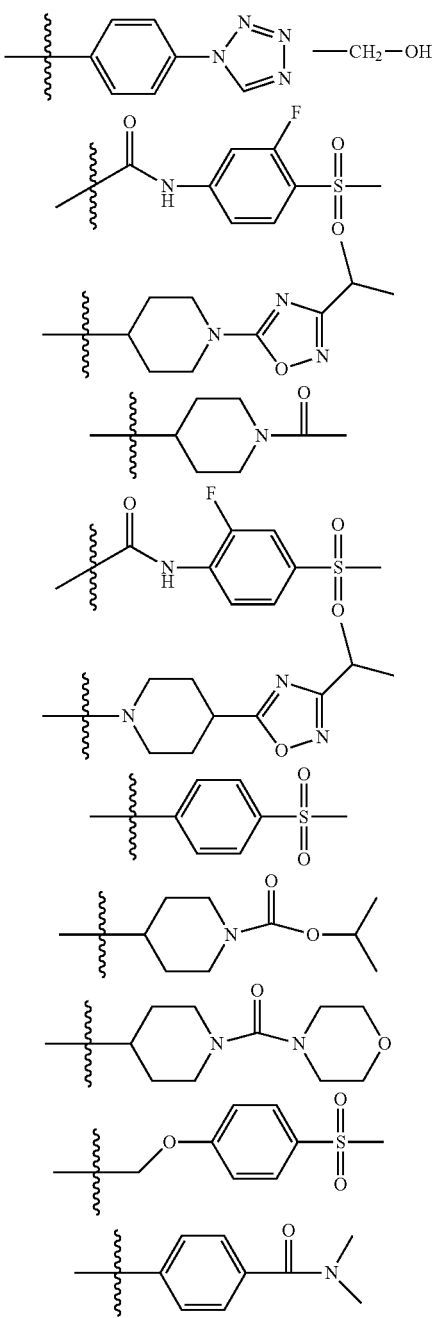
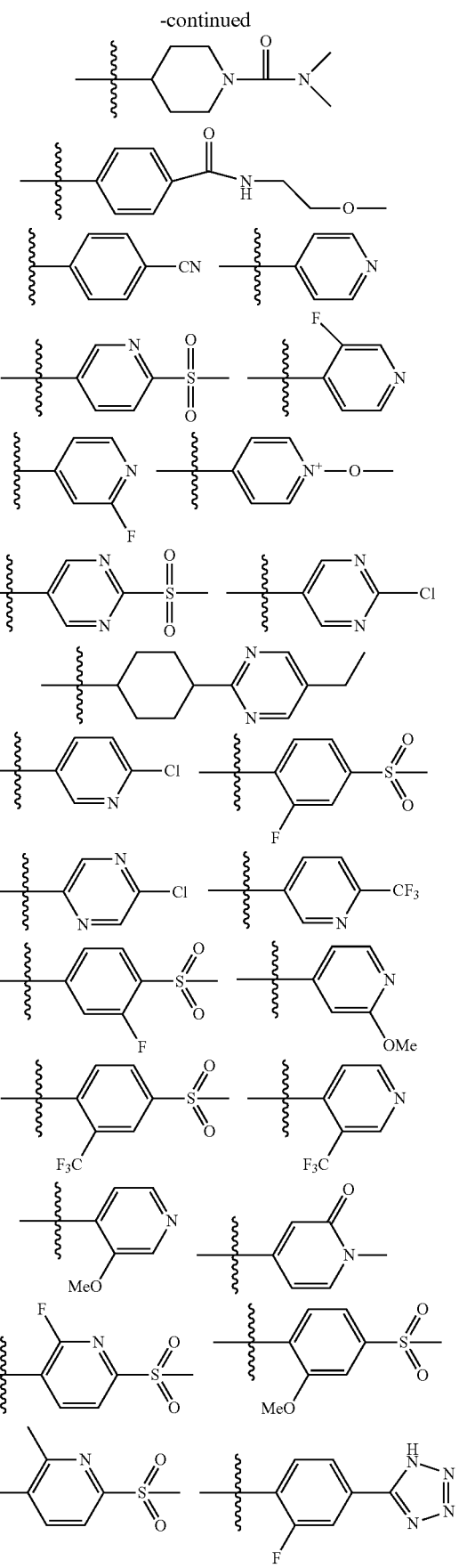

-continued

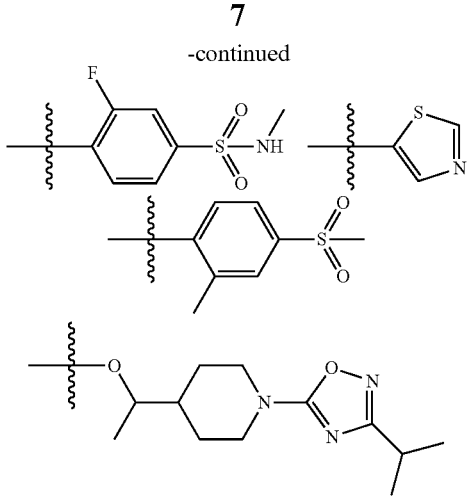

and pharmaceutically acceptable salts, hydrates and stereoisomers thereof.

In one embodiment, there are provided compounds having the formula (II):

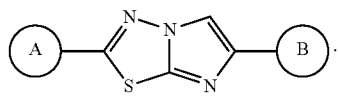

Individually comtemplated are compounds wherein A is

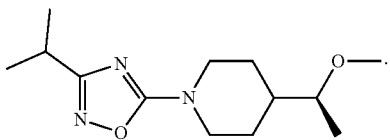 [SMILES: CO[C@@H](C)C1CCN(c2nc(C(C)C)no2)CC1]

Individually contemplated are compounds wherein A is

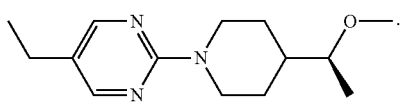 [SMILES: CCc1cnc(N2CCC([C@H](C)OC)CC2)nc1]

Individually contemplated are compounds wherein A is

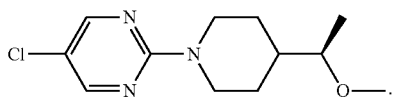

Also individually contemplated are compounds wherein A is

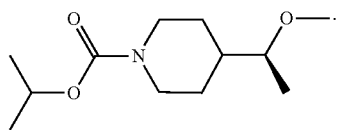 [SMILES: CO[C@@H](C)C1CCN(C(=O)OC(C)C)CC1]

In a variant, the invention provides compounds having significant dose dependent glucose reduction at both 3 mpk and 10 mpk in oral glucose tolerance test in rat model.

In another variant, the invention provides compounds showing significant dose dependent glucose reduction at both 3 mpk and 10 mpk in oral glucose tolerance test in mice.

In another cariant, the invention provides compounds showing active GLP-1 secretion greater than ~1 fold with respect to the vehicle.

In another aspect, the invention provides a method of treating diabetes comprising administering compounds of all embodiments and variants of the invention.

DETAILED DESCRIPTION OF THE INVENTION

A. Compounds of the Present Invention

The term "alkyl" refers to a linear or branched saturated monovalent hydrocarbon, wherein the alkylene may optionally be substituted as described herein. The term "alkyl" also encompasses both linear and branched alkyl, unless otherwise specified. In certain embodiments, the alkyl is a linear saturated monovalent hydrocarbon that has the specified number of carbon atoms, or branched saturated monovalent hydrocarbon of specified number of carbon atoms. As used herein, linear C1-C6 and branched C3-C6 alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, C1-C6 alkyl refers to a linear saturated monovalent hydrocarbon of 1 to 6 carbon atoms or a branched saturated monovalent hydrocarbon of 3 to 6 carbon atoms.

The term "alkoxy" refers to the group R'O— wherein R' is alkyl. The term "lower alkoxy" refers to alkoxy groups having from 1 to 3 carbon atoms; examples include methoxy, ethoxy, isopropoxy, and the like.

The term "aralkyl" or "aryl-alkyl" refers to a monovalent alkyl group substituted with aryl. In certain embodiments, the alkyl and aryl moieties are optionally substituted as described herein.

The term "halogen", "halide" or "halo" refers to fluorine, chlorine, bromine, and iodine.

The term "heteroatom" as used herein means an atom of any element other than carbon or hydrogen. Preferred heteroatoms are nitrogen, oxygen, sulfur, phosphorus and selenium.

The term "optionally substituted" is intended to mean that a group, such as an alkyl, alkylene, alkenyl, alkenylene, alkynyl, alkynylene, alkoxy, alkylamino, dialkylamino, carboxamido, cycloalkyl, cycloalkylene, aryl, arylene, heteroaryl, heteroarylene, heterocyclyl, or heterocyclylene, may be substituted with one or more substituents independently selected from, e.g., (a) C1-C6 alkyl, C2-C6 alkenyl, C2-C6 alkynyl, C3-C7 cycloalkyl, C6-C14 aryl, C7-C15aralkyl, heteroaryl, and heterocyclyl, each optionally substituted with one or more substituents; and (b) halo, cyano (—CN), nitro (—N02), —C(O)R3, —C(O)OR3, —C(O)NRbRC, —C(NR3)NR)RC, —OR3, —OC(O)R3, —OC(O)OR3, —OC(O)NRbRC, —OC(=NR3)NR)RC, —OS(O)R3, —OS(O)2R3, —OS(O)NRbRC, —OS(O) 2NRbRc, —NRbRc, —NR3C(O)Rd, —NR3C(O)ORd, —NR3C(O)NRbRC, —NR3C(=NRd)NRbRC, —NR3S (O)Rd, —NR3S(O)2Rd, —NR3S(O)NRbRC, —NR3S(O)

NRbRc, —SR3, —S(O)R3, —S(O)2R3, —S(O)NRbRC, and —S(O)2NRbRC, wherein each R3, Rb, Re, and Rd is independently (i) hydrogen; (ii) C1-C6 alkyl, C2-C6 alkenyl, C2-C6 alkynyl, C3-C7cycloalkyl, C6-C14 aryl, C7-C15 aralkyl, heteroaryl, or heterocyclyl, each optionally substituted with one or more substituents; or (iii) Rb and Re together with the N atom to which they are attached form heteroaryl or heterocyclyl, optionally substituted with one or more, in one embodiment, one, two, three, or four, substituents. As used herein, all groups that may be substituted are "optionally substituted," unless otherwise specified.

The use of terms "a" and "an" and "the" and similar references in the context of describing the invention (especially in the context of the following claims) are to be construed to cover both the singular and the plural, unless otherwise indicated herein or clearly contraindicated by context.

The term "salt(s)", as employed herein, denotes acidic and/or basic salts formed with inorganic and/or organic acids and bases.

The term "pharmaceutically acceptable salts" refers to the acid addition salt compound formed with a suitable acid selected from an inorganic acid such as hydrochloric acid, hydrobromic acid; or an organic acid such as benzene sulfonic acid, maleic acid, oxalic acid, fumaric acid, succinic acid, p-toluenesulfonic acid and malic acid.

The term "hydrate" as used herein designates a crystalline molecular compound in which water molecules are incorporated into the crystal lattice. Generally speaking, a hydrate thus designates a crystalline form of a molecular compound, whereby the only further molecules incorporated into the crystal lattice are water molecules.

The term "stereoisomer's" refers to at least two compounds having the same molecular formula and connectivity of atoms, but having a different arrangement of atoms in a three-dimensional space. In view of the present disclosure, a stereoisomer can be, for example, an enantiomer, a diastereomer, or a meso compound.

The term "GPR119" as used herein refers to the G protein-coupled receptor that in humans is encoded by the GPR119 gene.

The present invention provides compound represented by formula (1) that act as GPR119 agonist and is used in the treatment of diabetes, preferably type 2 diabetes mellitus.

The compounds of the present invention may be illustrated but not limited to the examples as provided at Table 1.

TABLE 1

Illustrative compounds of present invention

| Compound No. | IUPAC name | Structure |
|---|---|---|
| 1001 | 3,4-bis(4-(1H-tetrazol-1-yl)phenoxy)-1,2,5-thiadiazole | 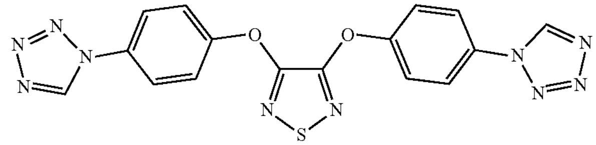 [SMILES: c1cc(-n2cnnn2)ccc1Oc1nsnc1Oc1ccc(-n2cnnn2)cc1] |
| 1002 | 3,4-bis((1-(3-isopropyl-1,2,4-oxadiazol-5-yl)piperidin-4-yl)oxy)-1,2,5-thiadiazole | 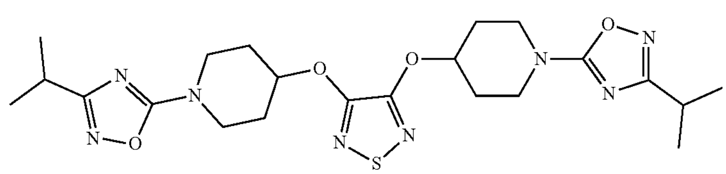 [SMILES: CC(C)c1noc(N2CCC(Oc3nsnc3OC3CCN(c4nc(C(C)C)no4)CC3)CC2)n1] |
| 1003 | 5-(1-(4-(4-(1H-tetrazol-1-yl)phenoxy)-1,2,5-thiadiazol-3-yl)piperidin-4-yl)-3-isopropyl-1,2,4-oxadiazole | 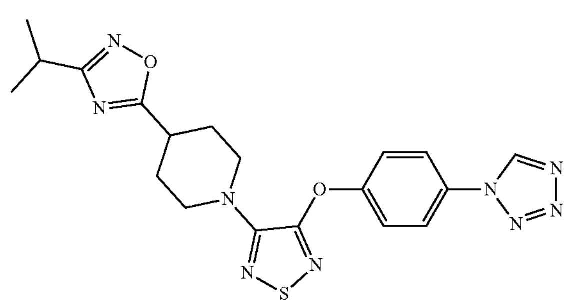 [SMILES: CC(C)c1noc(C2CCN(c3nsnc3Oc3ccc(-n4cnnn4)cc3)CC2)n1] |

TABLE 1-continued

Illustrative compounds of present invention

| Compound No. | IUPAC name | Structure |
| --- | --- | --- |
| 1004 | 3-(1-(5-ethylpyrimidin-2-yl)piperidin-4-yl)-4-(4-(methylsulfonyl)phenyl)-1,2,5-thiadiazole | 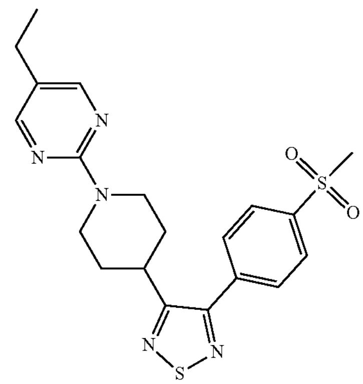 [SMILES: CCc1cnc(N2CCC(c3nsnc3-c3ccc(S(C)(=O)=O)cc3)CC2)nc1] |
| 1005 | 3-(4-(1H-tetrazol-1-yl)phenoxy)-4-(1-(5-ethylpyrimidin-2-yl)-1,2,3,6-tetrahydropyridin-4-yl)-1,2,5-thiadiazole | 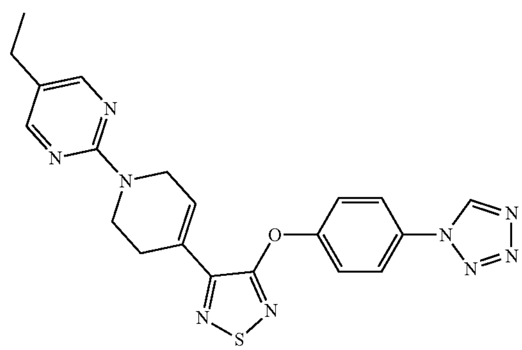 [SMILES: CCc1cnc(N2CC=C(c3nsnc3Oc3ccc(-n4cnnn4)cc3)CC2)nc1] |
| 1006 | 5-(1-(4-((2-fluoro-4-(methylsulfonyl)phenoxy)methyl)-1,2,5-thiadiazol-3-yl)piperidin-4-yl)-3-isopropyl-1,2,4-oxadiazole | 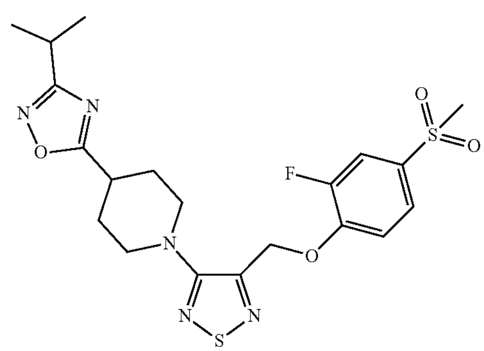 [SMILES: CC(C)c1noc(C2CCN(c3nsnc3COc3ccc(S(C)(=O)=O)cc3F)CC2)n1] |
| 1007 | 3-isopropyl-5-(1-(4-(4-(methylsulfonyl)phenyl)-1,2,5-thiadiazol-3-yl)piperidin-4-yl)-1,2,4-oxadiazole | 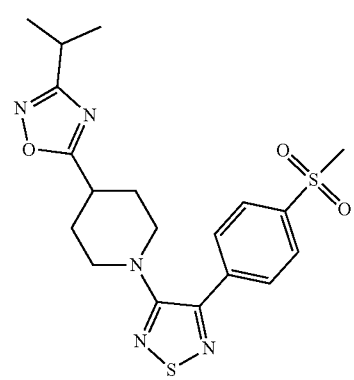 [SMILES: CC(C)c1noc(C2CCN(c3nsnc3-c3ccc(S(C)(=O)=O)cc3)CC2)n1] |

TABLE 1-continued

Illustrative compounds of present invention

| Compound No. | IUPAC name | Structure |
|---|---|---|
| 1008 | (4-(1-(5-ethylpyrimidin-2-yl)-1,2,3,6-tetrahydropyridin-4-yl)-1,2,5-thiadiazol-3-yl)methanol | 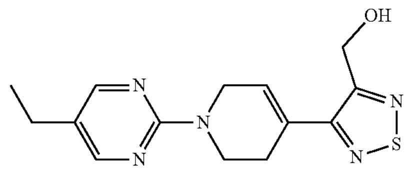 [SMILES: CCc1cnc(N2CC=C(c3nsnc3CO)CC2)nc1] |
| 1009 | 5-(1-(4-((4-(1H-tetrazol-1-yl)phenoxy)methyl)-1,2,5-thiadiazol-3-yl)piperidin-4-yl)-3-isopropyl-1,2,4-oxadiazole | 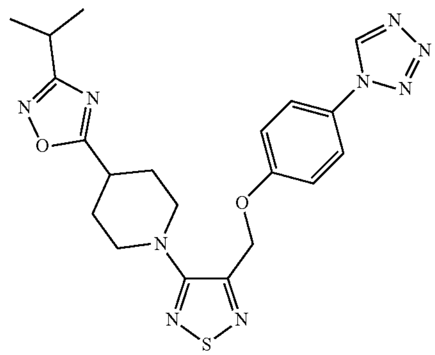 [SMILES: CC(C)c1noc(C2CCN(c3nsnc3COc3ccc(-n4cnnn4)cc3)CC2)n1] |
| 1010 | isopropyl 4-(4-(4-(1H-tetrazol-1-yl)phenoxy)-1,2,5-thiadiazol-3-yl)piperazine-1-carboxylate | 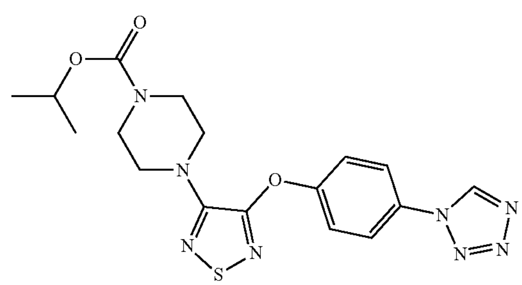 [SMILES: CC(C)OC(=O)N1CCN(c2nsnc2Oc2ccc(-n3cnnn3)cc2)CC1] |
| 1011 | 3,4-bis((1-(3-isopropyl-1,2,4-oxadiazol-5-yl)piperidin-4-yl)methoxy)-1,2,5-thiadiazole | 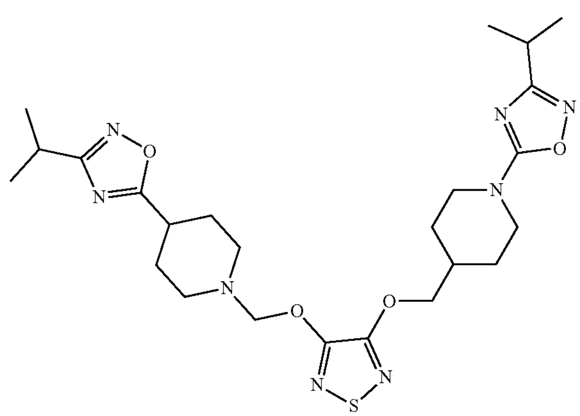 [SMILES: CC(C)c1noc(C2CCN(COc3nsnc3OCC3CCN(c4nc(C(C)C)no4)CC3)CC2)n1] |

TABLE 1-continued

Illustrative compounds of present invention

| Compound No. | IUPAC name | Structure |
|---|---|---|
| 1012 | N-(2-fluoro-4-(methylsulfonyl)phenyl)-4-(4-(3-isopropyl-1,2,4-oxadiazol-5-yl)piperidin-1-yl)-1,2,5-thiadiazole-3-carboxamide | 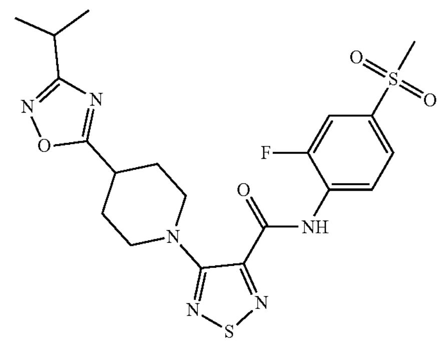 [SMILES: CC(C)c1noc(C2CCN(c3nsnc3C(=O)Nc3ccc(S(C)(=O)=O)cc3F)CC2)n1] |
| 1013 | N-(3-fluoro-4-(methylsulfonyl)phenyl)-4-(4-(3-isopropyl-1,2,4-oxadiazol-5-yl)piperidin-1-yl)-1,2,5-thiadiazole-3-carboxamide | 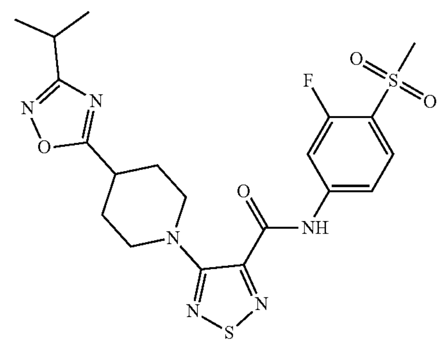 [SMILES: CC(C)c1noc(C2CCN(c3nsnc3C(=O)Nc3ccc(S(C)(=O)=O)c(F)c3)CC2)n1] |
| 1014 | 4-(1-(5-ethylpyrimidin-2-yl)-1,2,3,6-tetrahydropyridin-4-yl)-N-(2-fluoro-4-(methylsulfonyl)phenyl)-1,2,5-thiadiazole-3-carboxamide | 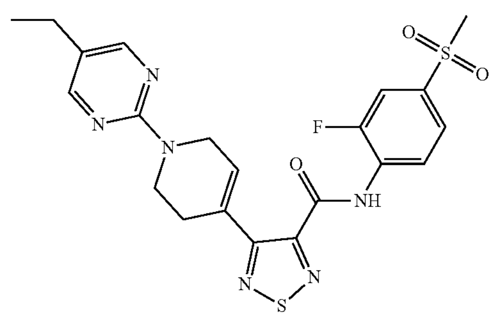 [SMILES: CCc1cnc(N2CC=C(c3nsnc3C(=O)Nc3ccc(S(C)(=O)=O)cc3F)CC2)nc1] |
| 1015 | 4-(1-(5-ethylpyrimidin-2-yl)piperidin-4-yl)-N-(2-fluoro-4-(methylsulfonyl)phenyl)-1,2,5-thiadiazole-3-carboxamide | 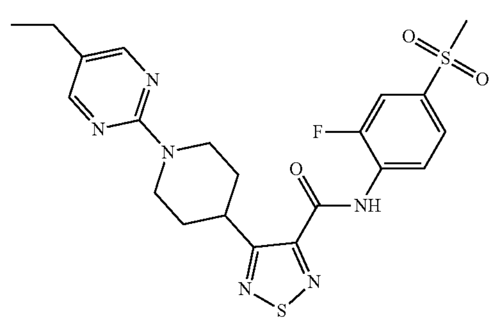 |
| 1016 | 3-isopropyl-5-(1-(6-(4-(methylsulfonyl)phenyl)imidazo[2,1-b][1,3,4]thiadiazol-2-yl)piperidin-4-yl)-1,2,4-oxadiazole | 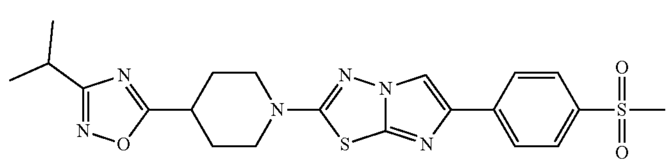 |

TABLE 1-continued

Illustrative compounds of present invention

| Compound No. | IUPAC name | Structure |
|---|---|---|
| 1017 | 3-isopropyl-5-(4-(((6-(4-(methylsulfonyl)phenyl)imidazo[2,1-b][1,3,4]thiadiazol-2-yl)oxy)methyl)piperidin-1-yl)-1,2,4-oxadiazole | 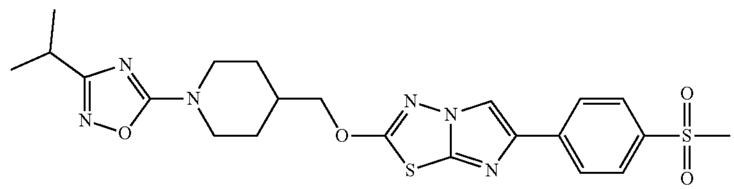 |
| 1018 | 3-isopropyl-5-(4-((6-(4-(methylsulfonyl)phenyl)imidazo[2,1-b][1,3,4]thiadiazol-2-yl)oxy)piperidin-1-yl)-1,2,4-oxadiazole | 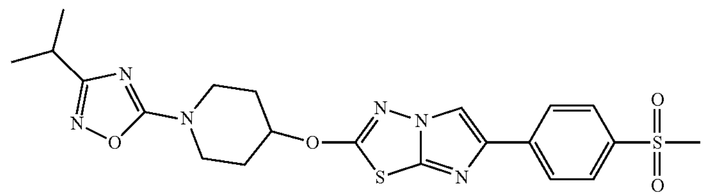 [SMILES: CC(C)c1noc(N2CCC(Oc3nn4cc(-c5ccc(S(C)(=O)=O)cc5)nc4s3)CC2)n1] |
| 1019 | 2-(1-benzylpiperidin-4-yl)-6-(4-(methylsulfonyl)phenyl)imidazo[2,1-b][1,3,4]thiadiazole | 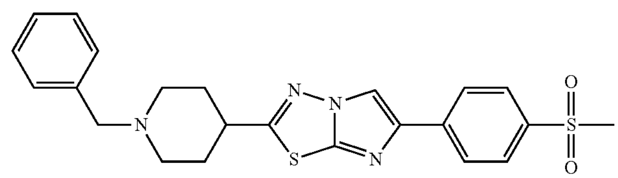 [SMILES: CS(=O)(=O)c1ccc(-c2cn3nc(C4CCN(Cc5ccccc5)CC4)sc3n2)cc1] |
| 1020 | isopropyl 4-(6-(4-(methylsulfonyl)phenyl)imidazo[2,1-b][1,3,4]thiadiazol-2-yl)piperazine-1-carboxylate | 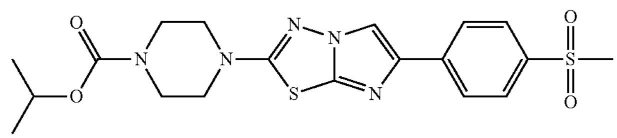 [SMILES: CC(C)OC(=O)N1CCN(c2nn3cc(-c4ccc(S(C)(=O)=O)cc4)nc3s2)CC1] |
| 1021 | isopropyl 4-((6-(4-(methylsulfonyl)phenyl)imidazo[2,1-b][1,3,4]thiadiazol-2-yl)amino)piperidine-1-carboxylate | 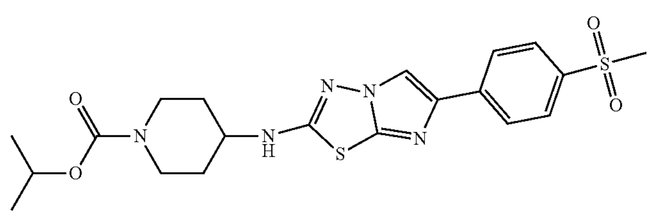 [SMILES: CC(C)OC(=O)N1CCC(Nc2nn3cc(-c4ccc(S(C)(=O)=O)cc4)nc3s2)CC1] |
| 1022 | isopropyl 4-(methyl(6-(4-(methylsulfonyl)phenyl)imidazo[2,1-b][1,3,4]thiadiazol-2-yl)amino)piperidine-1-carboxylate | 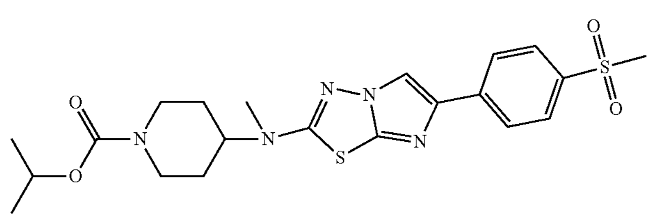 [SMILES: CC(C)OC(=O)N1CCC(N(C)c2nn3cc(-c4ccc(S(C)(=O)=O)cc4)nc3s2)CC1] |
| 1023 | N-(1-(5-ethylpyrimidin-2-yl)piperidin-4-yl)-6-(4-(methylsulfonyl)phenyl)imidazo[2,1-b][1,3,4]thiadiazol-2-amine | 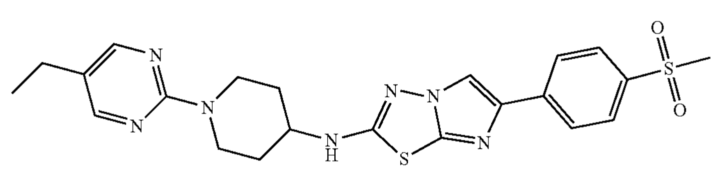 [SMILES: CCc1cnc(N2CCC(Nc3nn4cc(-c5ccc(S(C)(=O)=O)cc5)nc4s3)CC2)nc1] |
| 1024 | isopropyl 4-(6-(4-(methylsulfonyl)phenyl)imidazo[2,1-b][1,3,4]thiadiazol-2-yl)piperidine-1-carboxylate | 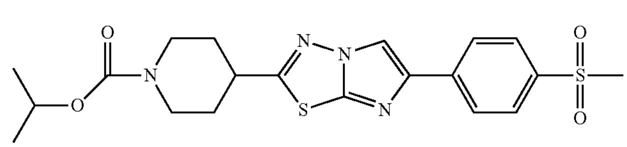 [SMILES: CC(C)OC(=O)N1CCC(c2nn3cc(-c4ccc(S(C)(=O)=O)cc4)nc3s2)CC1] |

TABLE 1-continued

Illustrative compounds of present invention

| Compound No. | IUPAC name | Structure |
|---|---|---|
| 1025 | 4-(methyl(6-(4-(methylsulfonyl)phenyl)imidazo[2,1-b][1,3,4]thiadiazol-2-yl)amino)piperidine-1-carboxamide | 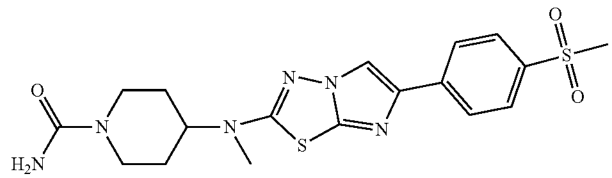 [SMILES: CN(c1nn2cc(-c3ccc(S(C)(=O)=O)cc3)nc2s1)C1CCN(C(N)=O)CC1] |
| 1026 | 4-(6-(4-(methylsulfonyl)phenyl)imidazo[2,1-b][1,3,4]thiadiazol-2-yl)piperidine-1-carboxamide | 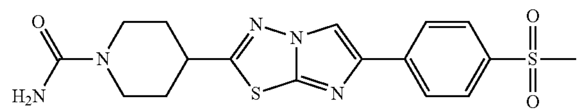 [SMILES: CS(=O)(=O)c1ccc(-c2cn3nc(C4CCN(C(N)=O)CC4)sc3n2)cc1] |
| 1027 | 3-isopropyl-5-(4-(6-(4-(methylsulfonyl)phenyl)imidazo[2,1-b][1,3,4]thiadiazol-2-yl)piperidin-1-yl)-1,2,4-oxadiazole | 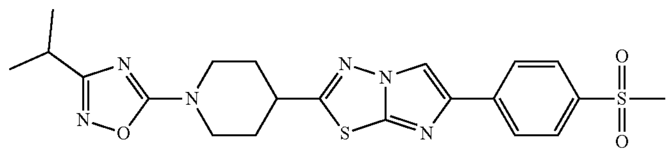 |
| 1028 | 1-(4-(2-(4-(methylsulfonyl)phenyl)imidazo[2,1-b][1,3,4]thiadiazol-6-yl)piperidin-1-yl)ethanone | 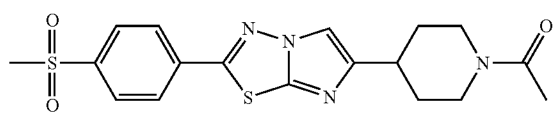 [SMILES: CC(=O)N1CCC(c2cn3nc(-c4ccc(S(C)(=O)=O)cc4)sc3n2)CC1] |
| 1029 | N-(1-(3-isopropyl-1,2,4-oxadiazol-5-yl)piperidin-4-yl)-N-methyl-6-(4-(methylsulfonyl)phenyl)imidazo[2,1-b][1,3,4]thiadiazol-2-amine | 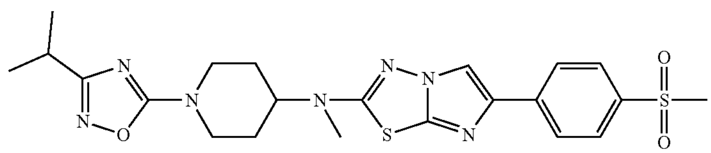 [SMILES: CC(C)c1noc(N2CCC(N(C)c3nn4cc(-c5ccc(S(C)(=O)=O)cc5)nc4s3)CC2)n1] |
| 1030 | isopropyl 4-(2-(4-(methylsulfonyl)phenyl)imidazo[2,1-b][1,3,4]thiadiazol-6-yl)piperidine-1-carboxylate | 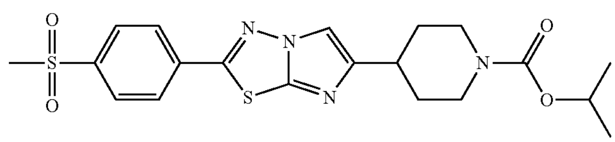 [SMILES: CC(C)OC(=O)N1CCC(c2cn3nc(-c4ccc(S(C)(=O)=O)cc4)sc3n2)CC1] |
| 1031 | 6-(4-(methylsulfonyl)phenyl)-2-(1-(methylsulfonyl)piperidin-4-yl)imidazo[2,1-b][1,3,4]thiadiazole | 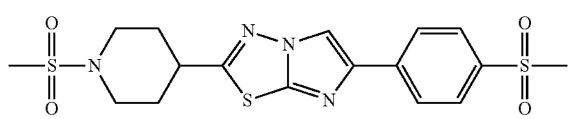 |
| 1032 | 3-isopropyl-5-(4-(2-(4-(methylsulfonyl)phenyl)imidazo[2,1-b][1,3,4]thiadiazol-6-yl)piperidin-1-yl)-1,2,4-oxadiazole | 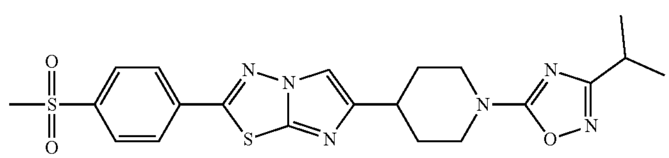 [SMILES: CC(C)c1noc(N2CCC(c3cn4nc(-c5ccc(S(C)(=O)=O)cc5)sc4n3)CC2)n1] |
| 1033 | N,N-dimethyl-4-(6-(4-(methylsulfonyl)phenyl)imidazo[2,1-b][1,3,4]thiadiazol-2-yl)piperidine-1-carboxamide | 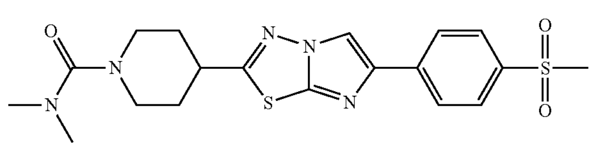 |
| 1034 | isopropyl 4-(2-(4-(dimethylcarbamoyl)phenyl)imidazo[2,1-b][1,3,4]thiadiazol-6-yl)piperidine-1-carboxylate | 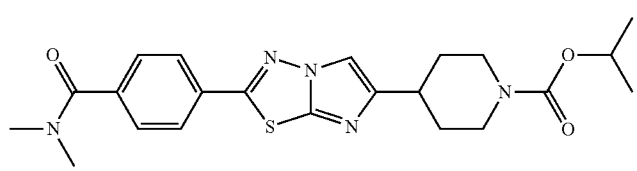 [SMILES: CC(C)OC(=O)N1CCC(c2cn3nc(-c4ccc(C(=O)N(C)C)cc4)sc3n2)CC1] |

TABLE 1-continued

Illustrative compounds of present invention

| Compound No. | IUPAC name | Structure |
|---|---|---|
| 1035 | isopropyl 4-(2-(4-((2-methoxyethyl)carbamoyl)phenyl)imidazo[2,1-b][1,3,4]thiadiazol-6-yl)piperidine-1-carboxylate | 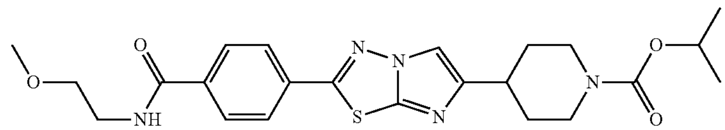 [SMILES: COCCNC(=O)c1ccc(-c2nn3cc(C4CCN(C(=O)OC(C)C)CC4)nc3s2)cc1] |
| 1036 | 4-(2-(4-(3-isopropyl-1,2,4-oxadiazol-5-yl)pipendin-1-yl)imidazo[2,1-b][1,3,4]thiadiazol-6-yl)-N,N-dimethylbenzamide | 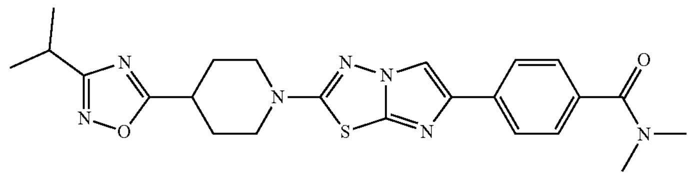 [SMILES: CC(C)c1noc(C2CCN(c3nn4cc(-c5ccc(C(=O)N(C)C)cc5)nc4s3)CC2)n1] |
| 1037 | (4-(2-(4-(3-isopropyl-1,2,4-oxadiazol-5-yl)piperidin-1-yl)imidazo[2,1-b][1,3,4]thiadiazol-6-yl)phenyl)(morpholino)methanone | 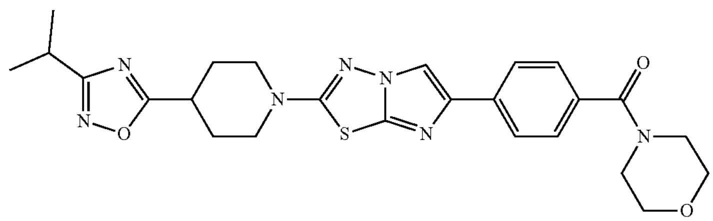 [SMILES: CC(C)c1noc(C2CCN(c3nn4cc(-c5ccc(C(=O)N6CCOCC6)cc5)nc4s3)CC2)n1] |
| 1038 | 2-(1-benzylpiperidin-4-yl)-6-((4-(methylsulfonyl)phenoxy)methyl)imidazo[2,1-b][1,3,4]thiadiazole | 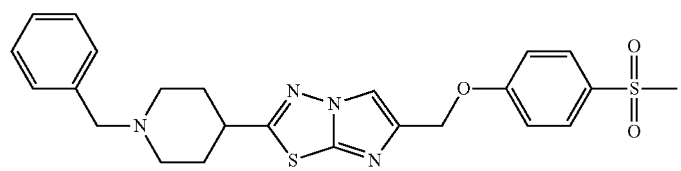 [SMILES: CS(=O)(=O)c1ccc(OCc2cn3nc(C4CCN(Cc5ccccc5)CC4)sc3n2)cc1] |
| 1039 | 4-(2-(4-(3-isopropyl-1,2,4-oxadiazol-5-yl)piperidin-1-yl)iidazo[2,1-b][1,3,4]thiadiazol-6-yl)-N-(2-methoxyethyl)benzamide | 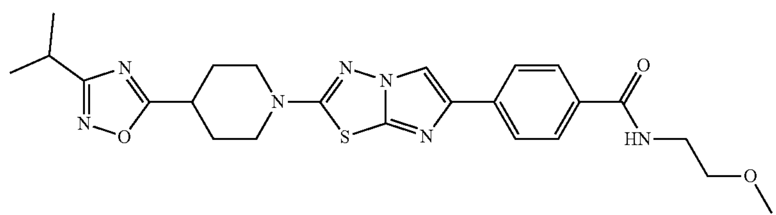 [SMILES: COCCNC(=O)c1ccc(-c2cn3nc(N4CCC(c5nc(C(C)C)no5)CC4)sc3n2)cc1] |
| 1040 | 3-isopropyl-5-(1-(6-((4-(methylsulfonyl)phenoxy)methyl)imidazo[2,1-b][1,3,4]thiadiazol-2-yl)piperidin-4-yl)-1,2,4-oxadiazole | 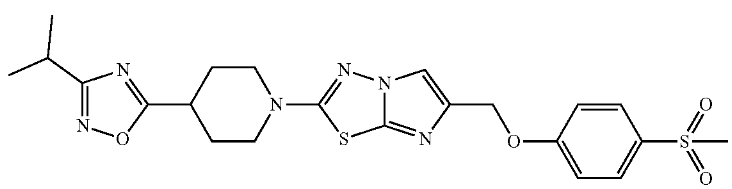 [SMILES: CC(C)c1noc(C2CCN(c3nn4cc(COc5ccc(S(C)(=O)=O)cc5)nc4s3)CC2)n1] |
| 1041 | isopropyl 4-(6-((4-(methylsulfonyl)phenoxy)methyl)imidazo[2,1-b][1,3,4]thiadiazol-2-yl)piperidine-1-carboxylate | 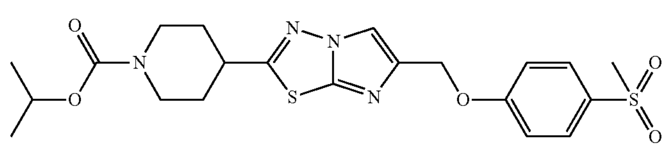 [SMILES: CC(C)OC(=O)N1CCC(c2nn3cc(COc4ccc(S(C)(=O)=O)cc4)nc3s2)CC1] |
| 1042 | 3-isopropyl-5-(4-((6-((4-(methylsulfonyl)phenoxy)methyl)imidazo[2,1-b][1,3,4]thiadiazol-2-yl)oxy)piperidin-1-yl)-1,2,4-oxadiazole | 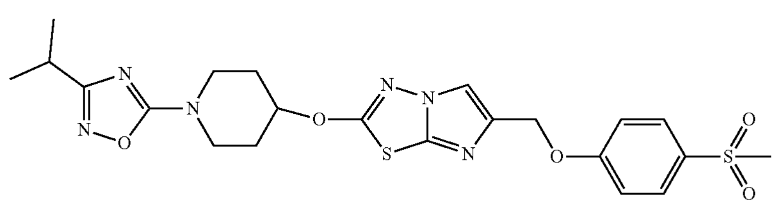 [SMILES: CC(C)c1noc(N2CCC(Oc3nn4cc(COc5ccc(S(C)(=O)=O)cc5)nc4s3)CC2)n1] |

TABLE 1-continued

Illustrative compounds of present invention

| Compound No. | IUPAC name | Structure |
|---|---|---|
| 1043 | 4-((2-(4-(3-isopropyl-1,2,4-oxadiazol-5-yl)piperidin-1-yl)imidazo[2,1-b][1,3,4]thiadiazol-6-yl)methoxy)-N,N-dimethylbenzamide | 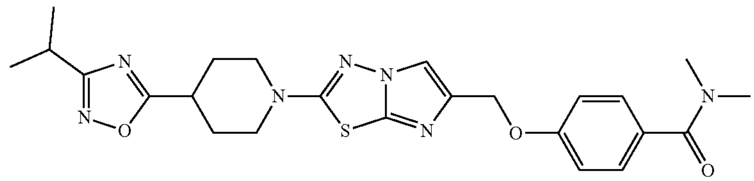 [SMILES: CC(C)c1noc(C2CCN(c3nn4cc(COc5ccc(C(=O)N(C)C)cc5)nc4s3)CC2)n1] |
| 1044 | 5-(1-(5-chloro-6-(4-(methylsulfonyl)phenyl)imidazo[2,1-b][1,3,4]thiadiazol-2-yl)piperidin-4-yl)-3-isopropyl-1,2,4-oxadiazole | 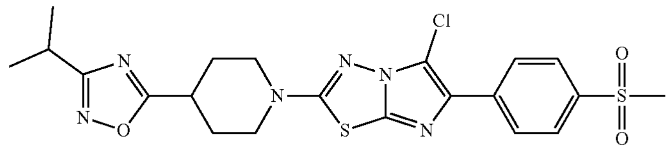 |
| 1045 | 3-cyclopropyl-5-(1-(6-(4-(methylsulfonyl)phenyl)imidazo[2,1-b][1,3,4]thiadiazol-2-yl)piperidin-4-yl)-1,2,4-oxadiazole | 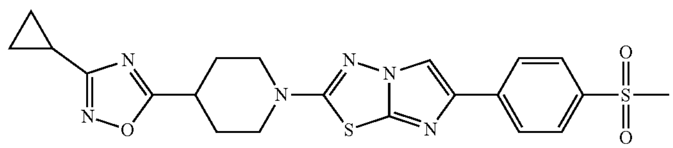 [SMILES: CS(=O)(=O)c1ccc(-c2cn3nc(N4CCC(c5nc(C6CC6)no5)CC4)sc3n2)cc1] |
| 1046 | 4-(2-(4-(3-isopropyl-1,2,4-oxadiazol-5-yl)piperidin-1-yl)imidazo[2,1-b][1,3,4]thiadiazol-6-yl)benzonitrile | 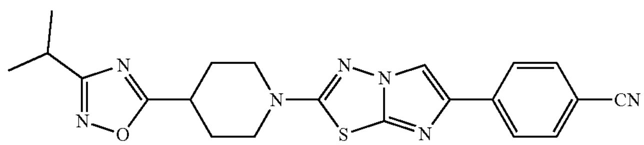 [SMILES: CC(C)c1noc(C2CCN(c3nn4cc(-c5ccc(C#N)cc5)nc4s3)CC2)n1] |
| 1047 | 4-(2-(1-(1-(3-isopropyl-1,2,4-oxadiazol-5-yl)piperidin-4-yl)ethoxy)imidazo[2,1-b][1,3,4]thiadiazol-6-yl)benzonitrile | 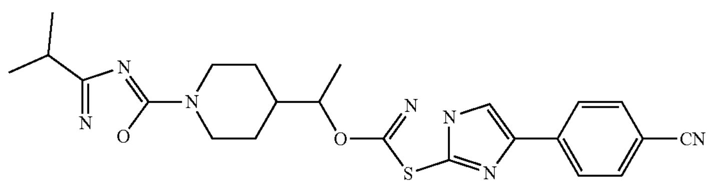 [SMILES: CC(C)C(=N)/N=C(\O)N1CCC(C(C)OC(=N)Sc2nc(-c3ccc(C#N)cc3)c[nH]2)CC1] |
| 1048 | 4-(2-(1-(1-(3-isopropyl-1,2,4-oxadiazol-5-yl)piperidin-4-yl)ethoxy)imidazo[2,1-b][1,3,4]thiadiazol-6-yl)-N,N-dimethylbenzamide | 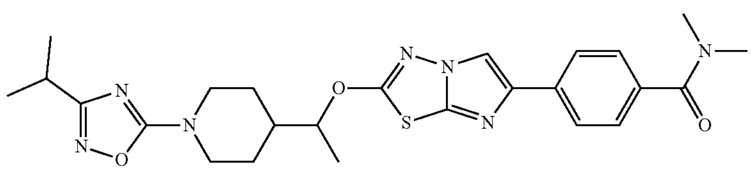 [SMILES: CC(C)c1noc(N2CCC(C(C)Oc3nn4cc(-c5ccc(C(=O)N(C)C)cc5)nc4s3)CC2)n1] |
| 1049 | N,N-dimethyl-4-(2-(1-(1-(5-propylpyrimidin-2-yl)piperidin-4-yl)ethoxy)imidazo[2,1-b][1,3,4]thiadiazol-6-yl)benzamide | 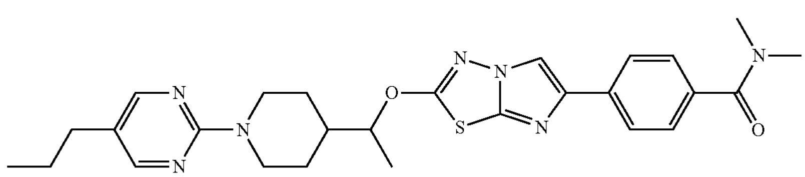 [SMILES: CCCc1cnc(N2CCC(C(C)Oc3nn4cc(-c5ccc(C(=O)N(C)C)cc5)nc4s3)CC2)nc1] |
| 1050 | 3-isopropyl-5-(4-(1-((6-(pyridin-4-yl)imidazo[2,1-b][1,3,4]thiadiazol-2-yl)oxy)ethyl)piperidin-1-yl)-1,2,4-oxadiazole | 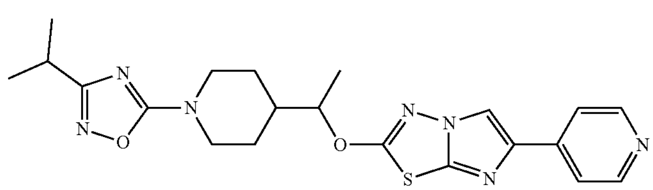 |
| 1051 | 3-isopropyl-5-(1-(6-(pyridin-4-yl)imidazo[2,1-b][1,3,4]thiadiazol-2-yl)piperidin-4-yl)-1,2,4-oxadiazole | 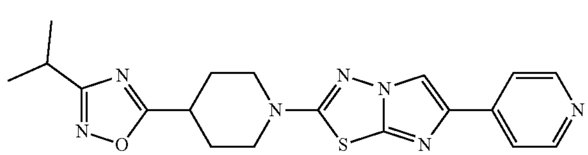 [SMILES: CC(C)c1noc(C2CCN(c3nn4cc(-c5ccncc5)nc4s3)CC2)n1] |

TABLE 1-continued

Illustrative compounds of present invention

| Compound No. | IUPAC name | Structure |
|---|---|---|
| 1052 | 5-(1-(5-chloro-6-(pyridin-4-yl)imidazo[2,1-b][1,3,4]thiadiazol-2-yl)piperidin-4-yl)-3-isopropyl-1,2,4-oxadiazole | 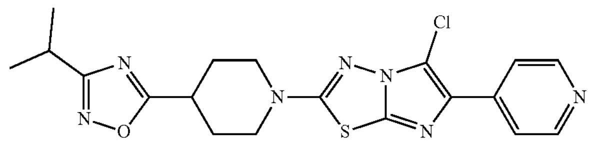 [SMILES: CC(C)c1noc(C2CCN(c3nn4c(Cl)c(-c5ccncc5)nc4s3)CC2)n1] |
| 1053 | 4-(2-((1-(3-isopropyl-1,2,4-oxadiazol-5-yl)piperidin-4-yl)methoxy)imidazo[2,1-b][1,3,4]thiadiazol-6-yl)benzonitrile | 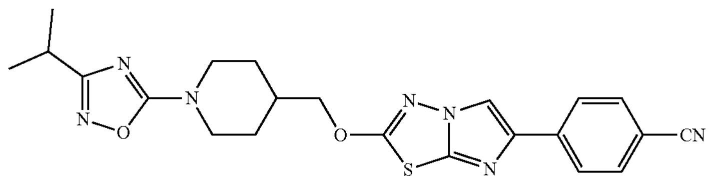 [SMILES: CC(C)c1noc(N2CCC(COc3nn4cc(-c5ccc(C#N)cc5)nc4s3)CC2)n1] |
| 1054 | 3-isopropyl-5-(4-(((6-(pyridin-4-yl)imidazo[2,1-b][1,3,4]thiadiazol-2-yl)oxy)methyl)piperidin-1-yl)-1,2,4-oxadiazole | 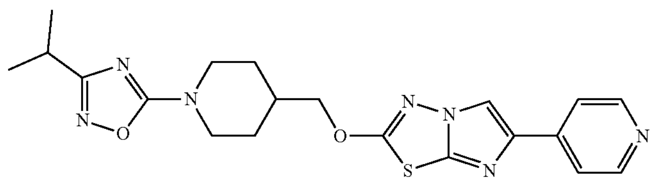 [SMILES: CC(C)c1noc(N2CCC(COc3nn4cc(-c5ccncc5)nc4s3)CC2)n1] |
| 1055 | 3-isopropyl-5-(4-(1-((6-(6-(methylsulfonyl)pyridin-3-yl)imidazo[2,1-b][1,3,4]thiadiazol-2-yl)oxy)ethyl)piperidin-1-yl)-1,2,4-oxadiazole | 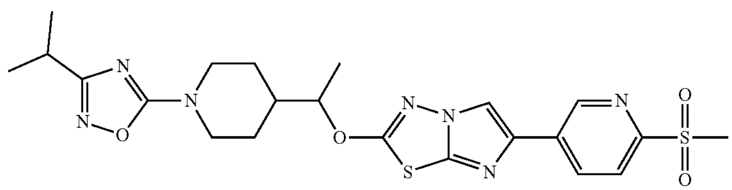 |
| 1056 | 2-(1-(1-(5-ethylpyrimidin-2-yl)piperidin-4-yl)ethoxy)-6-(pyridin-4-yl)imidazo[2,1-b][1,3,4]thiadiazole | 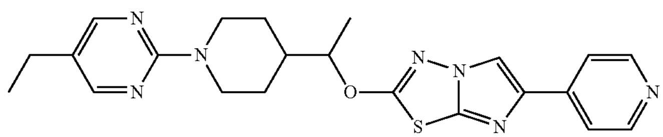 [SMILES: CCc1cnc(N2CCC(C(C)Oc3nn4cc(-c5ccncc5)nc4s3)CC2)nc1] |
| 1057 | 3-isopropyl-5-(4-(1-((6-(4-(methylsulfonyl)phenyl)imidazo[2,1-b][1,3,4]thiadiazol-2-yl)oxy)ethyl)piperidin-1-yl)-1,2,4-oxadiazole | 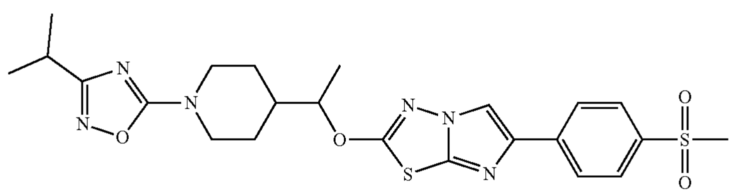 [SMILES: CC(C)c1noc(N2CCC(C(C)Oc3nn4cc(-c5ccc(S(C)(=O)=O)cc5)nc4s3)CC2)n1] |
| 1058 | (R)-3-isopropyl-5-(4-(1-((6-(6-(methylsulfonyl)pyridin-3-yl)imidazo[2,1-b][1,3,4]thiadiazol-2-yl)oxy)ethyl)piperidin-1-yl)-1,2,4-oxadiazole | 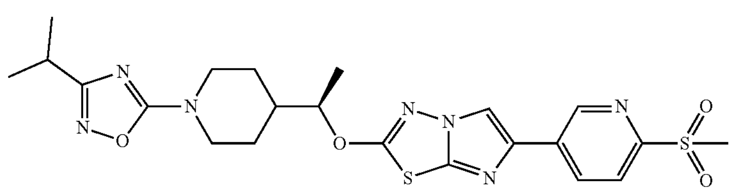 [SMILES: CC(C)c1noc(N2CCC([C@@H](C)Oc3nn4cc(-c5ccc(S(C)(=O)=O)nc5)nc4s3)CC2)n1] |
| 1059 | (R)-3-isopropyl-5-(4-(1-((6-(pyridin-4-yl)imidazo[2,1-b][1,3,4]thiadiazol-2-yl)oxy)ethyl)piperidin-1-yl)-1,2,4-oxadiazole | 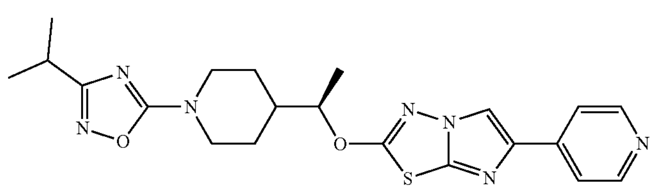 [SMILES: CC(C)c1noc(N2CCC([C@@H](C)Oc3nn4cc(-c5ccncc5)nc4s3)CC2)n1] |

TABLE 1-continued

Illustrative compounds of present invention

| Compound No. | IUPAC name | Structure |
|---|---|---|
| 1060 | (R)-3-isopropyl-5-(4-(1-((6-(4-(methylsulfonyl)phenyl)imidazo[2,1-b][1,3,4]thiadiazol-2-yl)oxy)ethyl)piperidin-1-yl)-1,2,4-oxadiazole | 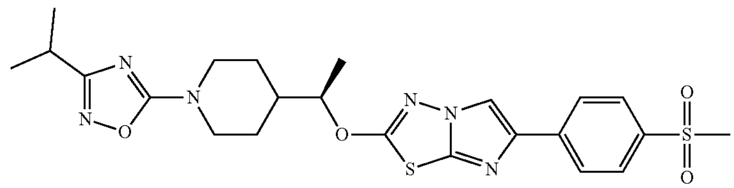 [SMILES: CC(C)c1noc(N2CCC([C@@H](C)Oc3nn4cc(-c5ccc(S(C)(=O)=O)cc5)nc4s3)CC2)n1] |
| 1061 | 5-(4-(1-((5-fluoro-6-(4-(methylsulfonyl)phenyl)imidazo[2,1-b][1,3,4]thiadiazol-2-yl)oxy)ethyl)piperidin-1-yl)-3-isopropyl-1,2,4-oxadiazole | 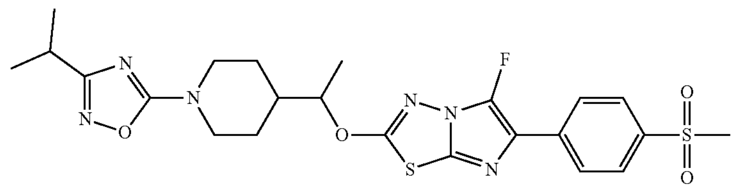 |
| 1062 | (R)-2-(1-(1-(5-ethylpyrimidin-2-yl)piperidin-4-yl)ethoxy)-6-(4-(methylsulfonyl)phenyl)imidazo[2,1-b][1,3,4]thiadiazole | 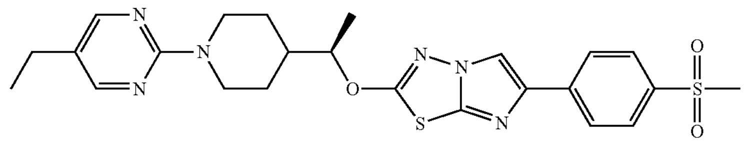 [SMILES: CCc1cnc(N2CCC([C@@H](C)Oc3nn4cc(-c5ccc(S(C)(=O)=O)cc5)nc4s3)CC2)nc1] |
| 1063 | 5-(4-(1-((5-chloro-6-(4-(methylsulfonyl)phenyl)imidazo[2,1-b][1,3,4]thiadiazol-2-yl)oxy)ethyl)piperidin-1-yl)-3-isopropyl-1,2,4-oxadiazole | 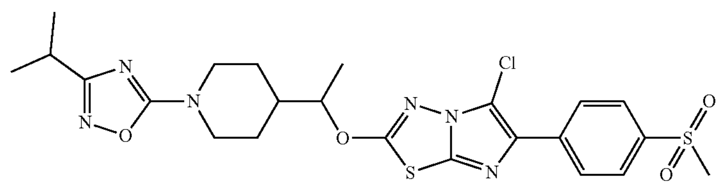 [SMILES: CC(C)c1noc(N2CCC(C(C)Oc3nn4c(Cl)c(-c5ccc(S(C)(=O)=O)cc5)nc4s3)CC2)n1] |
| 1064 | (S)-5-(4-(1-((6-(3-fluoropyridin-4-yl)imidazo[2,1-b][1,3,4]thiadiazol-2-yl)oxy)ethyl)piperidin-1-yl)-3-isopropyl-1,2,4-oxadiazole | 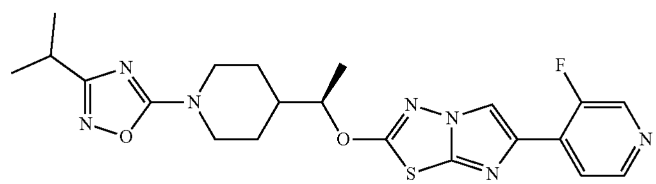 [SMILES: CC(C)c1noc(N2CCC([C@@H](C)Oc3nn4cc(-c5ccncc5F)nc4s3)CC2)n1] |
| 1065 | (R)-5-(4-(1-((6-(2-fluoropyridin-4-yl)imidazo[2,1-b][1,3,4]thiadiazol-2-yl)oxy)ethyl)piperidin-1-yl)-3-isopropyl-1,2,4-oxadiazole | 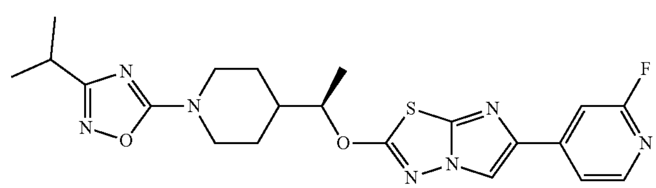 [SMILES: CC(C)c1noc(N2CCC([C@@H](C)Oc3nn4cc(-c5ccnc(F)c5)nc4s3)CC2)n1] |
| 1066 | (R)-5-(4-(1-((5-fluoro-6-(4-(methylsulfonyl)phenyl)imidazo[2,1-b][1,3,4]thiadiazol-2-yl)oxy)ethyl)piperidin-1-yl)-3-isopropyl-1,2,4-oxadiazole | 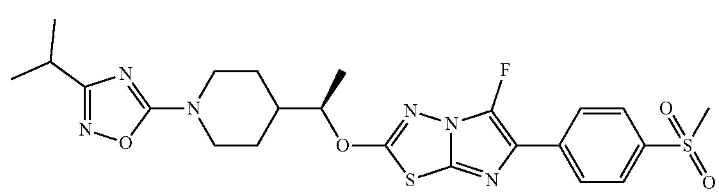 [SMILES: CC(C)c1noc(N2CCC([C@@H](C)Oc3nn4c(F)c(-c5ccc(S(C)(=O)=O)cc5)nc4s3)CC2)n1] |
| 1067 | (S)-6-(4-(methylsulfonyl)phenyl)-2-(1-(1-(5-propylpyrimidin-2-yl)piperidin-4-yl)ethoxy)imidazo[2,1-b][1,3,4]thiadiazole | 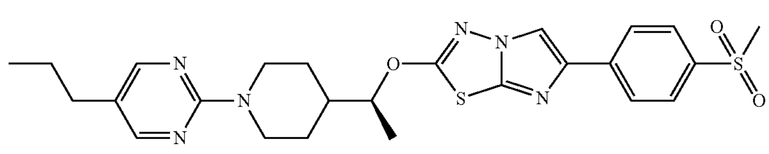 [SMILES: CCCc1cnc(N2CCC([C@H](C)Oc3nn4cc(-c5ccc(S(C)(=O)=O)cc5)nc4s3)CC2)nc1] |

TABLE 1-continued

Illustrative compounds of present invention

| Compound No. | IUPAC name | Structure |
|---|---|---|
| 1068 | (S)-4-(2-(1-(1-(3-isopropyl-1,2,4-oxadiazol-5-yl)piperidin-4-yl)ethoxy)imidazo[2,1-b][1,3,4]thiadiazol-6-yl)pyridine1-oxide | 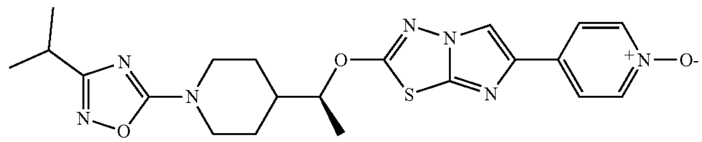 |
| 1069 | 2-(1-(1-(5-chloropyrimidin-2-yl)piperidin-4-yl)ethoxy)-6-(4-(methylsulfonyl)phenyl)imidazo[2,1-b][1,3,4]thiadiazole | 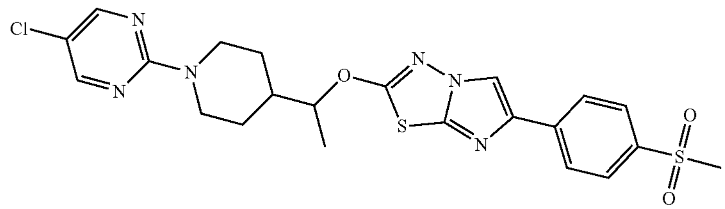 [SMILES: CC(Oc1nn2cc(-c3ccc(S(C)(=O)=O)cc3)nc2s1)C1CCN(c2ncc(Cl)cn2)CC1] |
| 1070 | 2-(1-(1-(5-isopropylpyrimidin-2-yl)piperidin-4-yl)ethoxy)-6-(4-(methylsulfonyl)phenyl)imidazo[2,1-b][1,3,4]thiadiazole | 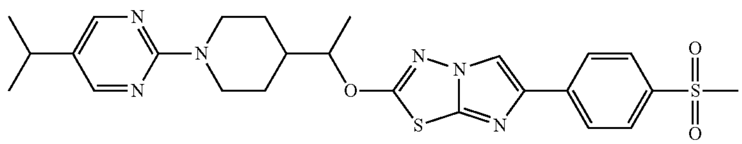 [SMILES: CC(C)c1cnc(N2CCC(C(C)Oc3nn4cc(-c5ccc(S(C)(=O)=O)cc5)nc4s3)CC2)nc1] |
| 1071 | (S)-5-(4-(1-((6-(2-chloropyrimidin-5-yl)imidazo[2,1-b][1,3,4]thiadiazol-2-yl)oxy)ethyl)piperidin-1-yl)-3-isopropyl-1,2,4-oxadiazole | 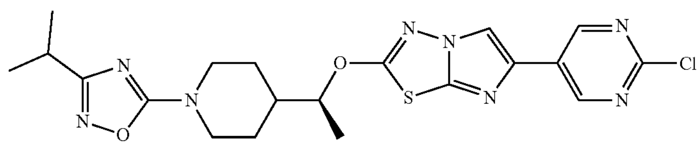 [SMILES: CC(C)c1noc(N2CCC([C@H](C)Oc3nn4cc(-c5cnc(Cl)nc5)nc4s3)CC2)n1] |
| 1072 | (S)-3-isopropyl-5-(4-(1-((6-(2-(methylsulfonyl)pyrimidin-5-yl)imidazo[2,1-b][1,3,4]thiadiazol-2-yl)oxy)ethyl)piperidin-1-yl)-1,2,4-oxadiazole | 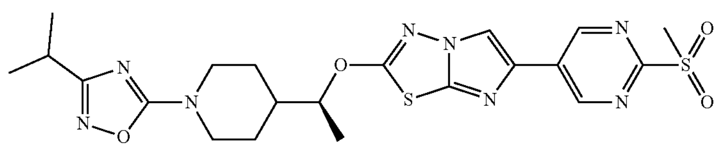 [SMILES: CC(C)c1noc(N2CCC([C@H](C)Oc3nn4cc(-c5cnc(S(C)(=O)=O)nc5)nc4s3)CC2)n1] |
| 1073 | 2-(1-(1-(3-(trifluoromethyl)-1,2,4-oxadiazol-5-yl)piperidin-4-yl)ethoxy)-6-(4-(methylsulfonyl)phenyl)imidazo[2,1-b][1,3,4]thiadiazole | 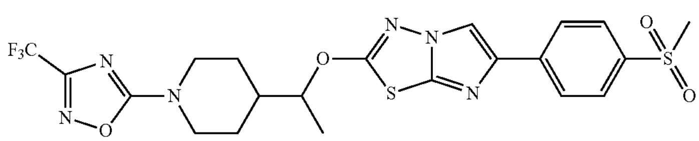 [SMILES: CC(Oc1nn2cc(-c3ccc(S(C)(=O)=O)cc3)nc2s1)C1CCN(c2nc(C(F)(F)F)no2)CC1] |
| 1074 | 2-(1-(1-(3-isopropyl-1,2,4-oxadiazol-5-yl)piperidin-4-yl)ethoxy)-6-(2-(methylsulfonyl)pyrimidin-5-yl)imidazo[2,1-b][1,3,4]thiadiazole | 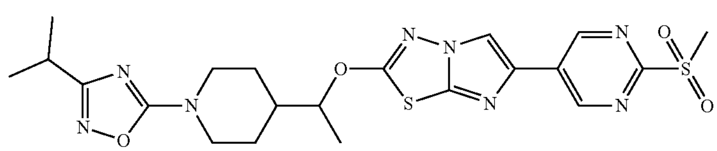 [SMILES: CC(C)c1noc(N2CCC(C(C)Oc3nn4cc(-c5cnc(S(C)(=O)=O)nc5)nc4s3)CC2)n1] |
| 1075 | 2-(1-(1-(3-isopropyl-1,2,4-oxadiazol-5-yl)piperidin-4-yl)ethoxy)-6-(6-chloropyridin-3-yl)imidazo[2,1-b][1,3,4]thiadiazole | 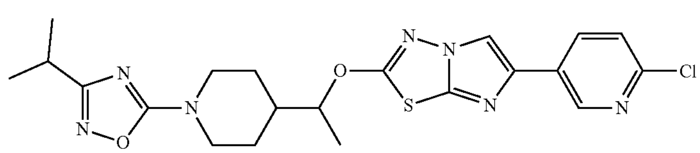 [SMILES: CC(C)c1noc(N2CCC(C(C)Oc3nn4cc(-c5ccc(Cl)nc5)nc4s3)CC2)n1] |
| 1076 | 2-((R)-1-(1-(3-(trifluoromethyl)-1,2,4-oxadiazol-5-yl)piperidin-4-yl)ethoxy)-6-(4-(methylsulfonyl)phenyl)imidazo[2,1-b][1,3,4]thiadiazole | 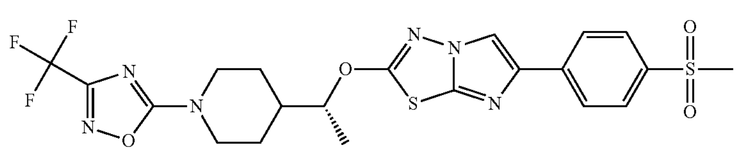 [SMILES: C[C@@H](Oc1nn2cc(-c3ccc(S(C)(=O)=O)cc3)nc2s1)C1CCN(c2nc(C(F)(F)F)no2)CC1] |

TABLE 1-continued

Illustrative compounds of present invention

| Compound No. | IUPAC name | Structure |
|---|---|---|
| 1077 | 2-((S)-1-(1-(3-(trifluoromethyl)-1,2,4-oxadiazol-5-yl)piperidin-4-yl)ethoxy)-6-(4-(methylsulfonyl)phenyl)imidazo[2,1-b][1,3,4]thiadiazole | 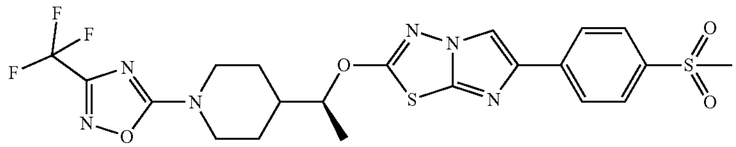 [SMILES: C[C@H](Oc1nn2cc(-c3ccc(S(C)(=O)=O)cc3)nc2s1)C1CCN(c2nc(C(F)(F)F)no2)CC1] |
| 1078 | 2-((S)-1-(1-(3-isopropyl-1,2,4-oxadiazol-5-yl)piperidin-4-yl)ethoxy)-6-(3-fluoro-4-(methylsulfonyl)phenyl)imidazo[2,1-b][1,3,4]thiadiazole | 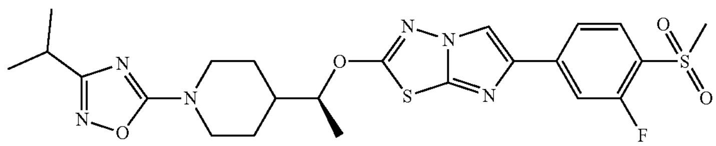 [SMILES: CC(C)c1noc(N2CCC([C@H](C)Oc3nn4cc(-c5ccc(S(C)(=O)=O)c(F)c5)nc4s3)CC2)n1] |
| 1079 | 2-(1-(1-(3-isopropyl-1,2,4-oxadiazol-5-yl)piperidin-4-yl)ethoxy)-6-(5-chloropyrazin-2-yl)imidazo[2,1-b][1,3,4]thiadiazole | 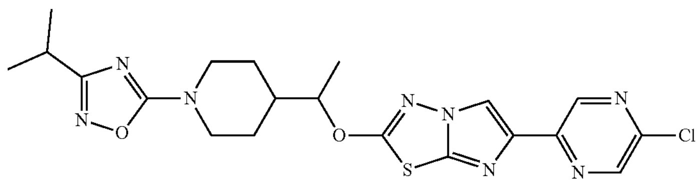 [SMILES: CC(C)c1noc(N2CCC(C(C)Oc3nn4cc(-c5cnc(Cl)cn5)nc4s3)CC2)n1] |
| 1080 | 2-((R)-1-(1-(5-ethylpyrimidin-2-yl)piperidin-4-yl)ethoxy)-6-(pyridin-4-yl)imidazo[2,1-b][1,3,4]thiadiazole | 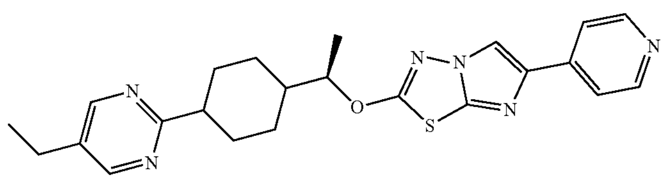 [SMILES: CCc1cnc(C2CCC([C@@H](C)Oc3nn4cc(-c5ccncc5)nc4s3)CC2)nc1] |
| 1081 | 2-((R)-1-(1-(5-propylpyrimidin-2-yl)piperidin-4-yl)ethoxy)-6-(6-(metliylsulfonyl)pyridin-3-yl)imidazo[2,1-b][1,3,4]thiadiazole | 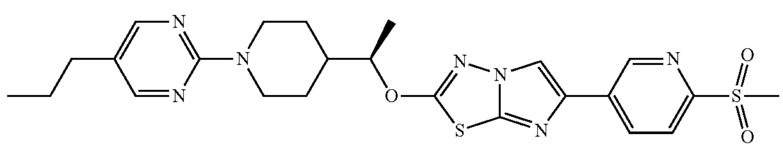 [SMILES: CCCc1cnc(N2CCC([C@@H](C)Oc3nn4cc(-c5ccc(S(C)(=O)=O)nc5)nc4s3)CC2)nc1] |
| 1082 | 2-((S)-1-(1-(5-propylpyrimidin-2-yl)piperidin-4-yl)ethoxy)-6-(3-fluoropyridin-4-yl)imidazo[2,1-b][1,3,4]thiadiazole | 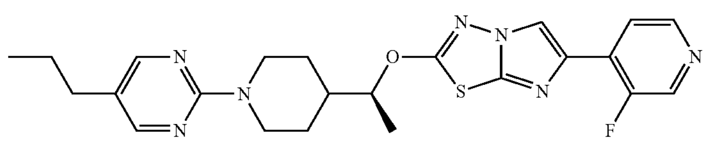 [SMILES: CCCc1cnc(N2CCC([C@H](C)Oc3nn4cc(-c5ccncc5F)nc4s3)CC2)nc1] |
| 1083 | 2-((S)-1-(1-(5-chloropyrimidin-2-yl)piperidin-4-yl)ethoxy)-6-(4-(methylsulfonyl)phenyl)imidazo[2,1-b][1,3,4]thiadiazole | 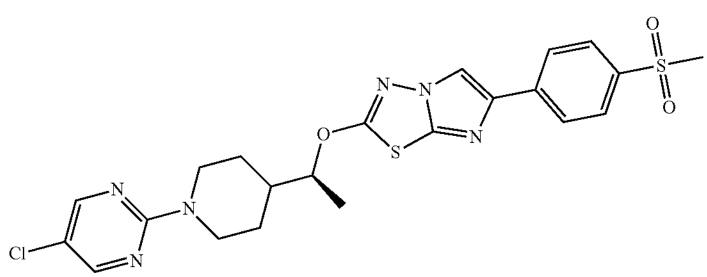 [SMILES: C[C@H](Oc1nn2cc(-c3ccc(S(C)(=O)=O)cc3)nc2s1)C1CCN(c2ncc(Cl)cn2)CC1] |
| 1084 | 2-((R)-1-(1-(3-isopropyl-1,2,4-oxadiazol-5-yl)piperidin-4-yl)ethoxy)-6-(6-(trifluoromethyl)pyridin-3-yl)imidazo[2,1-b][1,3,4]thiadiazole | 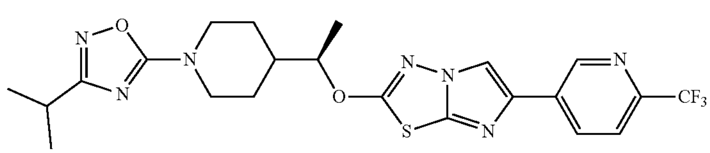 [SMILES: CC(C)c1noc(N2CCC([C@@H](C)Oc3nn4cc(-c5ccc(C(F)(F)F)nc5)nc4s3)CC2)n1] |

TABLE 1-continued

Illustrative compounds of present invention

| Compound No. | IUPAC name | Structure |
|---|---|---|
| 1085 | 2-((S)-1-(1-(5-propylpyrimidin-2-yl)piperidin-4-yl)ethoxy)-6-(2-fluoro-4-(methylsulfonyl)phenyl)imidazo[2,1-b][1,3,4]thiadiazole | 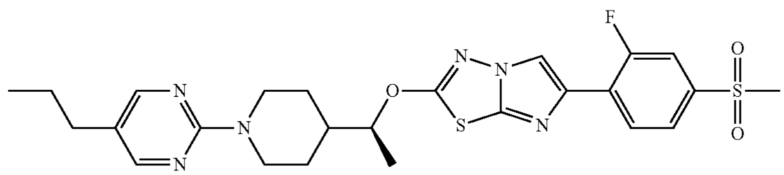 [SMILES: CCCc1cnc(N2CCC([C@H](C)Oc3nn4cc(-c5ccc(S(C)(=O)=O)cc5F)nc4s3)CC2)nc1] |
| 1086 | 2-((S)-1-(1-(5-ethylpyrimidin-2-yl)piperidin-4-yl)ethoxy)-6-(2-fluoro-4-(methylsulfonyl)phenyl)imidazo[2,1-b][1,3,4]thiadiazole | 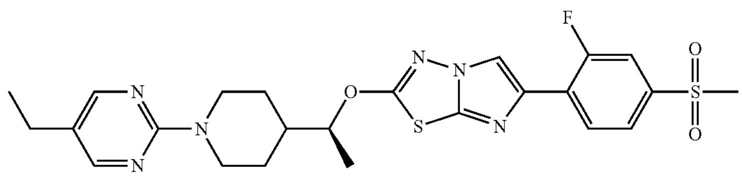 [SMILES: CCc1cnc(N2CCC([C@H](C)Oc3nn4cc(-c5ccc(S(C)(=O)=O)cc5F)nc4s3)CC2)nc1] |
| 1087 | 2-((R)-1-(1-(3-isopropyl-1,2,4-oxadiazol-5-yl)piperidin-4-yl)ethoxy)-6-(5-chloropyrazin-2-yl)imidazo[2,1-b][1,3,4]thiadiazole | 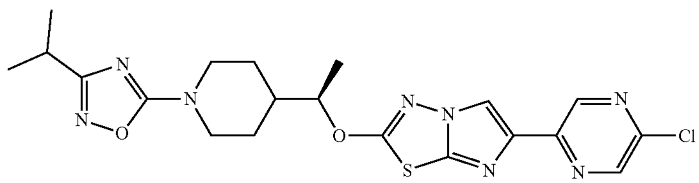 [SMILES: CC(C)c1noc(N2CCC([C@@H](C)Oc3nn4cc(-c5cnc(Cl)cn5)nc4s3)CC2)n1] |
| 1088 | 2-((R)-1-(1-(3-isopropyl-1,2,4-oxadiazol-5-yl)piperidin-4-yl)ethoxy)-6-(2-fluoro-4-(methylsulfonyl)phenyl)imidazo[2,1-b][1,3,4]thiadiazole | 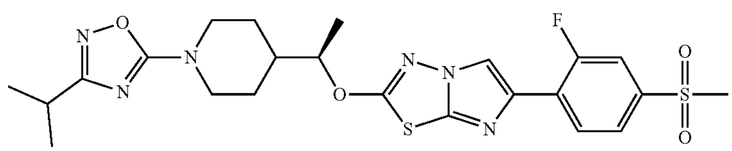 [SMILES: CC(C)c1noc(N2CCC([C@@H](C)Oc3nn4cc(-c5ccc(S(C)(=O)=O)cc5F)nc4s3)CC2)n1] |
| 1089 | 2-((S)-1-(1-(3-isopropyl-1,2,4-oxadiazol-5-yl)piperidin-4-yl)ethoxy)-6-(2-methoxypyridin-4-yl)imidazo[2,1-b][1,3,4]thiadiazole | 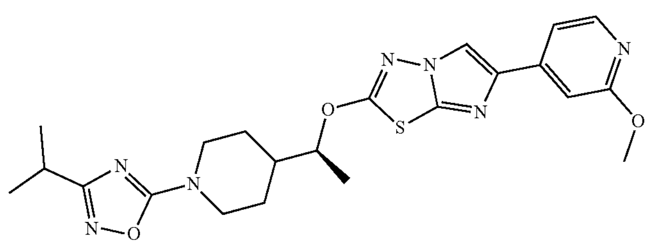 [SMILES: COc1cc(-c2cn3nc(O[C@@H](C)C4CCN(c5nc(C(C)C)no5)CC4)sc3n2)ccn1] |
| 1090 | 2-((R)-1-(1-(5-chloropyrimidin-2-yl)piperidin-4-yl)ethoxy)-6-(2-fluoro-4-(methylsulfonyl)phenyl)imidazo[2,1-b][1,3,4]thiadiazole | 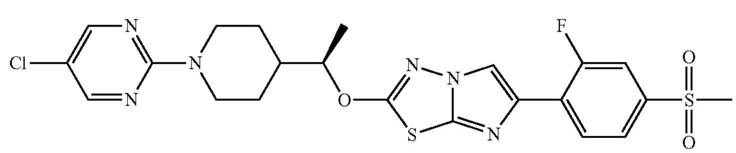 [SMILES: C[C@@H](Oc1nn2cc(-c3ccc(S(C)(=O)=O)cc3F)nc2s1)C1CCN(c2ncc(Cl)cn2)CC1] |
| 1091 | 2-(1-(1-(3-isopropyl-1,2,4-oxadiazol-5-yl)piperidin-4-yl)ethoxy)-6-(2-(trifluoromethyl)-4-(methylsulfonyl)phenyl)imidazo[2,1-b][1,3,4]thiadiazole | 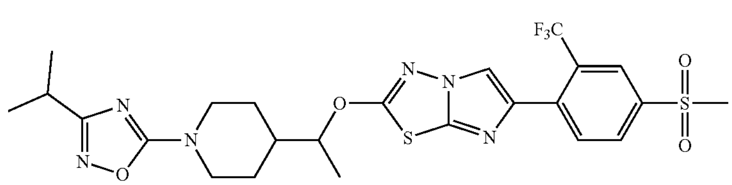 [SMILES: CC(C)c1noc(N2CCC(C(C)Oc3nn4cc(-c5ccc(S(C)(=O)=O)cc5C(F)(F)F)nc4s3)CC2)n1] |
| 1092 | 2-(1-(1-(3-isopropyl-1,2,4-oxadiazol-5-yl)piperidin-4-yl)ethoxy)-6-(3-(trifluoromethyl)pyridin-4-yl)imidazo[2,1-b][1,3,4]thiadiazole | 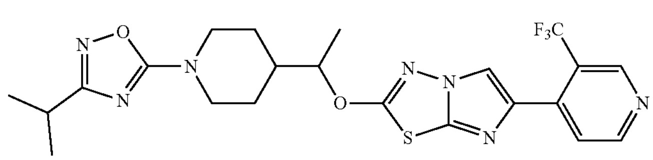 [SMILES: CC(C)c1noc(N2CCC(C(C)Oc3nn4cc(-c5ccncc5C(F)(F)F)nc4s3)CC2)n1] |

TABLE 1-continued

Illustrative compounds of present invention

| Compound No. | IUPAC name | Structure |
|---|---|---|
| 1093 | 2-((S)-1-(1-(5-ethylpyrimidin-2-yl)piperidin-4-yl)ethoxy)-6-(2-methoxypyridin-4-yl)imidazo[2,1-b][1,3,4]thiadiazole | 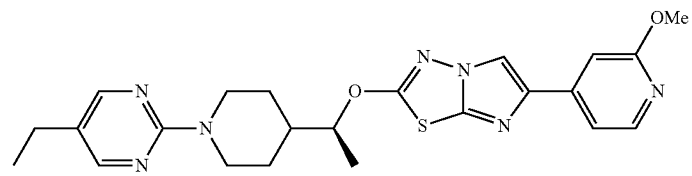 [SMILES: CCc1cnc(N2CCC([C@H](C)Oc3nn4cc(-c5ccnc(OC)c5)nc4s3)CC2)nc1] |
| 1094 | 2-((S)-1-(1-(5-propylpyrimidin-2-yl)piperidin-4-yl)ethoxy)-6-(2-methoxypyridin-4-yl)imidazo[2,1-b][1,3,4]thiadiazole | 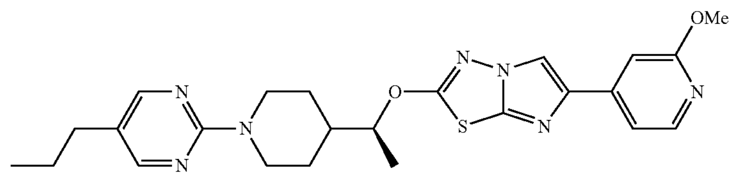 [SMILES: CCCc1cnc(N2CCC([C@H](C)Oc3nn4cc(-c5ccnc(OC)c5)nc4s3)CC2)nc1] |
| 1095 | 2-(1-(1-(3-isopropyl-1,2,4-oxadiazol-5-yl)piperidin-4-yl)ethoxy)-6-(3-methoxypyridin-4-yl)imidazo[2,1-b][1,3,4]thiadiazole | 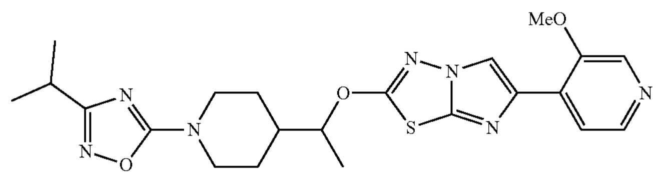 [SMILES: COc1cnccc1-c1cn2nc(OC(C)C3CCN(c4nc(C(C)C)no4)CC3)sc2n1] |
| 1096 | 4-(2-((S)-1-(1-(3-isopropyl-1,2,4-oxadiazol-5-yl)piperidin-4-yl)ethoxy)imidazo[2,1-b][1,3,4]thiadiazol-6-yl)-1-methylpyridin-2(1H)-one | 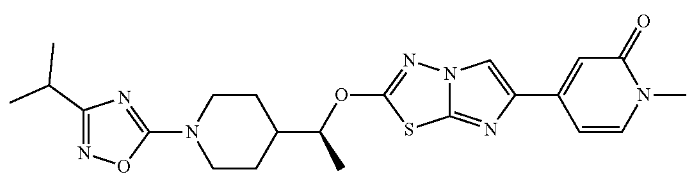 [SMILES: CC(C)c1noc(N2CCC([C@H](C)Oc3nn4cc(-c5ccn(C)c(=O)c5)nc4s3)CC2)n1] |
| 1097 | 2-((S)-1-(1-(3-isopropyl-1,2,4-oxadiazol-5-yl)piperidin-4-yl)ethoxy)-6-(3-fluoropyridin-4-yl)imidazo[2,1-b][1,3,4]thiadiazole hydrochloride | 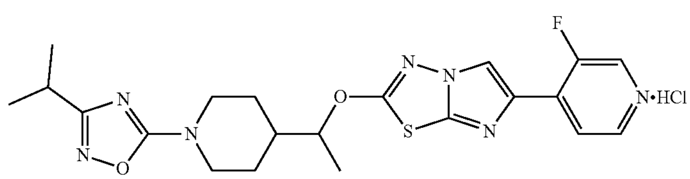 |
| 1098 | 2-((S)-1-(1-(5-(trifluoromethyl)pyrimidin-2-yl)piperidin-4-yl)ethoxy)-6-(2-fluoro-4-(methylsulfonyl)phenyl)imidazo[2,1-b][1,3,4]thiadiazole | 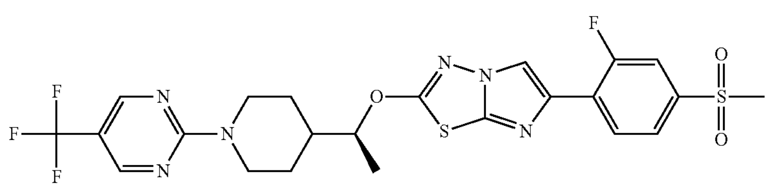 [SMILES: C[C@H](Oc1nn2cc(-c3ccc(S(C)(=O)=O)cc3F)nc2s1)C1CCN(c2ncc(C(F)(F)F)cn2)CC1] |
| 1099 | 4-(2-((R)-1-(1-(3-isopropyl-1,2,4-oxadiazol-5-yl)piperidin-4-yl)ethoxy)imidazo[2,1-b][1,3,4]thiadiazol-6-yl)-3-fluorobenzonitrile | 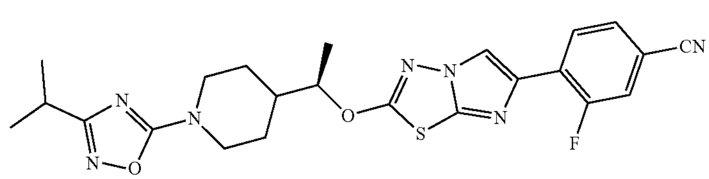 [SMILES: CC(C)c1noc(N2CCC([C@@H](C)Oc3nn4cc(-c5ccc(C#N)cc5F)nc4s3)CC2)n1] |
| 1100 | 2-((R)-1-(1-(3-isopropyl-1,2,4-oxadiazol-5-yl)piperidin-4-yl)ethoxy)-6-(2-fluoro-6-(methylsulfonyl)pyridin-3-yl)imidazo[2,1-b][1,3,4]thiadiazole | 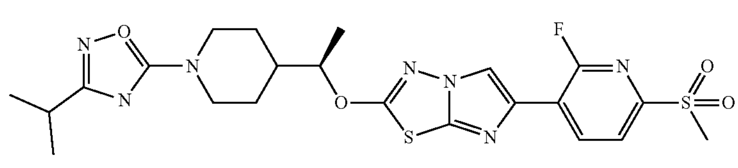 |

TABLE 1-continued

Illustrative compounds of present invention

| Compound No. | IUPAC name | Structure |
|---|---|---|
| 1101 | isopropyl 4-(1-(6-(2-fluoro-4-(methylsulfonyl)phenyl)imidazo[2,1-b][1,3,4]thiadiazol-2-yloxy)ethyl)piperidine-1-carboxylate | 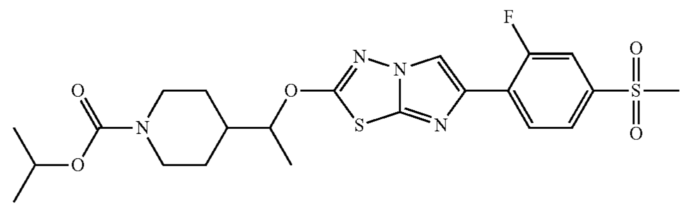 [SMILES: CC(C)OC(=O)N1CCC(C(C)Oc2nn3cc(-c4ccc(S(C)(=O)=O)cc4F)nc3s2)CC1] |
| 1102 | 2-((R)-1-(1-(5-ethylpyrimidin-2-yl)piperidin-4-yl)ethoxy)-6-(2-fluoro-6-(methylsulfonyl)pyridin-3-yl)imidazo[2,1-b][1,3,4]thiadiazole | 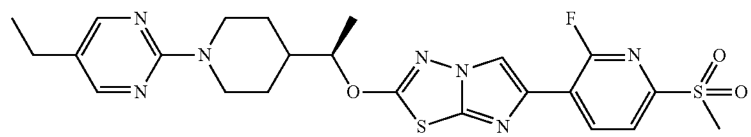 [SMILES: CCc1cnc(N2CCC([C@@H](C)Oc3nn4cc(-c5ccc(S(C)(=O)=O)nc5F)nc4s3)CC2)nc1] |
| 1103 | 2-((S)-1-(1-(3-isopropyl-1,2,4-oxadiazol-5-yl)piperidin-4-yl)ethoxy)-6-(2-methoxy-4-(methylsulfonyl)phenyl)imidazo[2,1-b][1,3,4]thiadiazole | 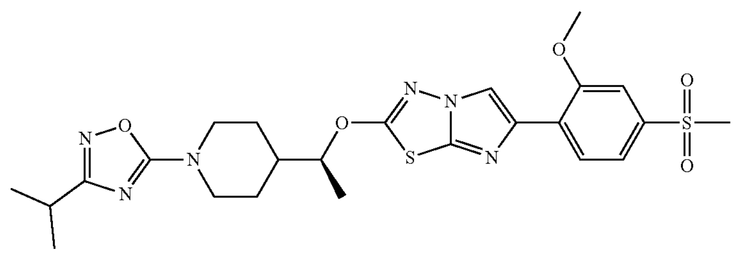 [SMILES: COc1cc(S(C)(=O)=O)ccc1-c1cn2nc(O[C@@H](C)C3CCN(c4nc(C(C)C)no4)CC3)sc2n1] |
| 1104 | 2-((S)-1-(1-(3-isopropyl-1,2,4-oxadiazol-5-yl)piperidin-4-yl)ethoxy)-6-(2-methyl-6-(methylsulfonyl)pyridin-3-yl)imidazo[2,1-b][1,3,4]thiadiazole | 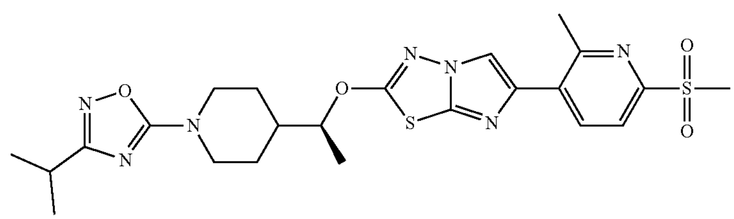 [SMILES: Cc1nc(S(C)(=O)=O)ccc1-c1cn2nc(O[C@@H](C)C3CCN(c4nc(C(C)C)no4)CC3)sc2n1] |
| 1105 | 2-((R)-1-(1-(3-isopropyl-1,2,4-oxadiazol-5-yl)piperidin-4-yl)ethoxy)-6-(2-fluoro-4-(1H-tetrazol-5-yl)phenyl)imidazo[2,1-b][1,3,4]thiadiazole hydrochloride | 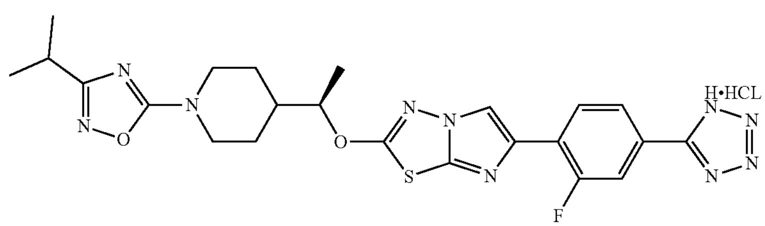 |
| 1106 | tert-butyl4-(1-(6-(6-fluoro-4-(methylsulfonyl)cyclohexa-1,5-dienyl)imidazo[2,1-b][1,3,4]thiadiazol-2-yloxy)ethyl)piperidine-1-carboxylate | 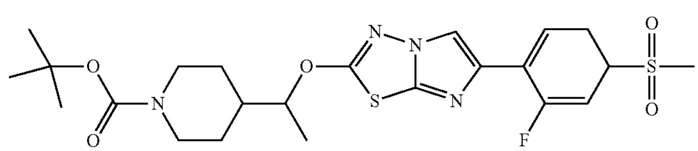 [SMILES: CC(Oc1nn2cc(C3=CCC(S(C)(=O)=O)C=C3F)nc2s1)C1CCN(C(=O)OC(C)(C)C)CC1] |
| 1107 | ethyl4-(1-(6-(2-fluoro-4-(methylsulfonyl)phenyl)imidazo[2,1-b][1,3,4]thiadiazol-2-yloxy)ethyl)piperidine-1-carboxylate | 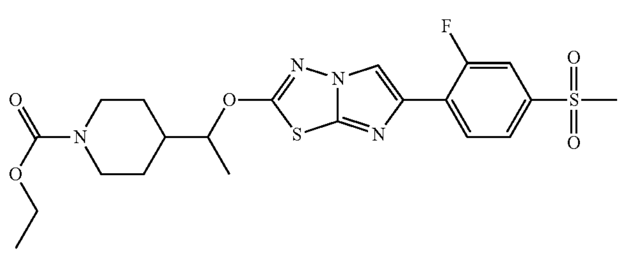 [SMILES: CCOC(=O)N1CCC(C(C)Oc2nn3cc(-c4ccc(S(C)(=O)=O)cc4F)nc3s2)CC1] |

TABLE 1-continued

Illustrative compounds of present invention

| Compound No. | IUPAC name | Structure |
|---|---|---|
| 1108 | isopropyl 4-((S)-1-(6-(2-fluoro-4-(methylsulfonyl)phenyl)imidazo[2,1-b][1,3,4]thiadiazol-2-yloxy)ethyl)piperidine-1-carboxylate | 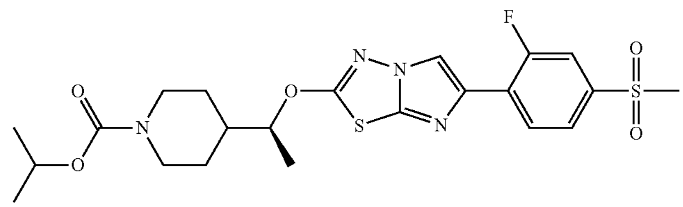 [SMILES: CC(C)OC(=O)N1CCC([C@H](C)Oc2nn3cc(-c4ccc(S(C)(=O)=O)cc4F)nc3s2)CC1] |
| 1109 | 3-fluoro-4-(2-(1-(1-(3-isopropyl-1,2,4-oxadiazol-5-yl)piperidin-4-yl)ethoxy)imidazo[2,1-b][1,3,4]thiadiazo1-6-yl)-N-methylbenzenesulfonamide | 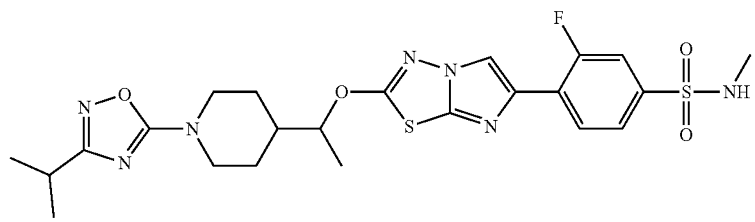 [SMILES: CNS(=O)(=O)c1ccc(-c2cn3nc(OC(C)C4CCN(c5nc(C(C)C)no5)CC4)sc3n2)c(F)c1] |
| 1110 | 1-methylcyclopropyl 4-(1-(6-(2-fluoro-4-(methylsulfonyl)phenyl)imidazo[2,1-b][1,3,4]thiadiazol-2-yloxy)ethyl)piperidine-1-carboxylate | 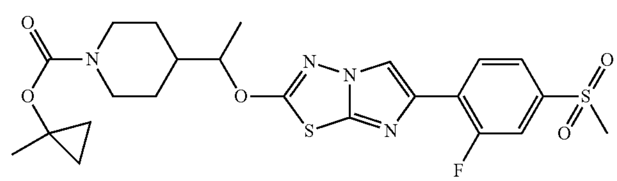 |
| 1111 | 2-(1-(1-(3-isopropyl-1,2,4-oxadiazol-5-yl)piperidin-4-yl)ethoxy)-6-(thiazol-5-yl)imidazo[2,1-b][1,3,4]thiadiazole | 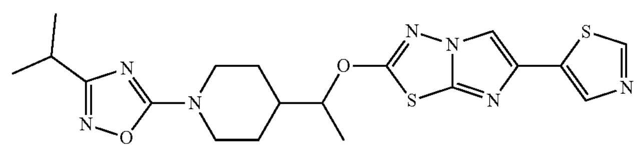 [SMILES: CC(C)c1noc(N2CCC(C(C)Oc3nn4cc(-c5cncs5)nc4s3)CC2)n1] |
| 1112 | 2-((S)-1-(1-(3-isopropyl-1,2,4-oxadiazol-5-yl)piperidin-4-yl)ethoxy)-6-(2-methyl-4-(methylsulfonyl)phenyl)imidazo[2,1-b][1,3,4]thiadiazole | 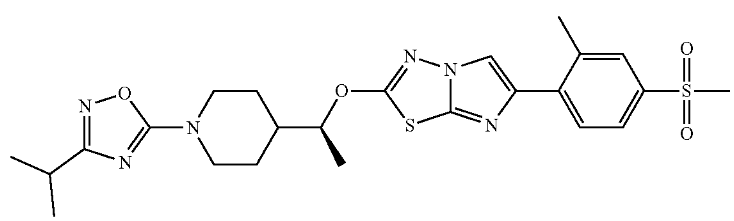 [SMILES: Cc1cc(S(C)(=O)=O)ccc1-c1cn2nc(O[C@@H](C)C3CCN(c4nc(C(C)C)no4)CC3)sc2n1] |
| 1113 | ethyl4-((S)-1-(6-(2-fluoro-4-(methylsulfonyl)phenyl)imidazo[2,1-b][1,3,4]thiadiazol-2-yloxy)ethyl)piperidine-1-carboxylate | 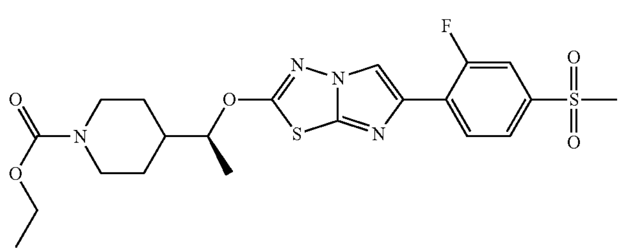 [SMILES: CCOC(=O)N1CCC([C@H](C)Oc2nn3cc(-c4ccc(S(C)(=O)=O)cc4F)nc3s2)CC1] |
| 1114 | 4-(3-isopropyl-1,2,4-oxadiazol-5-yl)-1-(3-(4-(methylsulfonyl)phenyl)-1,2,4-thiadiazol-5-yl)piperidine | 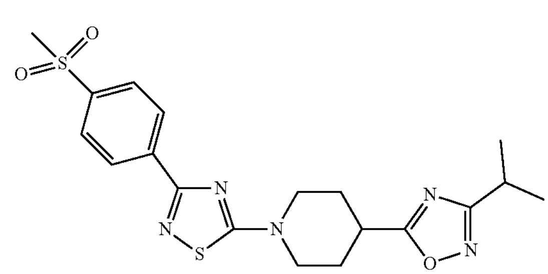 [SMILES: CC(C)c1noc(C2CCN(c3nc(-c4ccc(S(C)(=O)=O)cc4)ns3)CC2)n1] |

TABLE 1-continued

Illustrative compounds of present invention

| Compound No. | IUPAC name |
|---|---|
| 1115 | 4-(1-(3-(4-(methylsulfonyl)phenyl)-1,2,4-thiadiazol-5-yloxy)ethyl)-1-(3-isopropyl-1,2,4-oxadiazol-5-yl)piperidine |
| 1116 | 4-(3-(4-(methylsulfonyl)phenyl)-1,2,4-thiadiazol-5-yloxy)-1-(3-isopropyl-1,2,4-oxadiazol-5-yl)piperidine |
| 1117 | 4-((3-(4-(methylsulfonyl)phenyl)-1,2,4-thiadiazol-5-yloxy)methyl)-1-(3-isopropyl-1,2,4-oxadiazol-5-yl)piperidine |
| 1118 | 5-(3-(1-(1-(3-isopropyl-1,2,4-oxadiazol-5-yl)piperidin-4-yl)ethoxy)-1,2,4-thiadiazol-5-yl)-2-(methylsulfonyl)pyridine |
| 1119 | 5-(3-(1-(3-isopropyl-1,2,4-oxadiazol-5-yl)piperidin-4-yloxy)-1,2,4-thiadiazol-5-yl)-2-(methylsulfonyl)pyridine |

TABLE 1-continued

Illustrative compounds of present invention

| Compound No. | IUPAC name | Structure |
|---|---|---|
| 1120 | 5-(3-((1-(3-isopropyl-1,2,4-oxadiazol-5-yl)piperidin-4-yl)methoxy)-1,2,4-thiadiazol-5-yl)-2-(methylsulfonyl)pyridine | 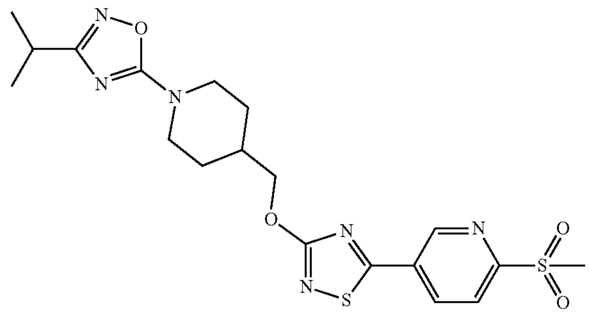 |
| 1121 | 5-(5-(1-(3-isopropyl-1,2,4-oxadiazol-5-yl)piperidin-4-yloxy)-1,2,4-thiadiazol-3-yl)-2-(methylsulfonyl)pyridine | 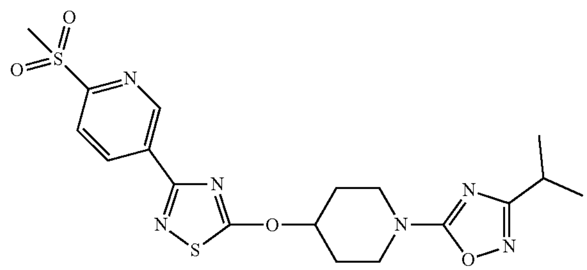 [SMILES: CC(C)c1noc(N2CCC(Oc3nc(-c4ccc(S(C)(=O)=O)cc4)ns3)CC2)n1] |
| 1122 | 2-(4-(3-(6-(methylsulfonyl)pyridin-3-yl)-1,2,4-thiadiazol-5-yloxy)piperidin-1-yl)-5-ethylpyrimidine | 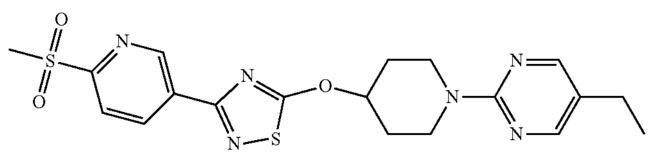 [SMILES: CCc1cnc(N2CCC(Oc3nc(-c4ccc(S(C)(=O)=O)nc4)ns3)CC2)nc1] |
| 1123 | 2-(4-(3-(6-(methylsulfonyl)pyridin-3-yl)-1,2,4-thiadiazol-5-yloxy)piperidin-1-yl)-5-propylpyrimidine | 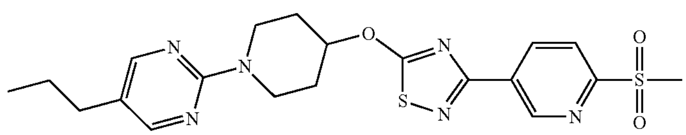 [SMILES: CCCc1cnc(N2CCC(Oc3nc(-c4ccc(S(C)(=O)=O)nc4)ns3)CC2)nc1] |
| 1124 | N-(5-(1-(3-isopropyl-1,2,4-oxadiazol-5-yl)piperidin-4-yloxy)-1,2,4-thiadiazol-3-yl)-N-methyl-6-(methylsulfonyl)pyridin-3-amine | 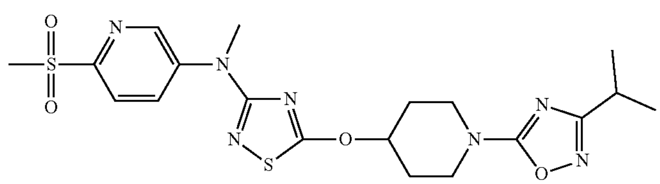 [SMILES: CC(C)c1noc(N2CCC(Oc3nc(N(C)c4ccc(S(C)(=O)=O)nc4)ns3)CC2)n1] |
| 1125 | 2-(4-(3-(2-fluoro-4-(methylsulfonyl)phenyl)-1,2,4-thiadiazol-5-yloxy)piperidin-1-yl)-5-ethylpyrimidine | 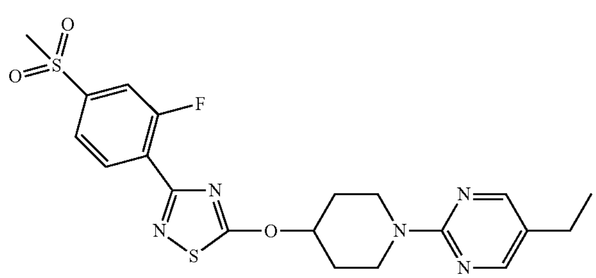 [SMILES: CCc1cnc(N2CCC(Oc3nc(-c4ccc(S(C)(=O)=O)cc4F)ns3)CC2)nc1] |

TABLE 1-continued

Illustrative compounds of present invention

| Compound No. | IUPAC name | Structure |
|---|---|---|
| 1126 | 1-(3-isopropyl-1,2,4-oxadiazol-5-yl)-N-(3-(6-(methylsulfonyl)pyridin-3-yl)-1,2,4-thiadiazol-5-yl)piperidin-4-amine | 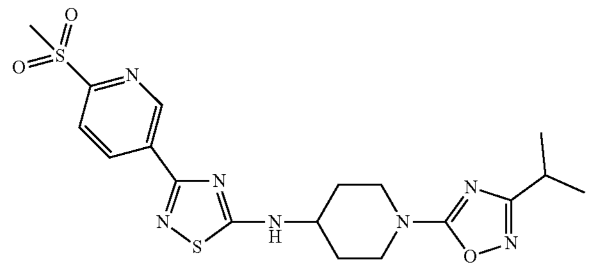 [SMILES: CC(C)c1noc(N2CCC(Nc3nc(-c4ccc(S(C)(=O)=O)nc4)ns3)CC2)n1] |
| 1127 | 1-(3-isopropyl-1,2,4-oxadiazol-5-yl)-N-methyl-N-(3-(6-(methylsulfonyl)pyridin-3-yl)-1,2,4-thiadiazol-5-yl)piperidin-4-amine | 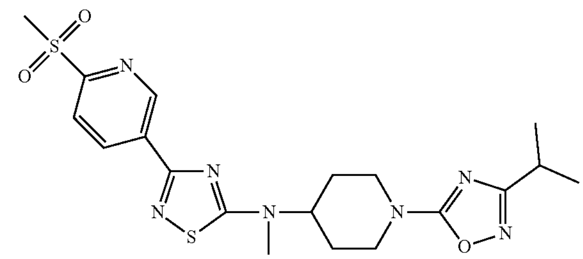 [SMILES: CC(C)c1noc(N2CCC(N(C)c3nc(-c4ccc(S(C)(=O)=O)nc4)ns3)CC2)n1] |

The present invention also provides for compounds of formula (1) as below:

i. 3,4-bis(4-(1H-tetrazol-1-yl)phenoxy)-1,2,5-thiadiazole
ii. 3,4-bis((1-(3-isopropyl-1,2,4-oxadiazol-5-yl)piperidin-4-yl)oxy)-1,2,5-thiadiazole
iii. 5-(1-(4-(4-(1H-tetrazol-1-yl)phenoxy)-1,2,5-thiadiazol-3-yl)piperidin-4-yl)-3-isopropyl-1,2,4-oxadiazole
iv. 3-(1-(5-ethylpyrimidin-2-yl)piperidin-4-yl)-4-(4-(methylsulfonyl)phenyl)-1,2,5-thiadiazole
v. 3-(4-(1H-tetrazol-1-yl)phenoxy)-4-(1-(5-ethylpyrimidin-2-yl)-1,2,3,6-tetrahydropyridin-4-yl)-1,2,5-thiadiazole
vi. 5-(1-(4-(((2-fluoro-4-(methylsulfonyl)phenoxy)methyl)-1,2,5-thiadiazol-3-yl)piperidin-4-yl)-3-isopropyl-1,2,4-oxadiazole
vii. 3-isopropyl-5-(1-(4-(4-(methylsulfonyl)phenyl)-1,2,5-thiadiazol-3-yl)piperidin-4-yl)-1,2,4-oxadiazole
viii. (4-(1-(5-ethylpyrimidin-2-yl)-1,2,3,6-tetrahydropyridin-4-yl)-1,2,5-thiadiazol-3-yl)methanol
ix. 5-(1-(4-(((4-(1H-tetrazol-1-yl)phenoxy)methyl)-1,2,5-thiadiazol-3-yl)piperidin-4-yl)-3-isopropyl-1,2,4-oxadiazole
x. isopropyl 4-(4-(4-(1H-tetrazol-1-yl)phenoxy)-1,2,5-thiadiazol-3-yl)piperazine-1-carboxylate
xi. 3,4-bis((1-(3-isopropyl-1,2,4-oxadiazol-5-yl)piperidin-4-yl)methoxy)-1,2,5-thiadiazole
xii. N-(2-fluoro-4-(methylsulfonyl)phenyl)-4-(4-(3-isopropyl-1,2,4-oxadiazol-5-yl)piperidin-1-yl)-1,2,5-thiadiazole-3-carboxamide
xiii. N-(3-fluoro-4-(methylsulfonyl)phenyl)-4-(4-(3-isopropyl-1,2,4-oxadiazol-5-yl)piperidin-1-yl)-1,2,5-thiadiazole-3-carboxamide
xiv. 4-(1-(5-ethylpyrimidin-2-yl)-1,2,3,6-tetrahydropyridin-4-yl)-N-(2-fluoro-4-(methylsulfonyl)phenyl)-1,2,5-thiadiazole-3-carboxamide
xv. 4-(1-(5-ethylpyrimidin-2-yl)piperidin-4-yl)-N-(2-fluoro-4-(methylsulfonyl)phenyl)-1,2,5-thiadiazole-3-carboxamide
xvi. 3-isopropyl-5-(1-(6-(4-(methylsulfonyl)phenyl)imidazo[2,1-b][1,3,4]thiadiazol-2-yl)piperidin-4-yl)-1,2,4-oxadiazole
xvii. 3-isopropyl-5-(4-(((6-(4-(methylsulfonyl)phenyl)imidazo[2,1-b][1,3,4]thiadiazol-2-yl)oxy)methyl)piperidin-1-yl)-1,2,4-oxadiazole
xviii. 3-isopropyl-5-(4-(((6-(4-(methylsulfonyl)phenyl)imidazo[2,1-b][1,3,4]thiadiazol-2-yl)oxy)piperidin-1-yl)-1,2,4-oxadiazole
xix. 2-(1-benzylpiperidin-4-yl)-6-(4-(methylsulfonyl)phenyl)imidazo[2,1-b][1,3,4]thiadiazole
xx. isopropyl-4-(6-(4-(methylsulfonyl)phenyl)imidazo[2,1-b][1,3,4]thiadiazol-2-yl)piperazine-1-carboxylate
xxi. isopropyl-4-(((6-(4-(methylsulfonyl)phenyl)imidazo[2,1-b][1,3,4]thiadiazol-2-yl)amino)piperidine-1-carboxylate
xxii. isopropyl 4-(methyl(6-(4-(methylsulfonyl)phenyl)imidazo[2,1-b][1,3,4]thiadiazol-2-yl)amino)piperidine-1-carboxylate
xxiii. N-(1-(5-ethylpyrimidin-2-yl)piperidin-4-yl)-6-(4-(methylsulfonyl) phenyl)imidazo[2,1-b][1,3,4]thiadiazol-2-amine
xxiv. isopropyl-4-(6-(4-(methylsulfonyl)phenyl)imidazo[2,1-b][1,3,4]thiadiazol-2-yl)piperidine-1-carboxylate
xxv. 4-(methyl(6-(4-(methylsulfonyl)phenyl)imidazo[2,1-b][1,3,4]thiadiazol-2-yl)amino)piperidine-1-carboxamide
xxvi. 4-(6-(4-(methylsulfonyl)phenyl)imidazo[2,1-b][1,3,4]thiadiazol-2-yl)piperidine-1-carboxamide
xxvii. 3-isopropyl-5-(4-(6-(4-(methylsulfonyl)phenyl)imidazo[2,1-b][1,3,4]thiadiazol-2-yl)piperidin-1-yl)-1,2,4-oxadiazole
xxviii. 1-(4-(2-(4-(methylsulfonyl)phenyl)imidazo[2,1-b][1,3,4]thiadiazol-6-yl)piperidin-1-yl)ethanone
xxix. N-(1-(3-isopropyl-1,2,4-oxadiazol-5-yl)piperidin-4-yl)-N-methyl-6-(4-(methylsulfonyl)phenyl)imidazo[2,1-b][1,3,4]thiadiazol-2-amine
xxx. isopropyl-4-(2-(4-(methylsulfonyl)phenyl)imidazo[2,1-b][1,3,4]thiadiazol-6-yl)piperidine-1-carboxylate xxxi. 6-(4-(methylsulfonyl)phenyl)-2-(1-(methylsulfonyl)piperidin-4-yl)imidazo[2,1-b][1,3,4]thiadiazole
xxxii. 3-isopropyl-5-(4-(2-(4-(methylsulfonyl)phenyl)imidazo[2,1-b][1,3,4]thiadiazol-6-yl)piperidin-1-yl)-1,2,4-oxadiazole
xxxiii. N,N-dimethyl-4-(6-(4-(methylsulfonyl)phenyl)imidazo[2,1-b][1,3,4]thiadiazol-2-yl)piperidine-1-carboxamide
xxxiv. isopropyl-4-(2-(4-(dimethylcarbamoyl)phenyl)imidazo[2,1-b][1,3,4]thiadiazol-6-yl)piperidine-1-carboxylate
xxxv. isopropyl-4-(2-(4-((2-methoxyethyl)carbamoyl)phenyl)imidazo[2,1-b][1,3,4]thiadiazol-6-yl)piperidine-1-carboxylate
xxxvi. 4-(2-(4-(3-isopropyl-1,2,4-oxadiazol-5-yl)piperidin-1-yl)imidazo[2,1-b][1,3,4]thiadiazol-6-yl)-N,N-dimethylbenzamide
xxxvii. (4-(2-(4-(3-isopropyl-1,2,4-oxadiazol-5-yl)piperidin-1-yl)imidazo[2,1-b][1,3,4]thiadiazol-6-yl)phenyl)(morpholino)methanone
xxxviii. 2-(1-benzylpiperidin-4-yl)-6-((4-(methylsulfonyl)phenoxy)methyl)imidazo[2,1-b][1,3,4]thiadiazole
xxxix. 4-(2-(4-(3-isopropyl-1,2,4-oxadiazol-5-yl)piperidin-1-yl)imidazo[2,1-b][1,3,4]thiadiazol-6-yl)-N-(2-methoxyethyl)benzamide
xl. 3-isopropyl-5-(1-(6-((4-(methylsulfonyl)phenoxy)methyl)imidazo[2,1-b][1,3,4]thiadiazol-2-yl)piperidin-4-yl)-1,2,4-oxadiazole
xli. isopropyl-4-(6-((4-(methylsulfonyl)phenoxy)methyl)imidazo[2,1-b][1,3,4]thiadiazol-2-yl)piperidine-1-carboxylate
xlii. 3-isopropyl-5-(4-((6-((4-(methylsulfonyl)phenoxy)methyl)imidazo[2,1-b][1,3,4]thiadiazol-2-yl)oxy)piperidin-1-yl)-1,2,4-oxadiazole
xliii. 4-((2-(4-(3-isopropyl-1,2,4-oxadiazol-5-yl)piperidin-1-yl)imidazo[2,1-b][1,3,4]thiadiazol-6-yl)methoxy)-N,N-dimethylbenzamide
xliv. 5-(1-(5-chloro-6-(4-(methylsulfonyl)phenyl)imidazo[2,1-b][1,3,4]thiadiazol-2-yl)piperidin-4-yl)-3-isopropyl-1,2,4-oxadiazole
xlv. 3-cyclopropyl-5-(1-(6-(4-(methylsulfonyl)phenyl)imidazo[2,1-b][1,3,4]thiadiazol-2-yl)piperidin-4-yl)-1,2,4-oxadiazole
xlvi. 4-(2-(4-(3-isopropyl-1,2,4-oxadiazol-5-yl)piperidin-1-yl)imidazo[2,1-b][1,3,4]thiadiazol-6-yl)benzonitrile
xlvii. 4-(2-(1-(1-(3-isopropyl-1,2,4-oxadiazol-5-yl)piperidin-4-yl)ethoxy)imidazo[2,1-b][1,3,4]thiadiazol-6-yl)benzonitrile
xlviii. 4-(2-(1-(1-(3-isopropyl-1,2,4-oxadiazol-5-yl)piperidin-4-yl)ethoxy)imidazo[2,1-b][1,3,4]thiadiazol-6-yl)-N,N-dimethylbenzamide
xlix. N,N-dimethyl-4-(2-(1-(1-(5-propylpyrimidin-2-yl)piperidin-4-yl)ethoxy)imidazo[2,1-b][1,3,4]thiadiazol-6-yl)benzamide
l. 3-isopropyl-5-(4-(1-((6-(pyridin-4-yl)imidazo[2,1-b][1,3,4]thiadiazol-2-yl)oxy)ethyl)piperidin-1-yl)-1,2,4-oxadiazole
li. 3-isopropyl-5-(1-(6-(pyridin-4-yl)imidazo[2,1-b][1,3,4]thiadiazol-2-yl)piperidin-4-yl)-1,2,4-oxadiazole
lii. 5-(1-(5-chloro-6-(pyridin-4-yl)imidazo[2,1-b][1,3,4]thiadiazol-2-yl)piperidin-4-yl)-3-isopropyl-1,2,4-oxadiazole
liii. 4-(2-((1-(3-isopropyl-1,2,4-oxadiazol-5-yl)piperidin-4-yl)methoxy)imidazo[2,1-b][1,3,4]thiadiazol-6-yl)benzonitrile
liv. 3-isopropyl-5-(4-(((6-(pyridin-4-yl)imidazo[2,1-b][1,3,4]thiadiazol-2-yl)oxy)methyl)piperidin-1-yl)-1,2,4-oxadiazole
lv. 3-isopropyl-5-(4-(1-((6-(6-(methylsulfonyl)pyridin-3-yl)imidazo[2,1-b][1,3,4]thiadiazol-2-yl)oxy)ethyl)piperidin-1-yl)-1,2,4-oxadiazole
lvi. 2-(1-(1-(5-ethylpyrimidin-2-yl)piperidin-4-yl)ethoxy)-6-(pyridin-4-yl)imidazo[2,1-b][1,3,4]thiadiazole
lvii. 3-isopropyl-5-(4-(1-((6-(4-(methylsulfonyl)phenyl)imidazo[2,1-b][1,3,4]thiadiazol-2-yl)oxy)ethyl)piperidin-1-yl)-1,2,4-oxadiazole
lviii. (R)-3-isopropyl-5-(4-(1-((6-(6-(methylsulfonyl)pyridin-3-yl)imidazo[2,1-b][1,3,4]thiadiazol-2-yl)oxy)ethyl)piperidin-1-yl)-1,2,4-oxadiazole
lix. (R)-3-isopropyl-5-(4-(1-((6-(pyridin-4-yl)imidazo[2,1-b][1,3,4]thiadiazol-2-yl)oxy)ethyl)piperidin-1-yl)-1,2,4-oxadiazole
lx. (R)-3-isopropyl-5-(4-(1-((6-(4-(methylsulfonyl)phenyl)imidazo[2,1-b][1,3,4]thiadiazol-2-yl)oxy)ethyl)piperidin-1-yl)-1,2,4-oxadiazole
lxi. 5-(4-(1-((5-fluoro-6-(4-(methylsulfonyl)phenyl)imidazo[2,1-b][1,3,4]thiadiazol-2-yl)oxy)ethyl)piperidin-1-yl)-3-isopropyl-1,2,4-oxadiazole
lxii. (R)-2-(1-(1-(5-ethylpyrimidin-2-yl)piperidin-4-yl)ethoxy)-6-(4-(methylsulfonyl)phenyl)imidazo[2,1-b][1,3,4]thiadiazole
lxiii. 5-(4-(1-((5-chloro-6-(4-(methylsulfonyl)phenyl)imidazo[2,1-b][1,3,4]thiadiazol-2-yl)oxy)ethyl)piperidin-1-yl)-3-isopropyl-1,2,4-oxadiazole
lxiv. (S)-5-(4-(1-((6-(3-fluoropyridin-4-yl)imidazo[2,1-b][1,3,4]thiadiazol-2-yl)oxy)ethyl)piperidin-1-yl)-3-isopropyl-1,2,4-oxadiazole
lxv. (R)-5-(4-(1-((6-(2-fluoropyridin-4-yl)imidazo[2,1-b][1,3,4]thiadiazol-2-yl)oxy)ethyl)piperidin-1-yl)-3-isopropyl-1,2,4-oxadiazole
lxvi. (R)-5-(4-(1-((5-fluoro-6-(4-(methylsulfonyl)phenyl)imidazo[2,1-b][1,3,4]thiadiazol-2-yl)oxy)ethyl)piperidin-1-yl)-3-isopropyl-1,2,4-oxadiazole
lxvii. (S)-6-(4-(methylsulfonyl)phenyl)-2-(1-(1-(5-propylpyrimidin-2-yl)piperidin-4-yl)ethoxy)imidazo[2,1-b][1,3,4]thiadiazole
lxviii. (S)-4-(2-(1-(1-(3-isopropyl-1,2,4-oxadiazol-5-yl)piperidin-4-yl)ethoxy)imidazo[2,1-b][1,3,4]thiadiazol-6-yl)pyridine 1-oxide
lxix. 2-(1-(1-(5-chloropyrimidin-2-yl)piperidin-4-yl)ethoxy)-6-(4-(methylsulfonyl)phenyl)imidazo[2,1-b][1,3,4]thiadiazole
lxx. 2-(1-(1-(5-isopropylpyrimidin-2-yl)piperidin-4-yl)ethoxy)-6-(4-(methylsulfonyl)phenyl)imidazo[2,1-b][1,3,4]thiadiazole
lxxi. (S)-5-(4-(1-((6-(2-chloropyrimidin-5-yl)imidazo[2,1-b][1,3,4]thiadiazol-2-yl)oxy)ethyl)piperidin-1-yl)-3-isopropyl-1,2,4-oxadiazole
lxxii. (S)-3-isopropyl-5-(4-(1-((6-(2-(methylsulfonyl)pyrimidin-5-yl)imidazo[2,1-b][1,3,4]thiadiazol-2-yl)oxy)ethyl)piperidin-1-yl)-1,2,4-oxadiazole
lxxiii. 2-((R)-1-(1-(3-isopropyl-1,2,4-oxadiazol-5-yl)piperidin-4-yl)ethoxy)-6-(pyridin-4-yl)imidazo[2,1-b][1,3,4]thiadiazole
lxxiv. 2-(1-(1-(3-(trifluoromethyl)-1,2,4-oxadiazol-5-yl)piperidin-4-yl)ethoxy)-6-(4-(methylsulfonyl)phenyl)imidazo[2,1-b][1,3,4]thiadiazole
lxxv. 2-(1-(1-(3-isopropyl-1,2,4-oxadiazol-5-yl)piperidin-4-yl)ethoxy)-6-(2-(methylsulfonyl)pyrimidin-5-yl)imidazo[2,1-b][1,3,4]thiadiazole
lxxvi. 2-(1-(1-(3-isopropyl-1,2,4-oxadiazol-5-yl)piperidin-4-yl)ethoxy)-6-(6-chloropyridin-3-yl)imidazo[2,1-b][1,3,4]thiadiazole
lxxvii. 2-((R)-1-(1-(3-(trifluoromethyl)-1,2,4-oxadiazol-5-yl)piperidin-4-yl)ethoxy)-6-(4-(methylsulfonyl)phenyl)imidazo[2,1-b][1,3,4]thiadiazole
lxxviii. 2-((S)-1-(1-(3-(trifluoromethyl)-1,2,4-oxadiazol-5-yl)piperidin-4-yl)ethoxy)-6-(4-(methylsulfonyl)phenyl)imidazo[2,1-b][1,3,4]thiadiazole
lxxix. 2-((S)-1-(1-(3-isopropyl-1,2,4-oxadiazol-5-yl)piperidin-4-yl)ethoxy)-6-(3-fluoro-4-(methylsulfonyl)phenyl)imidazo[2,1-b][1,3,4]thiadiazole lxxx. 2-(1-(1-(3-isopropyl-1,2,4-oxadiazol-5-yl)piperidin-4-yl)ethoxy)-6-(5-chloropyrazin-2-yl)imidazo[2,1-b][1,3,4]thiadiazole lxxxi. 2-((R)-1-(1-(5-ethylpyrimidin-2-yl)piperidin-4-yl)ethoxy)-6-(pyridin-4-yl)imidazo[2,1-b][1,3,4]thiadiazole lxxxii. 2-((R)-1-(1-(5-propylpyrimidin-2-yl)piperidin-4-yl)ethoxy)-6-(6-(methylsulfonyl)pyridin-3-yl)imidazo[2,1-b][1,3,4]thiadiazole lxxxiii. 2-((S)-1-(1-(5-propylpyrimidin-2-yl)piperidin-4-yl)ethoxy)-6-(3-fluoropyridin-4-yl)imidazo[2,1-b][1,3,4]thiadiazole lxxxiv. 2-((S)-1-(1-(5-chloropyrimidin-2-yl)piperidin-4-yl)ethoxy)-6-(4-(methylsulfonyl)phenyl)imidazo[2,1-b][1,3,4]thiadiazole lxxxv. 2-((R)-1-(1-(3-isopropyl-1,2,4-oxadiazol-5-yl)piperidin-4-yl)ethoxy)-6-(6-(trifluoromethyl)pyridin-3-yl)imidazo[2,1-b][1,3,4]thiadiazole lxxxvi. 2-((S)-1-(1-(5-propylpyrimidin-2-yl)piperidin-4-yl)ethoxy)-6-(2-fluoro-4-(methylsulfonyl)phenyl)imidazo[2,1-b][1,3,4]thiadiazole lxxxvii. 2-((S)-1-(1-(5-ethylpyrimidin-2-yl)piperidin-4-yl)ethoxy)-6-(2-fluoro-4-(methylsulfonyl)phenyl)imidazo[2,1-b][1,3,4]thiadiazole lxxxviii. 2-((R)-1-(1-(3-isopropyl-1,2,4-oxadiazol-5-yl)piperidin-4-yl)ethoxy)-6-(5-chloropyrazin-2-yl)imidazo[2,1-b][1,3,4]thiadiazole lxxxix. 2-((R)-1-(1-(3-isopropyl-1,2,4-oxadiazol-5-yl)piperidin-4-yl)ethoxy)-6-(2-fluoro-4-(methylsulfonyl)phenyl)imidazo[2,1-b][1,3,4]thiadiazole xc. 2-((S)-1-(1-(3-isopropyl-1,2,4-oxadiazol-5-yl)piperidin-4-yl)ethoxy)-6-(2-methoxypyridin-4-yl)imidazo[2,1-b][1,3,4]thiadiazole xci. 2-((R)-1-(1-(5-chloropyrimidin-2-yl)piperidin-4-yl)ethoxy)-6-(2-fluoro-4-(methylsulfonyl)phenyl)imidazo[2,1-b][1,3,4]thiadiazole xcii. 2-(1-(1-(3-isopropyl-1,2,4-oxadiazol-5-yl)piperidin-4-yl)ethoxy)-6-(2-(trifluoromethyl)-4-(methylsulfonyl)phenyl)imidazo[2,1-b][1,3,4]thiadiazole xciii. 2-(1-(1-(3-isopropyl-1,2,4-oxadiazol-5-yl)piperidin-4-yl)ethoxy)-6-(3-(trifluoromethyl)pyridin-4-yl)imidazo[2,1-b][1,3,4]thiadiazole xciv. 2-((S)-1-(1-(5-ethylpyrimidin-2-yl)piperidin-4-yl)ethoxy)-6-(2-methoxypyridin-4-yl)imidazo[2,1-b][1,3,4]thiadiazole xcv. 2-((S)-1-(1-(5-propylpyrimidin-2-yl)piperidin-4-yl)ethoxy)-6-(2-methoxypyridin-4-yl)imidazo[2,1-b][1,3,4]thiadiazole xcvi. 2-(1-(1-(3-isopropyl-1,2,4-oxadiazol-5-yl)piperidin-4-yl)ethoxy)-6-(3-methoxypyridin-4-yl)imidazo[2,1-b][1,3,4]thiadiazole xcvii. 4-(2-((S)-1-(1-(3-isopropyl-1,2,4-oxadiazol-5-yl)piperidin-4-yl)ethoxy)imidazo[2,1-b][1,3,4]thiadiazol-6-yl)-1-methylpyridin-2(1H)-one xcviii. 2-((S)-1-(1-(3-isopropyl-1,2,4-oxadiazol-5-yl)piperidin-4-yl)ethoxy)-6-(3-fluoropyridin-4-yl)imidazo[2,1-b][1,3,4]thiadiazole hydrochloride xcix. 2-((S)-1-(1-(5-(trifluoromethyl)pyrimidin-2-yl)piperidin-4-yl)ethoxy)-6-(2-fluoro-4-(methylsulfonyl)phenyl)imidazo[2,1-b][1,3,4]thiadiazole c. 4-(2-((R)-1-(1-(3-isopropyl-1,2,4-oxadiazol-5-yl)piperidin-4-yl)ethoxy)imidazo[2,1-b][1,3,4]thiadiazol-6-yl)-3-fluorobenzonitrile ci. 2-((R)-1-(1-(3-isopropyl-1,2,4-oxadiazol-5-yl)piperidin-4-yl)ethoxy)-6-(2-fluoro-6-(methylsulfonyl)pyridin-3-yl)imidazo[2,1-b][1,3,4]thiadiazole cii. isopropyl 4-(1-(6-(2-fluoro-4-(methylsulfonyl)phenyl)imidazo[2,1-b][1,3,4]thiadiazol-2-yloxy)ethyl)piperidine-1-carboxylate ciii. 2-((R)-1-(1-(5-ethylpyrimidin-2-yl)piperidin-4-yl)ethoxy)-6-(2-fluoro-6-(methylsulfonyl)pyridin-3-yl)imidazo[2,1-b][1,3,4]thiadiazole civ. 2-((S)-1-(1-(3-isopropyl-1,2,4-oxadiazol-5-yl)piperidin-4-yl)ethoxy)-6-(2-methoxy-4-(methylsulfonyl)phenyl)imidazo[2,1-b][1,3,4]thiadiazole cv. 2-((S)-1-(1-(3-isopropyl-1,2,4-oxadiazol-5-yl)piperidin-4-yl)ethoxy)-6-(2-methyl-6-(methylsulfonyl)pyridin-3-yl)imidazo[2,1-b][1,3,4]thiadiazole cvi. 2-((R)-1-(1-(3-isopropyl-1,2,4-oxadiazol-5-yl)piperidin-4-yl)ethoxy)-6-(2-fluoro-4-(1H-tetrazol-5-yl)phenyl)imidazo[2,1-b][1,3,4]thiadiazole hydrochloride cvii. tert-butyl 4-(1-(6-(6-fluoro-4-(methylsulfonyl)cyclohexa-1,5-dienyl)imidazo[2,1-b][1,3,4]thiadiazol-2-yloxy)ethyl)piperidine-1-carboxylate cviii. ethyl 4-(1-(6-(2-fluoro-4-(methylsulfonyl)phenyl)imidazo[2,1-b][1,3,4]thiadiazol-2-yloxy)ethyl)piperidine-1-carboxylate cix. isopropyl 4-((S)-1-(6-(2-fluoro-4-(methylsulfonyl)phenyl)imidazo[2,1-b][1,3,4]thiadiazol-2-yloxy)ethyl)piperidine-1-carboxylate cx. 1-methylcyclopropyl 4-(1-(6-(2-fluoro-4-(methylsulfonyl)phenyl)imidazo[2,1-b][1,3,4]thiadiazol-2-yloxy)ethyl)piperidine-1-carboxylate cxi. 2-(1-(1-(3-isopropyl-1,2,4-oxadiazol-5-yl)piperidin-4-yl)ethoxy)-6-(thiazol-5-yl)imidazo[2,1-b][1,3,4]thiadiazole cxii. 2-((S)-1-(1-(3-isopropyl-1,2,4-oxadiazol-5-yl)piperidin-4-yl)ethoxy)-6-(2-methyl-4-(methylsulfonyl)phenyl)imidazo[2,1-b][1,3,4]thiadiazole cxiii. ethyl 4-((S)-1-(6-(2-fluoro-4-(methylsulfonyl)phenyl)imidazo[2,1-b][1,3,4]thiadiazol-2-yloxy)ethyl)piperidine-1-carboxylate cxiv. 4-(3-isopropyl-1,2,4-oxadiazol-5-yl)-1-(3-(4-(methylsulfonyl)phenyl)-1,2,4-thiadiazol-5-yl)piperidine cxv. 4-(1-(3-(4-(methylsulfonyl)phenyl)-1,2,4-thiadiazol-5-yloxy)ethyl)-1-(3-isopropyl-1,2,4-oxadiazol-5-yl)piperidine cxvi. 4-(3-(4-(methylsulfonyl)phenyl)-1,2,4-thiadiazol-5-yloxy)-1-(3-isopropyl-1,2,4-oxadiazol-5-yl)piperidine cxvii. 4-((3-(4-(methylsulfonyl)phenyl)-1,2,4-thiadiazol-5-yloxy)methyl)-1-(3-isopropyl-1,2,4-oxadiazol-5-yl)piperidine cxviii. 5-(3-(1-(1-(3-isopropyl-1,2,4-oxadiazol-5-yl)piperidin-4-yl)ethoxy)-1,2,4-thiadiazol-5-yl)-2-(methylsulfonyl)pyridine cxix. 5-(3-(1-(3-isopropyl-1,2,4-oxadiazol-5-yl)piperidin-4-yloxy)-1,2,4-thiadiazol-5-yl)-2-(methylsulfonyl)pyridine cxx. 5-(3-((1-(3-isopropyl-1,2,4-oxadiazol-5-yl)piperidin-4-yl)methoxy)-1,2,4-thiadiazol-5-yl)-2-(methylsulfonyl)pyridine cxxi. 5-(5-(1-(3-isopropyl-1,2,4-oxadiazol-5-yl)piperidin-4-yloxy)-1,2,4-thiadiazol-3-yl)-2-(methylsulfonyl)pyridine cxxii. 2-(4-(3-(6-(methylsulfonyl)pyridin-3-yl)-1,2,4-thiadiazol-5-yloxy)piperidin-1-yl)-5-ethylpyrimidine cxxiii. 2-(4-(3-(6-(methylsulfonyl)pyridin-3-yl)-1,2,4-thiadiazol-5-yloxy)piperidin-1-yl)-5-propylpyrimidine cxxiv. N-(5-(1-(3-isopropyl-1,2,4-oxadiazol-5-yl)piperidin-4-yloxy)-1,2,4-thiadiazol-3-yl)-N-methyl-6-(methylsulfonyl)pyridin-3-amine cxxv. 2-(4-(3-(2-fluoro-4-(methylsulfonyl)phenyl)-1,2,4-thiadiazol-5-yloxy)piperidin-1-yl)-5-ethylpyrimidine cxxvi. 1-(3-isopropyl-1,2,4-oxadiazol-5-yl)-N-(3-(6-(methylsulfonyl)pyridin-3-yl)-1,2,4-thiadiazol-5-yl)piperidin-4-amine cxxvii. 1-(3-isopropyl-1,2,4-oxadiazol-5-yl)-N-methyl-N-(3-(6-(methylsulfonyl)pyridin-3-yl)-1,2,4-thiadiazol-5-yl)piperidin-4-amine B. Synthesis of Compounds of the Present Invention The present invention also relates to a process of preparing the compounds of formula (I). The compounds of present invention may be prepared by the schemes as here below:

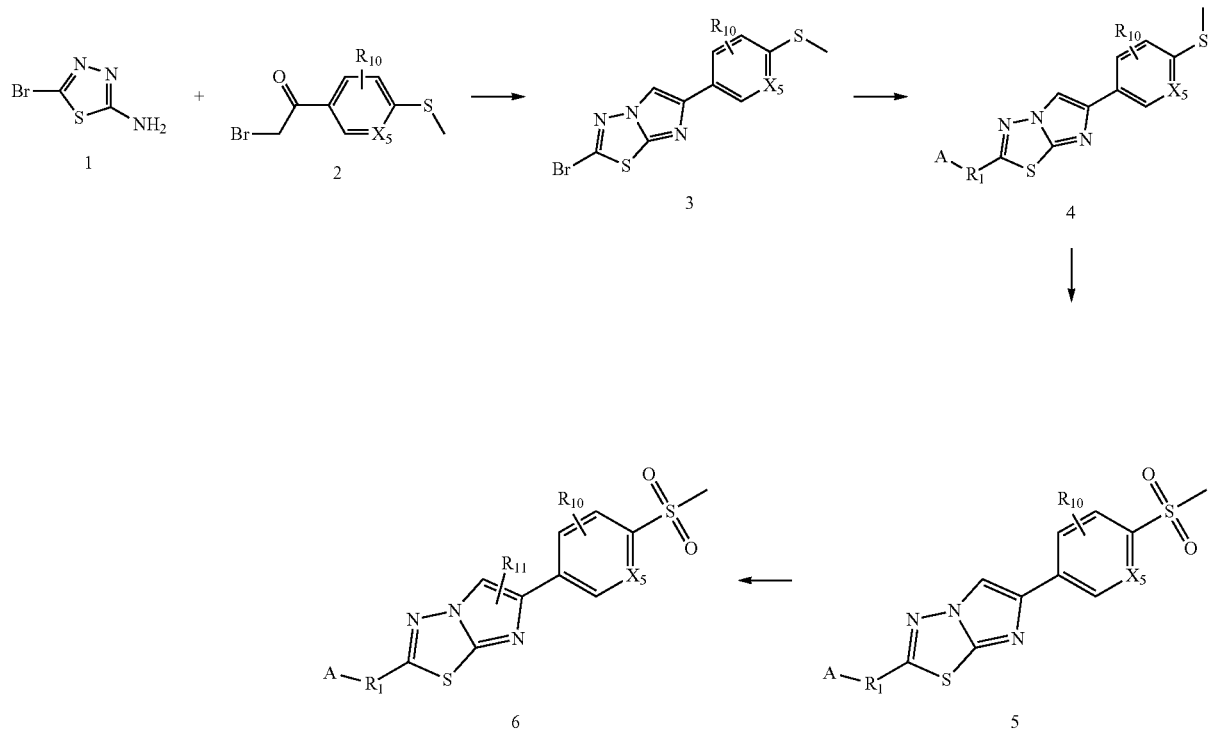
Wherein,
R₁ and A is as defined above;
$X_5$ is CH, N, O, S;
$R_{10}$ is H, OH, halogen, $C_{1-6}$ alkyl, $C_{1-6}$alkoxy, —$(CH_2)n$, amino, —CO, —CONH, —NH(Alkyl), —N(Alkyl)$_2$, —NH-aralkyl, —OCH(CH$_3$);
n is 0, 1, 2 or 3;
$R_{11}$ is halogen, H
Synthetic Scheme 2
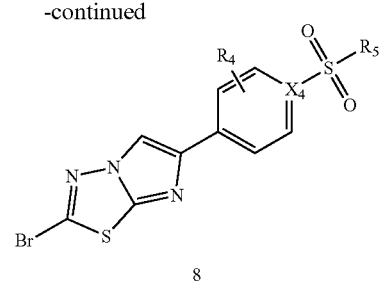
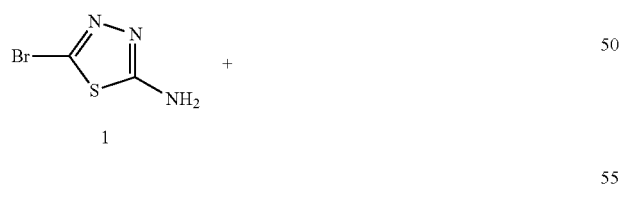
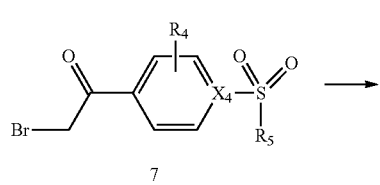
Wherein,
R₁ and A is as defined above;
$X_4$ is CH, N, O, S;
$R_4$ is H, OH, halogen, $C_{1-6}$ alkyl, $C_{1-6}$alkoxy, —$(CH_2)n$, amino, —CO, —CONH, —NH(Alkyl), —N(Alkyl)$_2$, —NH-aralkyl, —OCH(CH$_3$);
n is 0, 1, 2 or 3;

Synthetic Scheme 3
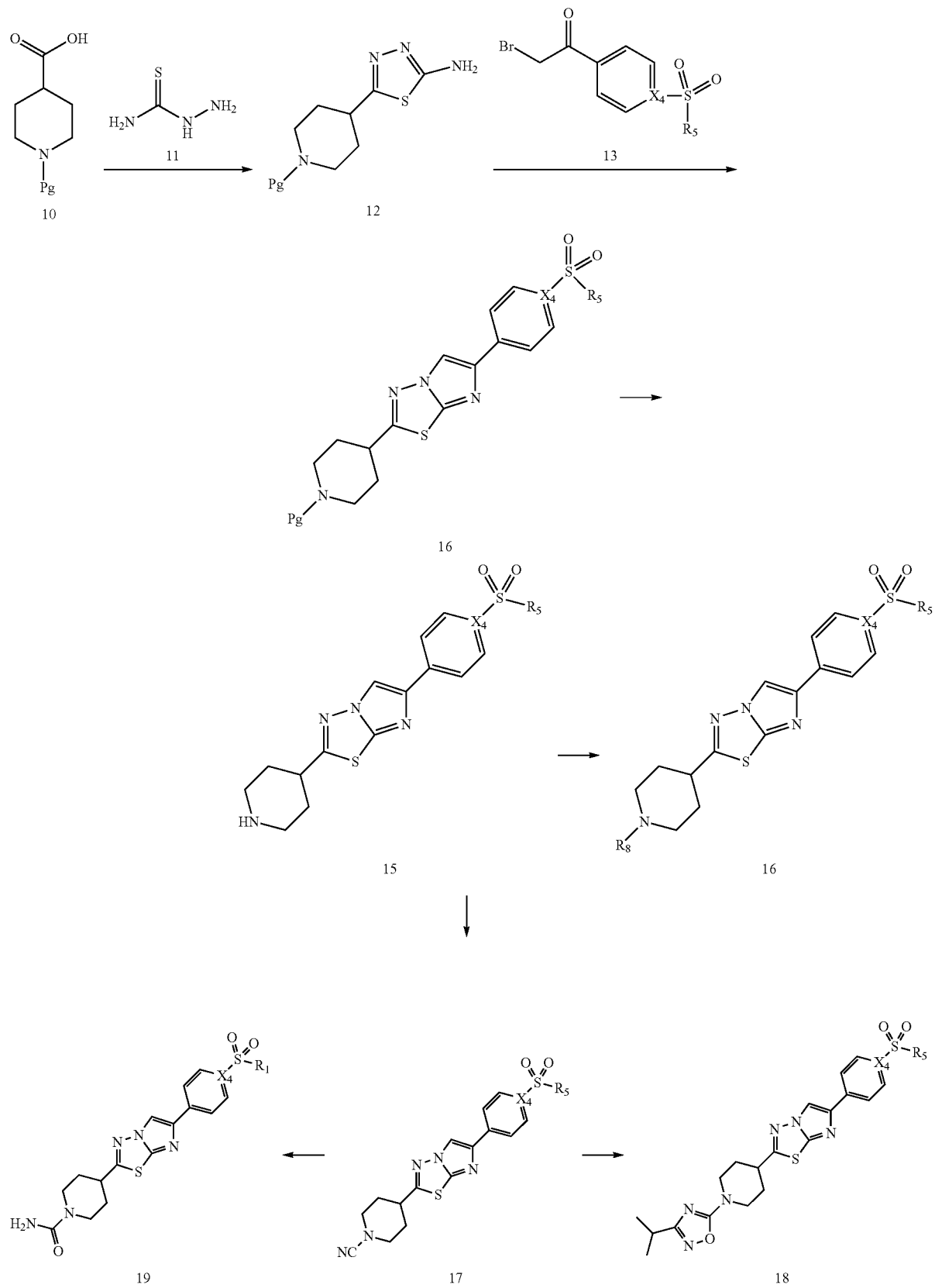

Wherein,
$X_4$ is CH, N, O, S;
$R_5$ is H, OH, halogen, $C_{1-6}$ alkyl, $C_{1-6}$ alkoxy, —$(CH_2)n$, amino, —CO, —CONH, —NH(Alkyl), —N(Alkyl)$_2$, —NH-aralkyl, —OCH(CH$_3$);
$R_8$ is
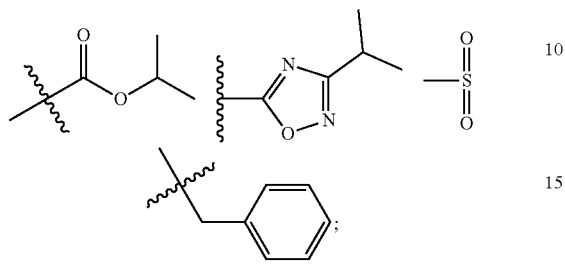
n is 0, 1, 2 or 3;

Synthetic Scheme 4
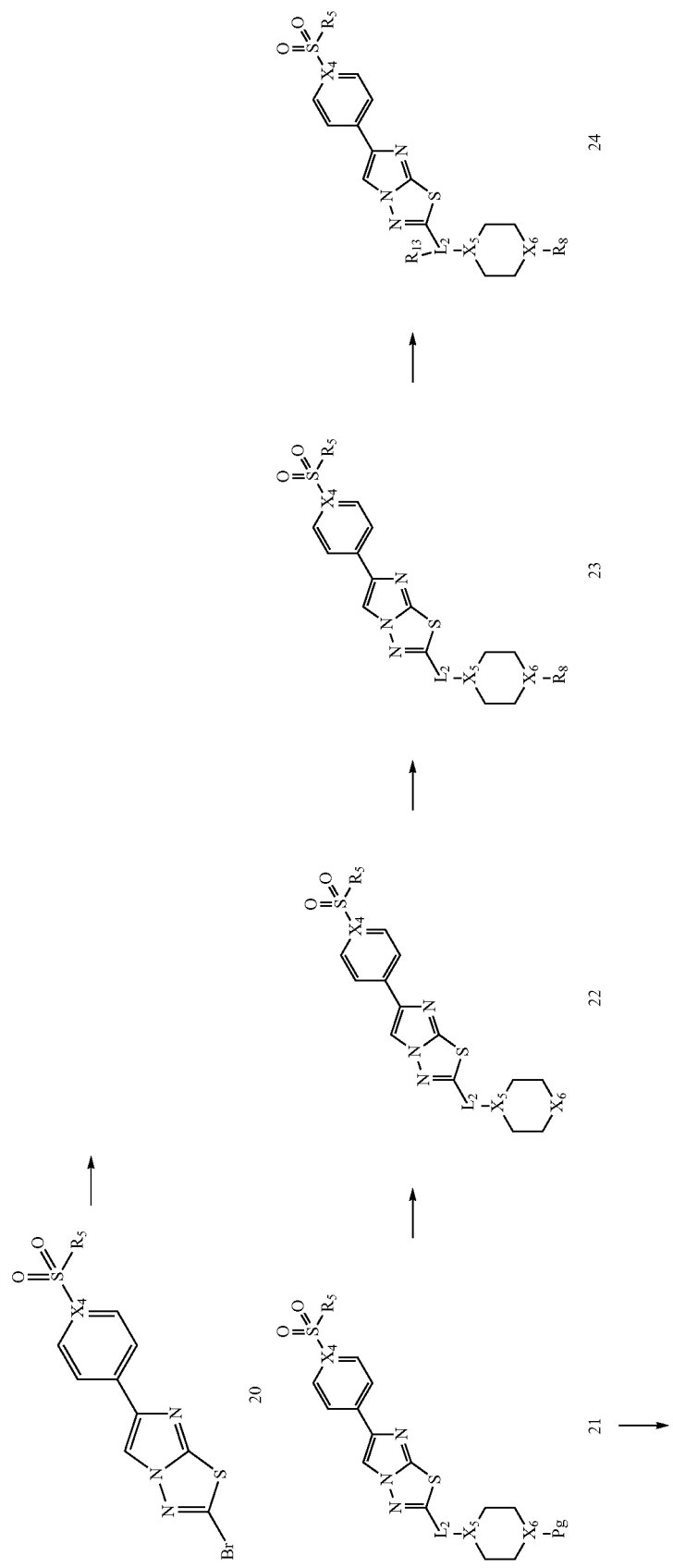

-continued
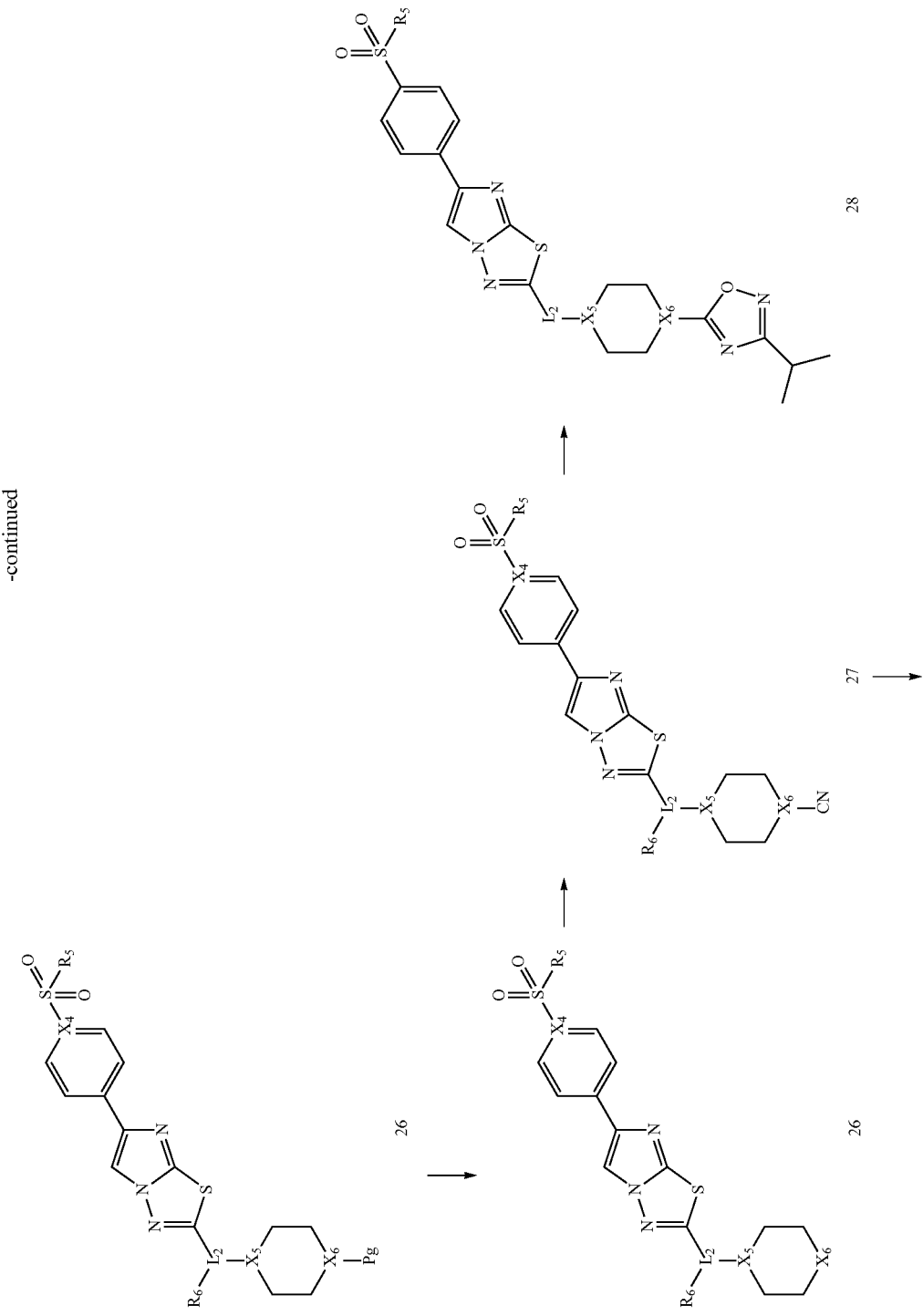

-continued
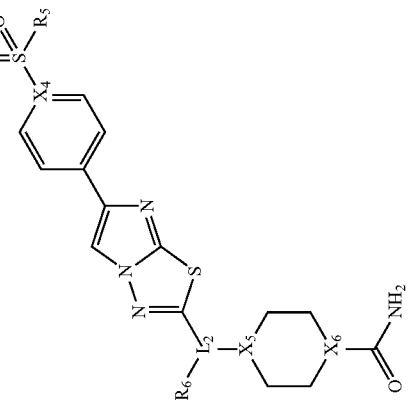
29

Wherein, $X_4$, $X_5$, $X_6$ and $L_2$ is CH, N, O, S;

$R_5$ and $R_6$ are H, OH, halogen, $C_{1-6}$ alkyl, $C_{1-6}$alkoxy, —$(CH_2)n$, amino, —CO, —CONH, —NH(Alkyl), —N(Alkyl)$_2$, —NH-aralkyl, —OCH(CH$_3$);

n is 0, 1, 2 or 3;

Synthetic Scheme 5

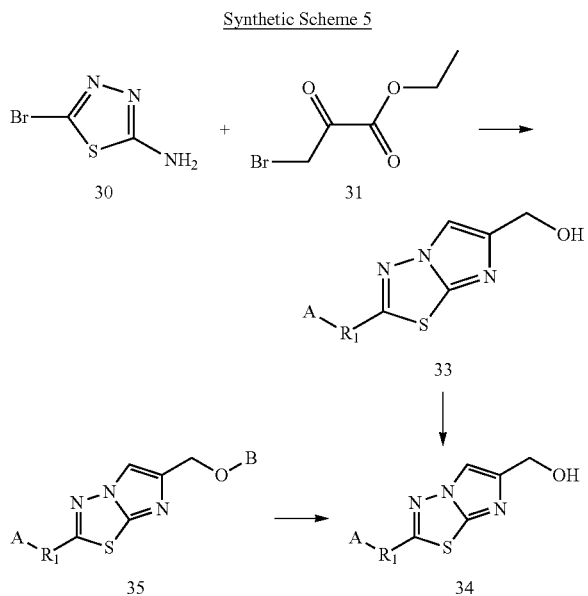

Wherein, $R_1$, A and B is as defined above;

$X_4$, $X_5$, $X_6$ and $L_2$ is CH, N, O, S;

$R_5$ and $R_6$ are H, OH, halogen, $C_{1-6}$ alkyl, $C_{1-6}$alkoxy, —$(CH_2)n$, amino, —CO, —CONH, —NH(Alkyl), —N(Alkyl)$_2$, —NH-aralkyl, —OCH(CH$_3$);

n is 0, 1, 2 or 3;

C. Salts and Isomers

The present invention includes within its scope the salts and isomers. Compounds of the present invention after being novel may in some cases form salts which are also within the scope of this invention. The term "salt(s)", as employed herein, denotes acidic and/or basic salts formed with inorganic and/or organic acids and bases. Pharmaceutically acceptable (i.e., non-toxic, physiologically acceptable) salts are preferred.

All stereoisomer's of the present compounds, such as those which may exist due to asymmetric carbons on the R substituents of the compound, including enantiomeric and diastereomeric forms, are contemplated within the scope of this invention.

The Compounds of the present invention may be present in their enantiomeric pure forms or their mixtures.

D. Methods of Use and Pharmaceutical Composition Containing the Novel Entities of the Invention The invention thus provides the use of the novel compounds as defined herein for use in human or veterinary medicine. The compounds of the present invention may be used in the treatment of diabetes. Particularly, the compounds of the present invention are effective in the treatment of type 2 diabetes mellitus. The compounds of present invention activates the GPR119 which increases the intracellular accumulation of cAMP, leading to enhanced glucose-dependent insulin secretion from pancreatic β-cells and increased release of the gut peptides GLP-1 (glucagon like peptide 1), GIP (glucose-dependent insulinotropic peptide) and PYY (polypeptide YY) and thus acts as GPR119 agonists.

The compound for use as a pharmaceutical may be presented as a pharmaceutical composition. The invention therefore provides in a further aspect a pharmaceutical composition comprising the novel compounds of the invention along with pharmaceutically acceptable excipients/carriers thereof and optionally other therapeutic and/or prophylactic ingredients. The excipients/carriers must be "acceptable" in the sense of being compatible with the other ingredients of the composition and not deleterious to the recipient thereof. Suitably the pharmaceutical composition will be in an appropriate formulation.

The pharmaceutical formulations may be any formulation and include those suitable for oral, intranasal, or parenteral (including intramuscular and intravenous) administration. The formulations may, where appropriate, be conveniently presented in discrete dosage units and may be prepared by any of the methods well known in the art of pharmacy. All methods include the step of bringing into association the active compound with liquid carriers or finely divided solid carriers or both, and then, if necessary, shaping the product into the desired formulation.

For these purposes the compounds of the present invention may be administered orally, topically, intranasally, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasteral injection or infusion techniques. In addition to the treatment of warm-blooded animals such as mice, rats, horses, dogs, cats, etc. The compounds of the present invention are effective in the treatment of humans.

In an aspect, compound of the present invention may be administered in a dose ranging from 0.1 to 100 mg/kg body weight per day. The compounds of the present invention are useful for the prevention and treatment of metabolic disorders, particularly for the treatment of type I and type II diabetes, obesity and related disorders.

Without being limited by theory, it is submitted that the novel compounds of the present invention exhibit substantially different pharmacokinetic and pharmacodynamic profiles. The invention is described in detail herein below with respect to the following examples which are provided merely for illustration. However, these examples may not be construed to restrict the scope of the invention. Any embodiments that may be apparent to a person skilled in the art are deemed to fall within the scope of present invention.

EXPERIMENTALS

Example 1: 3-(1-(5-ethylpyrimidin-2-yl)piperidin-4-yl)-4-(4-(methylsulfonyl) phenyl)-1,2,5-thiadiazole [1004]

Step-1: Synthesis of 3-chloro-4-(4-(methylsulfonyl) phenyl)-1,2,5-thiadiazole

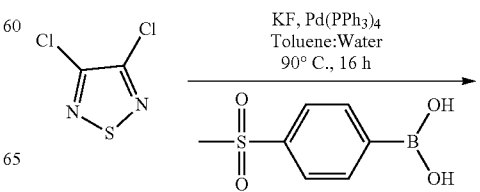

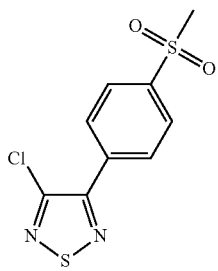

To a stirred solution of 3,4-dichloro-1,2,5-thiadiazole (0.2 g, 1.307 mmol) and 4-(methylsulfonyl)phenylboronic acid (0.259 g, 1.307 mmol) in toluene (5 mL) was added KF (0.226 g, 3.898 mmol) in water (5 mL), reaction mass was purged with nitrogen for 30 min. After 30 min Pd(PPh$_3$)$_4$ (0.0075 g, 0.0653 mmol) was added to reaction mixture, heated at 90° C. for 16 h. Reaction was monitored by TLC. On completion, reaction was quenched with water, extracted with ethyl acetate. Organic layer was washed with water, brine, dried over sodium sulphate, concentrated under reduced pressure obtained crude which was purified by Combiflash chromatography; eluent 15% EtOAc/Hexane to afford 3-chloro-4-(4-(methylsulfonyl)phenyl)-1,2,5-thiadiazole (0.075 g, 20.94%) as off white solid.

MS: 275.20 [M+1]

Step-2: Synthesis of t-butyl 5,6-dihydro-4-(4-(4-(methylsulfonyl)phenyl)-1,2,5-thiadiazol-3-yl)pyridine-1(2H)-carboxylate

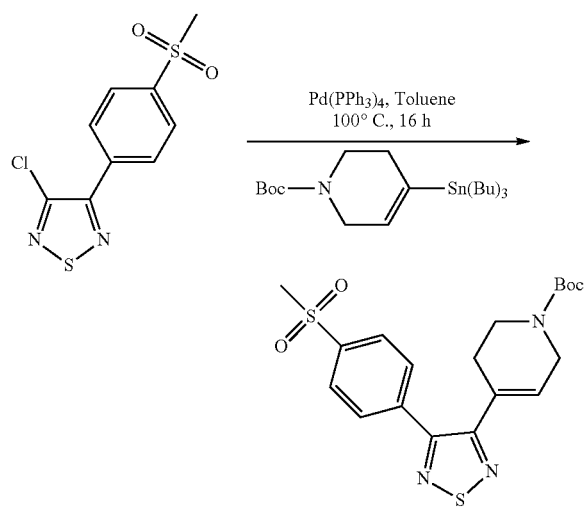

To a stirred solution of 3-chloro-4-(4-(methylsulfonyl)phenyl)-1,2,5-thiadiazole (0.07 g, 0.255 mmol) and t-butyl 4-(tributylstannyl)-5,6-dihydropyridine-1(2H)-carboxylate (0.145 g, 0.306 mmol) in toluene (10 mL), nitrogen was purged for 30 min. After 30 min Pd(PPh$_3$)$_4$ (0.029 g, 0.0255 mmol) was added to reaction mass and heated at 100° C. for 16 h. Reaction was monitored by TLC. On completion reaction was concentrated under reduced pressure obtained crude which was purified by Column chromatography (100-200 mesh); eluent 25% EtOAc/Hexane to afford t-butyl 5,6-dihydro-4-(4-(4-(methylsulfonyl)phenyl)-1,2,5-thiadiazol-3-yl)pyridine-1(2H)-carboxylate (0.065 g, 60.11%) as off white solid. MS: 422.11 [M$^+$+1]

Step-3: Synthesis of 1,2,3,6-tetrahydro-4-(4-(4-(methylsulfonyl)phenyl)-1,2,5-thiadiazol-3-yl)pyridine hydrochloride

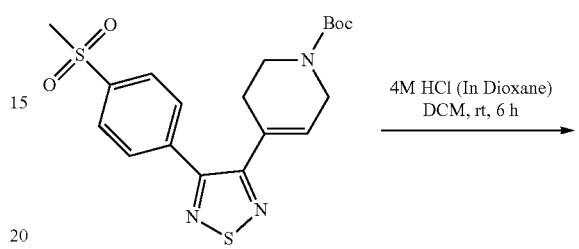

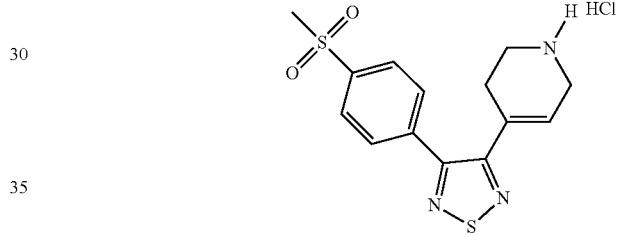

To t-butyl 5,6-dihydro-4-(4-(4-(methylsulfonyl)phenyl)-1,2,5-thiadiazol-3-yl)pyridine-1(2H)-carboxylate (0.06 g, 0.141 mmol) in DCM (5 mL) was added 4 M HCl in Dioxane (1 mL) and stirred at room temperature for 6 h. Reaction was monitored by TLC. On completion reaction mixture was concentrated under reduced pressure to afford 1,2,3,6-tetrahydro-4-(4-(4-(methylsulfonyl)phenyl)-1,2,5-thiadiazol-3-yl)pyridine hydrochloride (0.04, g 80.0%) as white solid.

MS: 322.06[M$^+$+1]

Step-4: Synthesis of 5-ethyl-2-(5,6-dihydro-4-(4-(4-(methylsulfonyl)phenyl)-1,2,5-thiadiazol-3-yl)pyridin-1(2H)-yl)pyrimidine

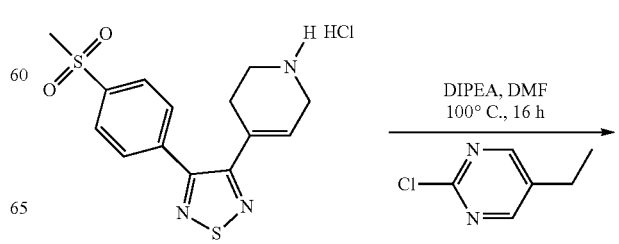

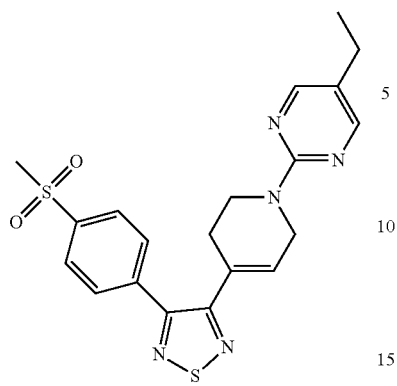

To a stirred solution of 1,2,3,6-tetrahydro-4-(4-(4-(methylsulfonyl)phenyl)-1,2,5-thiadiazol-3-yl)pyridine hydrochloride (0.04 g, 0.111 mmol) and 2-chloro-5-ethylpyrimidine (0.023 g, 0.166 mmol) in DMF (5 mL) was added DIPEA (0.45 mL, 0.555 mmol) and stirred at 100° C. for 16 h. Reaction was monitored by TLC. On completion reaction mass was quenched with water, extracted with ethyl acetate. The organic layer was washed with water, brine, dried over sodium sulphate evaporated under reduced pressure obtained crude which was purified by silica gel (100-200 Mesh) column chromatography, eluent 25% EtOAc/Hexane to afford 5-ethyl-2-(5,6-dihydro-4-(4-(4-(methylsulfonyl)phenyl)-1,2,5-thiadiazol-3-yl)pyridin-1(2H)-yl)pyrimidine (0.024 g, 51.06%) as off white solid.

MS: 428.11[M$^+$+1]

Step-5: Synthesis of 5-ethyl-2-(4-(4-(4-(methylsulfonyl)phenyl)-1,2,5-thiadiazol-3-yl)piperidin-1-yl)pyrimidine

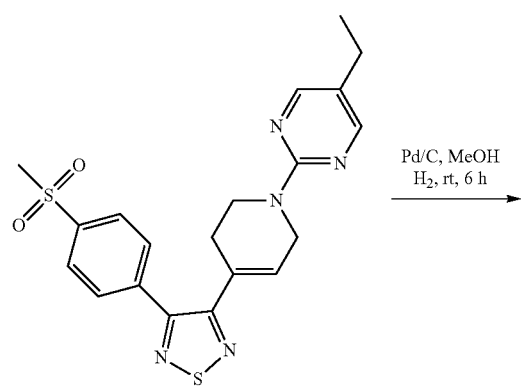

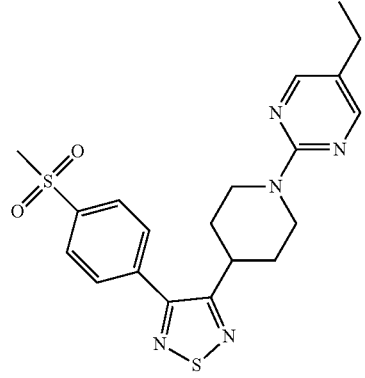

To a stirred solution of 5-ethyl-2-(5,6-dihydro-4-(4-(4-(methylsulfonyl)phenyl)-1,2,5-thiadiazol-3-yl)pyridin-1(2H)-yl)pyrimidine (0.2 g, 0.0467 mmol) in MeOH (5 mL) was added 10% Pd/C (0.04 g) reaction mass was purged with hydrogen for 6 h, and monitored by TLC. On completion, reaction was filtered on celite, filtrate was concentrated under reduced pressure obtained crude which was purified by Column chromatography (100-200 mesh); eluent 25% EtOAc in Hexane obtained 5-ethyl-2-(4-(4-(4-(methylsulfonyl)phenyl)-1,2,5-thiadiazol-3-yl)piperidin-1-yl)pyrimidine (0.005 g 25%) as off white solid.

MS: 430.13[M$^+$+1]

Example 2: 3-(4-(1H-tetrazol-1-yl)phenoxy)-4-(1-(5-ethylpyrimidin-2-yl)-1,2,3,6-tetrahydropyridin-4-yl)-1,2,5-thiadiazole [1005]

Step 1: Synthesis of 1-(4-(4-chloro-1,2,5-thiadiazol-3-yloxy)phenyl)-1H-tetrazole

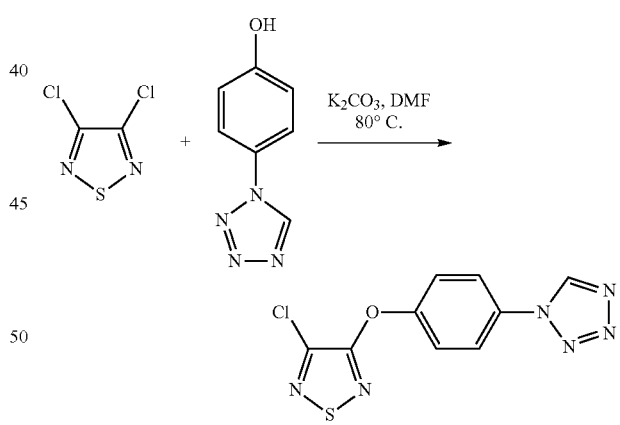

To a stirred solution of 3,4-dichloro-1,2,5-thiadiazole (0.3 g, 1.93 mmol) in DMF (10 mL) was added solution of 4-(1H-tetrazol-1-yl)phenol (0.313 g, 1.93 mmol) in DMF (2 mL) and heat reaction mass at 80° C. for 12 h. Reaction was monitored by TLC. On completion, reaction mass was diluted with water, extracted with EtOAc. Organic layer was washed with water, brine, dried over Na$_2$SO$_4$ and evaporated under reduced pressure to give crude product. Purification of the crude was done by silica gel (100-200 Mesh) column chromatography; eluent 25% EtOAc:hexane to obtain 1-(4-(4-chloro-1,2,5-thiadiazol-3-yloxy)phenyl)-1H-tetrazole (0.1 g, 18%) as white solid.

MS: 280.99[M$^+$+1]

Step 2: Synthesis of t-butyl 4-(4-(4-(1H-tetrazol-1-yl)phenoxy)-1,2,5-thiadiazol-3-yl)-5,6-dihydropyridine-1(2H)-carboxylate

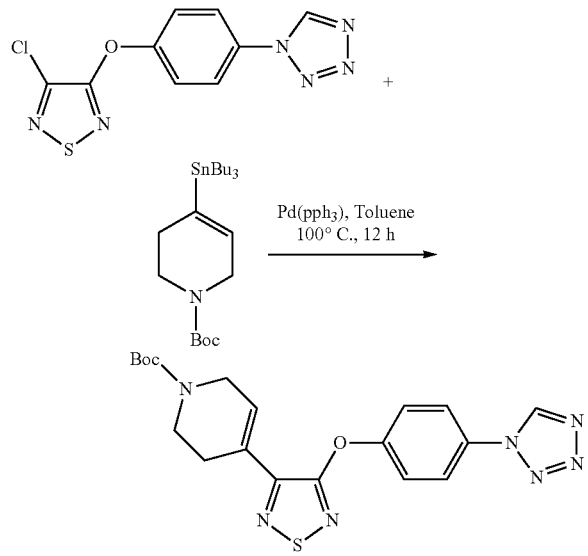

To a stirred solution of 1-(4-(4-chloro-1,2,5-thiadiazol-3-yloxy)phenyl)-1H-tetrazole (0.1 g, 0.36 mmol) and teroom temperature-butyl 4-(tributylstannyl)-5,6-dihydropyridine-1(2H)-carboxylate (0.2 g, 0.43 mmol) in toluene (10 mL), N2 was purged for 30 min. After 30 min, Pd(PPh$_3$)$_4$ (0.041 g, 0.035 mmol) was added to reaction mixture and heated at 100° C. for 12 h. Reaction was monitored by TLC. On completion, all volatiles were evaporated under reduced pressure to give crude which was purified by column chromatography (100-200 mesh); eluent 30% EtOAc/Hexane to obtain t-butyl 4-(4-(4-(1H-tetrazol-1-yl)phenoxy)-1,2,5-thiadiazol-3-yl)-5,6-dihydropyridine-1(2H)-carboxylate (0.05 g, 33%) as yellow sticky mass. MS: 428.14[M$^+$+1]

Step 3: Synthesis of 4-(4-(4-(1H-tetrazol-1-yl)phenoxy)-1,2,5-thiadiazol-3-yl)-1,2,3,6-tetrahydropyridinehydrochloride

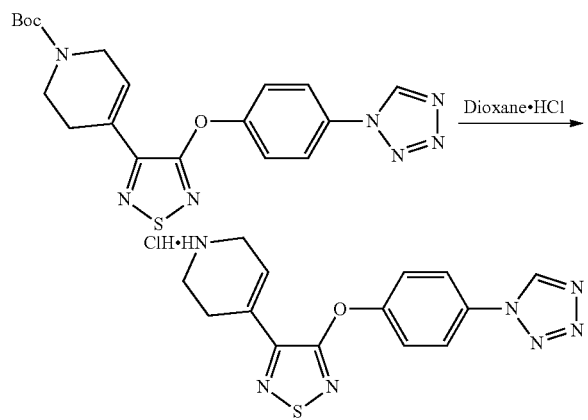

To a stirred solution of teroom temperature-butyl 4-(4-(4-(1H-tetrazol-1-yl)phenoxy)-1,2,5-thiadiazol-3-yl)-5,6-dihydro pyridine-1(2H)-carboxylate (0.05 g, 0.11 mmol) in DCM (10 mL) was added 4 M HCl in Dioxane (1 mL). Reaction mixture was allowed to stir at room temperature for 6 h. Reaction was monitored by TLC. On completion, reaction mixture was concentrated under reduced pressure to give of 4-(4-(4-(1H-tetrazol-1-yl)phenoxy)-1,2,5-thiadiazol-3-yl)-1,2,3,6-tetrahydropyridine hydrochloride (0.03 g, 78%) as off-white solid. MS: 328.14[M$^+$+1]

Step 4: Synthesis of 2-(4-(4-(4-(1H-tetrazol-1-yl)phenoxy)-1,2,5-thiadiazol-3-yl)-5,6-dihydropyridin-1(2H)-yl)-5-ethylpyrimidine

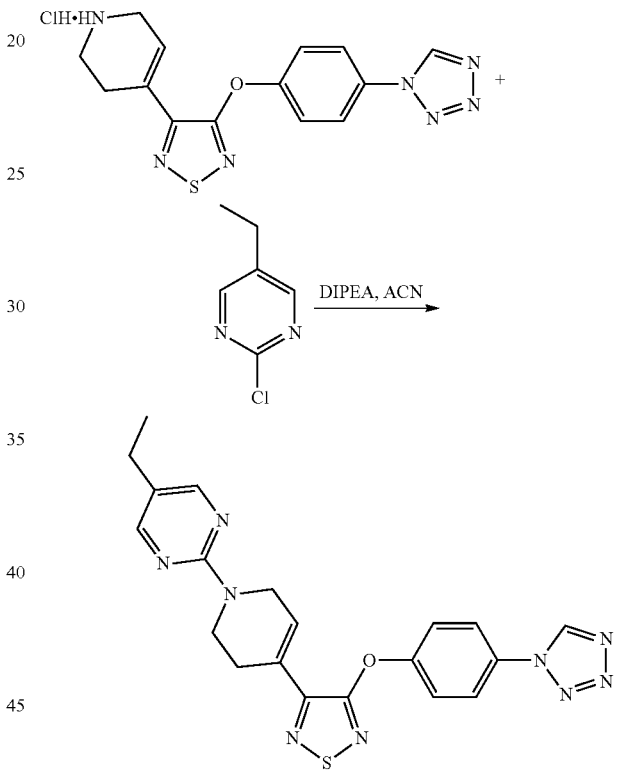

To a stirred solution of 4-(4-(4-(1H-tetrazol-1-yl) phenoxy)-1,2,5-thiadiazol-3-yl)-1,2,3,6-tetrahydro pyridine hydrochloride (0.03 g, 0.097 mmol) in ACN (7 mL) was added DIPEA (0.09 mL, 0.48 mmol) followed by 2-chloro-5-ethylpyrimidine (0.028 g, 0.19 mmol) at room temperature. Reaction mixture was allowed to stir at room temperature for 12 h. Reaction was monitored by TLC. On completion, reaction mixture was diluted with water and extracted with EtOAc. Organic layer was washed with water, brine, dried over sodium sulphate and evaporated under reduced pressure to give crude product. Purification of the crude was done by silica gel (100-200 Mesh) column chromatography; eluent 2% MeOH in DCM to obtain 2-(4-(4-(4-(1H-tetrazol-1-yl)phenoxy)-1,2,5-thiadiazol-3-yl)-5,6-dihydropyridin-1(2H)-yl)-5-ethylpyrimidine (0.01 g, 25%) as off-white solid.

MS: 434.14[M$^+$+1]

Example 3: Isopropyl 4-(4-(4-(1H-tetrazol-1-yl)phenoxy)-1,2,5-thiadiazol-3-yl)piperazine-1-carboxylate [1010]

Step 1: Synthesis of 1-(4-(4-chloro-1,2,5-thiadiazol-3-yloxy)phenyl)-1H-tetrazole.

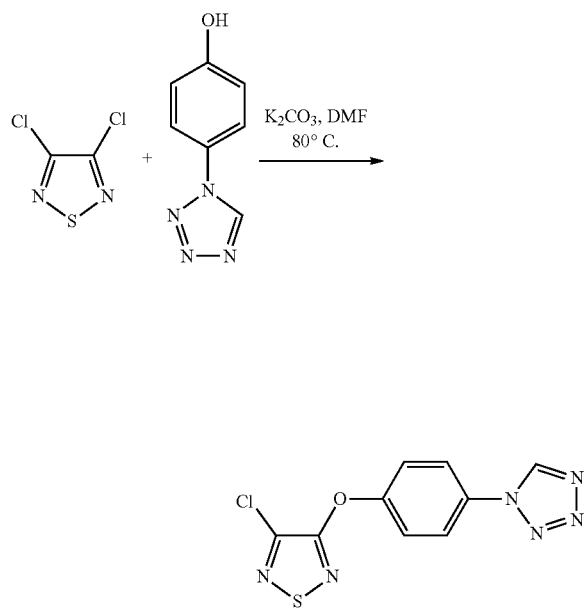

To a stirred solution of 3,4-dichloro-1,2,5-thiadiazole (0.3 g, 1.93 mmol) in DMF (10 mL) was added solution of 4-(1H-tetrazol-1-yl)phenol (0.313 g, 1.93 mmol) in DMF (2 mL) and heat reaction mass at 80° C. for 12 h. Reaction was monitored by TLC. On completion, reaction mass was diluted with water, extracted with EtOAc. Organic layer was washed with water, brine, dried over Na₂SO₄ and evaporated under reduced pressure to give crude product. Purification of the crude was done by silica gel (100-200 Mesh) column chromatography; eluent 25% EtOAc:hexane to obtain 1-(4-(4-chloro-1,2,5-thiadiazol-3-yloxy)phenyl)-1H-tetrazole (0.1 g, 18%) as white solid.

MS: 280.99[M⁺+1]

Step-2: Synthesis of t-butyl 4-(4-(4-(1H-tetrazol-1-yl)phenyl)-1,2,5-thiadiazol-3-yl)piperazine-1-carboxylate

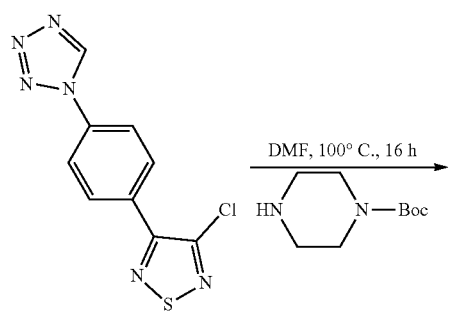

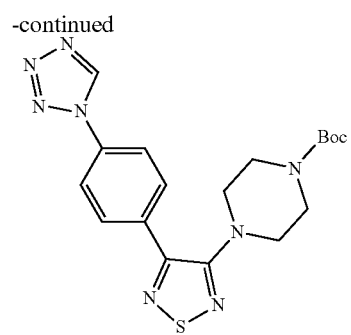

To a stirred solution of 1-(4-(4-chloro-1,2,5-thiadiazol-3-yl)phenyl)-1H-tetrazole (0.15 g, 0.534 mmol) and t-butyl piperazine-1-carboxylate (0.199 g, 1.068 mmol) in DMF (10 mL). Reaction was stirred at 100° C. for 16 h. Reaction was monitored by TLC. On completion reaction was quenched with water, extracted with ethyl acetate. The organic layer was washed with water, brine, dried over sodium sulphate, concentrated under reduced pressure obtained crude which was purified by silica gel (100-200 Mesh) column chromatography, eluent 30% EtOAc/Hexane obtained t-butyl 4-(4-(4-(1H-tetrazol-1-yl)phenyl)-1,2,5-thiadiazol-3-yl)piperazine-1-carboxylate (0.090 g, 39.13%) as off white solid.

MS: 415.16[M⁺+1]]

Step-3: Synthesis of 1-(4-(4-(1H-tetrazol-1-yl)phenyl)-1,2,5-thiadiazol-3-yl)piperazine hydrochloride To a stirred solution of t-butyl 4-(4-(4-(1H-tetrazol-1-yl)phenyl)-1,2,5-thiadiazol-3-yl)piperazine-1-carboxylate (0.09 g, 0.208 mmol) in DCM (5 mL) was added 4 M HCl in Dioxane (0.2 mL, 1.042 mmol) and reaction allowed to stirred at room temperature for 3 h. Reaction was monitored by TLC. On completion reaction mixture was concentrated under reduced pressure obtained 1-(4-(4-(1H-tetrazol-1-yl)phenyl)-1,2,5-thiadiazol-3-yl)piperazine hydrochloride (0.07 g, 80.00%) as Yellow solid.

MS: 314.13[M⁺+1]

Step-4: Synthesis of isopropyl 4-(4-(4-(1H-tetrazol-1-yl)phenyl)-1,2,5-thiadiazol-3-yl)piperazine-1-carboxylate

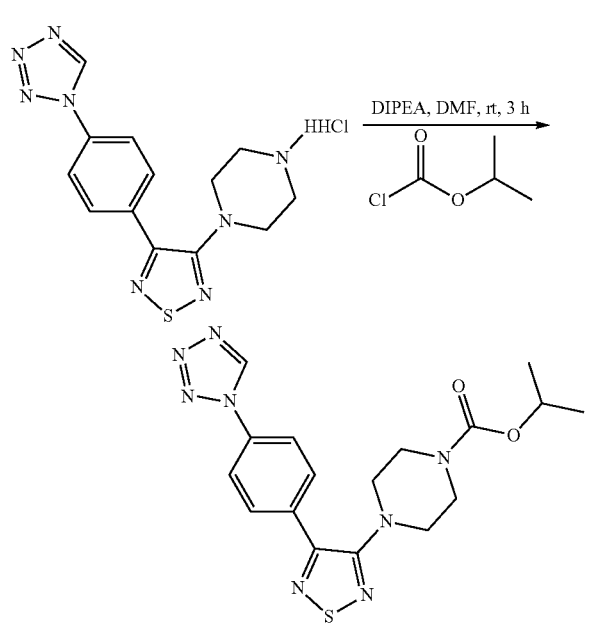

To a stirred solution of 1-(4-(4-(1H-tetrazol-1-yl)phenyl)-1,2,5-thiadiazol-3-yl)piperazine hydrochloride (0.04 g, 0.109 mmol) in DMF (5 mL) was added DIPEA (0.097 mL, 0.546 mmol) and reaction allowed to stirred at room temperature for 30 min then added isopropylchloroformate (2M in toluene) (0.109 mL, 0.218 mmol) and stirred for 3 h. Reaction was monitored by TLC. Reaction was quenched with ice cold water, extracted with ethyl acetate. The organic layer was washed with brine, dried over sodium sulphate, concentrated under reduced pressure obtained crude which was purified by silica gel (100-200 Mesh) column chromatography, eluent 20% EtOAc/Hexane to afford isopropyl 4-(4-(4-(1H-tetrazol-1-yl)phenyl)-1,2,5-thiadiazol-3-yl)piperazine-1-carboxylate (0.004 g, 8.88%) as off white solid.

MS: 401.14[M$^+$+1]

Example 4: 3-isopropyl-5-(1-(6-(4-(methylsulfonyl)phenyl)imidazo[2,1-b][1,3,4]thiadiazol-2-yl)piperidin-4-yl)-1,2,4-oxadiazole [1016]

Step-1: Synthesis of 5-bromo-1,3,4-thiadiazol-2-amine

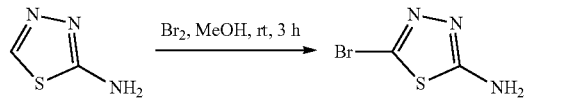

To a stirred solution of 1,3,4-thiadiazol-2-amine (5 g, 49.44 mmol) in MeOH (250 mL) was added bromine (23.70 g, 148.32 mmol) dropwise at room temperature and stirred for 3 h. Completion of reaction was monitored by TLC. Reaction mixture was evaporated under reduced pressure. After addition of water to reaction mass, solid precipitate out which was filtered off. Solid was washed with water, dried under vacuum to obtained 5-bromo-1,3,4-thiadiazol-2-amine (6.5 g, 72.95%) as yellow solid.
MS: 178.96[M+1]

Step 2: synthesis of 2-bromo-6-(4-(methylsulfonyl)phenyl)imidazo[2,1-b][1,3,4]thiadiazole

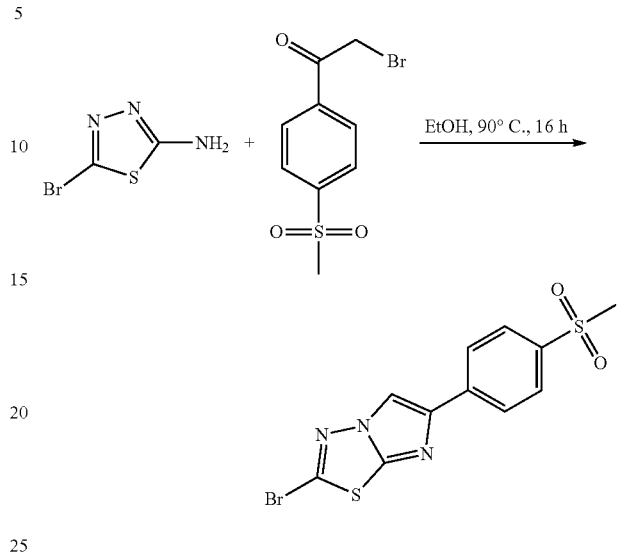

To a stirred solution of 5-amino-2-bromo-1,3,4-thiadiazole (1.0 g, 5.55 mmol) and 2-bromo-1-(4-(methylsulfonyl)phenyl) ethanone (1.53 g, 5.55 mmol) in ethanol (50 mL) was heated at 90° C. for 16 h. After cooled to room temperature, the precipitated solid was filtered off, washed with hot ethanol, dried under vacuum obtained 2-bromo-6-(4-(methylsulfonyl)phenyl)imidazo[2,1-b][1,3,4]thiadiazole (1.2 g, 60.60%) as off white solid.

MS: 358.1 [M+1]

Step-3: Synthesis of 2-(4-(3-isopropyl-1,2,4-oxadiazol-5-yl)piperidin-1-yl)-6-(4-(methylsulfonyl)phenyl)imidazo[2,1-b][1,3,4]thiadiazole

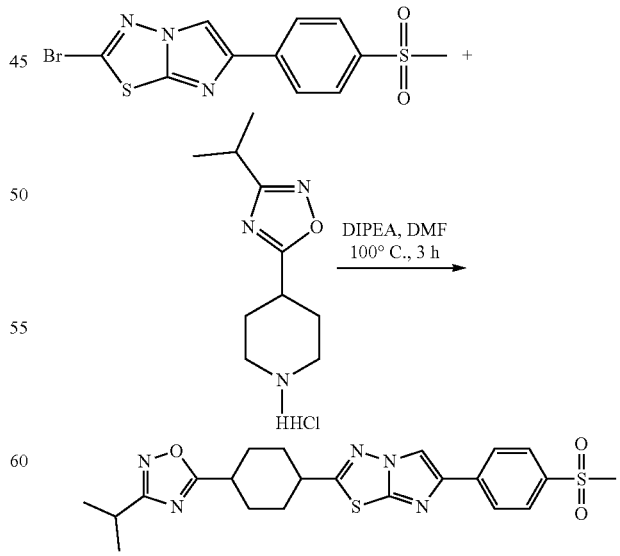

To a stirred solution of 2-bromo-6-(4-(methylsulfonyl)phenyl)imidazo[2,1-b][1,3,4]thiadiazole (0.03 g, 0.083 mmol) and 4-(3-isopropyl-1,2,4-oxadiazol-5-yl)piperidineHCl salt (0.03 g, 0.125 mmol) in DMF (10 mL) was added DIPEA (0.29 mL, 0.0167 mmol) and reaction heated at 100° C. for 6 h. Reaction was monitored by TLC. On completion, quenched with water, extracted with ethyl acetate. The organic layer was washed with water, brine, dried over sodium sulphate, concentrated under reduced pressure to obtained crude. Purification of the crude was done by silica gel (100-200 Mesh) column chromatography eluent 2% MeOH/DCM obtained 2-(4-(3-isopropyl-1,2,4-oxadiazol-5-yl)piperidin-1-yl)-6-(4-(methylsulfonyl)phenyl)imidazo[2,1-b][1,3,4]thiadiazole (0.014 g, 35.89%) as off white solid.

MS: 473.21[M$^+$+1]

Example 5: 2-(1-benzylpiperidin-4-yl)-6-(4-(methylsulfonyl)phenyl)imidazo [2,1-b][1,3,4]thiadiazole [1019]

Step 1:

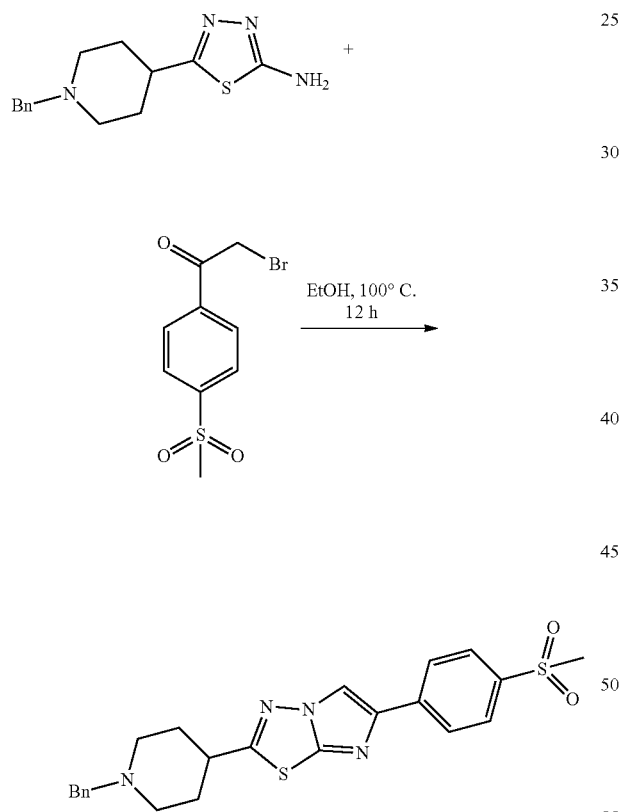

To a stirred solution of 5-(1-benzylpiperidin-4-yl)-1,3,4-thiadiazol-2-amine (0.1 g, 0.36 mmol) and 2-bromo-1-(4-(methylsulfonyl)phenyl)ethanone (0.11 g, 0.40 mmol) in EtOH (30 mL) was heated at 100° C. for 12 h. Reaction was cooled to room temperature, Obtained precipitates were filtered off, washed with boiling EtOH (10 mL) and dried under vacuum to obtain 2-(1-benzylpiperidin-4-yl)-6-(4-(methylsulfonyl)phenyl)imidazo[2,1-b][1,3,4]thiadiazole (0.04 g, 24%) as light yellow solid.

MS: 453.13[M$^+$+1]

Example 6: 1-(4-(2-(4-(methylsulfonyl)phenyl)imidazo[2,1-b][1,3,4]thiadiazol-6-yl)piperidin-1-yl)ethanone [1028]

Step-1: Synthesis of 1-acetylpiperidine-4-carboxylic acid

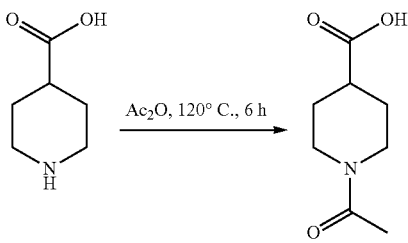

To a solution of piperidine-4-carboxylic acid (5.0 g) in acetic anhydride (50 mL) was heated at 130° C. for 6 h, Completion of reaction was monitored by TLC. On completion all volatiles were evaporated under reduced pressure obtained crude which was triturated with petroleum ethers solid precipitated out which was filtered off, solid was dried under vacuum obtained 1-acetylpiperidine-4-carboxylic acid (5.20 g, 78.43%) as off white solid.

MS: 171.98[M+1]

Step-2: Synthesis of 1-acetyl-N-methoxy-N-methylpiperidine-4-carboxamide

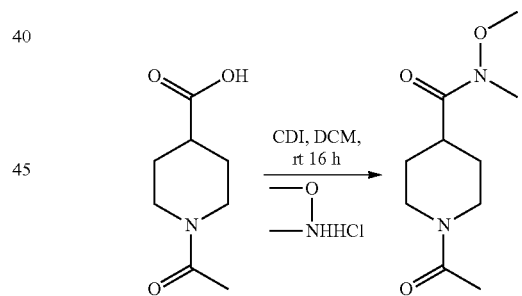

To a stirred solution of 1-acetylpiperidin-4-carboxylic acid (5.0 g, 29.207 mmol) in dichloromethane (100 mL) was added CDI (9.47 g, 58.414 mmol) and stirred for 0.5 h. After 0.5 h N-methoxymethanamine hydrochloride (4.27 g, 43.810 mmol) was added to reaction mass. The mixture was stirred at room temperature for 16 h. On completion, 4M HCl in Dioxane (20 mL) was added slowly. The slurry was agitated for 30 minutes and then filtered. Filtrate was washed twice with sodium bicarbonate solution, dried over sodium sulphate, concentrated under vacuum obtained 1-acetyl-N-methoxy-N-methylpiperidine-4-carboxamide (5.20 g, 83.20%) as yellow oil.

MS: 215.05[M+1]

Step-3: Synthesis of N-acetyl-1-(piperidin-4-yl) ethanone

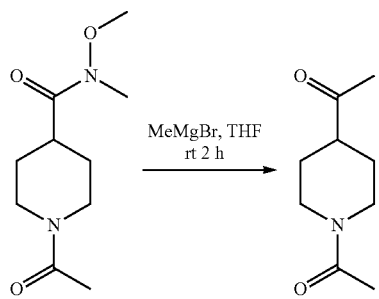

To a stirred solution of N-acetyl-N-methoxy-N-methylpiperidine-4-carboxamide (4.0 g, 18.668 mmol) in THF (100 mL) was added methyl magnesium bromide (2 M in THF) (28 mL, 56.006 mmol) at 0° C., after the addition the mixture was stirred at room temperature for 2 h. On completion, reaction mixture was quenched with NH$_4$Cl solution, extracted with EtOAc. The organic layer was washed with water, brine, dried over Na$_2$SO$_4$, evaporated under reduced pressure obtained N-acetyl-1-(piperidin-4-yl) ethanone (3.01 g, 95.55%) as yellow oil.

MS: 170.03[M$^+$+1]

Step-4: Synthesis of 1-(1-acetylpiperidin-4-yl)-2-bromoethanone

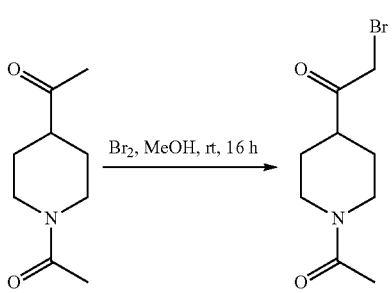

To a stirred solution of N-acetyl-1-(piperidin-4-yl) ethanone (2.0 g, 11.81 mmol) in MeOH (50 mL) was added bromine dropwise (1.88 g, 11.81 mmol) at room temperature, after the addition the mixture was stirred for 16 h. On completion, reaction mixture was quenched with water, extracted with EtOAc. The organic layer was washed with water, NaHCO$_3$ solution, dried over Na$_2$SO$_4$ and Concentrated under reduced pressure obtained 1-(1-acetylpiperidin-4-yl)-2-bromoethanone (1.60 g, 54.60%) as yellow oil.

MS: 247.91[M+1]

Step-5: Synthesis of 1-(4-(2-bromoimidazo[2,1-b][1,3,4]thiadiazol-6-yl)piperidin-1-yl)ethanone

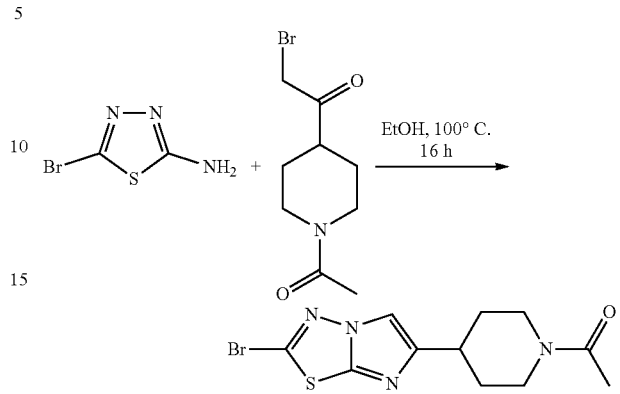

To a stirred solution of 5-amino-2-bromo-1,3,4-thiadiazole (1.0 g, 5.553 mmol) and 1-(1-acetylpiperidin-4-yl)-2-bromoethanone (1.37 g, 5.553 mmol) in ethanol (50 mL) was heated at 120° C. for 16 h. On completion, all volatiles were evaporated under reduced pressure obtained yellow sticky mass which was purified by silica gel (100-200 Mesh) column chromatography eluent 3% MeOH/DCM obtained 1-(4-(2-bromoimidazo[2,1-b][1,3,4]thiadiazol-6-yl)piperidin-1-yl)ethanone (0.495 g, 27.5%) as off white solid.

MS: 328.94[M+1]

Step-6: Synthesis of 1-(4-(2-(4-(methylsulfonyl)phenyl)imidazo[2,1-b][1,3,4]thiadiazol-6-yl)piperidin-1-yl)ethanone

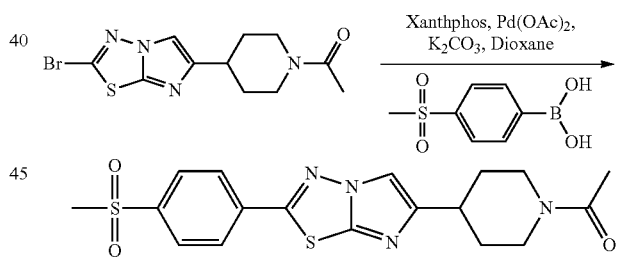

To a stirred solution of 1-(4-(2-bromoimidazo[2,1-b][1,3,4]thiadiazol-6-yl)piperidin-1-yl)ethanone (0.04 g, 0.121 mmol) and 4-(methylsulfonyl)phenylboronic acid (0.029 g, 0.145 mmol) in Dioxane (5 mL) were added K$_2$CO$_3$ (0.027 g, 0.19 mmol) and Xanthphos (0.0036 g, 0.006 mmol) and nitrogen was purged for 30 min. After 30 min Pd((OAc)2 (0.0013 g, 0.006 mmol) was added to reaction mass and heated at 100° C. for 6 h. Reaction was monitored by TLC. On completion, reaction was quenched with water, extracted with ethyl acetate. Organic layer was washed with water, brine dried over sodium sulphate, concentrated under reduced pressure obtained crude. Purification of the crude was done by silica gel (100-200 Mesh) column chromatography; eluent 2% MeOH/DCM to afford 1-(4-(2-(4-(methylsulfonyl)phenyl)imidazo[2,1-b][1,3,4]thiadiazol-6-yl)piperidin-1-yl)ethanone (0.011 g, 22.44%) as off white solid.

MS: 405.01[M+1]

Example 7: 4-(2-(4-(3-isopropyl-1,2,4-oxadiazol-5-yl)piperidin-1-yl)imidazo [2,1-b][1,3,4]thiadiazol-6-yl)-N,N-dimethylbenzamide [1036]

Step 1: Synthesis of methyl 4-(2-(4-(3-isopropyl-1,2,4-oxadiazol-5-yl)piperidin-1-yl)imidazo[2,1-b][1,3,4]thiadiazol-6-yl)benzoate

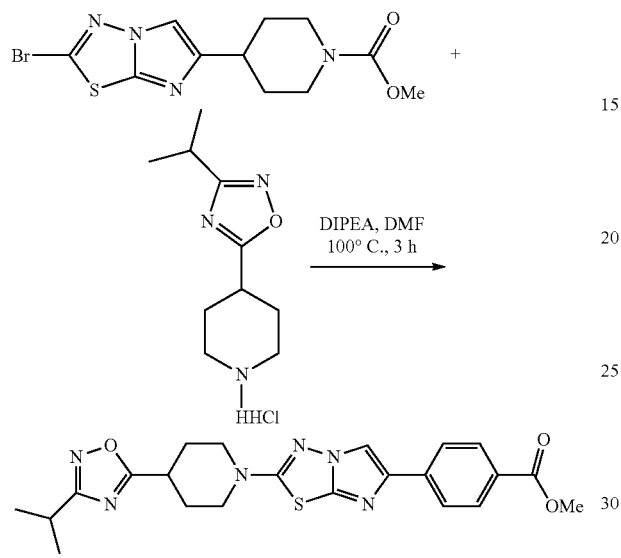

To a stirred solution of methyl 4-(2-bromoimidazo[2,1-b][1,3,4]thiadiazol-6-yl)benzoate (0.1 g, 0.29 mmol) and 4-(3-isopropyl-1,2,4-oxadiazol-5-yl)piperidine hydrochloride (0.07 g, 0.32 mmol) in DMF (10 ml) was added DIPEA (0.06 g, 0.44 mmol) and reaction was heated at 100° C. for 3 h. Reaction was monitored by TLC. On completion, reaction was quenched with water, extracted with ethyl acetate. The organic layer was washed with water, then brine, dried over Na$_2$SO$_4$ evaporated under reduced pressure to give crude. Purification of the compound was done by silica gel (100-200 Mesh) column chromatography, eluent 1% MeOH:DCM to obtain methyl 4-(2-(4-(3-isopropyl-1,2,4-oxadiazol-5-yl)piperidin-1-yl)imidazo[2,1-b][1,3,4]thiadiazol-6-yl)benzoate (0.1 g, 75%) as light yellow solid.

MS: 453.16[M$^+$+1]

Step 2: synthesis of 4-(2-(4-(3-isopropyl-1,2,4-oxadiazol-5-yl)piperidin-1-yl)imidazo[2,1-b][1,3,4]thiadiazol-6-yl)benzoic acid

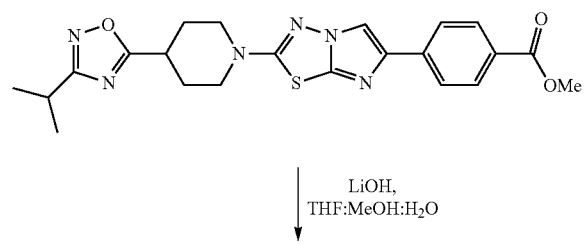

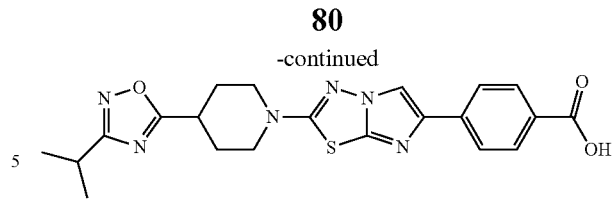

To a stirred solution of methyl 4-(2-(4-(3-isopropyl-1,2,4-oxadiazol-5-yl)piperidin-1-yl)imidazo[2,1-b][1,3,4]thiadiazol-6-yl)benzoate (0.1 g, 0.24 mmol) in mixture of THF:MeOH:H$_2$O (20 mL) was added LiOH (0.015 g, 0.33 mmol). After the addition, the mixture was stirred for 2 h at room temperature. On completion, all volatiles were evaporated under reduced pressure. Reaction mass diluted with water, acidify with 6N HCl and extracted with EtOAc. Organic poroomtemperatureions were combined, dried over Na$_2$SO$_4$, evaporated under reduced pressure to obtain 4-(2-(4-(3-isopropyl-1,2,4-oxadiazol-5-yl)piperidin-1-yl)imidazo[2,1-b][1,3,4]thiadiazol-6-yl)benzoic acid (0.07 g, 72%) as white solid.

MS: 439.15[M$^+$+1]

Step 3: synthesis of 4-(2-(4-(3-isopropyl-1,2,4-oxadiazol-5-yl)piperidin-1-yl)imidazo[2,1-b][1,3,4]thiadiazol-6-yl)-N,N-dimethylbenzamide

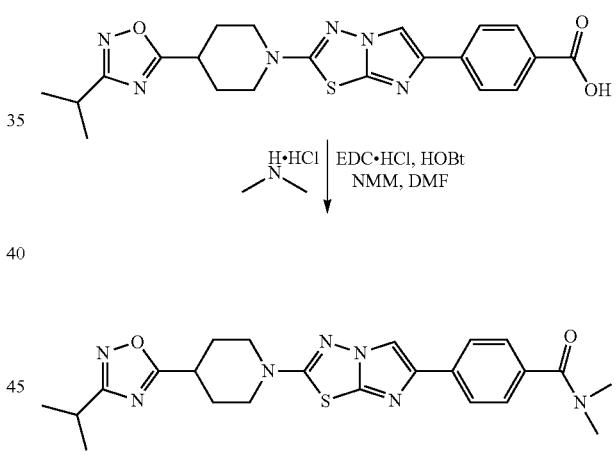

To a stirred solution of 4-(2-(4-(3-isopropyl-1,2,4-oxadiazol-5-yl)piperidin-1-yl)imidazo[2,1-b][1,3,4]thiadiazol-6-yl)benzoic acid (0.030 g, 0.068 mmol) and dimethyl amine hydrochloride (0.006 g, 0.068 mmol) in DMF (2 mL) were added EDC.HCl (0.02 g, 0.10 mmol), HOBT (0.014 g, 0.10 mmol) and NMM (0.014 g, 0.13 mmol). Reaction mixture was stirred at room temperature for 16 h. Reaction was monitored by TLC. On completion, reaction was quenched with water, extracted with ethyl acetate. Organic layer was washed with water, brine, dried over sodium sulphate and evaporated under reduced pressure to give crude product. Purification of the crude was done by silica gel (100-200 Mesh) column chromatography; eluent 3% MeOH:DCM to obtain 4-(2-(4-(3-isopropyl-1,2,4-oxadiazol-5-yl)piperidin-1-yl)imidazo[2,1-b][1,3,4]thiadiazol-6-yl)-N,N-dimethylbenzamide (0.012 g, 39%) as light yellow solid.

MS: 466.19[M$^+$+1]

Example 8: 2-(1-benzylpiperidin-4-yl)-6-((4-(methylsulfonyl)phenoxy)methyl) imidazo[2,1-b][1,3,4]thiadiazole [1038]

Step 1: Synthesis of 1-benzylpiperidine-4-carboxylic acid

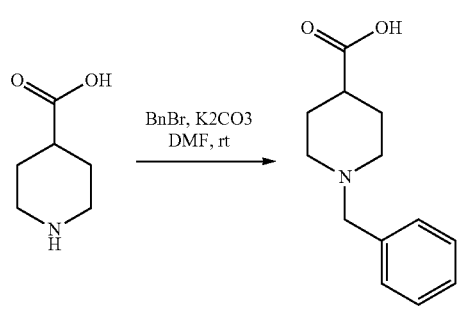 [SMILES: O=C(O)C1CCNCC1 ; O=C(O)C1CCN(Cc2ccccc2)CC1]

To a stirred solution of piperidine-4-carboxylic acid (5.0 g, 38.7 mmol) in DMF (20 mL) was added $K_2CO_3$ (13.3 g, 96.8 mmol) followed by drop wise addition of benzyl bromide (9.2 mL, 77.5 mmol). Reaction was allowed to stir at room temperature for 12 h. Reaction was monitored by TLC. On completion, reaction mass was diluted with cold water (100 mL) and extracted with EtOAc. The organic layer was washed with water, brine, dried over $Na_2SO_4$, evaporated under reduced pressure to give crude product. Purification of the compound was done by silica gel (100-200 Mesh) column chromatography eluent 20% EtOAc:hexane to obtain 1-benzylpiperidine-4-carboxylic acid (5.0 g, 59%) as light yellow oil.

MS: 220.14[M$^+$+1]

Step 2: Synthesis of 5-(1-benzylpiperidin-4-yl)-1,3,4-thiadiazol-2-amine

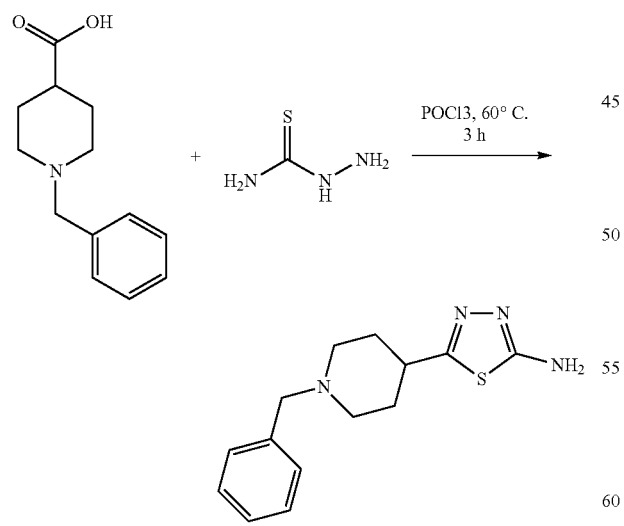

To a stirred solution of 1-benzylpiperidine-4-carboxylic acid (4.0 g, 18.2 mmol) in $POCl_3$ (20 mL) was added thiosemicarbazide (1.66 g, 18.2 mmol) and heated at 60° C. for 3 h. Reaction was monitored by TLC. On completion, reaction mass was quenched with saturated solution of $NaHCO_3$ (500 mL), extracted with EtOAc. The organic layer was combined, dried over $Na_2SO_4$, evaporated under reduced pressure to give crude product. Purification of the compound was done by silica gel (100-200 Mesh) column chromatography eluent 5% MeOH:DCM to obtain 5-(1-benzylpiperidin-4-yl)-1,3,4-thiadiazol-2-amine (1.8 g, 36%) as yellow solid.

MS: 275.14[M$^+$+1]

Step 3: Synthesis of ethyl 2-(1-benzylpiperidin-4-yl)imidazo[2,1-b][1,3,4]thiadiazole-6-carboxylate

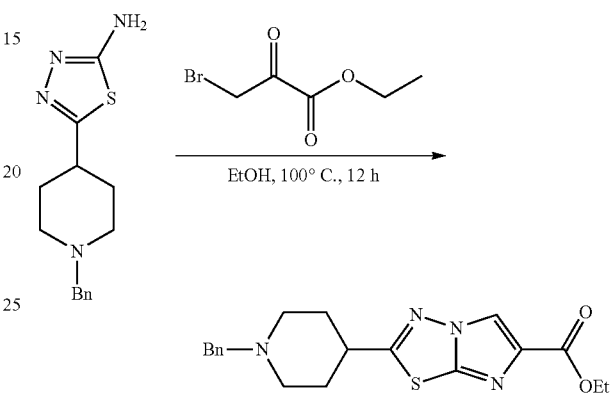

To a stirred solution of 5-(1-benzylpiperidin-4-yl)-1,3,4-thiadiazol-2-amine (0.6 g, 2.18 mmol) and ethyl 3-bromo-2-oxopropanoate (0.42 g, 2.18 mmol) in EtOH (50 mL) was heated at 100° C. for 12 h. Reaction was monitored by TLC On completion, EtOH was evaporated to give crude product. Purification of the compound was done by silica gel (100-200 Mesh) column chromatography, eluent 4% MeOH:DCM to obtain ethyl 2-(1-benzylpiperidin-4-yl)imidazo[2,1-b][1,3,4]thiadiazole-6-carboxylate (0.3 g, 37%) as yellow sticky mass.

MS: 371.15[M$^+$+1]

Step 4: Synthesis of ethyl 2-(piperidin-4-yl)imidazo[2,1-b][1,3,4]thiadiazole-6-carboxylate

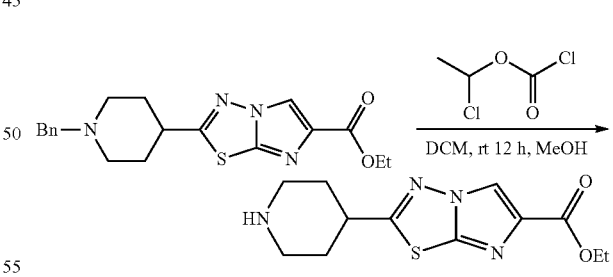

To a stirred solution of ethyl 2-(1-benzylpiperidin-4-yl)imidazo[2,1-b][1,3,4]thiadiazole-6-carboxylate (0.3 g, 0.81 mmol) in DCM (50 mL) was added 1-chloroethyl chloroformate (0.17 g, 1.21 mmol) and stir at room temperature for 12 h. Reaction was monitored by TLC. On completion, DCM was evaporated to give sticky mass which was dissolved in MeOH (10.0 mL) and heat at 50° C. for 1 h, then MeOH was evaporated under reduced pressure to obtain ethyl 2-(piperidin-4-yl)imidazo[2,1-b][1,3,4]thiadiazole-6-carboxylate (0.2 g, 26%) as yellow sticky mass.

MS: 281.1[M$^+$+1]

Step 5: Synthesis of (2-(1-benzylpiperidin-4-yl)imidazo[2,1-b][1,3,4]thiadiazol-6-yl)methanol

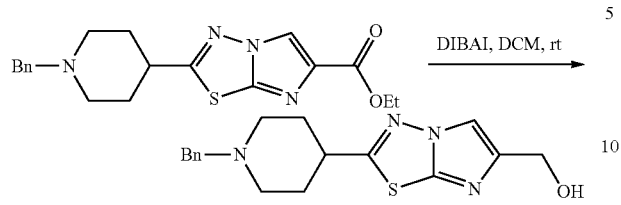

To a stirred solution of ethyl 2-(1-benzylpiperidin-4-yl)imidazo[2,1-b][1,3,4]thiadiazole-6-carboxylate (0.06 g, 0.16 mmol) in DCM (15 mL) was added DIBAL (1M in THF, 0.48 mL, 0.48 mmol) at 0° C. and reaction was allowed to stir at room temperature for 12 h. Reaction was monitored by TLC. On completion, reaction was quenched with addition of water, extracted with DCM. The organic layer was washed with water, dried over Na₂SO₄, evaporated under reduced pressure to obtain (2-(1-benzylpiperidin-4-yl)imidazo[2,1-b][1,3,4]thiadiazol-6-yl)methanol (0.040 g, 75%) as light yellow solid.

MS: 329.14[M$^+$+1]

Step 6: Synthesis of 6-((4-(methylsulfonyl)phenoxy)methyl)-2-(1-benzylpiperidin-4-yl)imidazo[2,1-b][1,3,4]thiadiazole

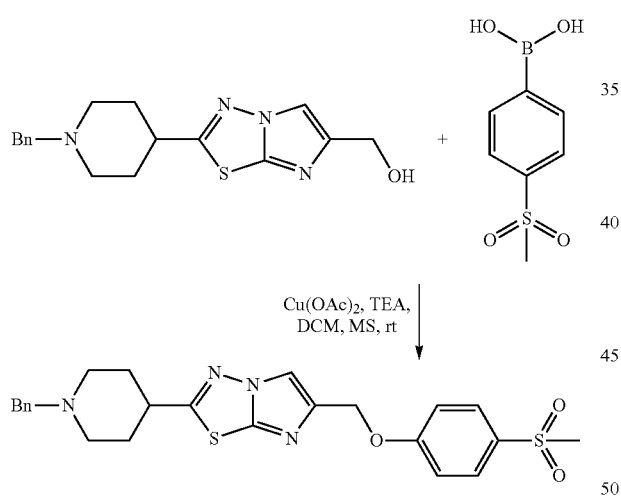

To a stirred solution of (2-(1-benzylpiperidin-4-yl)imidazo[2,1-b][1,3,4]thiadiazol-6-yl)methanol (0.04 g, 0.12 mmol) in DCM (20 mL) was added 4-(methylsulfonyl)phenylboronic acid (0.037 g, 0.18 mmol) followed by Cu(OAc)2 (0.025 g, 0.12 mmol), TEA (0.1 mL, 0.60 mmol), and molecular sieves 4° (0.015 g) at room temperature. Reaction mass was allowed to stir at room temperature for 12 h. Reaction was monitored by TLC. On completion, reaction mass was filtered, washed with DCM (20 mL). Filtrate was evaporated under reduced pressure to obtain crude product. Purification of crude was done by silica gel (100-200 Mesh) column chromatography; eluent 4% MeOH:DCM to obtain 6-((4-(methylsulfonyl)phenoxy)methyl)-2-(1-benzylpiperidin-4-yl)imidazo[2,1-b][1,3,4]thiadiazole (0.02 g, 34%) as light yellow solid.

MS: 483.14[M$^+$+1]

Example 9: 3-isopropyl-5-(1-(6-((4-(methylsulfonyl)phenoxy)methyl)imidazo[2,1-b][1,3,4]thiadiazol-2-yl)piperidin-4-yl)-1,2,4-oxadiazole [1040]

Step 1: Synthesis of ethyl 2-bromoimidazo[2,1-b][1,3,4]thiadiazole-6-carboxylate

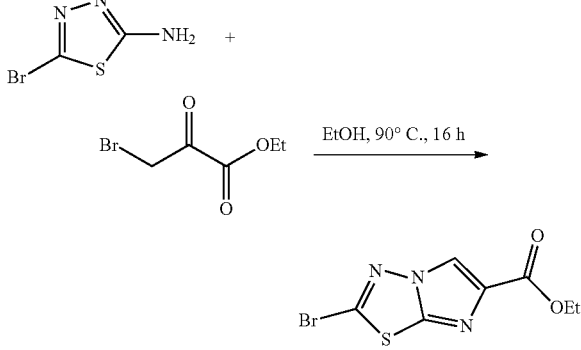

To a stirred solution of 5-amino-2-bromo-1,3,4-thiadiazole (0.5 g, 2.80 mmol) and ethyl 3-bromo-2-oxopropanoate (0.6 g, 3.08 mmol) in EtOH (50 mL) was heated at 90° C. for 16 h. Reaction was cooled to room temperature, the solid precipitated out which was filtered off, washed with boiling EtOH (10 mL) and dried under vacuum to obtain ethyl 2-bromoimidazo[2,1-b][1,3,4]thiadiazole-6-carboxylate (0.2 g, 26%) as light yellow solid.

MS: 276.11 [M$^+$+1]

Step 2: Synthesis of ethyl 2-(4-(3-isopropyl-1,2,4-oxadiazol-5-yl)piperidin-1-yl)imidazo[2,1-b][1,3,4]thiadiazole-6-carboxylate

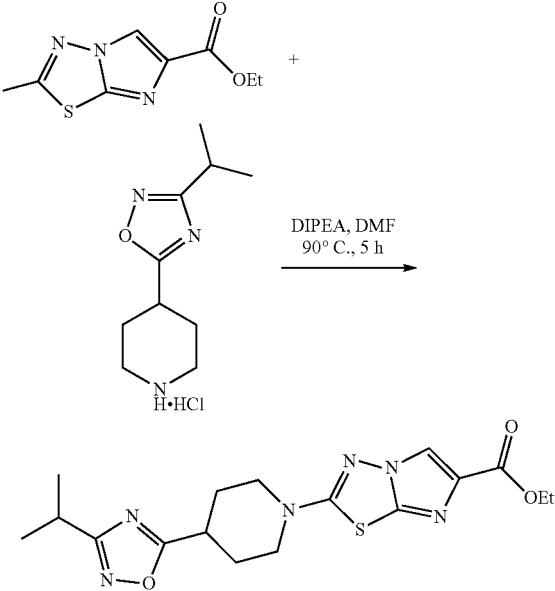

To a stirred solution of ethyl 2-bromoimidazo[2,1-b][1,3,4]thiadiazole-6-carboxylate (0.1 g, 3.62 mmol) and 4-(3-isopropyl-1,2,4-oxadiazol-5-yl)piperidine hydrochloride (0.1 g, 0.43 mmol) in DMF (10 mL) was added DIPEA (0.11 g, 0.90 mmol) and reaction was heated at 100° C. for 5 h. Reaction was monitored by TLC. On completion, reaction was quenched with water, extracted with ethyl acetate. The organic layer was washed with water, then brine, dried over Na$_2$SO$_4$ evaporated under reduced pressure to give crude. Purification of the compound was done by silica gel (100-200 Mesh) column chromatography eluent 20% EtOAc:hexane to obtain ethyl 2-(4-(3-isopropyl-1,2,4-oxadiazol-5-yl)piperidin-1-yl)imidazo[2,1-b][1,3,4]thiadiazole-6-carboxylate (0.08 g, 56%) as brown solid.

MS: 391.15[M$^+$+1]

Step 3: Synthesis of (2-(4-(3-isopropyl-1,2,4-oxadiazol-5-yl)piperidin-1-yl)imidazo[2,1-b][1,3,4]thiadiazol-6-yl)methanol

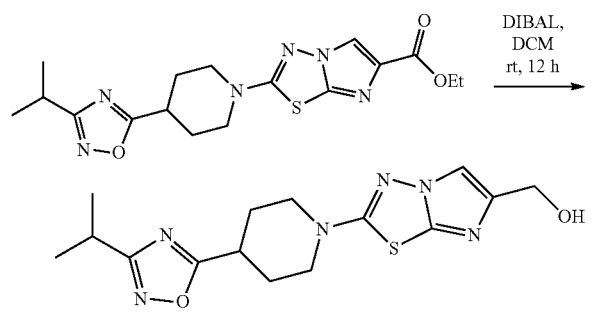

To a stirred solution of ethyl 2-(4-(3-isopropyl-1,2,4-oxadiazol-5-yl)piperidin-1-yl)imidazo[2,1-b][1,3,4]thiadiazole-6-carboxylate (0.08 g, 0.20 mmol) in DCM (20 mL) was added DIBAL (0.6 mL, 0.61 mmol, 1M in THF) at 0° C. and reaction was allowed to stir at room temperature for 12 h. Reaction was monitored by TLC. On completion, reaction was quenched with water, extracted with DCM. The organic layer was washed with water, dried over Na$_2$SO$_4$, evaporated under reduced pressure to give (2-(4-(3-isopropyl-1,2,4-oxadiazol-5-yl)piperidin-1-yl)imidazo[2,1-b][1,3,4]thiadiazol-6-yl)methanol (0.06 g, 84%) as light yellow solid.

MS: 349.14[M$^+$+1]

Step 4: Synthesis of 6-((4-(methylsulfonyl)phenoxy)methyl)-2-(4-(3-isopropyl-1,2,4-oxadiazol-5-yl)piperidin-1-yl)imidazo[2,1-b][1,3,4]thiadiazole

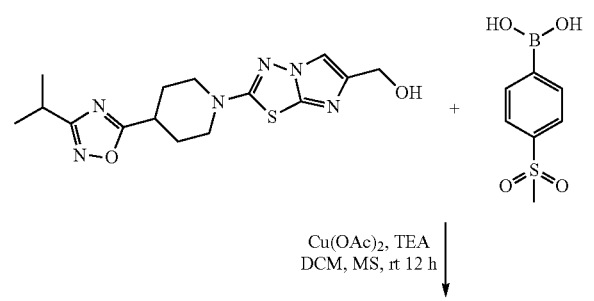

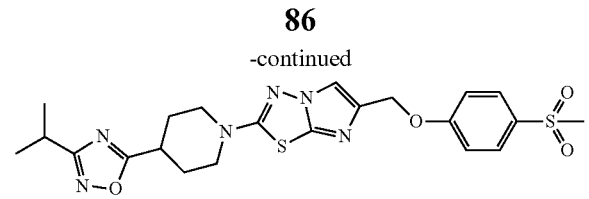

To a stirred solution of (2-(4-(3-isopropyl-1,2,4-oxadiazol-5-yl)piperidin-1-yl)imidazo[2,1-b][1,3,4]thiadiazol-6-yl)methanol (0.04 g, 0.11 mmol) in DCM (20 mL) was added 4-(methylsulfonyl)phenylboronic (0.035 g, 0.17 mmol) followed by Cu(OAc)2 (0.023 g, 0.11 mmol), TEA (0.08 mL, 0.57 mmol), and molecular sieves 4° (0.02 g). Reaction mixture was allowed to stir at room temperature for 12 h. Reaction was monitored by TLC. On completion, reaction mass was filtered, washed with DCM (20 mL), filtrate was evaporated under reduced pressure to obtain crude product. Purification of the compound was done by silica gel (100-200 Mesh) column chromatography eluent 2% MeOH:DCM to obtain 6-((4-(methylsulfonyl)phenoxy)methyl)-2-(4-(3-isopropyl-1,2,4-oxadiazol-5-yl)piperidin-1-yl)imidazo[2,1-b][1,3,4]thiadiazole (0.02 g, 35%) as off-white solid.

MS: 503.15[M$^+$+1]

Example 10: Isopropyl 4-(6-((4-(methylsulfonyl)phenoxy)methyl)imidazo[2,1-b][1,3,4]thiadiazol-2-yl)piperidine-1-carboxylate [1041]

Step 1: Synthesis of 1-benzylpiperidine-4-carboxylic acid

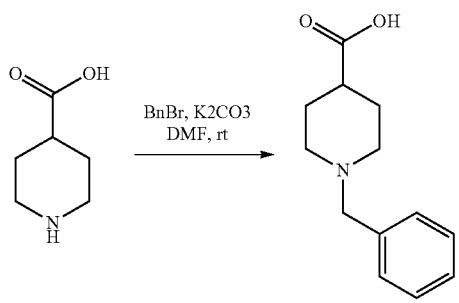 [SMILES: O=C(O)C1CCNCC1 ; O=C(O)C1CCN(Cc2ccccc2)CC1]

To a stirred solution of piperidine-4-carboxylic acid (5.0 g, 38.7 mmol) in DMF (20 mL) was added K$_2$CO$_3$ (13.3 g, 96.8 mmol) followed by drop wise addition of benzyl bromide (9.2 mL, 77.5 mmol). Reaction was allowed to stir at room temperature for 12 h. Reaction was monitored by TLC. On completion, reaction mass was diluted with cold water (100 mL) and extracted with EtOAc. The organic layer was washed with water, brine, dried over Na$_2$SO$_4$, evaporated under reduced pressure to give crude product. Purification of the compound was done by silica gel (100-200 Mesh) column chromatography eluent 20% EtOAc:hexane to obtain 1-benzylpiperidine-4-carboxylic acid (5.0 g, 59%) as light yellow oil.

MS: 220.14[M$^+$+1]

Step 2: Synthesis of 5-(1-benzylpiperidin-4-yl)-1,3,4-thiadiazol-2-amine

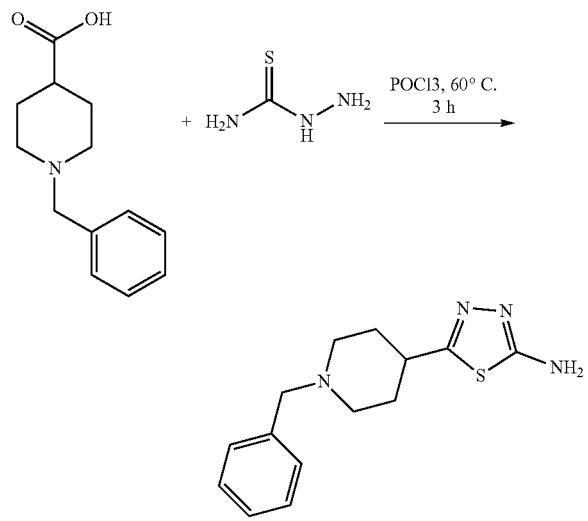

To a stirred solution of 1-benzylpiperidine-4-carboxylic acid (4.0 g, 18.2 mmol) in POCl$_3$ (20 mL) was added thiosemicarbazide (1.66 g, 18.2 mmol) and heated at 60° C. for 3 h. Reaction was monitored by TLC. On completion, reaction mass was quenched with saturated solution of NaHCO$_3$(500 mL), extracted with EtOAc. The organic layer was combined, dried over Na$_2$SO$_4$, evaporated under reduced pressure to give crude product. Purification of the compound was done by silica gel (100-200 Mesh) column chromatography eluent 5% MeOH:DCM to obtain 5-(1-benzylpiperidin-4-yl)-1,3,4-thiadiazol-2-amine (1.8 g, 36%) as yellow solid.
MS: 275.14[M$^+$+1]

Step 3: Synthesis of ethyl 2-(1-benzylpiperidin-4-yl)imidazo[2,1-b][1,3,4]thiadiazole-6-carboxylate

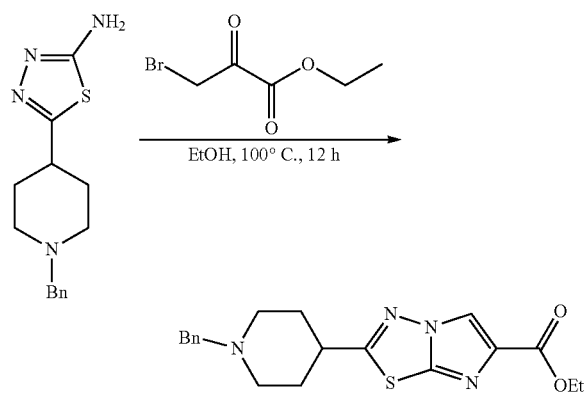

To a stirred solution of 5-(1-benzylpiperidin-4-yl)-1,3,4-thiadiazol-2-amine (0.6 g, 2.18 mmol) and ethyl 3-bromo-2-oxopropanoate (0.42 g, 2.18 mmol) in EtOH (50 mL) was heated at 100° C. for 12 h. Reaction was monitored by TLC On completion, EtOH was evaporated to give crude product. Purification of the compound was done by silica gel (100-200 Mesh) column chromatography, eluent 4% MeOH:DCM to obtain ethyl 2-(1-benzylpiperidin-4-yl)imidazo[2,1-b][1,3,4]thiadiazole-6-carboxylate (0.3 g, 37%) as yellow sticky mass.
MS: 371.15[M$^+$+1]

Step 4: Synthesis of ethyl 2-(piperidin-4-yl)imidazo[2,1-b][1,3,4]thiadiazole-6-carboxylate

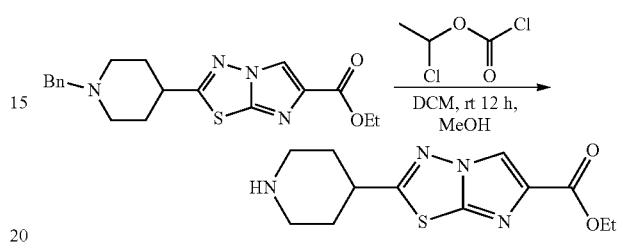

To a stirred solution of ethyl 2-(1-benzylpiperidin-4-yl)imidazo[2,1-b][1,3,4]thiadiazole-6-carboxylate (0.3 g, 0.81 mmol) in DCM (50 mL) was added 1-chloroethyl chloroformate (0.17 g, 1.21 mmol) and stir at room temperature for 12 h. Reaction was monitored by TLC. On completion, DCM was evaporated to give sticky mass which was dissolved in MeOH (10.0 mL) and heat at 50° C. for 1 h, then MeOH was evaporated under reduced pressure to obtain ethyl 2-(piperidin-4-yl)imidazo[2,1-b][1,3,4]thiadiazole-6-carboxylate (0.2 g, 26%) as yellow sticky mass. MS: 281.1 [M$^+$+1]

Step 5: Synthesis of ethyl 2-(1-(isopropoxycarbonyl)piperidin-4-yl)imidazo[2,1-b][1,3,4]thiadiazole-6-carboxylate

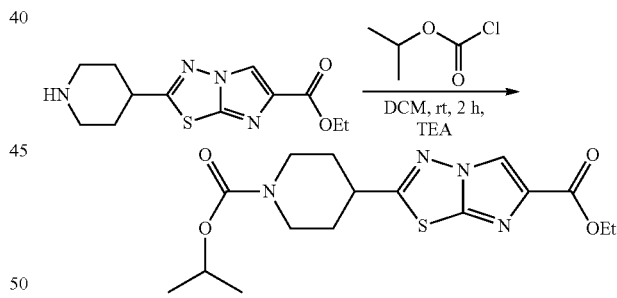

To a stirred solution of ethyl 2-(piperidin-4-yl)imidazo[2,1-b][1,3,4]thiadiazole-6-carboxylate (0.1 g, 0.35 mmol) in DCM (20 mL) was added TEA ((0.072 g, 0.71 mmol) followed by drop wise addition of isopropyl chloroformate (0.065 g, 0.53 mmol) and stir the reaction mass at room temperature for 2 h. Reaction was monitored by TLC. On completion, water was added to reaction mass, extracted with DCM. The organic layer were combined, dried over Na$_2$SO$_4$, evaporated under reduced pressure to give crude product. Purification of the compound was done by silica gel (100-200 Mesh) column chromatography eluent 30% EtOAc:DCM to obtain ethyl 2-(1-(isopropoxycarbonyl)piperidin-4-yl)imidazo[2,1-b][1,3,4]thiadiazole-6-carboxylate (0.06 g, 46%) as light yellow sticky mass.
MS: 367.14[M$^+$+1]

Step 6: Synthesis of isopropyl 4-(6-(hydroxymethyl)imidazo[2,1-b][1,3,4]thiadiazol-2-yl)piperidine-1-carboxylate

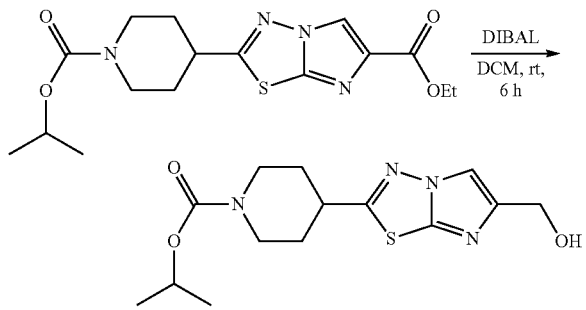

To a stirred solution of ethyl 2-(1-(isopropoxycarbonyl)piperidin-4-yl)imidazo[2,1-b][1,3,4]thiadiazole-6-carboxylate (0.06 g, 0.16 mmol) in DCM (15 mL) was added DIBAL (1M in THF) (0.5 mL, 0.49 mmol) at 0° C. and reaction was allowed to stir at room temperature for 6 h. Reaction was monitored by TLC. On completion, reaction was quenched with water, extracted with DCM. The organic layer was washed with water, dried over Na$_2$SO$_4$, evaporated under reduced pressure to obtain isopropyl 4-(6-(hydroxymethyl)imidazo[2,1-b][1,3,4]thiadiazol-2-yl)piperidine-1-carboxylate. (0.04 g, 75%) as light yellow solid.

MS: 325.13[M$^+$+1]

Step 7: Synthesis of isopropyl 4-(6-((4-(methylsulfonyl) phenoxy)methyl)imidazo[2,1-b][1,3,4]thiadiazol-2-yl)piperidine-1-carboxylate

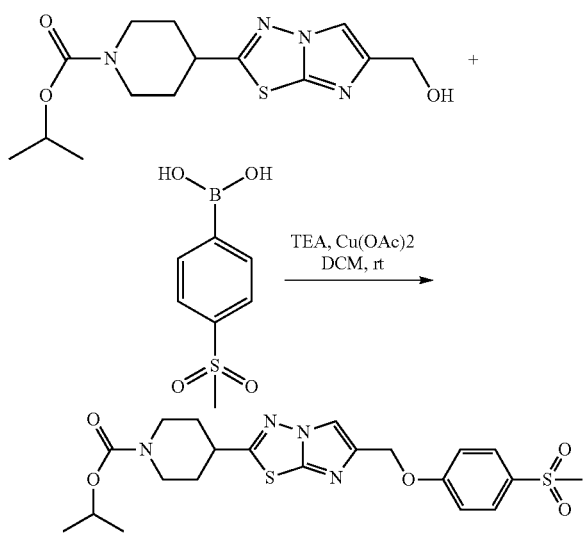

To a stirred solution of isopropyl 4-(6-(hydroxymethyl)imidazo[2,1-b][1,3,4]thiadiazol-2-yl)piperidine-1-carboxylate (0.05 g, 0.15 mmol) in DCM (20 mL) was added 4-(methylsulfonyl)phenylboronic acid (0.046 g, 0.23 mmol) followed by Cu(OAc)2 (0.031 g, 0.15 mmol), TEA (0.1 mL, 0.77 mmol), and molecular sieves 4° (0.015 g) at room temperature. Allowed the reaction mass to stir at room temperature for 12 h. Reaction was monitored by TLC. On completion, reaction mass was filtered, washed with DCM (20 mL), filtrate was evaporated under reduced pressure to obtain crude product. Purification of the compound was done by silica gel (100-200 Mesh) column chromatography eluent 2% MeOH:DCM to obtain isopropyl 4-(6-((4-(methylsulfonyl)phenoxy)methyl)imidazo[2,1-b][1,3,4]thiadiazol-2-yl)piperidine-1-carboxylate (0.02 g, 27%) as off-white solid.

MS: 479.13[M$^+$+1]

Example 11: 3-cyclopropyl-5-(1-(6-(4-(methylsulfonyl)phenyl)imidazo[2,1-b][1,3,4]thiadiazol-2-yl)piperidin-4-yl)-1,2,4-oxadiazole [1045]

Step 1: Synthesis of tert-butyl 4-(3-cyclopropyl-1,2,4-oxadiazol-5-yl)piperidine-1-carboxylate

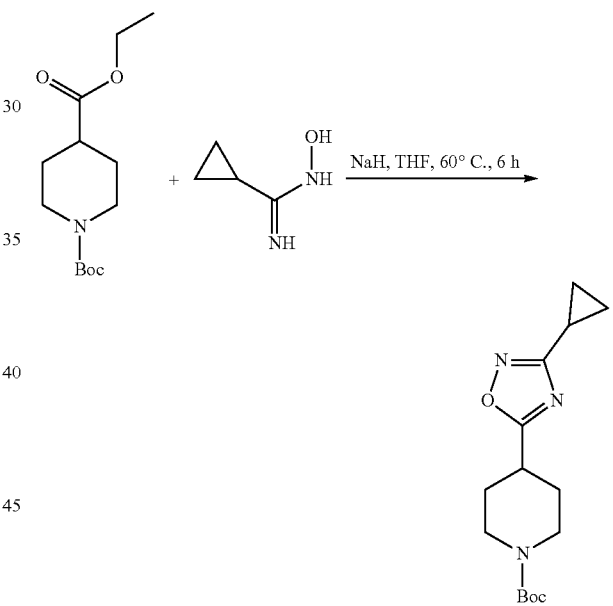

To a stirred solution of tert-butyl ethyl piperidine-1,4-dicarboxylate (0.5 g, 1.945 mmol) in THF (15 mL), was added NaH (60%) (0.31 g, 7.782 mmol) at 0° C. and stirred for 15 min. solution of N-hydroxycyclopropanecarboxamidine (0.39 g, 3.891 mmol) in THF (5 mL) was then added to the reaction mixture and heated at 60° C. for 6 h. Progress of reaction was monitored by TLC. After reaction completion reaction mass was quenched with water and extracted with ethyl acetate. Organic layer was washed with brine, dried over sodium sulphate and concentrated under reduced pressure to give tert-butyl 4-(3-cyclopropyl-1,2,4-oxadiazol-5-yl)piperidine-1-carboxylate (0.5 g, 87.6%) as yellow liquid.

Mass: 294.3 [M$^+$+1]

Step 2: Synthesis of 4-(3-cyclopropyl-1,2,4-oxadiazol-5-yl)piperidine trifluoroacetate

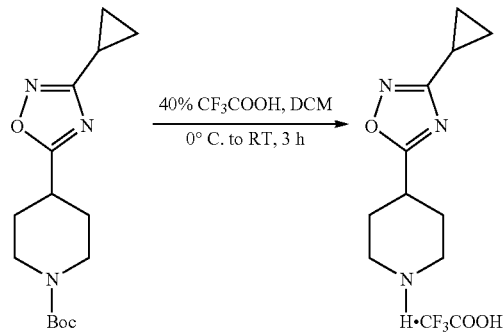

To a stirred solution of tert-butyl 4-(3-cyclopropyl-1,2,4-oxadiazol-5-yl)piperidine-1-carboxylate (0.24 g, 0.819 mol) in DCM (10 mL) was added 40% TFA (20 mL) at 0° C. and allowed the reaction to stir for 1 h at RT. Progress of reaction was monitored by TLC. After reaction completion reaction mass was concentrated under reduced pressure to give 4-(3-cyclopropyl-1,2,4-oxadiazol-5-yl)piperidinetrifluoroacetate (0.2 g, 79%) as off white solid. Mass: 308.2

Step 3: synthesis of 2-(4-(3-cyclopropyl-1,2,4-oxadiazol-5-yl)piperidin-1-yl)-6-(4-(methylsulfonyl)phenyl)imidazo[2,1-b][1,3,4]thiadiazole

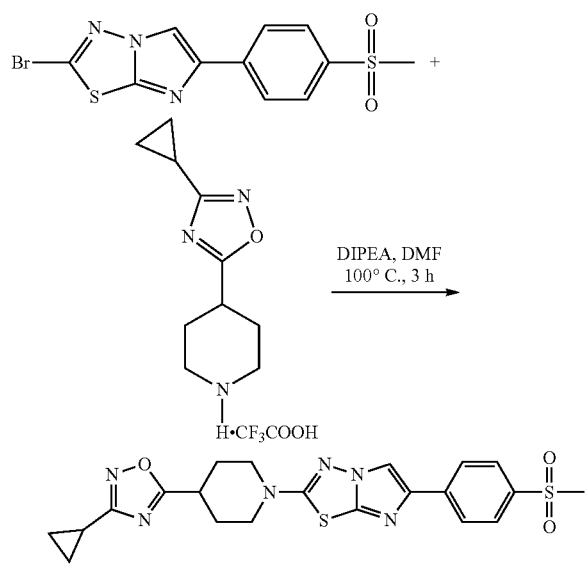

To a stirred solution of 2-bromo-6-(4-(methylsulfonyl)phenyl)imidazo[2,1-b][1,3,4]thiadiazole (0.025 g, 0.0698 mmol) and 4-(3-cyclopropyl-1,2,4-oxadiazol-5-yl)piperidinetrifluoroacetate (0.0257 g, 0.0837 mmol) in DMF (10 mL) was added DIPEA (0.045 g, 0.349 mmol) and reaction was heated at 100° C. for 6 h. Reaction was monitored by TLC. On completion, reaction was quenched with water and extracted with ethyl acetate. The organic layer was washed with water and brine, dried over sodium sulphate and concentrated under reduced pressure to give crude. Purification of the compound was done by silica gel (100-200 Mesh) column chromatography eluent 2% MeOH in DCM to give of 2-(4-(3-cyclopropyl-1,2,4-oxadiazol-5-yl)piperidin-1-yl)-6-(4-(methylsulfonyl)phenyl)imidazo[2,1-b][1,3,4]thiadiazole (0.02 g, 52.3%) as off white solid.

MS: 471.1 [M$^+$+1]

Example 12: N,N-dimethyl-4-(2-(1-(1-(5-propylpyrimidin-2-yl)piperidin-4-yl)ethoxy)imidazo[2,1-b][1,3,4]thiadiazol-6-yl)benzamide [1049]

Step 1: Synthesis of 4-acetylbenzoic acid

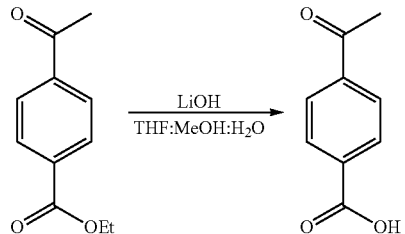

To a stirred solution of ethyl 4-acetylbenzoate (0.5 g, 2.8 mmol) in mixture of THF:MeOH:H$_2$O (18 mL, 5:3:1) was added LiOH (0.23 g, 5.61 mmol). And allowed to stir for 2 h at room temperature. On completion, all volatiles were evaporated under reduced pressure. Reaction mass diluted with water, acidify with 6N HCl and extracted with EtOAc. Organic portions were combined, dried over Na$_2$SO$_4$, evaporated under reduced pressure to obtain 4-acetylbenzoic acid (0.3 g, 76%) as white solid.

MS: 165.05[M$^+$+1]

Step 2: Synthesis of 4-acetyl-N,N-dimethylbenzamide

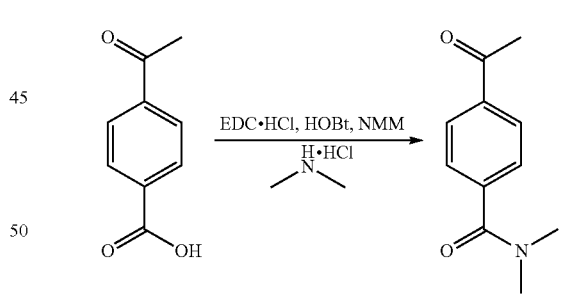

To a stirred solution of 4-acetylbenzoic acid (0.35 g, 2.13 mmol) and dimethyl amine hydrochloride (0.25 g, 3.20 mmol) in DMF (2 mL) were added EDC.HCl (0.61 g, 3.20 mmol), HOBT (0.43 g, 3.20 mmol) and NMM (0.43 g, 4.26 mmol). Then reaction mixture was stirred at room temperature for 16 h. Reaction was monitored by TLC. On completion, reaction was quenched with water, extracted with ethyl acetate. Organic layer was washed with water, brine, dried over sodium sulphate and evaporated under reduced pressure to give crude product. Purification of the crude was done by silica gel (100-200 Mesh) column chromatography; eluent 3% MeOH in DCM to obtain 4-acetyl-N,N-dimethylbenzamide (0.3 g, 74%) as light yellow solid. MS: 192.09 [M$^+$+1]

Step 3: Synthesis of 4-(2-bromoacetyl)-N,N-dimethylbenzamide

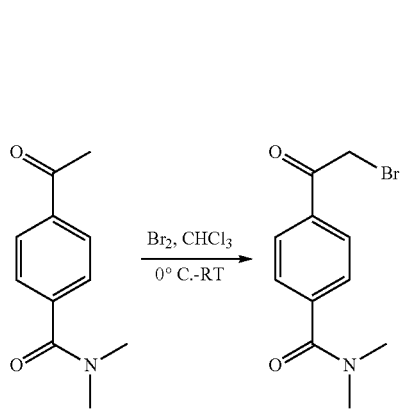

To a stirred solution of 4-acetyl-N,N-dimethylbenzamide (0.3 g, 1.57 mmol in CHCl3 (30 mL) was added bromine (0.081 mL, 1.57 mmol) drop wise at 0° C. and allowed to stir for 3 h at room temperature. Completion of reaction was monitored by TLC. Reaction mixture was evaporated under reduced pressure. Reaction mass was diluted with water, extracted with EtOAc. Organic layer was washed with water, brine, dried over sodium sulphate, evaporated under reduced pressure to obtain desired product 4-(2-bromo-acetyl)-N, N-dimethylbenzamide (0.3 g, 71%) as dark yellow sticky mass.

MS: 270.01[M$^+$+1]

Step 4: Synthesis of 4-(2-bromoimidazo [2,1-b][1,3, and 4]thiadiazol-6-yl)-N,N-dimethylbenzamide

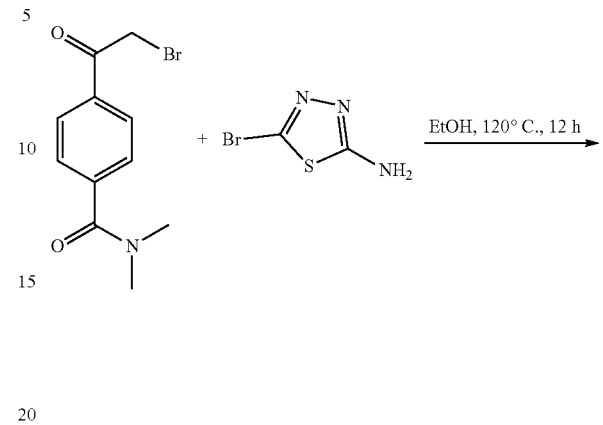

To a stirred solution of 5-amino-2-bromo-1,3,4-thiadiazole (0.4 g, 2.22 mmol) in EtOH (30 mL) was added 4-(2-bromoacetyl)-N,N-dimethylbenzamide (0.5 g, 2.22 mmol) and heated at 90° C. for 16 h. Reaction was cooled to room temperature, Precipitates were formed which was filtered off, washed with boiling EtOH (10 mL) and dried under vacuum to obtain pure product 4-(2-bromoimidazo [2,1-b][1,3,4]thiadiazol-6-yl)-N,N-dimethylbenzamid (0.2 g, 26%) as off white solid.

MS: [M+1] 351.22

Step 5: Synthesis of 4-(2-(1-(1-(5-propylpyrimidin-2-yl)piperidin-4-yl)ethoxy) imidazo[2,1-b][1,3,4]thiadiazol-6-yl)-N,N-dimethylbenzamide

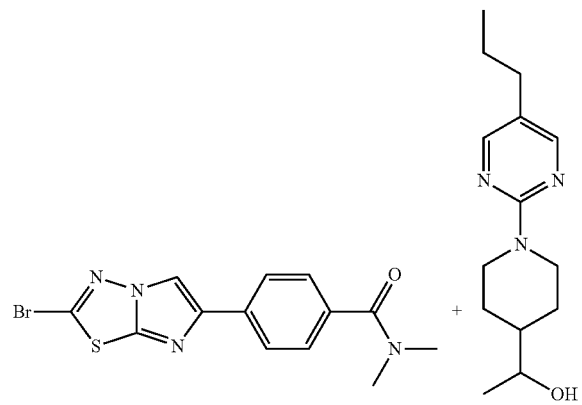

NaH, DMF
0° C.-rt, 3 h

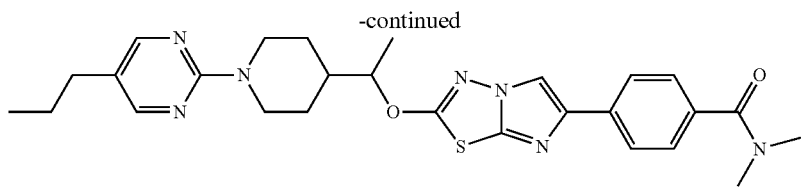

To a stirred solution of 1-(1-(5-propylpyrimidin-2-yl)piperidin-4-yl)ethanol (0.05 g, 0.20 mmol) in DMF (2 ml) was added sodium hydride (0.012 g, 0.30 mmol) at 0° C. and reaction allowed to stir at 0° C. for 30 min. After 30 min, 4-(2-bromoimidazo[2,1-b][1,3,4]thiadiazol-6-yl)-N,N-dimethylbenzamide (0.077 g, 0.22 mmol) in DMF (1 mL) was added to reaction mixture and stirred at room temperature for 3 h. Reaction was monitored by TLC. On completion reaction was quenched with ice cold water, extracted with ethyl acetate. The organic layer was washed with water, brine, dried over sodium sulphate and concentrated under reduced pressure to give crude desired product that was purified by silica gel (100 to 200 Mesh) chromatography, eluent 3% MeOH in DCM to obtain 4-(2-(1-(1-(5-propylpyrimidin-2-yl)piperidin-4-yl)ethoxy)imidazo[2,1-b][1,3,4]thiadiazol-6-yl)-N,N-dimethylbenzamide (0.02 g, 19%) as light yellow solid.

MS: 520.24[M$^+$+1]

Example 13: 2-(1-(1-(5-ethylpyrimidin-2-yl)piperidin-4-yl)ethoxy)-6-(pyridin-4-yl)imidazo[2,1-b][1,3,4]thiadiazole [1056]

Step 1: Synthesis of 2-(1-(1-(5-ethylpyrimidin-2-yl)piperidin-4-yl)ethoxy)-6-(pyridin-4-yl)imidazo[2,1-b][1,3,4]thiadiazole

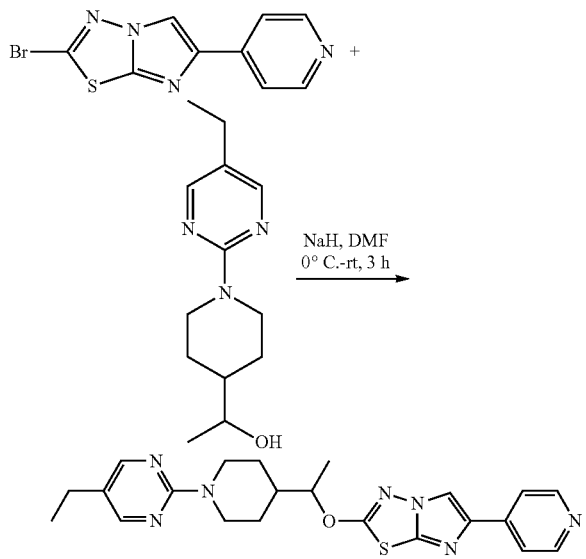

To a stirred solution of 1-(1-(5-ethylpyrimidin-2-yl)piperidin-4-yl)ethanol (0.03 g, 0.12 mmol) in DMF (2 mL) was added sodium hydride (0.08 g, 0.19 mmol) at 0° C. and reaction allowed to stir at 0° C. for 30 min. To it, 2-bromo-6-(pyridin-4-yl)imidazo[2,1-b][1,3,4]thiadiazole (0.035 g, 0.12 mmol) in DMF (1 mL) was added to reaction mixture and allowed to stir at room temperature for 3 h. Reaction was monitored by TLC. On completion, reaction was quenched with ice cold water, extracted with ethyl acetate. The organic layer was washed with water, brine, dried over sodium sulphate and concentrated under reduced pressure to give crude desired product which was purified by silica gel (100 to 200 mesh) chromatography, eluent 2% MeOH in DCM to obtain 2-(1-(1-(5-ethylpyrimidin-2-yl)piperidin-4-yl)ethoxy)-6-(pyridin-4-yl)imidazo[2,1-b][1,3,4]thiadiazole (0.012 g, 21%) as light yellow solid.

MS: 436.18[M$^+$+1]

Example 14: (R)-3-isopropyl-5-(4-(1-((6-(4-(methylsulfonyl)phenyl) imidazo [2,1-b][1,3,4]thiadiazol-2-yl)oxy)ethyl)piperidin-1-yl)-1,2,4-oxadiazole [1060]

Step 1: Synthesis of 2-((S)-1-(1-(3-isopropyl-1,2,4-oxadiazol-5-yl)piperidin-4-yl)ethoxy)-6-(4-(methylthio)phenyl)imidazo[2,1-b][1,3,4]thiadiazole

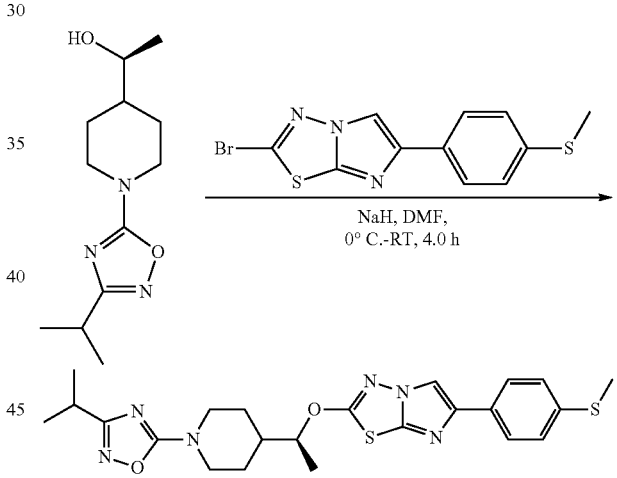

To a stirred solution of (S)-1-(1-(3-isopropyl-1,2,4-oxadiazol-5-yl)piperidin-4-yl)ethanol (0.03 g, 0.13 mmol) in DMF (5.0 mL), sodium hydride (0.008 g, 0.19 mmol) was added at 0° C. and allowed to stir the reaction at 0° C. for 30 min. Then to it, 2-bromo-6-(4-(methylthio)phenyl)imidazo[2,1-b][1,3,4]thiadiazole (0.05 g, 0.14 mmol) was added to reaction mixture and stirred at room temperature for 3.5 h. Reaction was monitored by TLC. On completion, reaction mixture was quenched with ice cold water and compound was extracted with ethyl acetate. The organic layer was washed with water, brine, dried over sodium sulphate and concentrated under reduced pressure to give crude product. Purification of the compound was done by silica gel (100-200 mesh) column chromatography using 5% methanol in DCM to give 2-((S)-1-(1-(3-isopropyl-1,2,4-oxadiazol-5-yl)piperidin-4-yl)ethoxy)-6-(4-(methylthio)phenyl)imidazo[2,1-b][1,3,4]thiadiazole (0.03 g, 49.34%) as yellow solid.

MS: 485.17[M$^+$+1].

Step 2: Synthesis of 2-((S)-1-(1-(3-isopropyl-1,2,4-oxadiazol-5-yl)piperidin-4-yl)ethoxy)-6-(4-(methyl-sulfonyl)phenyl)imidazo[2,1-b][1,3,4]thiadiazole

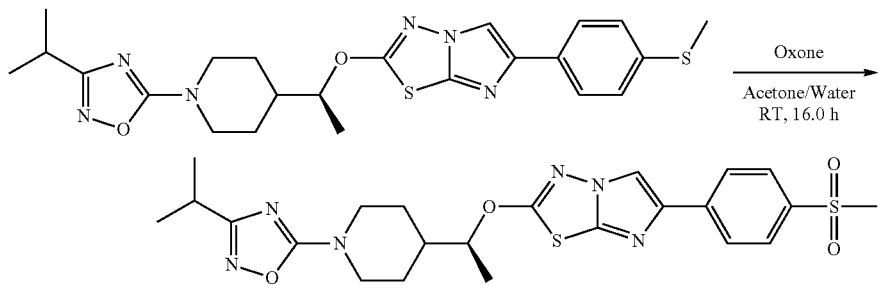

To a stirred solution of compound 2-((S)-1-(1-(3-isopropyl-1,2,4-oxadiazol-5-yl)piperidin-4-yl)ethoxy)-6-(4-(methylthio)phenyl)imidazo[2,1-b][1,3,4]thiadiazole (0.03 g, 0.06 mmol) in Acetone (5.0 mL), Oxone (0.08 g, 0.25 mmol) in Water (1.0 mL) was added and reaction continued at room temperature for 16 h. Progress of reaction was monitored by TLC. On completion, acetone was evaporated. Residue was quenched with water and extracted with ethyl acetate. The organic layer was concentrated under reduced pressure to give crude compound. Purification of the compound was done by silica gel (100-200 mesh) column chromatography using 5% methanol in DCM to give 2-((S)-1-(1-(3-isopropyl-1,2,4-oxadiazol-5-yl)piperidin-4-yl)ethoxy)-6-(4-(methylsulfonyl)phenyl)imidazo[2,1-b][1,3,4]thiadiazole (0.019 g, 59.41%) as yellow solid.

MS: 517.20[M$^+$+1].

Example 15: (R)-2-(1-(1-(5-ethylpyrimidin-2-yl)piperidin-4-yl)ethoxy)-6-(4-(methylsulfonyl)phenyl)imidazo[2,1-b][1,3,4]thiadiazole [1063]

Step 1: Synthesis of 2-((S)-1-(1-(5-ethylpyrimidin-2-yl)piperidin-4-yl)ethoxy)-6-(4-(methylthio)phenyl)imidazo[2,1-b][1,3,4]thiadiazole

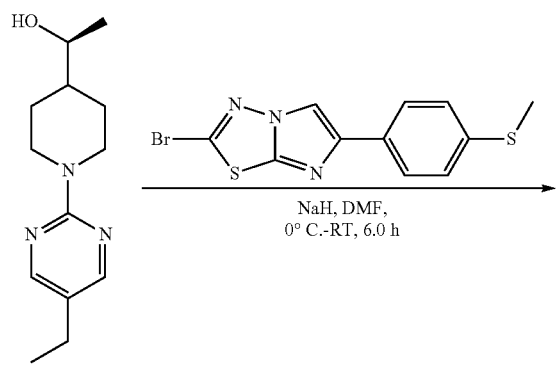

-continued

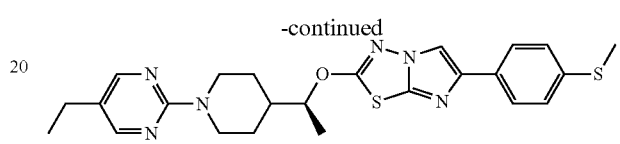

To a stirred solution of (S)-1-(1-(5-ethylpyrimidin-2-yl)piperidin-4-yl)ethanol (0.025 g, 0.11 mmol) in DMF (3.0 mL), sodium hydride (0.007 g, 0.16 mmol) was added at 0° C. and allowed the reaction to stir at 0° C. for 30 min. Then to it, 2-bromo-6-(4-(methylthio)phenyl)imidazo[2,1-b][1,3,4]thiadiazole (0.04 g, 0.12 mmol) was added to reaction mixture and stirred at room temperature for 5.30 h. Reaction was monitored by TLC. On completion, reaction mixture was quenched with ice cold water and compound was extracted with ethyl acetate. The organic layer was washed with water, brine, dried over sodium sulphate and concentrated under reduced pressure to give crude. Purification of the compound was done by silica gel (100-200 mesh) column chromatography using 1% methanol in DCM to give 2-((S)-1-(1-(5-ethylpyrimidin-2-yl)piperidin-4-yl)ethoxy)-6-(4-(methylthio)phenyl)imidazo [2,1-b][1,3,4]thiadiazole (0.022 g, 43.09%) as yellow semi solid.

MS: 481.18[M$^+$+1].

Step 2: Synthesis of 2-((S)-1-(1-(5-ethylpyrimidin-2-yl)piperidin-4-yl)ethoxy)-6-(4-(methylsulfonyl)phenyl)imidazo[2,1-b][1,3,4]thiadiazole

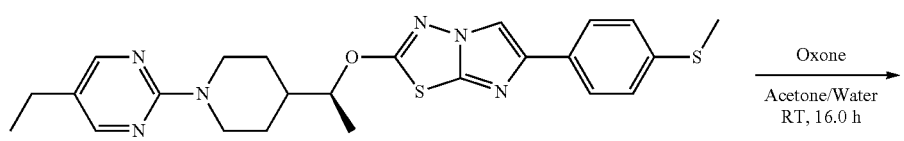

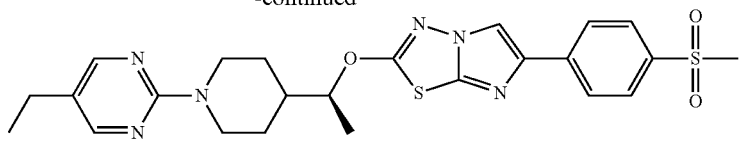

To a stirred solution of compound 2-((S)-1-(1-(5-ethylpyrimidin-2-yl)piperidin-4-yl)ethoxy)-6-(4-(methylthio)phenyl)imidazo[2,1-b][1,3,4]thiadiazole (0.02 g, 0.04 mmol) in Acetone (3.0 mL), Oxone (0.05 g, 0.17 mmol) in Water (0.5 mL) was added and reaction continued at room temperature for 16 h. Progress of reaction was monitored by TLC. On completion, acetone was evaporated from reaction mixture. Residue was quenched with water and extracted with ethyl acetate. The organic layer was concentrated under reduced pressure to give crude. Purification of the compound was done by silica gel (100-200 mesh) column chromatography using 1% methanol in DCM to give 2-((S)-1-(1-(5-ethylpyrimidin-2-yl)piperidin-4-yl)ethoxy)-6-(4-(methylsulfonyl)phenyl)imidazo[2,1-b][1,3,4]thiadiazole (0.009 g, 42.19%) as light brown solid.

MS: 513.30[M$^+$+1].

Example 16: (R)-5-(4-(1-((6-(2-fluoropyridin-4-yl)imidazo[2,1-b][1,3,4]thiadiazol-2-yl)oxy)ethyl)piperidin-1-yl)-3-isopropyl-1,2,4-oxadiazole [1065]

Step 1: Synthesis of 2-fluoro-N-methoxy-N-methylpyridine-4-carboxamide

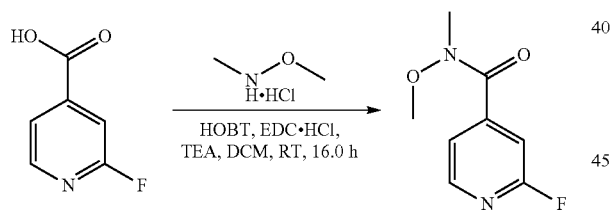

To a stirred solution of 2-fluoropyridine-4-carboxylic acid (1.0 g, 7.10 mmol) in DCM (20.0 mL), N-methoxymethanamine hydrochloride (1.03 g, 10.6 mmol), HOBT (1.19 g, 7.8 mmol), EDC.HCl (1.49 g, 7.8 mmol) and tri ethyl amine (3.94 mL, 28.4 mmol) was added at 25° C. and allowed to stir at room temperature for 16 h. Reaction was monitored by TLC. On completion, reaction mixture was quenched with ice cold water and compound was extracted with DCM. The organic layer was washed with water, brine, dried over sodium sulphate and concentrated under reduced pressure to give crude. Purification of the compound was done by silica gel (100-200 mesh) column chromatography using 20% ethyl acetate in hexane to give 2-fluoro-N-methoxy-N-methylpyridine-4-carboxamide (1.0 g, 76.92%) as yellow liquid.

MS: 185.04[M$^+$+1].

Step 2: Synthesis of 1-(2-fluoropyridin-4-yl)ethanone

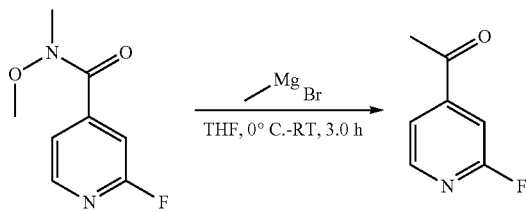

To a stirred solution of 2-fluoro-N-methoxy-N-methylpyridine-4-carboxamide (1.0 g, 5.4 mmol) in dry THF (30.0 mL), methyl magnesium bromide (8.15 mL, 16.3 mmol) was added at 0° C. and reaction allowed to stir at room temperature for 3 h. Reaction was monitored by TLC. On completion, reaction mixture was quenched with ice cold aqueous ammonium chloride solution and extracted with ethyl acetate. The organic layer was washed with water, dried over sodium sulphate and concentrated under reduced pressure to give 1-(2-fluoropyridin-4-yl) ethanone (0.69 g, 91.27%) as yellow solid.

MS: 139.94[M$^+$+1].

Step 3: Synthesis of 2-bromo-1-(2-fluoropyridin-4-yl)ethanone

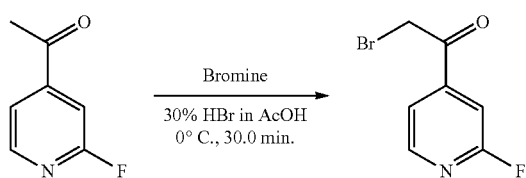

To a stirred solution of 1-(2-fluoropyridin-4-yl)ethanone (0.2 g, 1.44 mmol) in 30% HBr in Acetic acid (4.0 mL), Bromine (0.07 mL, 1.29 mmol) was added at 0° C. and allowed to stir at 0° C. for next 30 min. Reaction was monitored by TLC. On completion, reaction mixture was quenched with ice cold water and compound was extracted with di ethyl ether. The organic layer was washed with water, brine, dried over sodium sulphate and concentrated under reduced pressure to give 2-bromo-1-(2-fluoropyridin-4-yl)ethanone (0.32 g, Crude) as yellow liquid.

MS: 217.95[M$^+$+1].

Step 4: Synthesis of 5-chloro-1,3,4-thiadiazol-2-amine

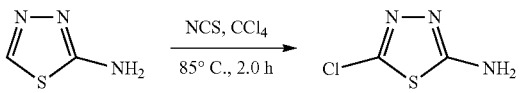

To a stirred solution of 1,3,4-thiadiazol-2-amine (0.5 g, 4.95 mmol) in CCl₄ (10.0 mL), N-Chlorosuccinimide (0.73 g, 5.45 mmol) was added at 25° C. and reaction allowed to stir at 85° C. for 2 h. Reaction was monitored by TLC. On completion, reaction mixture was quenched with ice cold water and compound was extracted with 10% methanol in DCM. The organic layer was washed with water, brine, dried over sodium sulphate and concentrated under reduced pressure to give crude. Purification of the compound was done by silica gel (100-200 mesh) column chromatography using 20% ethyl acetate in hexane to give 5-chloro-1,3,4-thiadiazol-2-amine (0.18 g, 26.94%) as light brown solid.

MS: 135.97[M⁺+1].

Step 5: Synthesis of 2-chloro-6-(2-fluoropyridin-4-yl)imidazo[2,1-b][1,3,4]thiadiazole

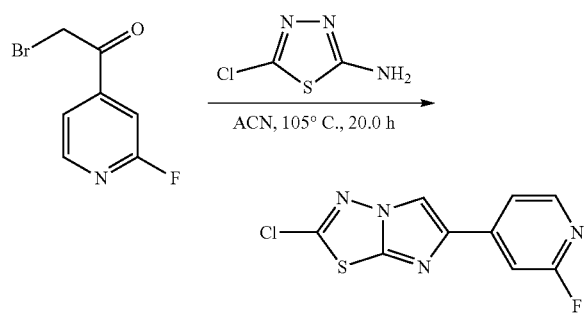

To a stirred solution of 2-bromo-1-(2-fluoropyridin-4-yl)ethanone (0.25 g, 1.15 mmol) in ACN (5.0 mL), 5-chloro-1,3,4-thiadiazol-2-amine (0.16 g, 1.15 mmol) was added at room temperature and allowed to stir at 105° C. for 20 h. Reaction was monitored by TLC. On completion reaction mixture was quenched with ice cold water and compound was extracted with ethyl acetate. The organic layer was washed with water, brine, dried over sodium sulphate and concentrated under reduced pressure to give crude product. Purification of the compound was done by silica gel (100-200 mesh) column chromatography using 15% ethyl acetate in hexane to give 2-chloro-6-(2-fluoropyridin-4-yl)imidazo[2,1-b][1,3,4]thiadiazole (0.055 g, 18.79%) as white solid.

MS: 254.83[M⁺+1].

Step 6: Synthesis of 2-((S)-1-(1-(3-isopropyl-1,2,4-oxadiazol-5-yl)piperidin-4-yl)ethoxy)-6-(2-fluoropyridin-4-yl)imidazo[2,1-b][1,3,4]thiadiazole

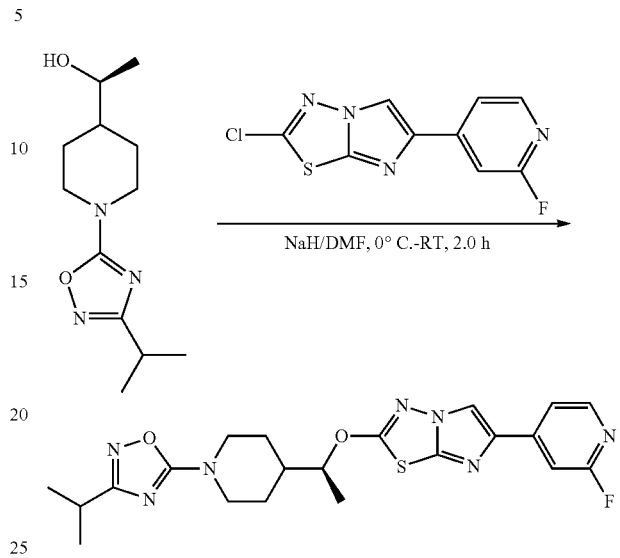

To a stirred solution of (S)-1-(1-(3-isopropyl-1,2,4-oxadiazol-5-yl)piperidin-4-yl)ethanol (0.02 g, 0.08 mmol) in DMF (3.0 mL), sodium hydride (0.005 g, 0.13 mmol) was added at 0° C. and allowed to stir at 0° C. for 30 min. Then to it, 2-chloro-6-(2-fluoropyridin-4-yl)imidazo[2,1-b][1,3,4]thiadiazole (0.028 g, 0.11 mmol) was added to reaction mixture and stirred at room temperature for 2 h. Reaction was monitored by TLC. On completion, reaction mixture was quenched with ice cold water and extracted with ethyl acetate. The organic layer was washed with water, brine, dried over sodium sulphate and concentrated under reduced pressure to give crude. Purification of the compound was done by silica gel (100-200 mesh) column chromatography using 45% ethyl acetate in hexane to give crude which was purified using prep. TLC (Mobile phase 50% EtOAc in Hexane) to give 2-((S)-1-(1-(3-isopropyl-1,2,4-oxadiazol-5-yl)piperidin-4-yl)ethoxy)-6-(2-fluoropyridin-4-yl)imidazo[2,1-b][1,3,4]thiadiazole (0.007 g, 18.31%) as white solid.

MS: 458.10[M⁺+1].

Example 17: 2-(1-(1-(3-(trifluoromethyl)-1,2,4-oxadiazol-5-yl)piperidin-4-yl)ethoxy)-6-(4-(methylsulfonyl)phenyl)imidazo[2,1-b][1,3,4]thiadiazole
[1073]

Step 1: Synthesis of 2-(1-(1-(3-(trifluoromethyl)-1,2,4-oxadiazol-5-yl)piperidin-4-yl)ethoxy)-6-(4-(methylthio)phenyl)imidazo[2,1-b][1,3,4]thiadiazole

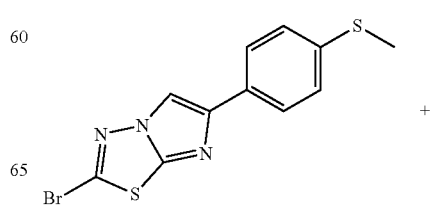

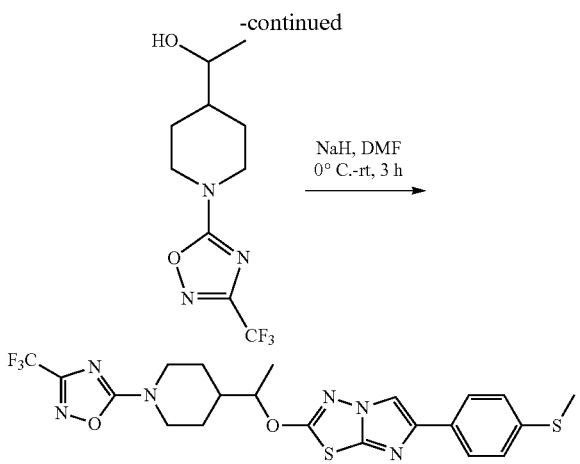

To compound 1-(1-(3-(trifluoromethyl)-1,2,4-oxadiazol-5-yl)piperidin-4-yl)ethanol (0.050 g, 0.20 mmol) in DMF (5 mL) was added sodium hydride (0.010 g, 0.33 mmol) at 0° C. and reaction allowed to run at 0° C. for 30 min. After 30 min 2-bromo-6-(4-(methylthio)phenyl)imidazo[2,1-b][1,3,4]thiadiazole (0.047 g, 0.23 mmol) dissolved in DMF was added to reaction mass, stirred at RT for 1 hr. Reaction was monitored by TLC. On completion reaction was quenched with ice cold water and reaction mixture extracted with ethyl acetate. The organic layer was washed with water, brine, dried over sodium sulphate, concentrated under reduced pressure to give crude desired product that was purified by silica gel (100 to 200 # column) chromatography, eluent 2% MeOH/DCM to afford (0.025 g, 18%) 2-(1-(1-(3-(trifluoromethyl)-1,2,4-oxadiazol-5-yl)piperidin-4-yl)ethoxy)-6-(4-(methylthio)phenyl)imidazo[2,1-b][1,3,4]thiadiazole as off white solid.

MS: 511.63 [M$^+$+1]

Step 2: Synthesis 2-(1-(1-(3-(trifluoromethyl)-1,2,4-oxadiazol-5-yl)piperidin-4-yl)ethoxy)-6-(4-(methylsulfonyl)phenyl)imidazo[2,1-b][1,3,4]thiadiazole To a stirred soln. of compound 2-(1-(1-(3-(trifluoromethyl)-1,2,4-oxadiazol-5-yl)piperidin-4-yl)ethoxy)-6-(4-(methylthio)phenyl)imidazo[2,1-b][1,3,4]thiadiazole (0.010 g, 0.020 mmol) in Acetone (5.0 mL), Oxone (0.012 g, 0.041 mmol) in Water (1.5 mL) was added and reaction continued at RT for 16.0 h. Progress of reaction was monitored by TLC. On completion acetone was evaporated from reaction mixture and residue was quenched with water, compound was extracted with ethyl acetate. The organic layer was concentrated under reduced pressure to give crude desired compound. Purification of the compound was done by silica gel (100-200 mess) column chromatography using 1.5% methanol in DCM that was concentrated to get compound 2-(1-(1-(3-(trifluoromethyl)-1,2,4-oxadiazol-5-yl)piperidin-4-yl)ethoxy)-6-(4-(methylsulfonyl)phenyl)imidazo[2,1-b][1,3,4]thiadiazole (0.004 g, 40%) white solid.

MS: 543.65[M$^+$+1].

Example 18: 2-(1-(1-(3-isopropyl-1,2,4-oxadiazol-5-yl)piperidin-4-yl)ethoxy)-6-(2-(methylsulfonyl)pyrimidin-5-yl)imidazo[2,1-b][1,3,4]thiadiazole [1074]

Step 1: Synthesis of 1-(2-(methylthio)pyrimidin-5-yl)ethanone

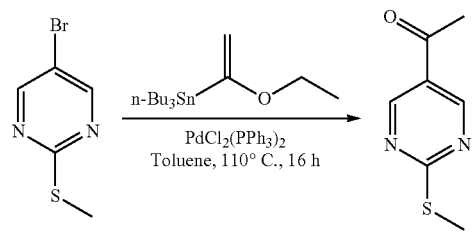

To a stirred solution of 5-bromo-2-(methylthio)pyrimidine (0.1 g, 0.48 mmol) and tributyl(1-ethoxyvinyl)stannane (0.193 g, 0.53 mmol) in toluene (10.0 ml), was degassed with N2 for 15 minute, after that PdCl2(PPh3)2 (0.017 g, 0.024 mmol) was added to reaction mass and stirred at 100° C. for 16 h. Reaction was monitored by TLC. On completion reaction mixture was quenched with water, extracted with ethyl acetate. The organic layer was dried over sodium sulphate, evaporated under reduced pressure to obtain crude desired product. Purification of the compound was done by silica gel (100-200 mesh) column chromatography using 20% ethyl acetate in hexane as a eluent to afford 1-(2-(methylthio)pyrimidin-5-yl)ethanone (0.06 g, 74%) as a white solid.

MS: 169.1[M$^+$+1].

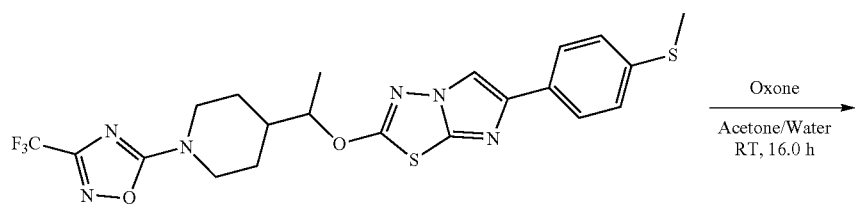

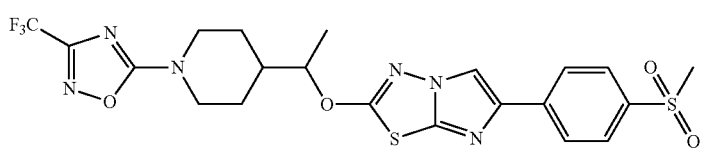

Step 2: Synthesis of 2-bromo-1-(2-(methylthio)pyrimidin-5-yl)ethanone

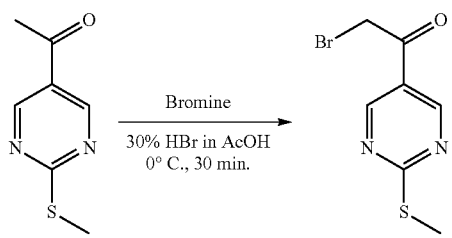

To a stirred solution of 1-(2-(methylthio)pyrimidin-5-yl)ethanone (0.150 g, 0.89 mmol) in 30% HBr in Acetic acid (5.0 mL), Bromine (0.04 mL, 0.8 mmol) was added at 0° C. and allowed to stir at 0° C. for next 30 min. Reaction was monitored by TLC. On completion, reaction mixture was quenched with ice cold water and extracted with EtOAc. The organic layer was washed with water, brine, dried over sodium sulphate and concentrated under reduced pressure to afford 2-bromo-1-(2-(methylthio)pyrimidin-5-yl)ethanone (0.15 g, 57%) as light yellow solid.

MS: 247.1[M$^+$+1].

Step 3: Synthesis of 2-bromo-6-(2-(methylthio)pyrimidin-5-yl)imidazo[2,1-b][1,3,4]thiadiazole

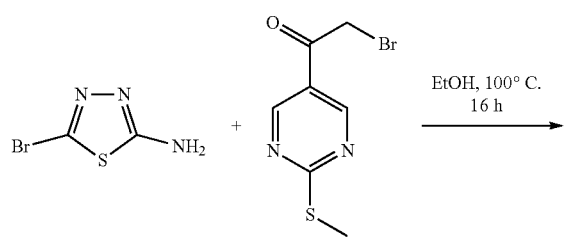

To a stirred solution of 5-amino-2-bromo-1,3,4-thiadiazole (0.250 g, 1.38 mmol) and 2-bromo-1-(2-(methylthio)pyrimidin-5-yl)ethanone (0.341 g, 1.38 mmol) in ethanol (20 mL) was heated at 120° C. for 16 h. On completion, all volatiles were evaporated under reduced pressure obtained yellow sticky mass which was purified by silica gel (100-200 Mesh) column chromatography eluent 2% MeOH/DCM obtained 2-bromo-6-(2-(methylthio)pyrimidin-5-yl)imidazo[2,1-b][1,3,4]thiadiazole (0.15 g, 33%) as light yellow solid.

MS: 328.1[M$^+$+1]

Step 4: Synthesis of 2-(1-(1-(3-isopropyl-1,2,4-oxadiazol-5-yl)piperidin-4-yl)ethoxy)-6-(2-(methylthio)pyrimidin-5-yl)imidazo[2,1-b][1,3,4]thiadiazole

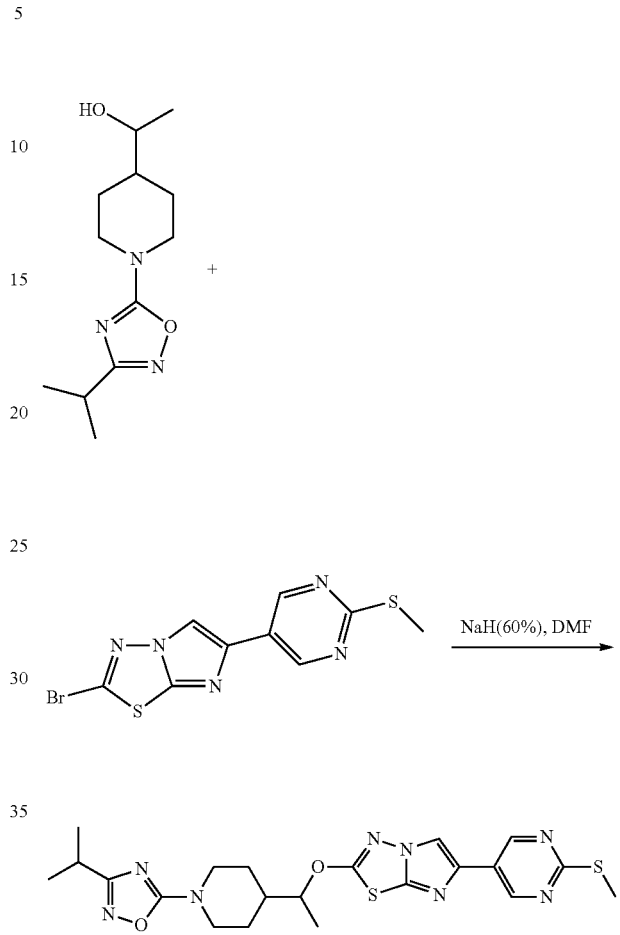

To 1-(1-(3-isopropyl-1,2,4-oxadiazol-5-yl)piperidin-4-yl)ethanol (0.03 g, 0.12 mmol) in DMF (1 mL) was added sodium hydride (0.008 g, 0.18 mmol) at 0° C. and allowed the reaction to stir at 0° C. for 30 min. After 30 min, 2-bromo-6-(2-(methylthio)pyrimidin-5-yl)imidazo[2,1-b][1,3,4]thiadiazole (0.045 g, 0.13 mmol) in DMF (1 mL) was added to reaction mixture and stirred it at room temperature for 2 h. Reaction was monitored by TLC. On completion, reaction was quenched with ice cold water (2 mL) and extracted with EtOAc. The organic layer was washed with water, brine, dried over Na$_2$SO$_4$, evaporated under reduced pressure to give crude product that was purified by silica gel (100 to 200 mesh) chromatography, eluent 50% EtOAc/Hexane to obtain 2-(1-(1-(3-isopropyl-1,2,4-oxadiazol-5-yl)piperidin-4-yl)ethoxy)-6-(2-(methylthio)pyrimidin-5-yl)imidazo[2,1-b][1,3,4]thiadiazole (0.015 g, 24%) as light yellow solid.

MS: 487.1[M$^+$+1]

Step 5: Synthesis of 2-(1-(1-(3-isopropyl-1,2,4-oxadiazol-5-yl)piperidin-4-yl)ethoxy)-6-(2-(methylsulfonyl)pyrimidin-5-yl)imidazo[2,1-b][1,3,4]thiadiazole

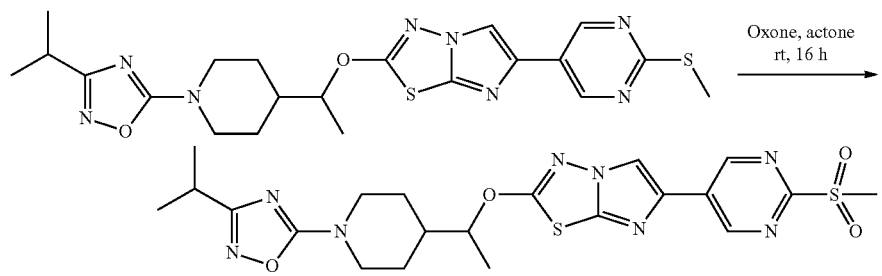

To a stirred solution of 2-(1-(1-(3-isopropyl-1,2,4-oxadiazol-5-yl)piperidin-4-yl)ethoxy)-6-(2-(methylthio)pyrimidin-5-yl)imidazo[2,1-b][1,3,4]thiadiazole (0.02 g, 0.04 mmol) in acetone (5.0 mL), Oxone (0.025 g, 0.08 mmol) in water (2 mL) was added drop wise at room temperature. Allowed the reaction to stir for 16 h. Completion of reaction was monitored by TLC. Reaction mass was evaporated, diluted with water, extracted with EtOAc. Organic portions were combined, dried over $Na_2SO_4$, evaporated under reduced pressure to obtain crude product as yellow solid which was purified by column chromatography using silica gel (100-200 mesh); eluent 2% MeOH in DCM to obtain 2-(1-(1-(3-isopropyl-1,2,4-oxadiazol-5-yl)piperidin-4-yl)ethoxy)-6-(2-(methylsulfonyl)pyrimidin-5-yl)imidazo[2,1-b][1,3,4]thiadiazole (0.01 g, 47%) as off-white solid.

MS: 519.28[M$^+$+1]

Example 19: 2-((S)-1-(1-(3-isopropyl-1,2,4-oxadiazol-5-yl)piperidin-4-yl)ethoxy)-6-(3-fluoro-4-(methylsulfonyl)phenyl)imidazo[2,1-b][1,3,4]thiadiazole [1078]

Step 1: Synthesis of 2-bromo-1-(3-fluoro-4-(methylthio) phenyl) ethanone

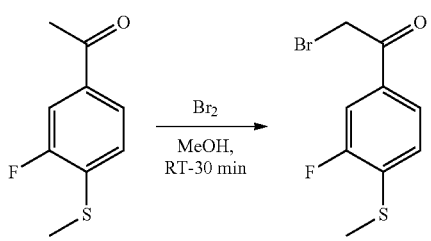

To a stirred solution of 1-(3-fluoro-4-(methylthio) phenyl) ethanone (0.500 g, 3.44 mmol) in MeOH (10 mL) was added $Br_2$ (0.052 mL, 1.07 mmol) in MeOH (2 mL) drop wise at RT, stirred at room temperature for 0.5 hr. Completion of reaction was monitored by TLC. Diethyl ether was added to reaction mass, solid precipitate out which was filtered on Buchner funnel, solid was washed with diethyl ether, dried under vacuum to afford (0.200 gm, 25%) 2-bromo-1-(3-fluoro-4-(methylthio)phenyl)ethanone as off white solid.

MS: 263[M$^+$+2]

Step 2: Synthesis 2-bromo-6-(3-fluoro-4-(methylthio) phenyl) imidazo [2,1-b][1,3,4] thiadiazole

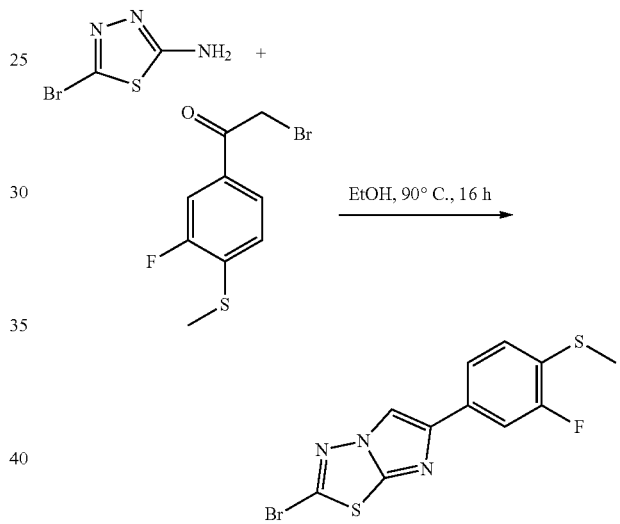

To a stirred solution of 5-amino-2-bromo-1,3,4-thiadiazole (0.174 gm, 0.982 mmol) and 2-bromo-1-(3-fluoro-4-(methylthio)phenyl)ethanone (0.200 gm, 0892 mmol) in Ethanol (50 mL), Reaction mass was heated at 90° C. for 16 h. cooled to room temperature, the precipitated solid was filtered off, washed with hot ethanol, dried under vacuum to afford 2-bromo-6-(3-fluoro-4-(methylthio)phenyl)imidazo[2,1-b][1,3,4]thiadiazole as off white solid.

MS: [M$^+$+2] 345.92

Step 3: Synthesis of 2-((R)-1-(1-(3-isopropyl-1,2,4-oxadiazol-5-yl)piperidin-4-yl)ethoxy)-6-(3-fluoro-4-(methylthio)phenyl)imidazo[2,1-b][1,3,4]thiadiazole

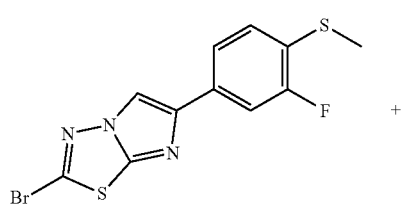

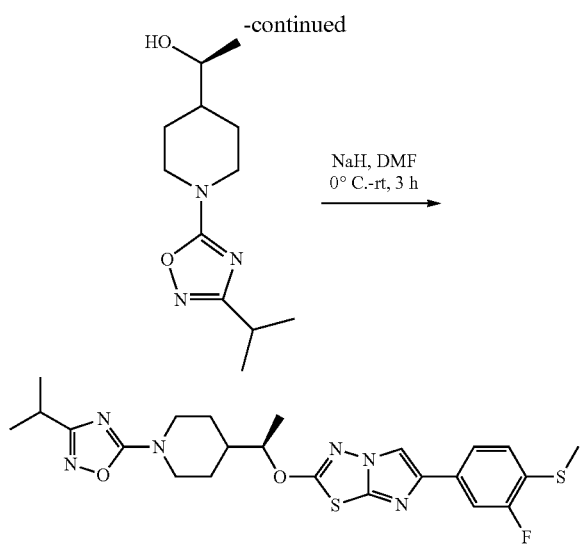

To compound 1-(3-isopropyl-1,2,4-oxadiazol-5-yl)piperidin-4-ol (0.050 g, 0.20 mmol) in DMF (5 mL) was added sodium hydride (0.010 g, 0.33 mmol) at 0° C. and reaction allowed to run at 0° C. for 30 min. After 30 min 2-bromo-6-(3-fluoro-4-(methylthio)phenyl)imidazo[2,1-b][1,3,4]thiadiazole (0.047 g, 0.23 mmol) dissolved in DMF was added to reaction mass, stirred at RT for 1 hr. Reaction was monitored by TLC. On completion reaction was quenched with ice cold water and reaction mixture extracted with ethyl acetate. The organic layer was washed with water, brine, dried over sodium sulphate, concentrated under reduced pressure to give crude desired product that was purified by silica gel (100 to 200 # column) chromatography, eluent 2% MeOH\DCM giving 0.025 g (18%) 2-((R)-1-(1-(3-isopropyl-1,2,4-oxadiazol-5-yl)piperidin-4-yl)ethoxy)-6-(3-fluoro-4-(methylthio)phenyl)imidazo[2,1-b][1,3,4]thiadiazole as off white solid.

MS: 503.63[M$^+$+1]

Step 4: Synthesis of 2-((R)-1-(1-(3-isopropyl-1,2,4-oxadiazol-5-yl)piperidin-4-yl)ethoxy)-6-(3-fluoro-4-(methylsulfonyl)phenyl)imidazo[2,1-b][1,3,4]thiadiazole

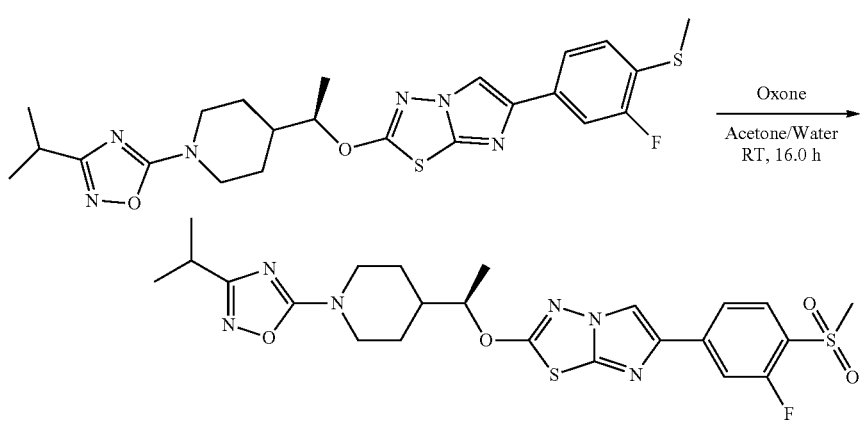

To a stirred soln. of compound 2-((R)-1-(1-(3-isopropyl-1,2,4-oxadiazol-5-yl)piperidin-4-yl)ethoxy)-6-(3-fluoro-4-(methylthio)phenyl)imidazo[2,1-b][1,3,4]thiadiazole (0.010 g, 0.020 mmol) in Acetone (5.0 mL), Oxone (0.012 g, 0.041 mmol) in Water (1.5 mL) was added and reaction continued at RT for 16.0 h. Progress of reaction was monitored by TLC. On completion acetone was evaporated from reaction mixture and residue was quenched with water, compound was extracted with ethyl acetate. The organic layer was concentrated under reduced pressure to give crude desired compound. Purification of the compound was done by silica gel (100-200 mess) column chromatography using 1.5% methanol in DCM that was concentrated to get compound 2-((R)-1-(1-(3-isopropyl-1,2,4-oxadiazol-5-yl)piperidin-4-yl)ethoxy)-6-(3-fluoro-4-(methylsulfonyl)phenyl)imidazo[2,1-b][1,3,4]thiadiazole (0.004 g, 40%) white solid.

MS: 535.65[M$^+$+1].

Example 20: 2-((S)-1-(1-(5-ethylpyrimidin-2-yl)piperidin-4-yl)ethoxy)-6-(pyridin-4-yl)imidazo[2,1-b][1,3,4]thiadiazole [1080]

Step 1: Synthesis of 2-((S)-1-(1-(5-ethylpyrimidin-2-yl)piperidin-4-yl)ethoxy)-6-(pyridin-4-yl)imidazo[2,1-b][1,3,4]thiadiazole

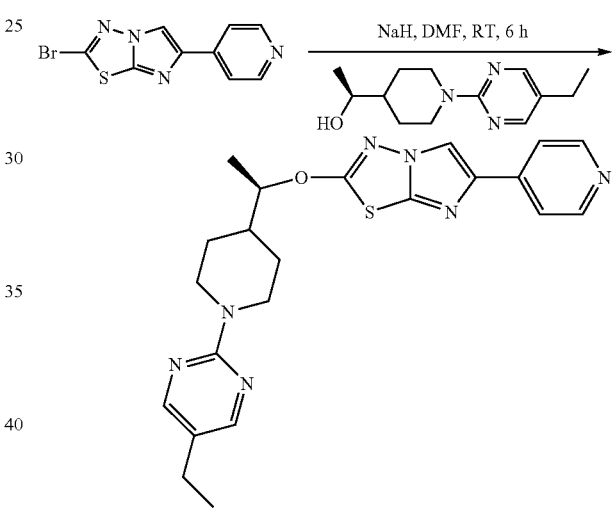

To a stirred solution of (S)-1-(1-(5-ethylpyrimidin-2-yl)piperidin-4-yl)ethanol (0.03 g, 0.107 mmol) in DMF (3 mL) was added sodium hydride (0.0085 g, 0.214 mmol) at 0° C.

and stirred for 30 min at room temperature. After 30 min solution of 2-bromo-6-(pyridin-4-yl)imidazo[2,1-b][1,3,4]thiadiazole (0.027 g, 0.117 mmol) in DMF (2 mL) was added to the reaction mixture and stirred for 6 h. Progress of reaction was monitored by TLC. After completion reaction mass was quenched with ice cold water and extracted with ethyl acetate. The organic layer was washed with water, brine, dried over sodium sulphate and concentrated under reduced pressure to give crude product. Crude was purified by neutral alumina column chromatography using 28% ethyl acetate in hexane as eluent to give 2-(1-(1-(5-chloropyrazin-2-yl)piperidin-4-yl)ethoxy)-5-bromothiazolo[5,4-b]pyridine (0.004 g, 8.58%) as white solid.

MS: 436.5 [M+1]

Example 21: 2-((S)-1-(1-(5-propylpyrimidin-2-yl)piperidin-4-yl)ethoxy)-6-(6-(methylsulfonyl)pyridin-3-yl)imidazo[2,1-b][1,3,4]thiadiazole [1081]

Step 1: Synthesis of
1-(6-bromopyridin-3-yl)ethanone

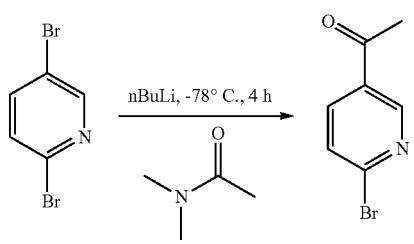

To a stirred solution of 2,5-dibromopyridine (1.0 g, 4.219 mmol) in diethyl ether (10 mL) at −78° C. was added n-Butyl lithium (2.0 mL, 5.0 mmol, 2.5M in hexane) under nitrogen and stirred for 1 h at the same temperature. Dimethyl acetamide (0.58 g, 6.3 mmol) was then added drop wise to the reaction mixture, stirred for 4 h at −78° C. Progress of reaction was monitored by TLC. After completion reaction mass was quenched with ice cold water and partitioned between saturated NH$_4$Cl solution and EtOAc. The organic layer was washed with brine, dried over sodium sulphate and concentrated under reduced pressure to give 1-(6-bromopyridin-3-yl) ethanone (0.4 g, 47%) as yellow solid

MS: 200.1 [M$^+$+1]

Step 2: Synthesis of
1-(6-(methylthio)pyridin-3-yl)ethanone

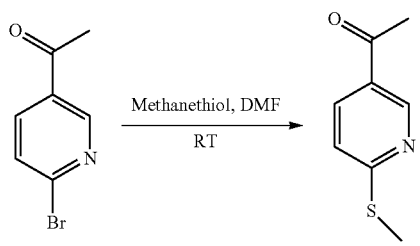

To a stirred solution of 1-(6-bromopyridin-3-yl) ethanone (0.5 g, 2.5 mmol) in DMF (10 mL) was added sodium thiomethoxide soln (1.25 mL, 3.75 mmol) at room temperature and allowed to stir for 6 h at same temperature. Progress of reaction was monitored by TLC. After completion reaction mass was quenched with ice cold water and partitioned with EtOAc. The organic layer was washed with brine, dried over sodium sulphate and concentrated under reduced pressure to give 1-(6-(methylthio)pyridin-3-yl)ethanone (0.4 g, 95%) as yellow solid

MS: 168.1 [M$^+$+1]

Step 3: Synthesis of
2-bromo-1-(6-(methylthio)pyridin-3-yl)ethanone

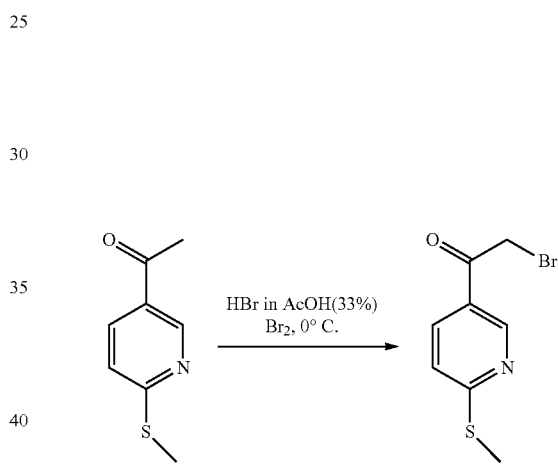

To a stirred solution of 1-(6-(methylthio)pyridin-3-yl) ethanone (0.4 g, 2.39 mmol) in 30% HBr in Acetic acid (5.0 mL), Bromine (0.344 g, 2.15 mmol) was added at 0° C. and allowed to stir at 0° C. for next 30 min. Reaction was monitored by TLC. On completion, diethyl ether was added to reaction mixture, solid precipitate out which was filtered off, washed with diethyl ether to afford 2-bromo-1-(6-(methylthio)pyridin-3-yl)ethanone (0.4 g, 68%) as light yellow solid.

MS: 246.1[M$^+$+1].

Step 4: Synthesis of 2-bromo-6-(6-(methylthio)pyridin-3-yl)imidazo[2,1-b][1,3,4]thiadiazole

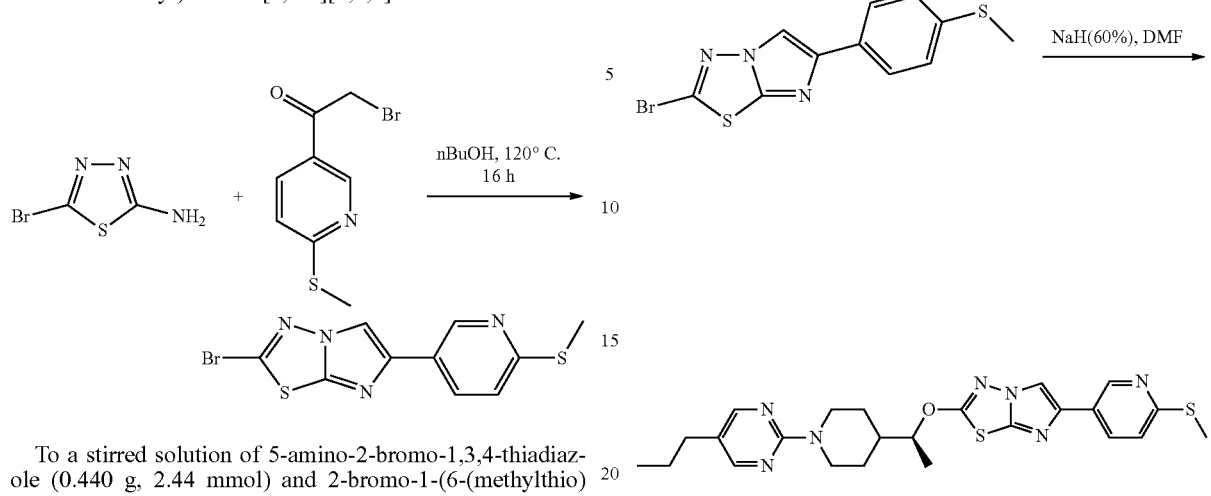

To a stirred solution of 5-amino-2-bromo-1,3,4-thiadiazole (0.440 g, 2.44 mmol) and 2-bromo-1-(6-(methylthio)pyridin-3-yl)ethanone (0.6 g, 2.44 mmol) in n-butanol (20 mL) was heated at 120° C. for 16 h. On completion, all volatiles were evaporated under reduced pressure obtained yellow sticky mass which was purified by silica gel (100-200 Mesh) column chromatography eluent 2% MeOH/DCM obtained 2-bromo-6-(6-(methylthio)pyridin-3-yl)imidazo[2,1-b][1,3,4]thiadiazole (0.25 g, 31%) as yellow solid.

MS: 327.1[M$^+$+1]

Step 5: Synthesis of 2-((S)-1-(1-(5-propylpyrimidin-2-yl)piperidin-4-yl)ethoxy)-6-(6-(methylthio)pyridin-3-yl)imidazo[2,1-b][1,3,4]thiadiazole To (S)-1-(1-(5-propylpyrimidin-2-yl)piperidin-4-yl)ethanol (0.04 g, 0.16 mmol) in DMF (1 mL) was added sodium hydride (0.009 g, 0.24 mmol) at 0° C. and allowed the reaction to stir at 0° C. for 30 min. After 30 min, 2-bromo-6-(6-(methylthio)pyridin-3-yl)imidazo[2,1-b][1,3,4]thiadiazole (0.062 g, 0.19 mmol) in DMF (1 mL) was added to reaction mixture and stirred it at room temperature for 6 h. Reaction was monitored by TLC. On completion, reaction was quenched with ice cold water (2 mL) and extracted with EtOAc. The organic layer was washed with water, brine, dried over Na$_2$SO$_4$, evaporated under reduced pressure to give crude product that was purified by silica gel (100 to 200 mesh) chromatography, eluent 2% MeOH/DCM to obtain 2-((S)-1-(1-(5-propylpyrimidin-2-yl)piperidin-4-yl)ethoxy)-6-(6-(methylthio)pyridin-3-yl)imidazo[2,1-b][1,3,4]thiadiazole (0.02 g, 25%) as off-white solid.

MS: 496.1[M$^+$+1]

Step 6: Synthesis of 2-((S)-1-(1-(5-propylpyrimidin-2-yl)piperidin-4-yl)ethoxy)-6-(6-(methylsulfonyl)pyridin-3-yl)imidazo[2,1-b][1,3,4]thiadiazole

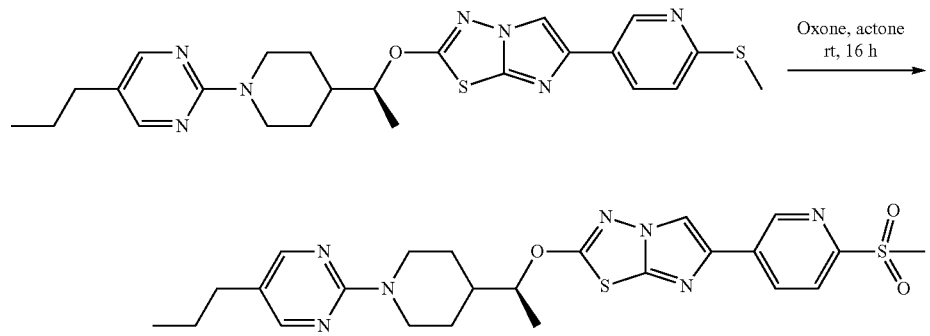

To a stirred solution of 2-((S)-1-(1-(5-propylpyrimidin-2-yl)piperidin-4-yl)ethoxy)-6-(6-(methylthio)pyridin-3-yl)imidazo[2,1-b][1,3,4]thiadiazole (0.02 g, 0.04 mmol) in acetone (5.0 mL), Oxone (0.025 g, 0.08 mmol) in water (2 mL) was added drop wise at room temperature. Allowed the reaction to stir for 16 h. Completion of reaction was monitored by TLC. Reaction mass was evaporated, diluted with water, extracted with EtOAc. Organic portions were combined, dried over Na$_2$SO$_4$, evaporated under reduced pressure to obtain crude product as yellow solid which was purified by column chromatography using silica gel (100-200 mesh); eluent 20% acetone in DCM to obtain 2-((S)-1-(1-(5-propylpyrimidin-2-yl)piperidin-4-yl)ethoxy)-6-(6-(methylsulfonyl)pyridin-3-yl)imidazo[2,1-b][1,3,4]thiadiazole (0.01 g, 47%) as off-white solid.

MS: 528.2 [M$^+$+1]

Example 22: 2-((S)-1-(1-(3-isopropyl-1,2,4-oxadiazol-5-yl)piperidin-4-yl)ethoxy)-6-(6-(trifluoromethyl)pyridin-3-yl)imidazo[2,1-b][1,3,4]thiadiazole
[1084]

Step-1: Synthesis of 5-bromo-2-(trifluoromethyl)pyridine

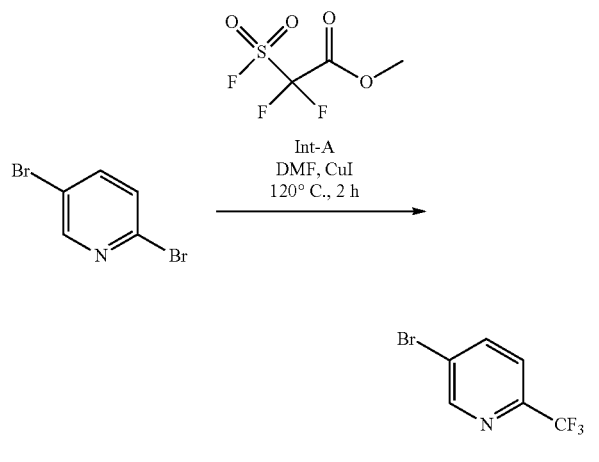

To a stirred solution of 2,5-dibromopyridine (0.3 g, 1.27 mmol) in DMF (10 mL), CuI (1.69 g, 8.8 mmol) was added and allow to stirred for 30 min. To resultant reaction mass Int-A (1.22 g, 6.3 mmol) was added and stirred for 2 h at RT. Completion of reaction was monitored by TLC. On completion, quenched with ice water, extracted with pentane. The organic layer was washed with water, brine, dried over sodium sulphate, concentrated under reduced pressure obtained crude. Purification of the crude was done via silica gel (100-200 Mesh) column chromatography eluent 15% MDC/n-Hexane to obtained 5-bromo-2-(trifluoromethyl)pyridine (0.07 g, 24.64%) as colourless oily mass.

Mass: 226.2 [M$^+$+1]

Step-2: Synthesis of 1-(6-(trifluoromethyl)pyridin-3-yl)ethanone

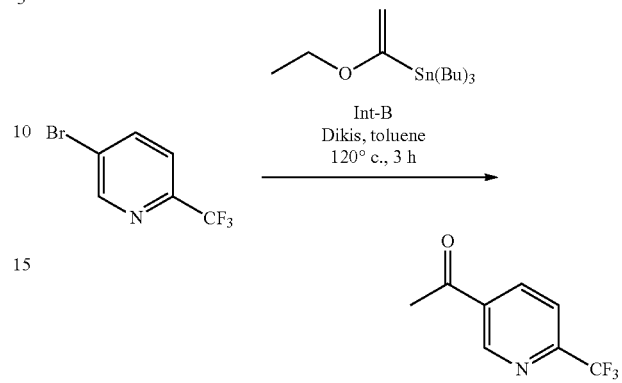

To a stirred solution of 5-bromo-2-(trifluoromethyl) pyridine (0.07 g, 0.31 mmol) in dry toluene (10 mL), Int-B (0.124 g, 0.34 mmol) was added. Purged reaction mass with nitrogen for 30 min. To resultant reaction mass Dikis (0.01 g, 0.015 mmol) was added and stirred at 120° C. for 3 h. Completion of reaction was monitored by TLC. On completion, quenched with ice water, extracted with ether. The organic layer was washed with water, brine, dried over sodium sulphate, concentrated under reduced pressure obtained crude. Purification of the crude was done via silica gel (100-200 Mesh) column chromatography and desired compound eluted at 15% ethyl acetate/n-Hexane to obtained 1-(6-(trifluoromethyl)pyridin-3-yl)ethanone (0.035 g, 59.25%) as off white solid.

Mass: 190.08 [M$^+$+1]

Step-3: Synthesis of 2-bromo-1-(6-(trifluoromethyl)pyridin-3-yl)ethanone

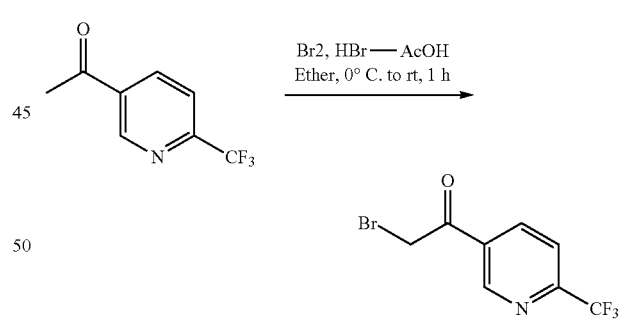

To a stirred solution of 1-(6-(trifluoromethyl)pyridin-3-yl)ethanone (0.035 g, 0.18 mmol) in ether (2 mL) was added HBr—AcOH (0.5 mL). To resultant reaction mass Br2 (diluted in 0.5 mL HBr—AcOH) (0.027 g, 0.17 mmol) was added at 0° C. and stirred for 30 min. Allow temp to increase gradually to RT. Completion of reaction was monitored by TLC. On completion, quenched with ice water, extracted with ether. The organic layer was washed with aqueous-bicarbonate, brine, dried over sodium sulphate, concentrated under reduced pressure obtained 2-bromo-1-(6-(trifluoromethyl) pyridin-3-yl)ethanone (0.26 g, 86.66%) as semisolid brownish gummy mass.

Mass: 268.2 [M$^+$+1]

Step-4: Synthesis of 2-chloro-6-(6-(trifluoromethyl) pyridin-3-yl)imidazo[2,1-b][1,3,4]thiadiazole

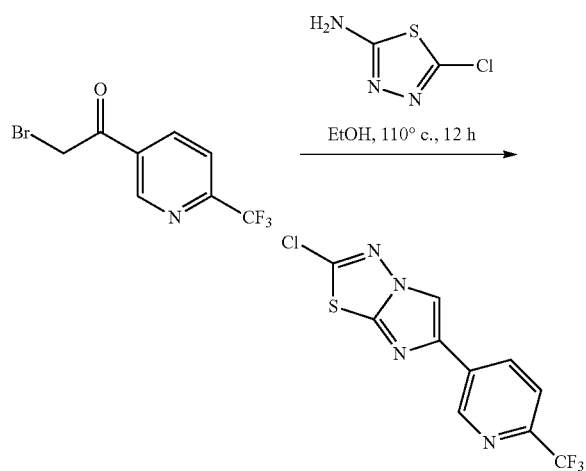

To a stirred solution of 5-amino-2-chloro-1,3,4-thiadiazole (0.179 g, 0.8 mmol) and 2-bromo-1-(6-(trifluoromethyl)pyridin-3-yl)ethanone (0.16 g, 0.84 mmol) in EtOH (5 mL) was heated at 110° C. for 16 h. After cooled to room temperature, concentrated under reduced pressure to obtained crude mass. Purification of the crude was done via silica gel (100-200 Mesh) column chromatography and desired compound eluted at 7% acetone/n-Hexane to obtained 2-chloro-6-(6-(trifluoromethyl)pyridin-3-yl)imidazo[2,1-b][1,3,4]thiadiazole (0.050 g, 32.0%) as off white solid.

MS: 351.0 [M+1]

Step-5: Synthesis of 2-((S)-1-(1-(3-isopropyl-1,2,4-oxadiazol-5-yl)piperidin-4-yl)ethoxy)-6-(6-(trifluoromethyl)pyridin-3-yl)imidazo[2,1-b][1,3,4]thiadiazole To a stirred solution of (S)-1-(1-(3-isopropyl-1,2,4-oxadiazol-5-yl)piperidin-4-yl)ethanol (0.035 g, 0.13 mmol) in DMF (2.5 mL), NaH (0.010 mg, 0.30 mmol) was added at 0° C. and stirred for 1 h. To resultant reaction mass, 2-chloro-6-(6-(trifluoromethyl)pyridin-3-yl)imidazo[2,1-b][1,3,4]thiadiazole (0.045 g, 0.143 mmol) was added and stirred for 1 h at RT. Reaction was monitored by TLC. On completion, quenched with water, extracted with ethyl acetate. The organic layer was washed with water, brine, dried over sodium sulphate, concentrated under reduced pressure obtained crude. Purification of the crude was done by silica gel (100-200 Mesh) column chromatography and desired compound eluted at 12% acetone/n-Hexane to obtained 2-((S)-1-(1-(3-isopropyl-1,2,4-oxadiazol-5-yl)piperidin-4-yl)ethoxy)-6-(6-(trifluoromethyl)pyridin-3-yl)imidazo[2,1-b][1,3,4]thiadiazole (0.005 g, 6.70%) as off white solid.

MS: 508.2 [M+1]

Example 23: 2-((S)-1-(1-(5-propylpyrimidin-2-yl)piperidin-4-yl)ethoxy)-6-(2-fluoro-4-(methylsulfonyl)phenyl)imidazo[2,1-b][1,3,4]thiadiazole [1085]

Step 1: Synthesis of 4-bromo-3-fluorobenzenethiol

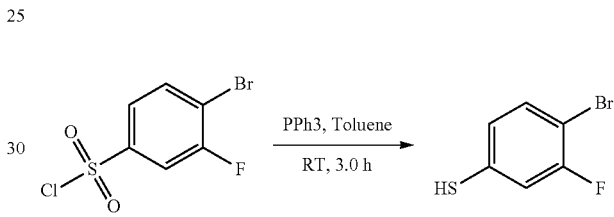

To a stirred soln. of Triphenylphosphine (1.4 gm, 5.48 mmol) in Toluene, compound 4-bromo-3-fluorobenzene-1-sulfonyl chloride (0.5 gm, 1.83 mmol) was added at room temperature and reaction allowed to run at same temperature for 3.0 h. Reaction was monitored by TLC. On completion reaction mixture and quenched by 1N HCl and compound was extracted with DCM. The organic layer was dried over sodium sulphate and concentrated under reduced pressure to give crude desired product. Purification of the compound was done by silica gel (100-200 mess) column chromatography using 1% ethyl acetate in hexane that was concentrated to get compound 4-bromo-3-fluorobenzenethiol (0.23 g, 61.09%) as yellow liquid.

MS: 205.0[M−−1].

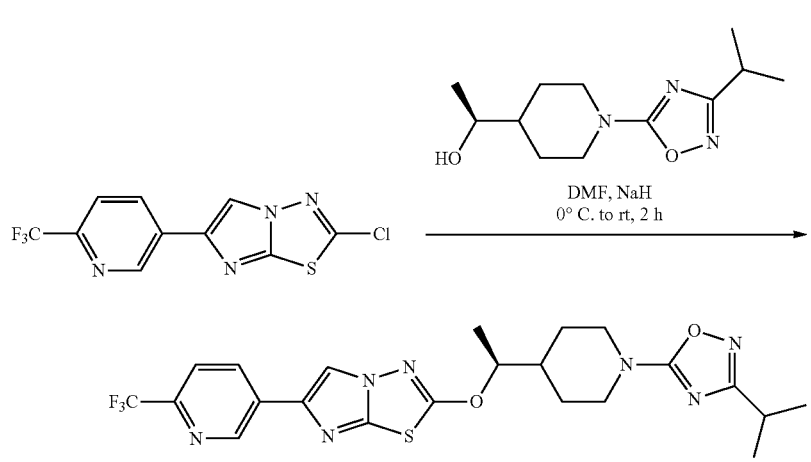

Step 2: Synthesis of (4-bromo-3-fluorophenyl)(methyl)sulfane

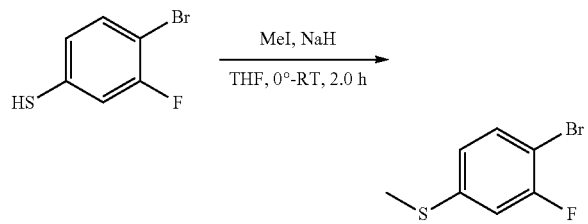

To a stirred soln. of 4-bromo-3-fluorobenzenethiol (0.23 gm, 1.12 mmol) in Dry THF (4.0 ml), sodium hydride (0.05 gm, 1.34 mmol) at 0° C. and reaction allowed to run at 0° C. for 10.0 min. then methyl iodide (0.08 ml, 1.23 mmol) was added to reaction mixture and reaction continued at RT for next 1.5 h. Reaction was monitored by TLC. On completion reaction mixture was quenched with ice cold water and compound was extracted with ethyl acetate. The organic layer was washed with water, brine, dried over sodium sulphate and concentrated under reduced pressure to give desired product (4-bromo-3-fluorophenyl)(methyl)sulfane (0.24 g, 97.69%) as yellow liquid.

MS: 220.94[M$^+$+1].

Step 3: Synthesis of 1-(2-fluoro-4-(methylthio)phenyl)ethanone

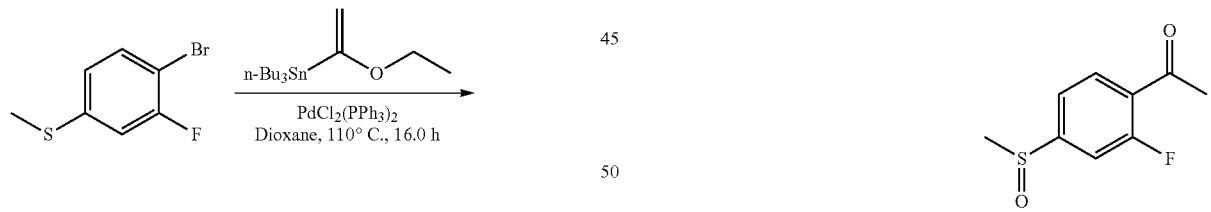

To a stirred soln. of compound (4-bromo-3-fluorophenyl)(methyl)sulfane (0.24 gm, 1.09 mmol) and tributyl(1-ethoxyvinyl)stannane (0.39 gm, 1.09 mmol) in Dioxane (5.0 ml), PdCl2(PPh3)2 (0.04 gm, 0.05 mmol) was added under nitrogen degassing. Reaction allowed to run at 110° C. for 16.0 h. Reaction was monitored by TLC. On completion solvent was evaporated from reaction mixture. Residue was quenched with water, compound was extracted with ethyl acetate. The organic layer was concentrated under reduced pressure to get crude desired product. Purification of the compound was done by silica gel (100-200 mess) column chromatography using 3% ethyl acetate in hexane that was concentrated to get compound 1-(2-fluoro-4-(methylthio)phenyl)ethanone (0.12 g, 59.76%) as yellow solid.

MS: 185.1[M$^+$+1].

Step 4: Synthesis of 1-(2-fluoro-4-(methylsulfinyl)phenyl)ethanone

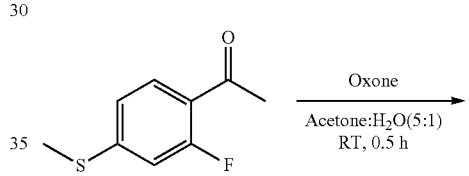

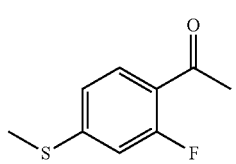

To a stirred soln. of compound 1-(2-fluoro-4-(methylthio)phenyl)ethanone (0.2 gm, 1.09 mmol) in Acetone (5.0 ml), Oxone (0.34 gm, 1.09 mmol) in Water (1.0 ml) was added and reaction continued at RT for 0.5 h. Progress of reaction was monitored by TLC. On completion acetone was evaporated from reaction mixture and residue was quenched with water, compound was extracted with ethyl acetate. The organic layer was concentrated under reduced pressure to get compound 1-(2-fluoro-4-(methylsulfinyl)phenyl)ethanone (0.2 g, 92.02%) white semi solid. MS: 201.1[M$^+$+1].

Step 5: Synthesis of 2-bromo-1-(2-fluoro-4-(methylthio)phenyl)ethanone

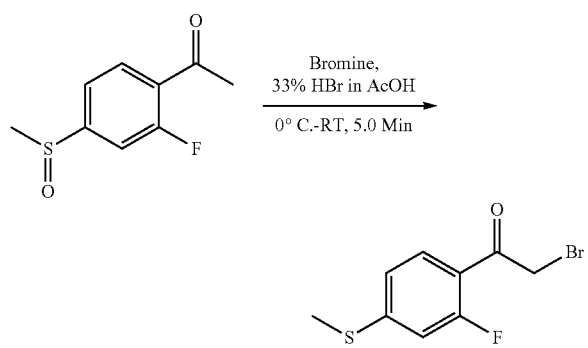

To a stirred soln. of 1-(2-fluoro-4-(methylsulfinyl)phenyl)ethanone (0.05 gm, 0.25 mmol) in 33% HBr in Acetic acid (0.5 ml), Bromine (0.04 gm, 0.22 mmol) in 0.2 ml HBr in AcOH was added at 0° C. and reaction allowed to run at RT for next 5.0 min. Reaction was monitored by TLC. On completion reaction mixture was quenched with ice cold water and compound was extracted with di ethyl ether. The organic layer was washed with water, brine, dried over sodium sulphate and concentrated under reduced pressure to get crude compound 2-bromo-1-(2-fluoro-4-(methylthio)phenyl)ethanone (0.05 g, Crude) as yellow semi solid.

MS: 262.95[M$^+$+1].

Step 6: Synthesis of 2-chloro-6-(2-fluoro-4-(methylthio)phenyl)imidazo[2,1-b][1,3,4]thiadiazole

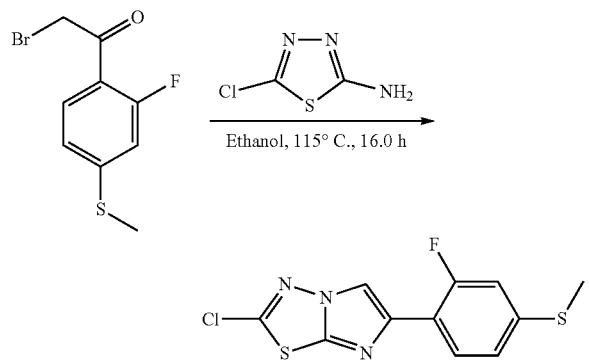

To a stirred soln. of 2-bromo-1-(2-fluoro-4-(methylthio)phenyl)ethanone (0.3 gm, 1.15 mmol) in Ethanol (6.0 ml), 5-chloro-1,3,4-thiadiazol-2-amine (0.15 gm, 1.15 mmol) was added at RT and reaction allowed to run at 115° C. for 16.0 h. Reaction was monitored by TLC. On completion reaction mixture was concentrated under reduced pressure to get crude desired product. Purification of the compound was done by silica gel (100-200 mess) column chromatography using 15% ethyl acetate in hexane that was concentrated to get compound 2-chloro-6-(2-fluoro-4-(methylthio)phenyl)imidazo[2,1-b][1,3,4]thiadiazole (0.06 g, 17.52%) as yellow solid.

MS: 300.0[M$^+$+1].

Step 7: Synthesis of 2-((S)-1-(1-(5-propylpyrimidin-2-yl)piperidin-4-yl)ethoxy)-6-(2-fluoro-4-(methylthio)phenyl)imidazo[2,1-b][1,3,4]thiadiazole

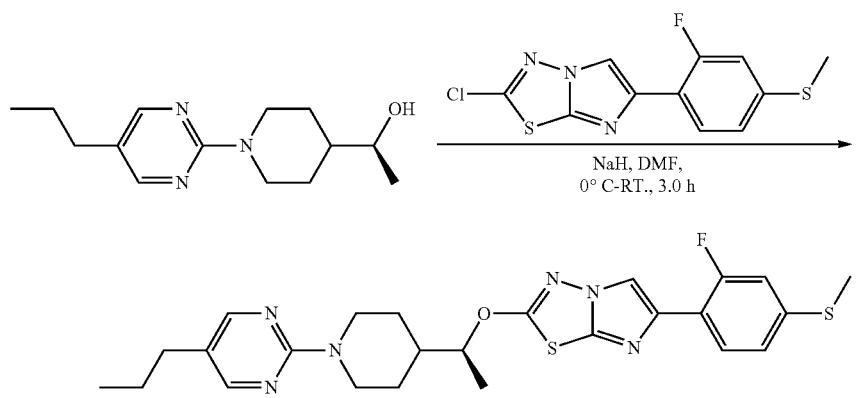

To a stirred soln. of (S)-1-(1-(5-propylpyrimidin-2-yl)piperidin-4-yl)ethanol (0.015 gm, 0.06 mmol) in DMF (3.0 ml), sodium hydride (0.004 gm, 0.09 mmol) at 0° C. and reaction allowed to run at 0° C. for 30.0 min. then 2-chloro-6-(2-fluoro-4-(methylthio)phenyl)imidazo[2,1-b][1,3,4]thiadiazole (0.02 gm, 0.07 mmol) was added to reaction mixture and reaction continued at RT for next 3.0 h. Reaction was monitored by TLC. On completion reaction mixture was quenched with ice cold water and compound was extracted with ethyl acetate. The organic layer was washed with water, brine, dried over sodium sulphate and concentrated under reduced pressure to give crude desired product. Purification of the compound was done by silica gel (100-200 mess) column chromatography using 20% Acetone in hexane that was concentrated to get compound 2-((S)-1-(1-(5-propylpyrimidin-2-yl)piperidin-4-yl)ethoxy)-6-(2-fluoro-4-(methylthio)phenyl)imidazo[2,1-b][1,3,4]thiadiazole (0.012 g, 38.92%) as white solid.

MS: 513.18[M$^+$+1].

Step 8: Synthesis of 2-((S)-1-(1-(5-propylpyrimidin-2-yl)piperidin-4-yl)ethoxy)-6-(2-fluoro-4-(methylsulfonyl)phenyl)imidazo[2,1-b][1,3,4]thiadiazole

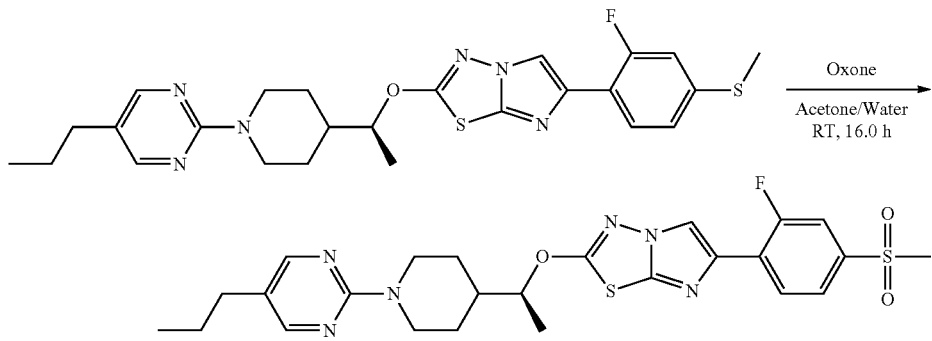

To a stirred soln. of compound 2-((S)-1-(1-(5-propylpyrimidin-2-yl)piperidin-4-yl)ethoxy)-6-(2-fluoro-4-(methylthio)phenyl)imidazo[2,1-b][1,3,4]thiadiazole (0.01 gm, 0.02 mmol) in Acetone (2.0 ml), Oxone (0.01 gm, 0.04 mmol) in Water (0.5 ml) was added and reaction continued at RT for 16.0 h. Progress of reaction was monitored by TLC. On completion acetone was evaporated from reaction mixture and residue was quenched with water, compound was extracted with ethyl acetate. The organic layer was concentrated under reduced pressure to give crude desired compound. Purification of the compound was done by silica gel (100-200 mess) column chromatography using 20% Acetone in hexane that was concentrated to get compound 2-((S)-1-(1-(5-propylpyrimidin-2-yl)piperidin-4-yl)ethoxy)-6-(2-fluoro-4-(methylsulfonyl)phenyl)imidazo[2,1-b][1,3,4]thiadiazole (0.008 g, 75.33%) white solid.

MS: 545.17[M$^+$+1].

Example 24: 2-((S)-1-(1-(5-ethylpyrimidin-2-yl)piperidin-4-yl) ethoxy)-6-(2-fluoro-4-(methylsulfonyl)phenyl)imidazo[2,1-b][1,3,4]thiadiazole [1086]

Step 1: Synthesis of 1-(2-fluoro-4-(methylthio)phenyl)ethenone (37)

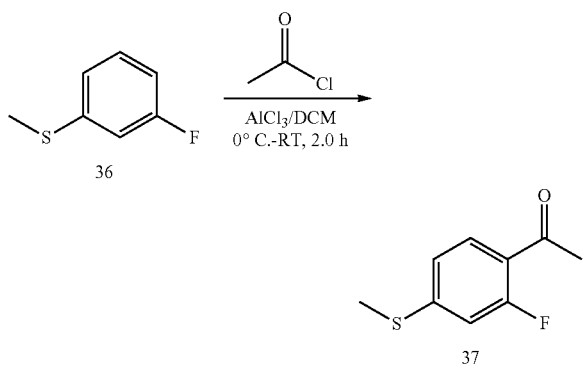

To a stirred soln. of compound (3-fluorophenyl)(methyl)sulfane (36) (1.0 gm, 7.0 mmol) in Dry DCM (20.0 mL) at 0° C., acetyl chloride (0.65 ml, 9.2 mmol) and AlCl$_3$ (2.05 gm, 15.4 mmol) were added at same temperature and reaction continued at RT for 2.0 h. Progress of reaction was monitored by TLC. On completion, reaction quenched with water, compound was extracted with DCM. The organic layer was concentrated under reduced pressure to get crude desired product. Purification of the compound was done by silica gel (100-200 mess) column chromatography using 5% ethyl acetate in hexane that was concentrated to get compound 1-(2-fluoro-4-(methylthio)phenyl)ethenone (37) (0.9 gm, 69.77%) as white solid.

MS: 185.04[M$^+$+1].

Step 2: Synthesis of 2-bromo-1-(2-fluoro-4-(methylthio) phenyl) ethenone (38)

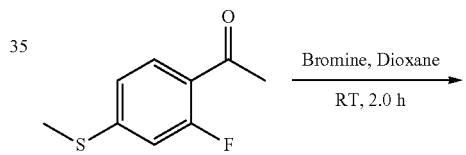

To a stirred solution of 1-(2-fluoro-4-(methylthio)phenyl) ethanone (0.9 gm, 4.89 mmol) (37) in Dioxane (40.0 ml), Bromine (0.70 gm, 4.40 mmol) in 5 ml Dioxane was added at RT and reaction allowed to run at RT for next 2.0 h. Reaction was monitored by TLC. On completion reaction mixture was quenched with ice cold water and compound was extracted with DCM. The organic layer was washed with water, brine, dried over sodium sulphate and concentrated under reduced pressure to get compound 2-bromo-1-(2-fluoro-4-(methylthio)phenyl)ethanone (38) (1.0 gm, 78.12%) as off white solid after pentane wash.

MS: 262.95[M$^+$+1].

Step 3: Synthesis of 5-chloro-1,3,4-thiadiazol-2-amine (40)

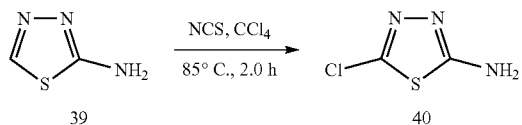 [SMILES: Nc1nncs1 ; Nc1nnc(Cl)s1]

To a stirred solution of 1,3,4-thiadiazol-2-amine (39) (0.5 g, 4.95 mmol) in CCl₄ (10.0 mL), N-Chloro succinimide (0.73 g, 5.45 mmol) was added at 25° C. and reaction allowed to stir at 85° C. for 2 h. Reaction was monitored by TLC. On completion, reaction mixture was quenched with ice cold water and compound was extracted with 10% methanol in DCM. The organic layer was washed with water, brine, dried over sodium sulphate and concentrated under reduced pressure to give crude. Purification of the compound was done by silica gel (100-200 mesh) column chromatography using 20% ethyl acetate in hexane to give 5-chloro-1,3,4-thiadiazol-2-amine (40) (0.18 g, 26.94%) as light brown solid.

MS: 135.97[M$^+$+1].

Step 4: 2-chloro-6-(2-fluoro-4-(methylthio)phenyl)imidazo[2,1-b][1,3,4]thiadiazole (41)

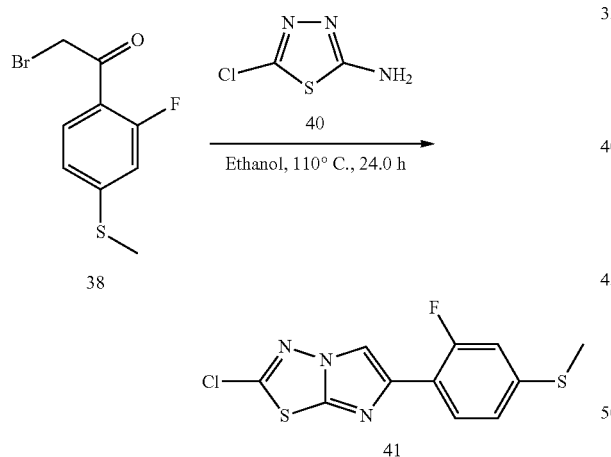

To a stirred soln. of 2-bromo-1-(2-fluoro-4-(methylthio)phenyl)ethanone (38) (1.0 gm, 3.8 mmol) in Ethanol (15.0 ml), 5-chloro-1,3,4-thiadiazol-2-amine (40) (0.52 gm, 3.8 mmol) was added at RT and reaction allowed to run at 110° C. for 24.0 h. Reaction was monitored by TLC. On completion reaction mixture was concentrated under reduced pressure to get crude desired product. Purification of the compound was done by neutral alumina column chromatography using 4% Acetone in hexane that was concentrated to get compound 2-chloro-6-(2-fluoro-4-thio)phenyl)imidazo[2,1-b][1,3,4]thiadiazole (41) (0.59 gm, 51.75%) as off white solid. MS: 299.99[M$^+$+1].

Step 5: Synthesis of ethyl piperidine-4-carboxylate hydrochloride (43)

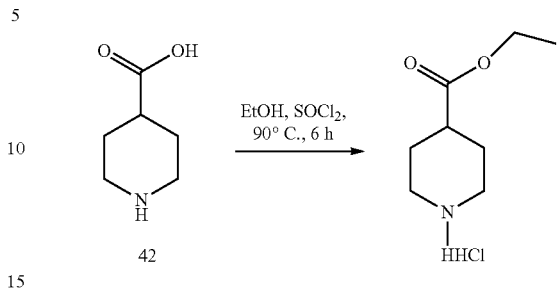

To a stirred solution of piperidine-4-carboxylic acid (42) (10.0 g) in ethanol (500 mL), added SOCl₂ (22.4 mL, 310 mmol) dropwise at 0° C., then reaction mixture was heated at 90° C. for 6 h, Reaction was monitored by TLC. On completion all volatiles were evaporated obtained sticky mass, triturated with pentane, Solid ppt out which was filtered off, solid dried under vacuum to afford ethyl piperidine-4-carboxylate hydrochloride (43) (12.0 g, 80.05%) as off white solid.

MS: 158.11 [M$^+$+1].

Step 6: Synthesis of t-butyl ethyl piperidine-1,4-dicarboxylate (44)

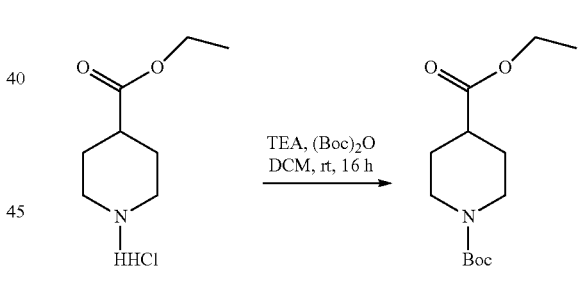

To a stirred solution of ethyl piperidine-4-carboxylate hydrochloride (43) (12.0 g, 62.33 mmol) in DCM (200 mL) was added TEA (18.92 g, 187.01 mmol) dropwise at room temperature and reaction allowed to stir for 15 min. After 15 min Boc anhydride (20.40 g, 93.50 mmol) was added it and stirred for 16 h. Reaction was monitored by TLC. On completion reaction was quenched with water, extracted with DCM. The organic layer was washed with water, NaHCO₃, brine, dried over Na₂SO₄, evaporated under reduced pressure obtained t-butyl ethyl piperidine-1,4-dicarboxylate (44) (20.15 g, 92.98%) as white solid.

MS: 258.16 [M$^+$+1].

Step 7: Synthesis of t-butyl 4-(hydroxymethyl) piperidine-1-carboxylate (45)

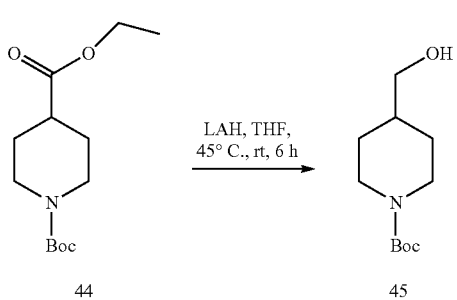 [SMILES: CCOC(=O)C1CCN(C(=O)OC(C)(C)C)CC1 ; CC(C)(C)OC(=O)N1CCC(CO)CC1]

To a stirred solution of t-butyl ethyl piperidine-1,4-dicarboxylate (44) (20 g, 77.72 mmol) in THF (200 mL) was added LAH (14.74 g, 0.926 mmol) at 0° C. and reaction allowed to stir at 45° C. for 6 h. Reaction was monitored by TLC. On completion reaction mass was diluted with EtOAc, water and extracted with EtOAc. The organic layer was washed with water, brine, dried over $Na_2SO_4$, and evaporated under reduced pressure obtained t-butyl 4-(hydroxymethyl) piperidine-1-carboxylate (45) (12.15 g, 72.53%) as white solid.

MS: 216.15 [$M^+$+1].

Step 8: t-butyl 4-formylpiperidine-1-carboxylate (46)

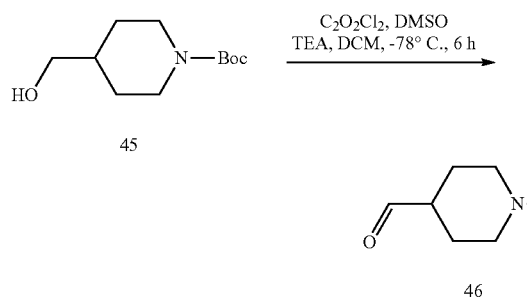

To DCM (50 mL) was added oxalyl chloride (7.07 g, 55.74 mmol) at −78° C. and reaction allowed to stir at −78° C. for 15 min. After 15 min. DMSO (5.27 g, 74.32 mmol) was added slowly dropwise and stir at −78° C. for 2 h. After 2 h t-butyl 4-(hydroxymethyl) piperidine-1-carboxylate (45) (4.0 g, 18.58 mmol) in DCM (10 mL) was added to reaction mass at −78° C. and stir 2 h. Then, TEA (6.24 g, 61.67 mmol) was added to it and stir at −78° C. for 30 min. Reaction was monitored by TLC. Reaction was quenched with water, extracted with DCM. The organic layer was washed with brine, dried over sodium sulphate, concentrated under reduced pressure obtained t-butyl 4-formylpiperidine-1-carboxylate (46) (4.0 g, % yield) of as yellow oil.

MS: 214.14 [$M^+$+1].

Step 9: t-butyl 4-(1-hydroxyethyl) piperidine-1-carboxylate (47)

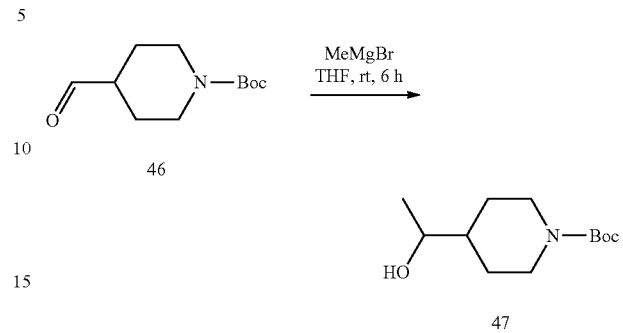

To a stirred solution of t-butyl 4-(1-hydroxyethyl) piperidine-1-carboxylate (46) (4 g, 18.75 mmol) in THF (200 mL) was added MeMgBr (2M in THF) (46.88 mL, 93.77 mmol) at 0° C. and reaction allowed to stir at room temperature for 3 h. Reaction was monitored by TLC. Reaction was quenched with aq. $NH_4Cl$, and extracted with ethyl acetate. The organic layer was washed with brine, dried over sodium sulphate, concentrated under reduced pressure obtained crude which was purified by silica gel (100-200 Mesh) column chromatography eluent 25% EtOAc/Hexane to afford t-butyl 4-(1-hydroxyethyl)piperidine-1-carboxylate (47) (2.6 g, 60.46%) as yellow oil.

MS: 230.1 [$M^+$+1].

Step 10: 1-(piperidin-4-yl) ethanol hydrochloride (48)

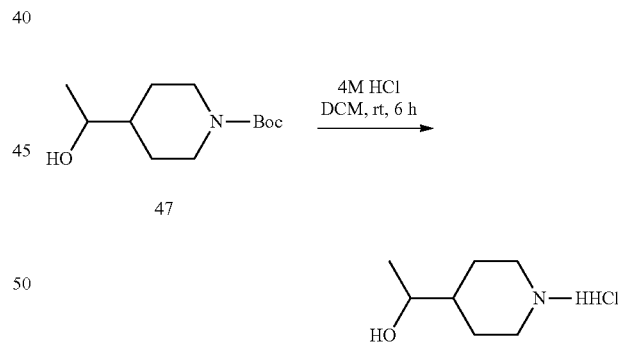

To a stirred solution of t-butyl 4-(1-hydroxyethyl) piperidine-1-carboxylate (47) (2.5 g, 10.90 mmol) in DCM (50 mL) was added 4 M HCl in Dioxane (13.62 mL, 54.50 mmol) and reaction allowed to stir at room temperature for 6 h. Reaction was monitored by TLC. On completion all volatiles were evaporated under reduced pressure obtained 1-(piperidin-4-yl) ethanol hydrochloride (48) (1.5 g, 83.79%) as off white solid.

MS: 130.2 [$M^+$+1].

Step 11: 1-(1-(5-ethylpyrimidin-2-yl) piperidin-4-yl) ethanol (50)

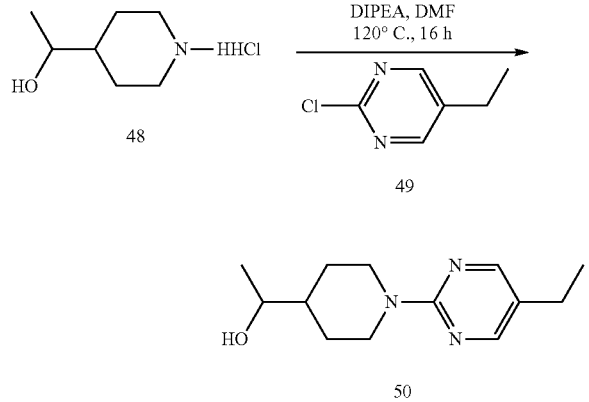

To a stirred solution of 1-(piperidin-4-yl) ethanol hydrochloride (48) (0.1 g, 0.603 mmol) in DMF (5 mL) was added DIPEA (0.234 g, 1.811 mmol) and stir at room temperature for 30 min. Then 2-chloro-5-ethylpyrimidine (49) (0.129 g, 0.905 mmol) was added and stir at 120° C. for 16 h. Reaction was monitored by TLC. Reaction was quenched ice cold water, extracted with ethyl acetate. The organic layer was washed with brine, dried over sodium sulphate, concentrated under reduced pressure obtained crude which was purified by combiflesh (Lumen) chromatography eluent 18% EtOAc/Hexane to afford 1-(1-(5-ethylpyrimidin-2-yl)piperidin-4-yl)ethanol (50) (0.06, 42.25%) as yellow oil.

MS: 236.2 [M$^+$+1].

Step 12: (2R)-(S)-1-(1-(5-ethylpyrimidin-2-yl) piperidin-4-yl) ethyl 2-methoxy-2-phenylacetate (52 a) and (2R)-(R)-1-(1-(5-ethylpyrimidin-2-yl) piperidin-4-yl) ethyl 2-methoxy-2-phenylacetate (52 b)

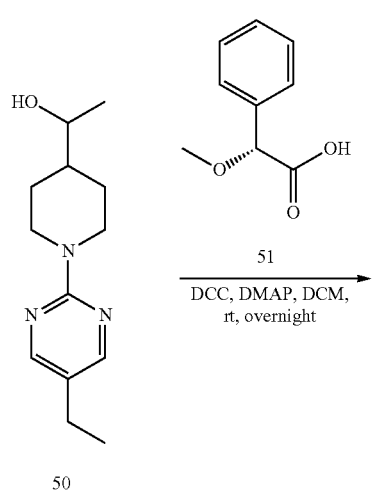

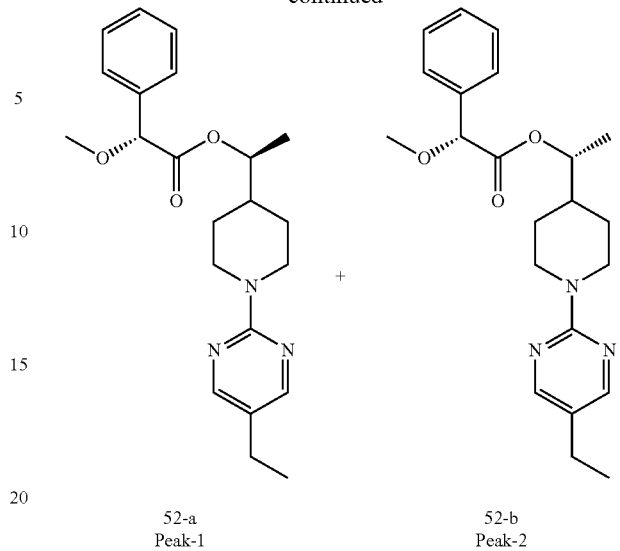

To a stirred solution of 1-(1-(5-ethylpyrimidin-2-yl)piperidin-4-yl)ethanol (50) (0.8 g, 3.404 mmol) and (S)-(+)-α-Methoxyphenylacetic acid (51) (0.678 g, 4.085 mmol) in DCM (15 mL) were added DCC (1.05 g, 5.106 mmol) and DMAP (0.16 g, 1.361 mmol) under nitrogen at room temperature. The resulting reaction mixture was stirred at room temperature for 16 h. Progress of reaction was monitored by TLC. After reaction completion reaction mass was filtered and the filtrate was concentrated under reduced pressure to give crude which was purified by column chromatography silica gel (100-200 Mesh) using 15% ethyl acetate in hexane as eluent to obtain mixture (1.2 g, 92.3%) of (2R)-(S)-1-(1-(5-ethylpyrimidin-2-yl)piperidin-4-yl)ethyl 2-methoxy-2-phenylacetate (52a) (peak-1) and (2R)-(R)-1-(1-(5-ethylpyrimidin-2-yl)piperidin-4-yl)ethyl 2-methoxy-2-phenylacetate (52b) (peak-2). The two diastereomer were separated by preparative Chiral HPLC to yield (0.37 g, 28.46%) and (0.41 g, 31.53%) of each diastereomer respectively.

MS: 384.3 [M$^+$+1].

Step 13: (S)-1-(1-(5-propylpyrimidin-2-yl) piperidin-4-yl) ethanol (53)

-continued

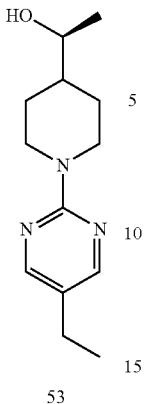

53

To a stirred solution of (2R)-(S)-1-(1-(5-ethylpyrimidin-2-yl) piperidin-4-yl) ethyl 2-methoxy-2-phenylacetate (52a) (0.37 g, 0.966 mmol) in MeOH (5 mL) was added $K_2CO_3$ (0.33 g, 2.415 mmol) in water (5 mL) at room temperature and the reaction mixture was heated at 45° C. for 48 h. Progress of reaction was monitored by TLC. After reaction completion reaction mass was diluted with water and extracted with ethyl acetate. The organic layer was washed with brine, dried over sodium sulphate and concentrated under reduced pressure to give crude product. Crude was purified by silica gel (100-200 mesh) column chromatography using 30% ethyl acetate in hexane as eluent to obtain (S)-1-(1-(5-ethylpyrimidin-2-yl)piperidin-4-yl)ethanol (53) (0.2 g, 88.1%) as off white solid. MS: 236.3 [M$^+$+1].

Step 14: 2-((S)-1-(1-(5-ethylpyrimidin-2-yl)piperidin-4-yl)ethoxy)-6-(2-fluoro-4-(methylthio)phenyl) imidazo[2,1-b][1,3,4]thiadiazole (54)

To a stirred soln. of (S)-1-(1-(5-ethylpyrimidin-2-yl)piperidin-4-yl)ethanol (53) (0.02 gm, 0.09 mmol) in DMF (3.0 ml), sodium hydride (0.005 gm, 0.13 mmol) at 0° C. and reaction allowed to run at 0° C. for 30.0 min. then 2-chloro-6-(2-fluoro-4-(methylthio)phenyl)imidazo[2,1-b][1,3,4] thiadiazole (41) (0.03 gm, 0.10 mmol) was added to reaction mixture and reaction continued at RT for next 4.0 h. Reaction was monitored by TLC. On completion reaction mixture was quenched with ice cold water and compound was extracted with ethyl acetate. The organic layer was washed with water, brine, dried over sodium sulphate and concentrated under reduced pressure to give crude desired product. Purification of the compound was done by silica gel (100-200 mess) column chromatography using 15% Acetone in hexane that was concentrated to get compound 2-((S)-1-(1-(5-ethylpyrimidin-2-yl)piperidin-4-yl)ethoxy)-6-(2-fluoro-4-(methylthio)phenyl)imidazo[2,1-b][1,3,4]thiadiazole (54) (0.017 gm, 40.13%) as white solid.

MS: 499.17 [M$^+$+1].

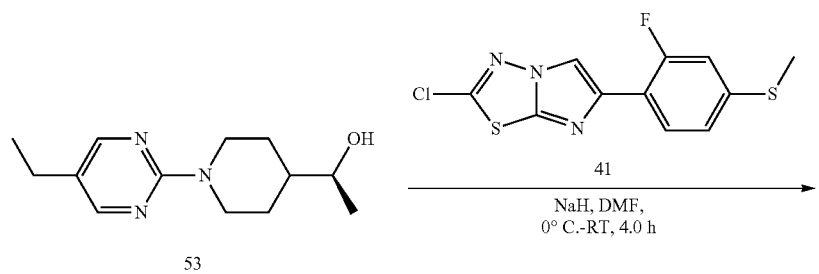

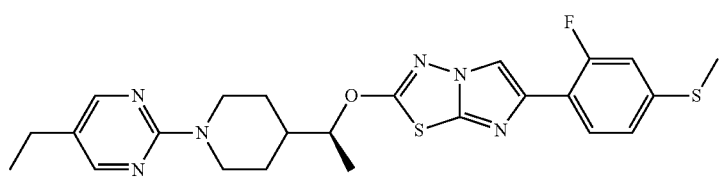

54

Step 15: 2-((S)-1-(1-(5-ethylpyrimidin-2-yl)piperidin-4-yl)ethoxy)-6-(2-fluoro-4-(methylsulfonyl)phenyl)imidazo[2,1-b][1,3,4]thiadiazole (1086)

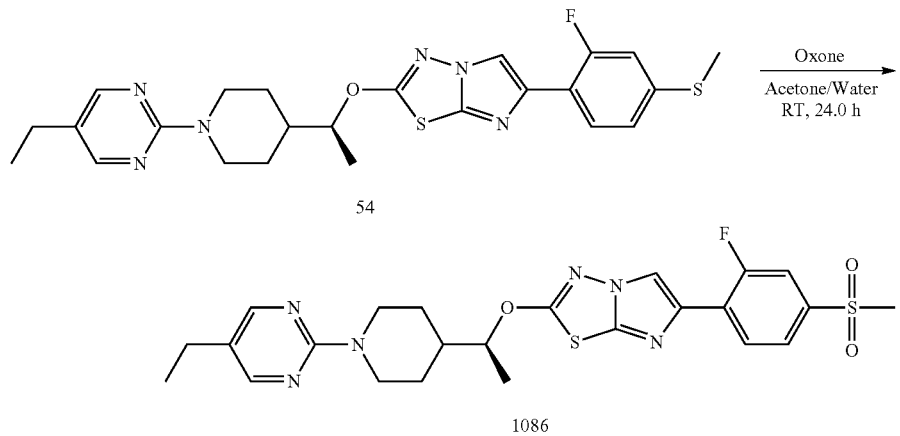

To a stirred solution of compound 2-((S)-1-(1-(5-ethylpyrimidin-2-yl)piperidin-4-yl)ethoxy)-6-(2-fluoro-4-(methylthio)phenyl)imidazo[2,1-b][1,3,4]thiadiazole (54) (0.017 gm, 0.03 mmol) in Acetone (3.0 ml), Oxone (0.03 gm, 0.09 mmol) in Water (0.7 ml) was added and reaction continued at RT for 24.0 h. Progress of reaction was monitored by TLC. On completion acetone was evaporated from reaction mixture and residue was quenched with water, compound was extracted with ethyl acetate. The organic layer was concentrated under reduced pressure to give crude desired compound. Purification of the compound was done by silica gel (100-200 mess) column chromatography using 15% Acetone in hexane that was concentrated to get compound 2-((S)-1-(1-(5-ethylpyrimidin-2-yl)piperidin-4-yl)ethoxy)-6-(2-fluoro-4-(methylsulfonyl)phenyl) imidazo[2,1-b][1,3,4]thiadiazole (1086) (0.016 gm, 88.45%) as white solid. MS: 531.3 [M$^+$+1].

Example 25: 2-((S)-1-(1-(5-ethylpyrimidin-2-yl) piperidin-4-yl)ethoxy)-6-(2-methoxypyridin-4-yl) imidazo[2,1-b][1,3,4]thiadiazole [1089]

Step 1: Synthesis of 3-fluoro-N-methoxy-N-methylpyridine-4-carboxamide

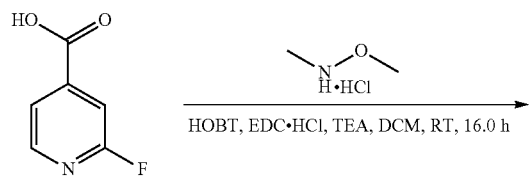

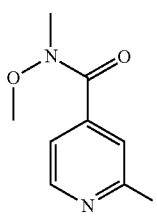

To a stirred solution of 3-fluoropyridine-4-carboxylic acid (1 g, 7.09 mmol) and N-methoxymethanamine hydrochloride (1 g, 10.63 mmol) in DCM (20 mL) was added EDCI (1.3 g, 10.63 mmol), HOBT (1.4 g, 10.63 mmol) and DIPEA (3.6 mL, 21.01 mmol) then reaction mixture was stirred at rt for 16 hr. Reaction was monitored by TLC. On completion reaction was quenched with water and reaction mixture extracted with ethyl acetate. Organic layer was washed with water, brine dried over sodium sulphate and concentrated under reduced pressure to give crude. Purification of the crude was done by silica gel (100-200 Mesh) column chromatography; eluent 1% EA/HEX give (1.2 g) (99%) 3-fluoro-N-methoxy-N-methylpyridine-4-carboxamide of as reddish colour sticky solid.

MS: 186[M$^+$+1]

Step 2: Synthesis of 1-(2-fluoropyridin-4-yl)ethanone

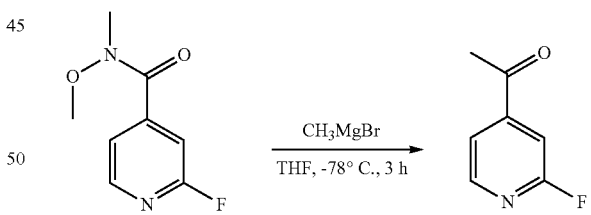

To a stirred solution of 3-fluoro-N-methoxy-N-methylpyridine-4-carboxamide (1.2 g, 0.65 mmol) in THF (15 mL) was added methyl magnesium bromide (2 M in THF) (16 mL, 32.5 mmol) at 0° C., after the addition the mixture was stirred at rt for 2 h. On completion reaction mixture was quenched with NH4Cl solution and reaction mixture was extracted with EtOAc. The organic layer was washed with water, brine, dried over Na$_2$SO$_4$ and evaporated under reduced pressure to give 0.650 gm. (92%) 1-(3-fluoropyridin-4-yl) ethanone as colourless oil

MS: 140.1[M$^+$+1]

Step 3: Synthesis of 1-(2-methoxypyridin-4-yl) ethanone

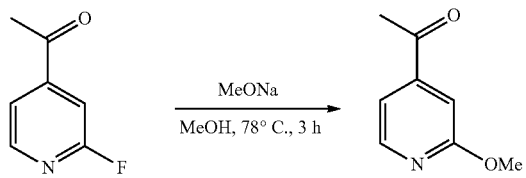

To a stirred solution of 1-(2-fluoropyridin-4-yl) ethanone (1.2 g, 0.65 mmol) in MeOH (15 mL) was added Sodium methoxide (1.6, 32.5 mmol) at 0° C., after the addition the mixture was stirred at 90° C. for 2 h. On completion reaction mixture was concentrated solution and reaction mixture was extracted with EtOAc. The organic layer was washed with water, brine, dried over $Na_2SO_4$ and evaporated under reduced pressure to give 0.650 gm. (92%) 1-(2-methoxy-pyridin-4-yl) ethanone as colourless oil

MS: 152.1[$M^+$+1]

Step 4: Synthesis of 2-bromo-1-(2-methoxypyridin-4-yl) ethanone

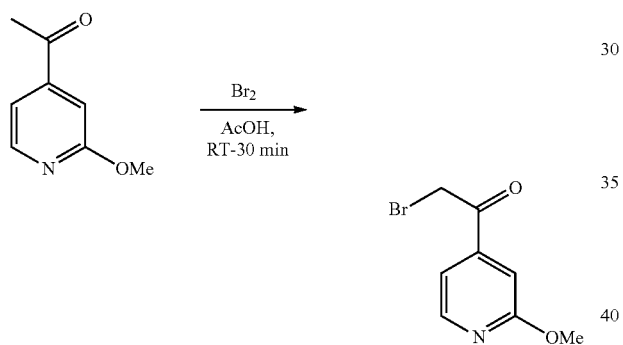

To a stirred solution of 1-(2-methoxypyridin-4-yl) ethanone (0.15 g, 1.07 mmol) in HBr:AcOH (10:5 mL) was added Br2 (0.052 mL, 1.07 mmol) in AcOH 1.0 mL) drop wise at 0° C. and stirred for 1 hr. Completion of reaction was monitored by TLC. Diethyl ether was added to reaction mass, solid precipitate out which was filtered off through Buchner funnel, solid was washed with diethyl ether, dried under vacuum to obtained pure product (0.2 g, 90%) 2-bromo-1-(2-methoxypyridin-4-yl)ethanone as yellow solid.

MS: 230.96[$M^+$+2]

Step 5: Synthesis of 2-bromo-6-(2-methoxypyridin-4-yl) imidazo [2,1-b][1,3,4]thiadiazole

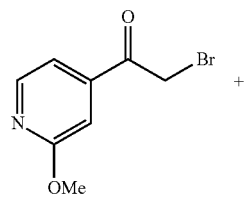

+

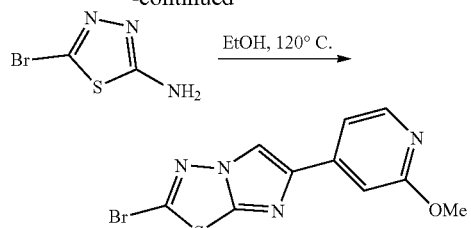

To a stirred solution of 2-bromo-1-(2-methoxypyridin-4-yl) ethanone (0.2 g, 0.92 mmol) in EtOH (10 mL) was added 5-bromo-1,3,4-thiadiazol-2-amine (0.2 g, 1.11 mmol) and heated at 120° C. for 12 hr. Completion of reaction was monitored by TLC. After 12 hr. of heating solid precipitate out at rt which was filtered off through Buchner funnel, solid product was washed with diethyl ether, dried under vacuum to obtained pure product 2-bromo-6-(2-methoxypyridin-4-yl)imidazo[2,1-b][1,3,4]thiadiazole (0.080 g, 28%) as light yellow solid.

MS: 311.95 [$M^+$+2]

Step 6: Synthesis of 2-((R)-1-(1-(5-ethylpyrimidin-2-yl)piperidin-4-yl)ethoxy)-6-(2-methoxypyridin-4-yl)imidazo[2,1-b][1,3,4]thiadiazole

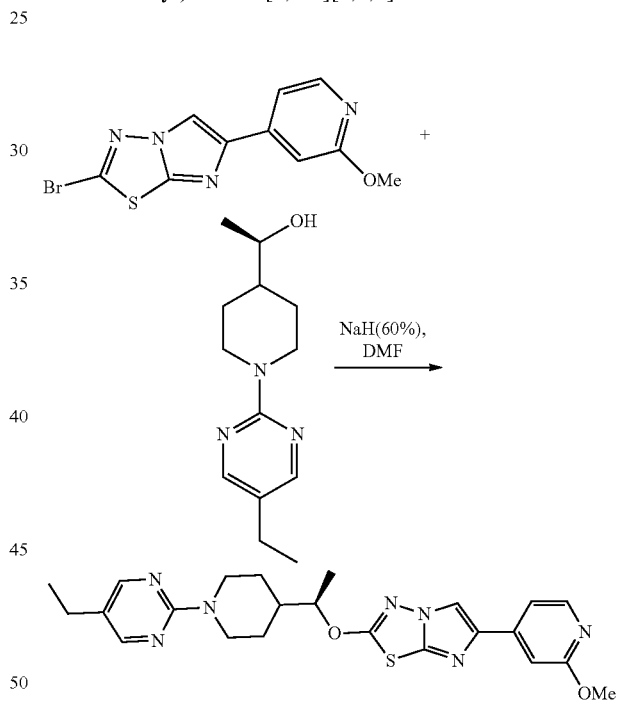

To(S)-1-(1-(3-isopropyl-1,2,4-oxadiazol-5-yl)piperidin-4-yl)ethanol (0.020 g, 0.15 mmol) in DMF (1 ml) was added sodium hydride (0.009 g, 0.23 mmol) at 0° C. and reaction allowed to run at 0° C. for 30 min. After 30 min 2-bromo-6-(3-fluoropyridin-4-yl)imidazo[2,1-b][1,3,4]thiadiazole (0.036 g, 0.15 mmol) in DMF (1 mL) was added to reaction mixture and reaction stirred at RT for 2 hr. Reaction was monitored by TLC. On completion, reaction was quenched with ice cold water (2 mL) and reaction mixture extracted with EtOAc. The organic layer was washed with water, brine, dried over Na2SO4, evaporated under reduced pressure to give crude desired product that was purified by silica gel (100 to 200 mesh) chromatography, eluent 1% MeOH/DCM to obtained pure product 2-((R)-1-(1-(3-isopropyl-1,2,4-oxadiazol-5-yl)piperidin-4-yl)ethoxy)-6-(3-fluoropyridin-4-yl)imidazo[2,1-b][1,3,4]thiadiazole (0.003 g, 27%) as off white solid.

MS: 466.23[$M^+$+1]

Example 26: 2-((S)-1-(1-(5-chloropyrimidin-2-yl) piperidin-4-yl)ethoxy)-6-(2-fluoro-4-(methylsulfonyl)phenyl)imidazo[2,1-b][1,3,4]thiadiazole [1090]

Step 1: Synthesis of 2-((S)-1-(1-(5-chloropyrimidin-2-yl)piperidin-4-yl)ethoxy)-6-(2-fluoro-4-(methylthio)phenyl)imidazo[2,1-b][1,3,4]thiadiazole

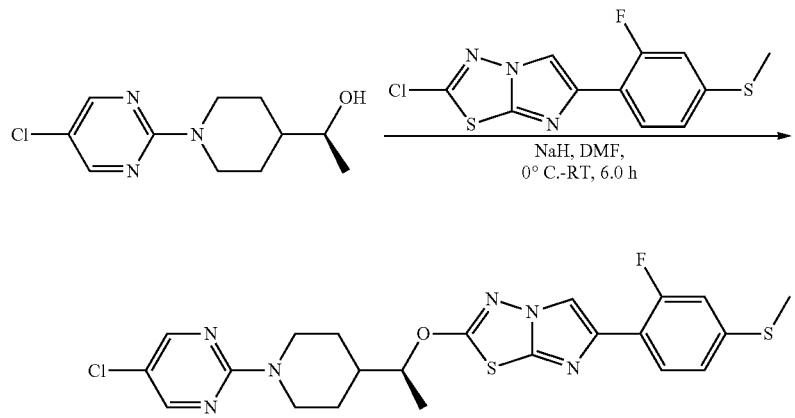

To a stirred soln. of (S)-1-(1-(5-chloropyrimidin-2-yl)piperidin-4-yl)ethanol (0.015 gm, 0.06 mmol) in DMF (2.0 ml), sodium hydride (0.004 gm, 0.09 mmol) at 0° C. and reaction allowed to run at 0° C. for 30.0 min. then 2-chloro-6-(2-fluoro-4-(methylthio)phenyl)imidazo[2,1-b][1,3,4] thiadiazole (0.023 gm, 0.07 mmol) was added to reaction mixture and reaction continued at RT for next 6.0 h. Reaction was monitored by TLC. On completion reaction mixture was quenched with ice cold water and compound was extracted with ethyl acetate. The organic layer was washed with water, brine, dried over sodium sulphate and concentrated under reduced pressure to give crude desired product. Purification of the compound was done by silica gel (100-200 mess) column chromatography using 15% Acetone in hexane that was concentrated to get compound 2-((S)-1-(1-(5-chloropyrimidin-2-yl)piperidin-4-yl)ethoxy)-6-(2-fluoro-4-(methylthio)phenyl)imidazo[2,1-b][1,3,4]thiadiazole (0.015 g, 47.83%) as light yellow semi solid.

MS: 505.10[M$^+$+1].

Step 2: Synthesis of 2-((S)-1-(1-(5-chloropyrimidin-2-yl)piperidin-4-yl)ethoxy)-6-(2-fluoro-4-(methylsulfonyl)phenyl)imidazo[2,1-b][1,3,4]thiadiazole

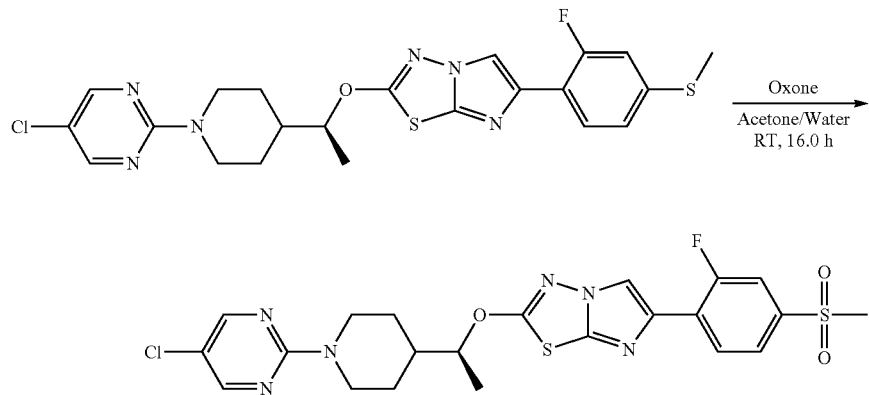

To a stirred soln. of compound 2-((S)-1-(1-(5-chloropyrimidin-2-yl)piperidin-4-yl)ethoxy)-6-(2-fluoro-4-(methylthio)phenyl)imidazo[2,1-b][1,3,4]thiadiazole (0.015 g, 0.03 mmol) in Acetone (3.0 ml), Oxone (0.018 g, 0.06 mmol) in water (0.7 ml) was added and reaction continued at RT for 16.0 h. Progress of reaction was monitored by TLC. On completion acetone was evaporated from reaction mixture and residue was quenched with water, compound was extracted with ethyl acetate. The organic layer was concentrated under reduced pressure to give crude desired compound. Purification of the compound was done by silica gel (100-200 mess) column chromatography using 15% Acetone in hexane that was concentrated to get compound 2-((S)-1-(1-(5-chloropyrimidin-2-yl)piperidin-4-yl)ethoxy)-6-(2-fluoro-4-(methylsulfonyl)phenyl)imidazo[2,1-b][1,3,4]thiadiazole (0.006 g, 37.62%) white solid.

MS: 537.09[M$^+$+1].

Example 27: 2-(1-(1-(3-isopropyl-1,2,4-oxadiazol-5-yl)piperidin-4-yl)ethoxy)-6-(2-(trifluoromethyl)-4-(methylsulfonyl)phenyl)imidazo[2,1-b][1,3,4]thiadiazole [1091]

Step 1:
1-(4-bromo-2-(trifluoromethyl)phenyl)ethanone

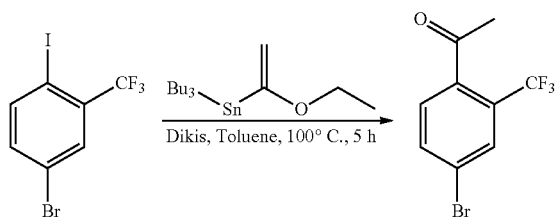

MS: 266.9 [M$^+$+1]

Step 2: 1-(2-(trifluoromethyl)-4-(methylthio)phenyl)ethanone

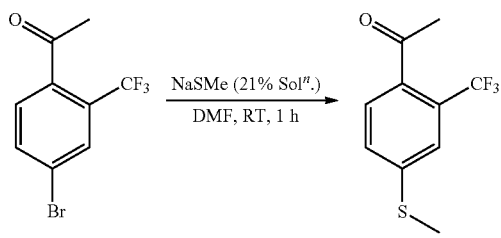

To a stirred solution of 1-(4-bromo-2-(trifluoromethyl)phenyl)ethanone (0.630 g, 2.359 mmol) in DMF (10 mL) was added 21% aq. solution of sodium thiomethoxide (0.215 mg, 3.06 mmol) at 0° C. and stirred for 1 h at room temperature. Progress of reaction was monitored by TLC. On completion, D.M. water was added to reaction mixture and extracted with EtOAc. Organic layers were combined, dried over sodium sulphate and concentrated under reduced pressure to give crude product. Crude product was purified by column chromatography using (silica gel, 100-200 mesh, 0-8% EtOAc in hexane as eluent) to give 1-(2-(trifluoromethyl)-4-(methylthio)phenyl)ethanone (0.4 g, 72.4%) as yellow oil.

MS: 235.03 [M$^+$+1]

Step-3:2-bromo-1-(2-(trifluoromethyl)-4-(methylthio)phenyl)ethanone

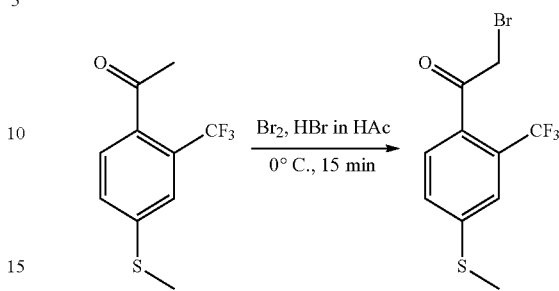

To a stirred solution of 1-(2-(trifluoromethyl)-4-(methylthio)phenyl)ethanone (0.250 g, 1.068 mmol) in acetic acid (5 mL) was added solution of bromine (0.154 g, 0.961 mmol) in 47% HBr in acetic acid (0.8 mL) at 0° C. and stirred for 15 min. Progress of reaction was monitored by TLC. On completion, cold D.M. water was added to reaction mixture and extracted with Diethyl ether. Organic layers were combined, dried over sodium sulphate and concentrated under reduced pressure to give 2-bromo-1-(2-(trifluoromethyl)-4-(methylthio)phenyl)ethanone (0.32 g, 95.69%) as Brown gum.

MS: 312.9 [M$^+$+1]

Step-4:2-chloro-6-(2-(trifluoromethyl)-4-(methylthio)phenyl)imidazo[2,1-b][1,3,4]thiadiazole

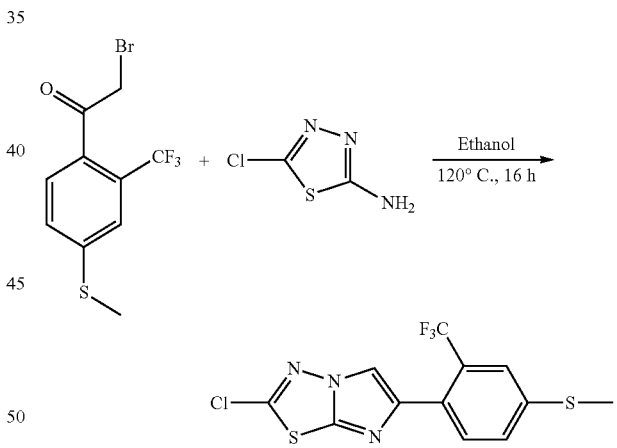

Solution of 2-bromo-1-(2-(trifluoromethyl)-4-(methylthio)phenyl)ethanone (0.320 g, 1.022 mmol) and 5-chloro-1,3,4-thiadiazol-2-amine (0.138 g, 1.022 mmol) in ethanol (10 mL) was heated to 120° C. for 16 h in a sealed tube. Progress of reaction was monitored by TLC. After reaction completion reaction mixture was concentrated to dryness. D.M. water was added to reaction mixture and extracted with EtOAc. Organic layers were combined, washed with brine, dried over sodium sulphate and concentrated under reduced pressure to give crude product. Crude product was purified by column chromatography using (silica gel, 100-200 mesh, 0-2% MeOH in DCM as eluent) to give 2-chloro-6-(2-(trifluoromethyl)-4-(methylthio)phenyl)imidazo[2,1-b][1,3,4]thiadiazole (0.028 g, 7.94%) as brown solid.

MS: 349.9 [M$^+$+1]

Step 5: 2-(1-(1-(3-isopropyl-1,2,4-oxadiazol-5-yl)
piperidin-4-yl)ethoxy)-6-(2-(trifluoromethyl)-4-
(methylthio)phenyl)imidazo[2,1-b][1,3,4]thiadiazole

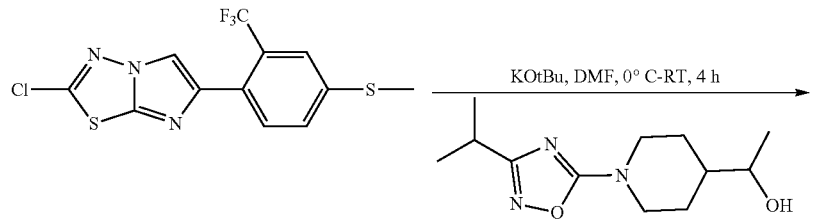

To a stirred solution of 1-(1-(3-isopropyl-1,2,4-oxadiazol-5-yl)piperidin-4-yl)ethanol (0.015 g, 0.063 mmol) in DMF (3 mL) was added KOtBu (0.010 g, 0.094 mmol) at 0° C. and stirred for 45 min at 0° C. Then to it, solution of 2-chloro-6-(2-(trifluoromethyl)-4-(methylthio)phenyl)imidazo[2,1-b][1,3,4] thiadiazole (0.022 g, 0.063 mmol) in DMF (1 mL) was added to the reaction mixture and stirred for 4 h at room temperature. Progress of reaction was monitored by TLC. After completion of reaction mass was quenched with ice cold water and extracted with ethyl acetate. The organic layer was washed with water, dried over sodium sulphate and concentrated under reduced pressure to give crude product which was purified by column chromatography using (silica gel, 100-200 mesh, 0-2% MeOH in DCM as eluent) to give 2-(1-(1-(3-isopropyl-1,2,4-oxadiazol-5-yl)piperidin-4-yl)ethoxy)-6-(2-(trifluoromethyl)-4 (methylthio)phenyl)imidazo[2,1-b][1,3,4]thiadiazole (0.012 g, 34.2%) as colourless gum.

MS: 513.16 [M⁺+1]

Step 6: 2-(1-(1-(3-isopropyl-1,2,4-oxadiazol-5-yl)
piperidin-4-yl)ethoxy)-6-(2-(trifluoromethyl)-4-
(methylsulfonyl)phenyl)imidazo[2,1-b][1,3,4]thiadi-
azole To a stirred solution of 2-(1-(1-(3-isopropyl-1,2,4-oxadiazol-5-yl)piperidin-4-yl)ethoxy)-6-(2-(trifluoromethyl)-4 (methylthio)phenyl)imidazo[2,1-b][1,3,4]thiadiazole (0.012 g, 0.021 mmol) in acetone (8 mL) and water (2 mL) was added oxone (0.020 g, 0.065 mmol) and the mixture was stirred at room temperature for 16 h and then heated at 40° C. for 3 h. Progress of reaction was monitored by TLC. D.M. water was added to reaction mixture and extracted with EtOAc. Organic layers were combined, washed with brine, dried over sodium sulphate and concentrated under reduced pressure to give crude product. Crude product was purified by column chromatography using (silica gel, 100-200 mesh, 0-2% MeOH in DCM as eluent) followed by (Neutral alumina, 0-4% Acetone:DCM as eluent) to give 2-(1-(1-(3-isopropyl-1,2,4-oxadiazol-5-yl)piperidin-4-yl)ethoxy)-6-(2-(trifluoromethyl)-4-(methylsulfonyl) phenyl)imidazo[2,1-b][1,3,4]thiadiazole (0.002 g, 14.97%) as off white sticky solid.

MS: 553.16 [M⁺+1]

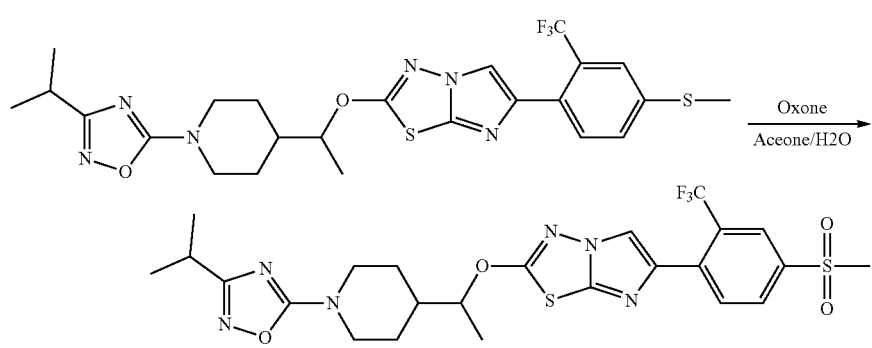

Example 28: 4-(2-((S)-1-(1-(5-ethylpyrimidin-2-yl)piperidin-4-yl)ethoxy)imidazo[2,1-b][1,3,4]thiadiazol-6-yl)-1-methylpyridin-2(1H)-one [1096]

Step 1: Synthesis of 4-(2-((S)-1-(1-(5-ethylpyrimidin-2-yl) piperidin-4-yl) ethoxy) imidazo[2,1-b][1,3,4]thiadiazol-6-yl)-1-methylpyridin-2(1H)-one

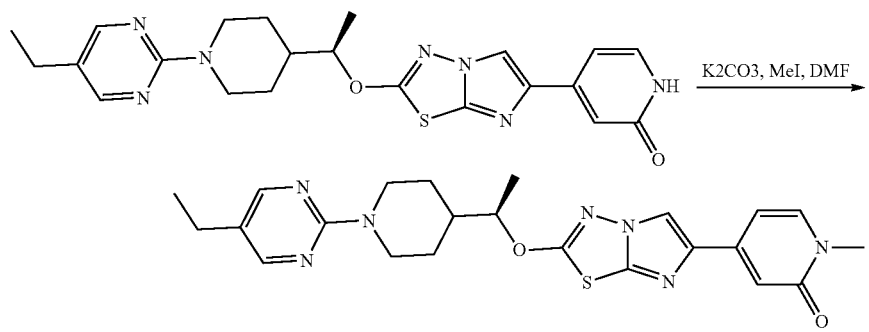

To a stirred soln. 4-(2-((S)-1-(1-(5-ethylpyrimidin-2-yl)piperidin-4-yl)ethoxy)imidazo[2,1-b][1,3,4]thiadiazol-6-yl)pyridin-2(1H)-one (0.015 gm, 0.0655 mmol) in DMF (3.0 ml), potassium carbonate (0.006 gm, 0.15 mmol) at 0° C. and reaction allowed to run at 0° C. for 30.0 min. then Me (0.021 gm, 0.720 mmol) followed by 18 crown 6 (catalytic) was added to reaction mixture and reaction continued at RT for next 5.0 h. Reaction was monitored by TLC. On completion reaction mixture was quenched with water and compound was extracted with ethyl acetate. The organic layer was washed with water, brine, dried over sodium sulphate and concentrated under reduced pressure to give crude desired product. Purification of the compound was done by silica gel (100-200 mess) column chromatography using 15% Acetone in hexane that was concentrated to get compound 4-(2-((S)-1-(1-(5-ethylpyrimidin-2-yl)piperidin-4-yl)ethoxy)imidazo[2,1-b][1,3,4]thiadiazol-6-yl)-1-methylpyridin-2(1H)-one (0.015 gm, 32.50%) as Greenish colour solid.
MS: 465.23 [M$^+$+1]

Example 29: 2-((S)-1-(1-(5-(trifluoromethyl)pyrimidin-2-yl)piperidin-4-yl)ethoxy)-6-(2-fluoro-4-(methylsulfonyl)phenyl)imidazo[2,1-b][1,3,4]thiadiazole [1098]

Step 1: Synthesis of 2-((S)-1-(1-(5-(trifluoromethyl)pyrimidin-2-yl)piperidin-4-yl)ethoxy)-6-(2-fluoro-4-(methylthio)phenyl)imidazo[2,1-b][1,3,4]thiadiazole

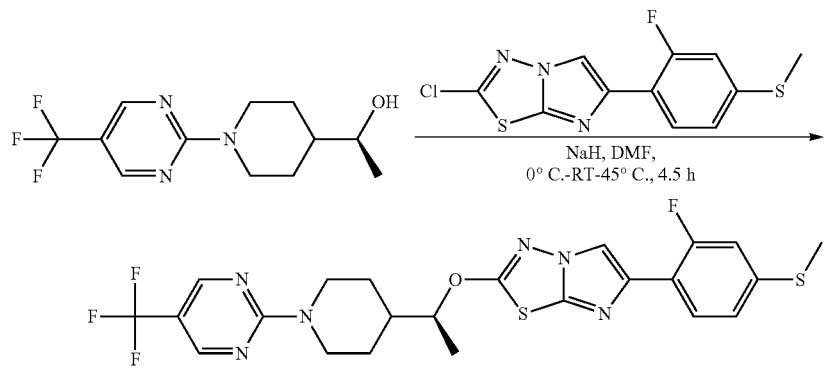

To a stirred soln. of (S)-1-(1-(5-(trifluoromethyl)pyrimidin-2-yl)piperidin-4-yl)ethanol (0.015 gm, 0.05 mmol) in DMF (2.0 ml), sodium hydride (0.012 gm, 0.33 mmol) at 0° C. and reaction allowed to run at 0° C. for 30.0 min. then 2-chloro-6-(2-fluoro-4-(methylthio)phenyl)imidazo[2,1-b][1,3,4]thiadiazole (0.026 gm, 0.09 mmol) was added to reaction mixture and reaction continued at RT to 45° C. for next 4.0 h. Reaction was monitored by TLC. On completion reaction mixture was quenched with ice cold water and compound was extracted with ethyl acetate. The organic layer was washed with water, brine, dried over sodium sulphate and concentrated under reduced pressure to give crude desired product. Purification of the compound was done by silica gel (100-200 mess) column chromatography using 15% Acetone in hexane that was concentrated to get compound 2-((S)-1-(1-(5-(trifluoromethyl)pyrimidin-2-yl)piperidin-4-yl)ethoxy)-6-(2-fluoro4(methylthio)phenyl)imidazo[2,1-b][1,3,4]thiadiazole (0.015 gm, 51.12%) as light yellow semisolid.

MS: 539.66 [M$^+$+1].

Step 2: Synthesis of 2-((S)-1-(1-(5-(trifluoromethyl)pyrimidin-2-yl)piperidin-4-yl)ethoxy)-6-(2-fluoro-4-(methylsulfonyl)phenyl)imidazo[2,1-b][1,3,4]thiadiazole (MKP10275.01).

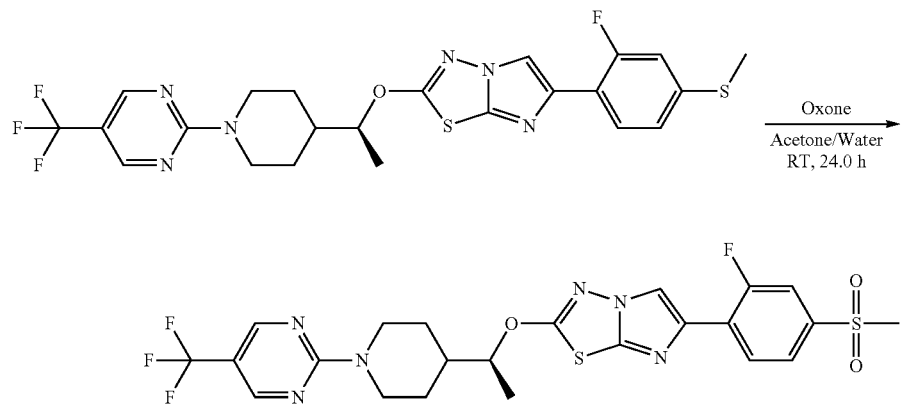

To a stirred soln. of compound 2-((S)-1-(1-(5-(trifluoromethyl)pyrimidin-2-yl)piperidin-4-yl)ethoxy)-6-(2-fluoro-4-(methylthio)phenyl)imidazo[2,1-b][1,3,4]thiadiazole (0.015 g, 0.03 mmol) in Acetone (4.0 ml), Oxone (0.017 g, 0.06 mmol) in water (0.5 ml) was added and reaction continued at RT for 24.0 h. Progress of reaction was monitored by TLC. On completion acetone was evaporated from reaction mixture and residue was quenched with water, compound was extracted with ethyl acetate. The organic layer was concentrated under reduced pressure to give crude desired compound. Purification of the compound was done by silica gel (100-200 mess) column chromatography using 20% Acetone in hexane that was concentrated to get compound 2-((S)-1-(1-(5-(trifluoromethyl)pyrimidin-2yl)piperidin4yl)ethoxy)6(2fluoro4(methylsulfonyl)phenyl)imidazo[2,1-b][1,3,4]thiadiazole (0.01 g, 62.93%) white solid.

MS: 571.73[M$^+$+1].

Example 30: 4-(2-((S)-1-(1-(3-isopropyl-1,2,4-oxadiazol-5-yl)piperidin-4-yl)ethoxy)imidazo[2,1-b][1,3,4]thiadiazol-6-yl)-3-fluorobenzonitrile [1099]

Step 1: Synthesis of 4-amino-3-fluorobenzonitrile

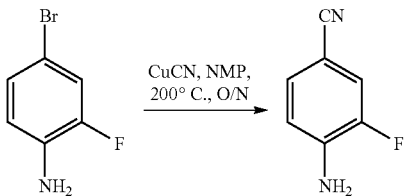

To a solution of 4-bromo-2-fluorobenzenamine (3 g, 15.789 mmol) in NMP (6 mL) was added copper cyanide (2.8 g, 31.578 mmol) and heated overnight at 2000° C. in a sealed tube. Progress of reaction was monitored by TLC. After reaction completion 1,2-diaminoethane (3 mL) and reaction mixture was poured into water. Product was extracted with ethyl acetate and washed with 10% 1,2-diaminoethane solution in water and then with water. Organic layer was dried over sodium sulphate, concentrated under reduced pressure. Crude was purified by silica (100-200) column chromatography using 15% ethyl acetate in hexane as eluent to give 4-amino-3-fluorobenzonitrile (1.6 g, 74.76%) as white solid.

MS: 137.1 [M+1]

Step 2: Synthesis of 4-bromo-3-fluorobenzonitrile

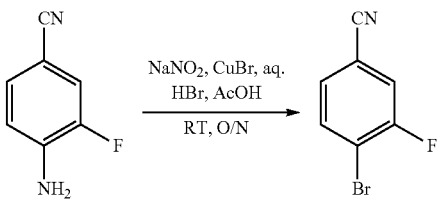 [SMILES: N#Cc1ccc(N)c(F)c1 ; N#Cc1ccc(Br)c(F)c1]

To conc. sulphuric acid (6 mL) was added sodium nitrite (0.97 g, 14.117 mmol) portion wise at 5° C. and stirred for 30 min at RT. Mixture was cooled to 0° C. and acetic acid (9.8 mL) was added dropwise, stirred for 5 min and then 4-amino-3-fluorobenzonitrile (1.6 g, 11.764 mmol) was added in small portions. Mixture was stirred for 1 h at RT. Solution of copper (I) bromide (2.5 g, 17.647 mmol) in aq. HBr (6 mL) was then added at 10° C. The resulting mixture was stirred overnight at RT. Progress of reaction was monitored by TLC. After reaction completion water was added and extracted with diethyl ether. The organic layer was dried over sodium sulphate and concentrated under reduced pressure. Crude was purified by silica (100-200) column chromatography using 2% ethyl acetate in hexane as eluent to give 4-bromo-3-fluorobenzonitrile (0.8 g, 34.7%) as white solid.
MS: 201.1 [M+1]

Step 3: Synthesis of 4-acetyl-3-fluorobenzonitrile

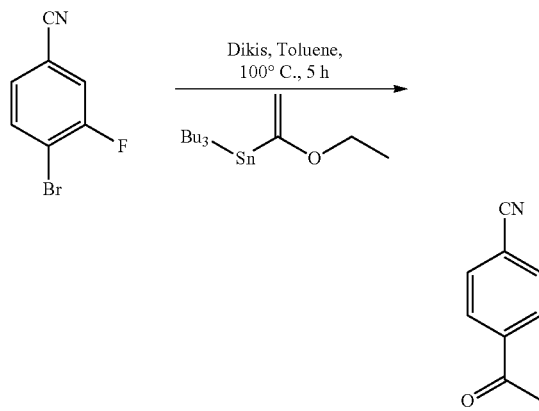

To a stirred solution of 4-bromo-3-fluorobenzonitrile (0.5 g, 2.512 mmol) in toluene (5 mL) was added tributyl(1-ethoxyvinyl)stannane (0.99 g, 2.763). Dikis (0.088 g, 0.125 mmol) was added after degassing the mixture for 30 min. with nitrogen. The resulting mixture was then heated to 110° C. for 4 h. Progress of reaction was monitored by TLC. After reaction completion water (5 mL) was added to the reaction mixture and the product extracted with ethyl acetate. The organic layer was dried over sodium sulphate, concentrated under reduced pressure. Crude was purified by silica (100-200) column chromatography using 2% ethyl acetate in hexane as eluent to give 4-acetyl-3-fluorobenzonitrile (0.3 g, 70.5%) as white solid.
MS: 164.1 [M+1]

Step 4: Synthesis of 4-(2-bromoacetyl)-3-fluorobenzonitrile

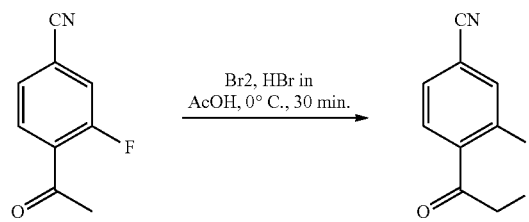

To a stirred solution of 4-acetyl-3-fluorobenzonitrile (0.3 g, 1.84 mmol) in 47% HBr in acetic acid (3 mL) was added solution of bromine (0.26 g, 1.656 mmol) in 47% HBr in acetic acid (0.3 mL) at 0° C. and stirred for 15 min. Progress of reaction was monitored by TLC. After reaction completion added water and product extracted with ethyl acetate. Organic washed with saturated aq. solution of sodium bicarbonate, dried over sodium sulphate and concentrated to give 4-(2-bromoacetyl)-3-fluorobenzonitrile (0.3 g, 67.4%) as yellow solid.
MS: 243.08 [M+1]

Step 5: Synthesis of 4-(2-chloroimidazo[2,1-b][1,3,4]thiadiazol-6-yl)-3-fluorobenzonitrile

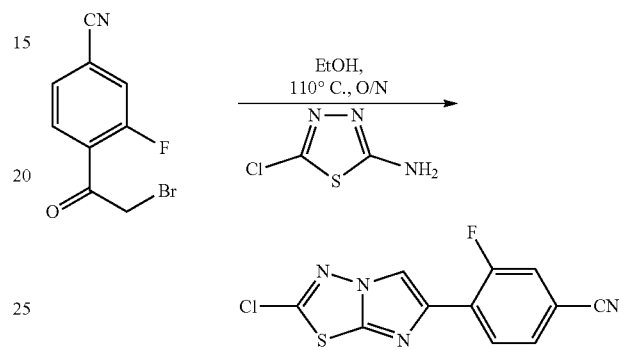

Solution of 4-(2-bromoacetyl)-3-fluorobenzonitrile (0.3 g, 1.239 mmol) and 5-chloro-1,3,4-thiadiazol-2-amine (0.13 g, 0.991 mmol) in ethanol (3 mL) was heated to 110° C. for 16 h in a sealed tube. Progress of reaction was monitored by TLC. After reaction completion reaction mixture was concentrated to dryness. Crude was purified by silica (100-200) column chromatography using 70% DCM/hexane to DCM as eluent to give 4-(2-chloroimidazo[2,1-b][1,3,4]thiadiazol-6-yl)-3-fluorobenzonitrile (0.15 g, 43.6%) as white solid.
MS: 279.6 [M+1]

Step 6: Synthesis of 4-(2-((S)-1-(1-(3-isopropyl-1,2,4-oxadiazol-5-yl)piperidin-4-yl)ethoxy)imidazo[2,1-b][1,3,4]thiadiazol-6-yl)-3-fluorobenzonitrile

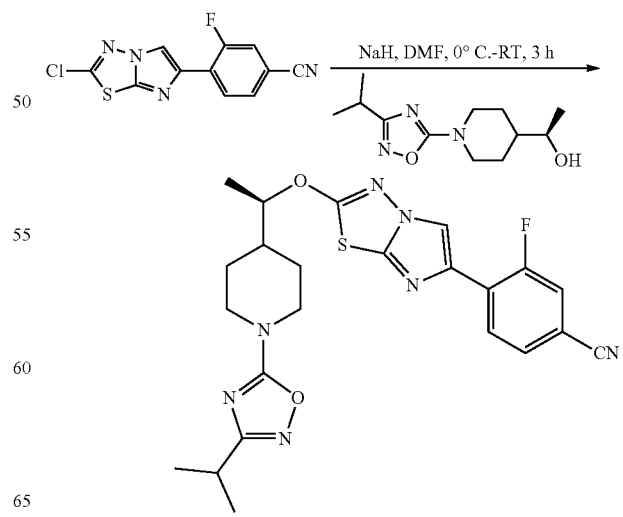

To a stirred solution of (R)-1-(1-(3-isopropyl-1,2,4-oxadiazol-5-yl)piperidin-4-yl)ethanol (0.02 g, 0.089 mmol) in DMF (3 mL) was added sodium hydride (0.0072 g, 0.179 mmol) at 0° C. and stirred for 30 min at room temperature. After 30 min solution of 4-(2-chloroimidazo[2,1-b][1,3,4] thiadiazol-6-yl)-3-fluorobenzonitrile (0.025 g, 0.089 mmol) in DMF (2 mL) was added to the reaction mixture and stirred for 3 h. Progress of reaction was monitored by TLC. After completion reaction mass was quenched with ice cold water and extracted with ethyl acetate. The organic layer was washed with water, brine, dried over sodium sulphate and concentrated under reduced pressure to give crude product. Crude was purified by neutral alumina column chromatography using 10% acetone in hexane as eluent to give 4-(2-((R)-1-(1-(3-isopropyl-1,2,4-oxadiazol-5-yl)piperidin-4-yl)ethoxy)imidazo[2,1-b][1,3,4]thiadiazol-6-yl)-3-fluorobenzonitrile (0.004 g, 9.23%) as white solid.

MS: 482.5 [M+1]

Example 31: 2-((S)-1-(1-(3-isopropyl-1,2,4-oxadiazol-5-yl)piperidin-4-yl)ethoxy)-6-(2-fluoro-6-(methylsulfonyl)pyridin-3-yl)imidazo[2,1-b][1,3,4]thiadiazole 1100]

Step-1: Synthesis of 2-fluoro-6-(methylthio)pyridine

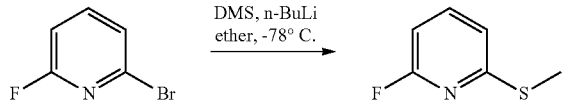

To a stirred solution of 2-bromo-6-fluoropyridine (0.1 g, 0.69 mmol) in ether (03 mL), n-BuLi (2.5 M) (0.29 mL, 0.74 mmol) was added dropwise at −78° C. and stirred for 30 min. To resultant reaction mixture, DMDS (dimethyl disulphide) (0.129 g, 0.72 mmol) was added and stirred for 2 h at RT. Completion of reaction was monitored by TLC. On completion, quenched with ice water, extracted with ether. The organic layer was washed with water, brine, dried over sodium sulphate, concentrated under reduced pressure obtained crude reaction mass. Purification of the crude was done via silica gel (100-200 Mesh) column chromatography and desired compound eluted at 10% ether/n-Hexane to obtained 2-fluoro-6-(methylthio)pyridine (0.05 g, 60.97%) as colourless oily mass.

MS: 144.2 [M+1]

Step-2: Synthesis of 3-bromo-2-fluoro-6-(methylthio) pyridine

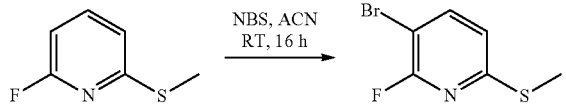

To a stirred solution of 2-fluoro-6-(methylthio)pyridine (0.05 g, 0.34 mmol) in ACN (2.5 mL), NBS (0.074 g, 0.41 mmol) was added portion-wise at −0° C. and allow to stirred for 30 min. Resultant reaction mass was then placed at RT and stirred for 16 h. Completion of reaction was monitored by TLC. On completion, concentrated under reduced pressure to obtained crude mass. Purification of the crude was done via silica gel (100-200 Mesh) column chromatography and desired compound eluted at 5% ether/n-Hexane to obtained 3-bromo-2-fluoro-6-(methylthio)pyridine (0.26 g, 33.76%) as colourless oily mass.

MS: 222.1 [M+1]

Step-3: Synthesis of 1-(2-fluoro-6-(methylthio) pyridin-3-yl)ethanone

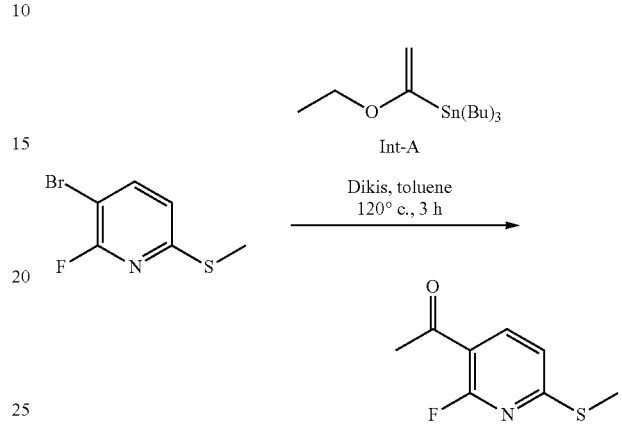

To a stirred solution of 3-bromo-2-fluoro-6-(methylthio) pyridine (0.10 g, 0.45 mmol) in dry toluene (10 mL), Int-A (0.21 g, 0.58 mmol) was added and purged with nitrogen for 30 min. To resultant reaction mixture Dikis (0.0015 g, 0.0062 mmol) was added and stirred at 120° C. for 3 h. Completion of reaction was monitored by TLC. On completion, quenched with ice water, extracted with ether. The organic layer was washed with water, brine, dried over sodium sulphate, concentrated under reduced pressure obtained crude. Purification of the crude was done via silica gel (100-200 Mesh) column chromatography and desired compound eluted at 1.5% ethyl acetate/n-Hexane to obtained 1-(2-fluoro-6-(methylthio)pyridin-3-yl)ethanone (0.040 g, 47.99%) as off white solid.

MS: 186.1 [M+1]

Step-4: Synthesis of 2-bromo-1-(2-fluoro-6-(methylthio)pyridin-3-yl)ethanone

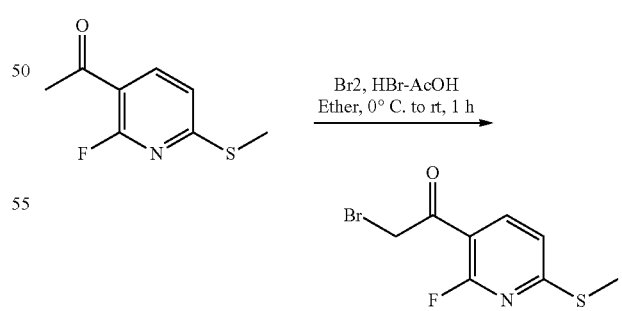

To a stirred solution of 1-(2-fluoro-6-(methylthio) pyridin-3-yl)ethanone (0.020 g, 0.10 mmol) in ether (2 mL), HBr—AcOH (0.5 mL) was added. To resultant reaction mass Br2 (diluted in 0.5 mL HBr—AcOH) (0.015 g, 0.097 mmol) was added at 0° C. and stirred for 30 min. Allow temp. to increase gradually to RT. Completion of reaction was monitored by TLC. On completion, quenched with ice water, extracted with ether. The organic layer was washed with aqueous-bicarbonate, brine, dried over sodium sulphate, concentrated under reduced pressure obtained 2-bromo-1-(2-fluoro-6-(methylthio)pyridin-3-yl)ethanone (0.004 g, 13.7%) as semisolid brownish gummy mass.

MS: 264.3 [M+1]

Step-5: Synthesis of 2-chloro-6-(2-fluoro-6-(methylthio)pyridin-3-yl) imidazo [2,1-b] [1,3,4] thiadiazole

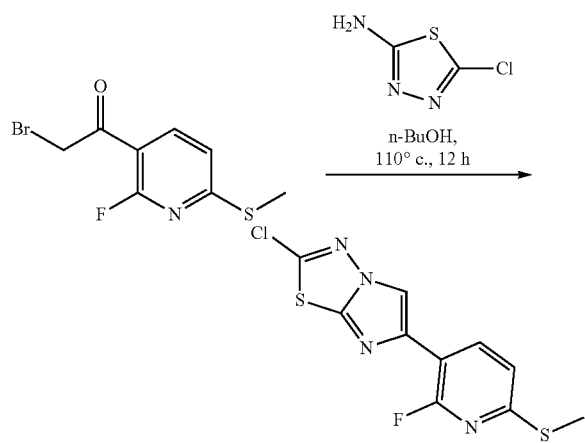

To a stirred solution of 5-amino-2-chloro-1,3,4-thiadiazole (0.135 g, 0.60 mmol) and 2-bromo-1-(2-fluoro-6-(methylthio)pyridin-3-yl)ethanone (0.20 g, 0.75 mmol) in n-BuOH (3 mL), heated at 110° C. for 16 h. After cooled to room temperature, concentrated under reduced pressure to obtained crude mass. Purification of the crude was done via silica gel (100-200 Mesh) column chromatography and desired compound eluted at 3% ethyl acetate/n-Hexane to obtained 2-chloro-6-(2-fluoro-6-(methylthio)pyridin-3-yl) imidazo [2,1-b] [1,3,4] thiadiazole (0.05 g, 22.0%) as off white solid (1.2 g, 60.60%) as off white solid.

MS: 300 [M+1]

Step-6: Synthesis of 2-((S)-1-(1-(3-isopropyl-1,2,4-oxadiazol-5-yl)piperidin-4-yl)ethoxy)-6-(2-fluoro-6-(methylthio)pyridin-3-yl)imidazo[2,1-b][1,3,4]thiadiazole

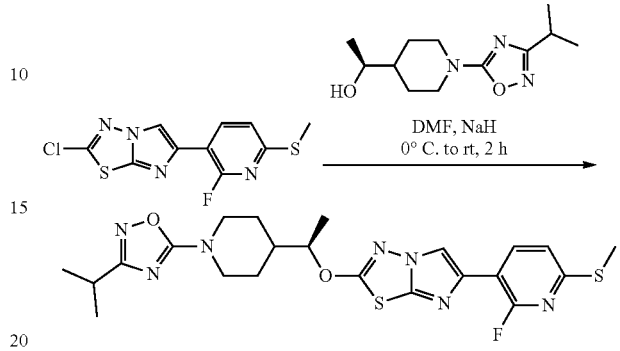

To a stirred solution of (S)-1-(1-(3-isopropyl-1,2,4-oxadiazol-5-yl)piperidin-4-yl)ethanol (0.021 g, 0.09 mmol) in DMF (3 mL), NaH (0.010 g, 0.27 mmol) was added at 0° C. and stirred for 1 h. To resultant reaction mass, 2-chloro-6-(2-fluoro-6-(methylthio)pyridin-3-yl) imidazo [2,1-b] [1,3,4] thiadiazole (0.03 g, 0.1 mmol) was added and stirred for 1 h at RT. Reaction was monitored by TLC. On completion, quenched with water, extracted with ethyl acetate. The organic layer was washed with water, brine, dried over sodium sulphate, concentrated under reduced pressure obtained crude. Purification of the crude was done via silica gel (100-200 Mesh) column chromatography and desired compound eluted at 12% acetone/n-Hexane to obtained 2-((S)-1-(1-(3-isopropyl-1,2,4-oxadiazol-5-yl)piperidin-4-yl)ethoxy)-6-(2-fluoro-6-(methylthio)pyridin-3-yl)imidazo [2,1-b][1,3,4]thiadiazole (0.025 g, 49.51%) as off white solid.

MS: 504.75 [M$^+$+1]

Step-7: Synthesis of 2-((S)-1-(1-(3-isopropyl-1,2,4-oxadiazol-5-yl)piperidin-4-yl)ethoxy)-6-(2-fluoro-6-(methylsulfonyl)pyridin-3-yl)imidazo[2,1-b][1,3,4]thiadiazole

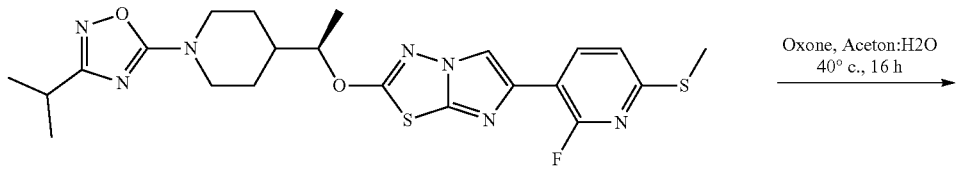

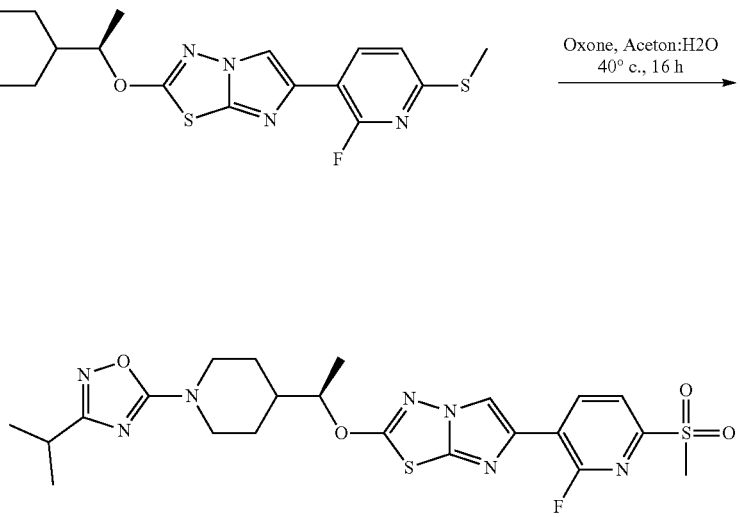

To a stirred solution of 2-((S)-1-(1-(3-isopropyl-1,2,4-oxadiazol-5-yl) piperidin-4-yl)ethoxy)-6-(2-fluoro-6-(methylthio)pyridin-3-yl)-5,6-dihydroimidazo [2,1-b][1,3,4]thiadiazole (0.025 g, 0.04 mmol) in Acetone:H₂O (15:05 mL), oxone (0.045 g, 0.14 mmol) was added at rt and stirred for 30 min. After 30 min, place reaction mass at 40° C. and stirred for 16 h. Reaction was monitored by TLC. On completion, quenched with ice cold water, extracted with ethyl acetate. The organic layer was washed with water, brine, dried over sodium sulphate, concentrated under reduced pressure obtained crude desired product which was purified via silica gel (100 to 200 Mesh) column chromatography and desired compound eluted at 20% acetone/DCM obtained 2-((S)-1-(1-(3-isopropyl-1,2,4-oxadiazol-5-yl)piperidin-4-yl)ethoxy)-6-(2-fluoro-6-(methylsulfonyl)pyridin-3-yl) imidazo[2,1-b][1,3,4] thiadiazole (0.007 g, 16.66%) as white solid.

MS: 535.9 [M⁺+1]

Example 32: Isopropyl 4-(1-(6-(2-fluoro-4-(methylsulfonyl)phenyl)imidazo[2,1-b][1,3,4]thiadiazol-2-yloxy)ethyl)piperidine-1-carboxylate [1101]

Step 1: Synthesis of isopropyl 4-(1-hydroxyethyl)piperidine-1-carboxylate

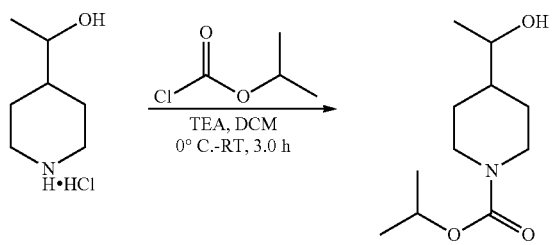

To a stirred soln. of compound 1-(piperidin-4-yl)ethanol hydrochloride (0.2 gm, 1.55 mmol) in DCM (5.0 ml), Triethylamine (0.64 ml, 4.65 mmol) was added at 0° C. and reaction allowed to run at same temperature for 0.5 h, then followed by 2.0 M isopropyl chloroformate (0.77 ml, 1.55 mmol) and reaction further continued for next 3.0 h at RT. Reaction was monitored by TLC. On completion reaction mixture was quenched with ice cold water and compound was extracted with DCM. The organic layer was washed with water, brine, dried over sodium sulphate and concentrated under reduced pressure to give crude desired product. Purification of the compound was done by silica gel (100-200 mess) column chromatography using 20% Acetone in hexane, that was concentrated to get compound isopropyl 4-(1-hydroxyethyl)piperidine-1-carboxylate (0.12 gm, 36.01%) as light yellow semi solid.

MS: 216.1[M⁺+1].

Step 2: Synthesis of isopropyl 4-(1-(6-(2-fluoro-4-(methylthio)phenyl)imidazo[2,1-b][1,3,4]thiadiazol-2-yloxy)ethyl)piperidine-1-carboxylate

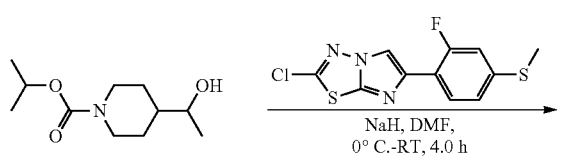

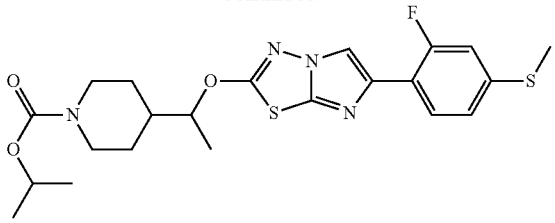

To a stirred soln. of isopropyl 4-(1-hydroxyethyl)piperidine-1-carboxylate (0.025 g, 0.12 mmol) in DMF (3.0 ml), sodium hydride (0.007 g, 0.17 mmol) at 0° C. and reaction allowed to run at 0° C. for 30.0 min. then 2-chloro-6-(2-fluoro-4-(methylthio)phenyl)imidazo[2,1-b][1,3,4]thiadiazole (0.042 g, 0.14 mmol) was added to reaction mixture and reaction continued at RT for next 4.0 h. Reaction was monitored by TLC. On completion reaction mixture was quenched with ice cold water and compound was extracted with ethyl acetate. The organic layer was washed with water, brine, dried over sodium sulphate and concentrated under reduced pressure to give crude desired product. Purification of the compound was done by silica gel (100-200 mesh) column chromatography using 15% Acetone in hexane that was concentrated to get compound isopropyl 4-(1-(6-(2-fluoro-4-(methylthio)phenyl)imidazo[2,1-b][1,3,4]thiadiazol-2-yloxy)ethyl)piperidine-1-carboxylate (0.025 gm, 44.99%) as light yellow semi solid.

MS: 478.8[M⁺+1].

Step 3: Synthesis of isopropyl 4-(1-(6-(2-fluoro-4-(methylsulfonyl)phenyl)imidazo[2,1-b][1,3,4]thiadiazol-2-yloxy)ethyl)piperidine-1-carboxylate

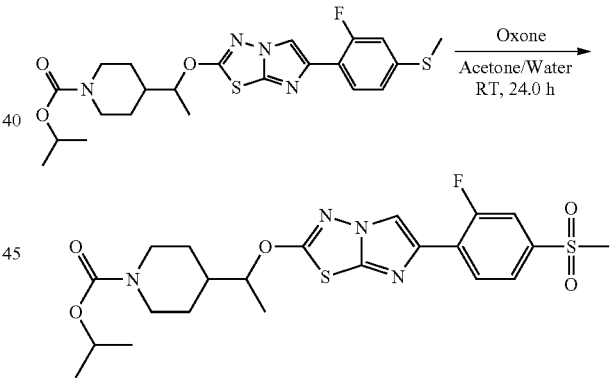

To a stirred soln. of compound isopropyl 4-(1-(6-(2-fluoro-4-(methylthio)phenyl)imidazo[2,1-b][1,3,4]thiadiazol-2-yloxy)ethyl)piperidine-1-carboxylate (0.025 g, 0.05 mmol) in Acetone (4.0 ml), Oxone (0.03 g, 0.10 mmol) in water (0.8 ml) was added and reaction continued at RT for 24.0 h. Progress of reaction was monitored by TLC. On completion acetone was evaporated from reaction mixture and residue was quenched with water, compound was extracted with ethyl acetate. The organic layer was concentrated under reduced pressure to give crude desired compound. Purification of the compound was done by silica gel (100-200 mesh) column chromatography using 15% Acetone in hexane that was concentrated to get compound isopropyl 4-(1-(6-(2-fluoro-4-(methylsulfonyl)phenyl)imidazo[2,1-b][1,3,4]thiadiazol-2-yloxy)ethyl)piperidine-1-carboxylate (0.023 g, 86.24%) off white solid.

MS: 510.9[M⁺+1].

Example 33: 2-((S)-1-(1-(5-ethylpyrimidin-2-yl)piperidin-4-yl)ethoxy)-6-(2-fluoro-6-(methylsulfonyl)pyridin-3-yl)imidazo[2,1-b][1,3,4]thiadiazole [1102]

Step-1: Synthesis of 2-((S)-1-(1-(5-ethylpyrimidin-2-yl)piperidin-4-yl)ethoxy)-6-(2-fluoro-6-(methylthio)pyridin-3-yl)imidazo[2,1-b][1,3,4]thiadiazole

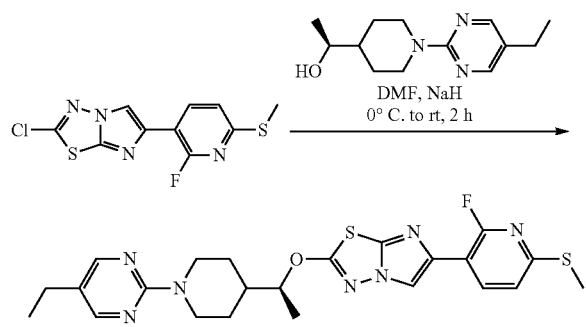

To a stirred solution of (S)-1-(1-(5-ethylpyrimidin-2-yl)piperidin-4-yl)ethanol (0.019 g, 0.074 mmol) in DMF (2 mL), NaH (0.004 mg, 0.0167 mmol) was added at 0° C. and stirred for 1 h. To resultant reaction mass, 2-chloro-6-(2-fluoro-6-(methylthio)pyridin-3-yl) imidazo [2,1-b] [1,3,4] thiadiazole (0.025 g, 0.083 mmol) was added and stirred for 1 h at RT. Reaction was monitored by TLC. On completion, quenched with water, extracted with ethyl acetate. The organic layer was washed with water, brine, dried over sodium sulphate, concentrated under reduced pressure obtained crude. Purification of the crude was done via silica gel (100-200 Mesh) column chromatography and desired compound eluted at 18% acetone/n-Hexane to obtained 2-((S)-1-(1-(5-ethylpyrimidin-2-yl)piperidin-4-yl)ethoxy)-6-(2-fluoro-6-(methylthio)pyridin-3-yl)imidazo[2,1-b][1,3,4]thiadiazole (0.014 g, 35.89%) as off white solid.

MS: 500.43[M$^+$+1]

Step-2: Synthesis of 2-((S)-1-(1-(5-ethylpyrimidin-2-yl)piperidin-4-yl)ethoxy)-6-(2-fluoro-6-(methylsulfonyl)pyridin-3-yl)imidazo[2,1-b][1,3,4]thiadiazole

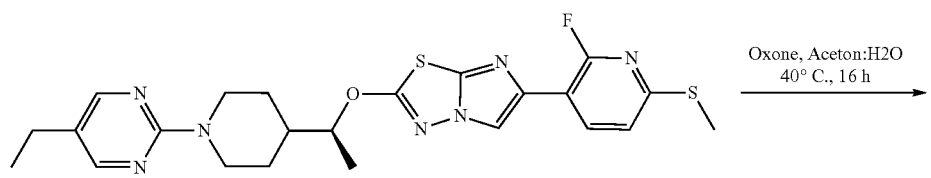

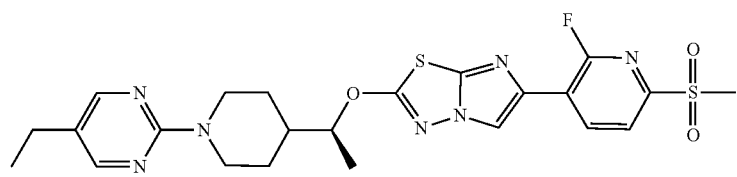

To a stirred solution of 2-((S)-1-(1-(5-ethylpyrimidin-2-yl)piperidin-4-yl)ethoxy)-6-(2-fluoro-6-(methylthio)pyridin-3-yl)imidazo[2,1-b][1,3,4]thiadiazole (0.024 g, 0.05 mmol) in Acetone:H$_2$O (10:03 mL), oxone (0.053 g, 0.17 mmol) was added at rt and stirred for 30 min. After 30 min, place reaction mass at 40° C. and stirred for 16 h. Reaction was monitored by TLC. On completion, quenched with ice cold water, extracted with ethyl acetate. The organic layer was washed with water, brine, dried over sodium sulphate, concentrated under reduced pressure to obtained crude which was purified via silica gel (100 to 200 Mesh) column chromatography, and desired compound eluted at 2% MeOH/DCM to obtained 2-((1-(3-isopropyl-1,2,4-oxadiazol-5-yl)piperidin-4-yl)methoxy)-6-(4-(methylsulfonyl)phenyl)imidazo[2,1-b][1,3,4]thiadiazole (0.010 g, 22.55%) as off white solid.

MS: 532[M$^+$+1]

Example 34: 2-((S)-1-(1-(3-isopropyl-1,2,4-oxadiazol-5-yl)piperidin-4-yl)ethoxy)-6-(2-methyl-6-(methylsulfonyl)pyridin-3-yl)imidazo[2,1-b][1,3,4]thiadiazole [1104]

Step 1: Synthesis of 1-(2-methyl-6-(methylthio)pyridin-3-yl)ethanone

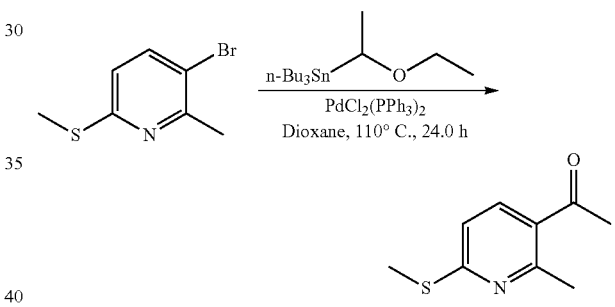

To a stirred soln. of compound 3-bromo-2-methyl-6-(methylthio)pyridine (0.35 g, 1.61 mmol) and tributyl(1-ethoxyvinyl)stannane (0.7 g, 1.94 mmol) in Dioxane (10.0 ml), PdCl2(PPh3)2 (0.12 gm, 0.16 mmol) was added under nitrogen degassing. Reaction allowed to run at 110° C. for 24.0 h. Reaction was monitored by TLC. On completion solvent was evaporated from reaction mixture. Residue was quenched with water, compound was extracted with ethyl acetate. The organic layer was concentrated under reduced pressure to get crude desired product. Purification of the compound was done by silica gel (100-200 mesh) column chromatography using 5% ethyl acetate in hexane that was concentrated to get compound 1-(2-methyl-6-(methylthio) pyridin-3-yl)ethanone (0.14 g, 47.93%) as yellow liquid.

MS: 182.0[M$^+$+1].

Step 2: Synthesis of 2-bromo-1-(2-methyl-6-(methylthio)pyridin-3-yl)ethanone

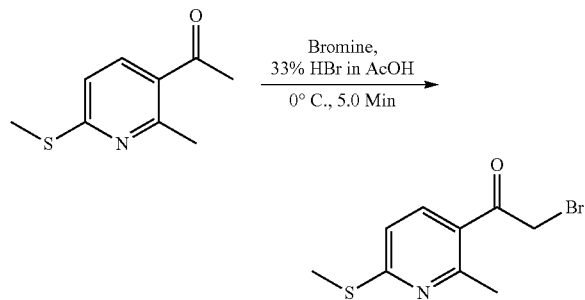

To a stirred soln. of 1-(2-methyl-6-(methylthio)pyridin-3-yl)ethanone (0.14 g, 0.77 mmol) in 33% HBr in Acetic acid (1.5 ml), Bromine (0.11 g, 0.69 mmol) in 0.5 ml HBr in AcOH was added at 0° C. and reaction allowed to run at same temp for next 5.0 min. Reaction was monitored by TLC. On completion reaction mixture was quenched with ice cold water and compound was extracted with di ethyl ether. The organic layer was washed with water, bicarbonate, brine, dried over sodium sulphate and concentrated under reduced pressure to get crude compound 2-bromo-1-(2-methyl-6-(methylthio)pyridin-3-yl)ethanone (0.15 g, 74.91%) as yellow semi solid.

MS: 259.80[M$^+$+1].

Step 3: Synthesis of 2-chloro-6-(2-methyl-6-(methylthio)pyridin-3-yl)imidazo[2,1-b][1,3,4]thiadiazole

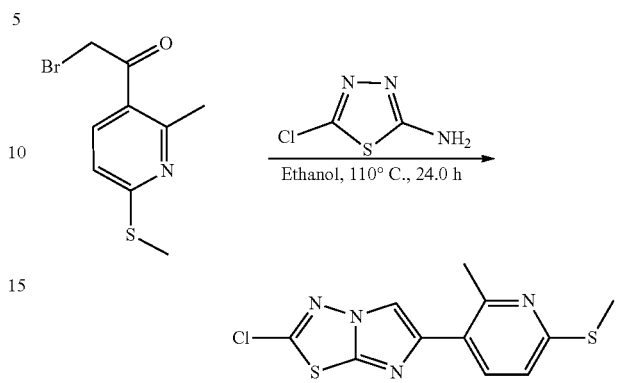

To a stirred soln. of 2-bromo-1-(2-methyl-6-(methylthio) pyridin-3-yl)ethanone (0.14 g, 0.54 mmol) in Ethanol (4.0 ml), 5-chloro-1,3,4-thiadiazol-2-amine (0.07 g, 0.54 mmol) was added at RT and reaction allowed to run at 110° C. for 24.0 h. Reaction was monitored by TLC. On completion reaction mixture was concentrated under reduced pressure to get crude desired product. Purification of the compound was done by silica gel (100-200 mesh) column chromatography using 10% ethyl acetate in hexane that was concentrated to get compound 2-chloro-6-(2-methyl-6-(methylthio)pyridin-3-yl)imidazo[2,1-b][1,3,4]thiadiazole (0.06 gm, 37.49%) as light yellow semi solid.

MS: 296.9[M$^+$+1].

Step 4: Synthesis of 2-((S)-1-(1-(3-isopropyl-1,2,4-oxadiazol-5-yl)piperidin-4-yl)ethoxy)-6-(2-methyl-6-(methylthio)pyridin-3-yl)imidazo[2,1-b][1,3,4]thiadiazole

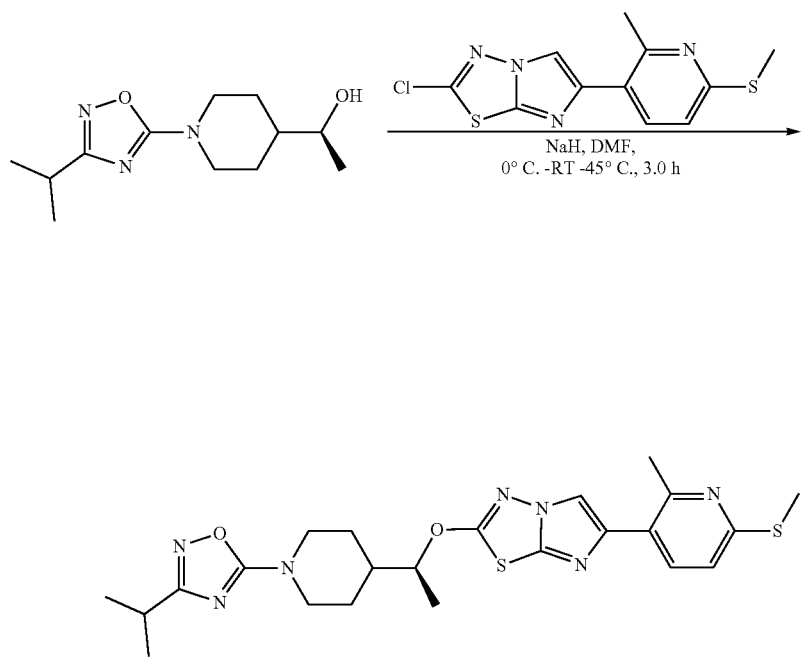

To a stirred soln. of (S)-1-(1-(3-isopropyl-1,2,4-oxadiazol-5-yl)piperidin-4-yl)ethanol (0.02 g, 0.08 mmol) in DMF (3.0 ml), sodium hydride (0.005 g, 0.13 mmol) at 0° C. and reaction allowed to run at 0° C. for 30.0 min. then 2-chloro-6-(2-methyl-6-(methylthio)pyridin-3-yl)imidazo[2,1-b][1,3,4]thiadiazole (0.03 g, 0.10 mmol) was added to reaction mixture and reaction continued at RT to 45° C. for next 3.0 h. Reaction was monitored by TLC. On completion reaction mixture was quenched with ice cold water and compound was extracted with ethyl acetate. The organic layer was washed with water, brine, dried over sodium sulphate and concentrated under reduced pressure to give crude desired product. Purification of the compound was done by silica gel (100-200 mess) column chromatography using 15% Acetone in hexane that was concentrated to get compound 2-((S)-1-(1-(3-isopropyl-1,2,4-oxadiazol-5-yl)piperidin-4-yl)ethoxy)-6-(2-methyl-6-(methylthio)pyridin-3-yl)imidazo[2,1-b][1,3,4]thiadiazole (0.024 g, 57.49%) as light yellow semi solid.

MS: 499.90[M$^+$+1].

Step 5: Synthesis of 2-((S)-1-(1-(3-isopropyl-1,2,4-oxadiazol-5-yl)piperidin-4-yl)ethoxy)-6-(2-methyl-6-(methylsulfonyl)pyridin-3-yl)imidazo[2,1-b][1,3,4]thiadiazole

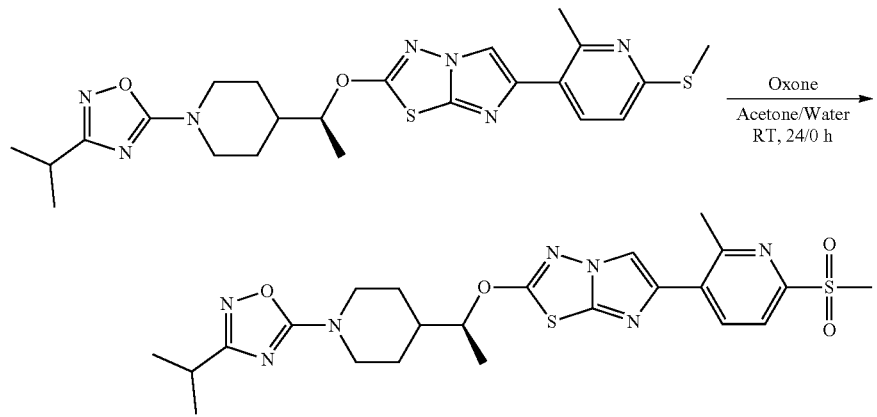

To a stirred soln. of compound 2-((S)-1-(1-(3-isopropyl-1,2,4-oxadiazol-5-yl)piperidin-4-yl)ethoxy)-6-(2-methyl-6-(methylthio)pyridin-3-yl)imidazo[2,1-b][1,3,4]thiadiazole (0.022 g, 0.04 mmol) in Acetone (4.0 ml), Oxone (0.03 gm, 0.09 mmol) in Water (0.8 ml) was added and reaction continued at RT for 24.0 h. Progress of reaction was monitored by TLC. On completion acetone was evaporated from reaction mixture and residue was quenched with water, compound was extracted with ethyl acetate. The organic layer was concentrated under reduced pressure to give crude desired compound. Purification of the compound was done by silica gel (100-200 mess) column chromatography using 20% Acetone in hexane that was concentrated to get compound 2-((S)-1-(1-(3-isopropyl-1,2,4-oxadiazol-5-yl)piperidin-4-yl)ethoxy)-6-(2-methyl-6-(methylsulfonyl)pyridin-3-yl)imidazo[2,1-b][1,3,4]thiadiazole (0.015 g, 64.08%) light yellow solid.

MS: 531.90[M$^+$+1].

Example 35: tert-butyl 4-((S)-1-(6-(2-fluoro-4-(methylsulfonyl)phenyl)imidazo[2,1-b][1,3,4]thiadiazol-2-yloxy)ethyl)piperidine-1-carboxylate [1106]

Step 1: Synthesis of tert-butyl 4-(1-(6-(2-fluoro-4-(methylthio)phenyl)imidazo[2,1-b][1,3,4]thiadiazol-2-yloxy)ethyl)piperidine-1-carboxylate

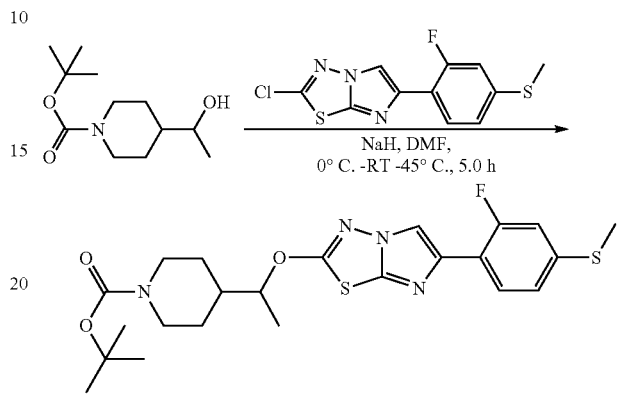

To a stirred soln. of ethyl 4-(1-hydroxyethyl)piperidine-1-carboxylate (0.015 gm, 0.0655 mmol) in DMF (3.0 ml), sodium hydride (0.006 gm, 0.15 mmol) at 0° C. and reaction allowed to run at 0° C. for 30.0 min. then 2-chloro-6-(2-fluoro-4-(methylthio)phenyl)imidazo[2,1-b][1,3,4]thiadiazole (0.021 gm, 0.720 mmol) was added to reaction mixture and reaction continued at RT to 45° C. for next 5.0 h. Reaction was monitored by TLC. On completion reaction mixture was quenched with ice cold water and compound was extracted with ethyl acetate. The organic layer was washed with water, brine, dried over sodium sulphate and concentrated under reduced pressure to give crude desired product. Purification of the compound was done by silica gel (100-200 mess) column chromatography using 15% Acetone in hexane that was concentrated to get compound tert-butyl 4-(1-(6-(2-fluoro-4-(methylthio)phenyl)imidazo[2,1-b][1,3,4]thiadiazol-2-yloxy)ethyl)piperidine-1-carboxylate (0.015 g, 32.50%) as yellow semi solid.

MS: 493.17[M$^+$+1].

Step 2: Synthesis of tert-butyl 4-(1-(6-(2-fluoro-4-(methylsulfonyl)phenyl)imidazo[2,1-b][1,3,4]thiadiazol-2-yloxy)ethyl)piperidine-1-carboxylate

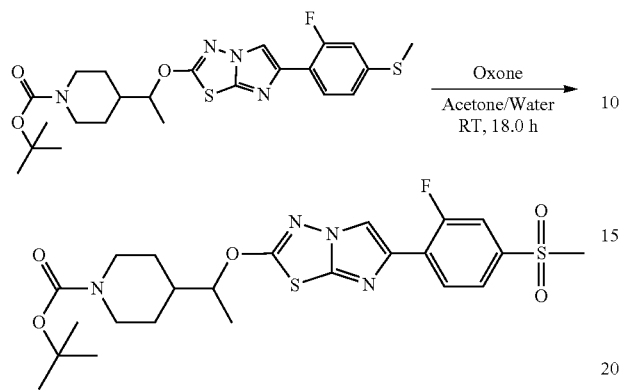

To a stirred soln. of compound ethyl 4-(1-(6-(2-fluoro-4-(methylthio)phenyl)imidazo[2,1-b][1,3,4]thiadiazol-2-yloxy)ethyl)piperidine-1-carboxylate (0.015 gm, 0.03 mmol) in Acetone (4.0 ml), Oxone (0.02 g, 0.06 mmol) in water (0.8 ml) was added and reaction continued at room temperature for 18 h. Progress of reaction was monitored by TLC. On completion acetone was evaporated from reaction mixture and residue was quenched with water, compound was extracted with ethyl acetate. The organic layer was concentrated under reduced pressure to give crude desired compound. Purification of the compound was done by silica gel (100-200 mess) column chromatography using 15% Acetone in hexane that was concentrated to get compound tert-butyl 4-(1-(6-(2-fluoro-4-(methylsulfonyl)phenyl)imidazo[2,1-b][1,3,4]thiadiazol-2-yloxy)ethyl)piperidine-1-carboxylate (0.008 g, 49.90%) off white solid.

MS: 496.8[M$^+$+1].

Example 36: Ethyl 4-(1-(6-(2-fluoro-4-(methylsulfonyl)phenyl)imidazo[2,1-b][1,3,4]thiadiazol-2-yloxy)ethyl)piperidine-1-carboxylate [1107]

Step 1: Synthesis of ethyl 4-(1-hydroxyethyl)piperidine-1-carboxylate

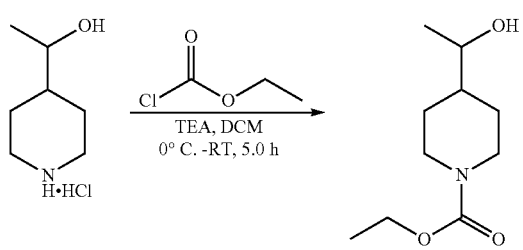

To a stirred soln. of compound 1-(piperidin-4-yl)ethanol hydrochloride (0.15 g, 1.16 mmol) in DCM (4.0 ml), Tri-ethylamine (0.5 ml, 3.49 mmol) was added at 0° C. and reaction allowed to run at same temperature for 0.5 h, then followed by ethyl chloroformate (0.1 ml, 1.16 mmol) and reaction further continued for next 5.0 h at RT. Reaction was monitored by TLC. On completion reaction mixture was quenched with ice cold water and compound was extracted with DCM. The organic layer was washed with water, brine, dried over sodium sulphate and concentrated under reduced pressure to give crude desired product. Purification of the compound was done by silica gel (100-200 mess) column chromatography using 50% EtOAc in hexane, that was concentrated to get compound ethyl 4-(1-hydroxyethyl)piperidine-1-carboxylate (0.09 g, 38.52%) as light yellow liquid.

MS: 202.1[M$^+$+1].

Step 2: Synthesis of ethyl 4-(1-(6-(2-fluoro-4-(methylthio)phenyl)imidazo[2,1-b][1,3,4]thiadiazol-2-yloxy)ethyl)piperidine-1-carboxylate

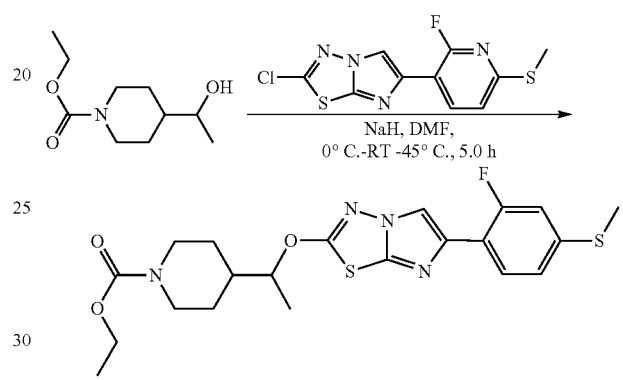

To a stirred soln. of ethyl 4-(1-hydroxyethyl)piperidine-1-carboxylate (0.02 gm, 0.09 mmol) in DMF (3.0 ml), sodium hydride (0.006 g, 0.15 mmol) at 0° C. and reaction allowed to run at 0° C. for 30.0 min. then 2-chloro-6-(2-fluoro-4-(methylthio)phenyl)imidazo[2,1-b][1,3,4]thiadiazole (0.04 g, 0.12 mmol) was added to reaction mixture and reaction continued at RT to 45° C. for next 5.0 h. Reaction was monitored by TLC. On completion reaction mixture was quenched with ice cold water and compound was extracted with ethyl acetate. The organic layer was washed with water, brine, dried over sodium sulphate and concentrated under reduced pressure to give crude desired product. Purification of the compound was done by silica gel (100-200 mesh) column chromatography using 15% Acetone in hexane that was concentrated to get compound ethyl 4-(1-(6-(2-fluoro-4-(methylthio)phenyl)imidazo[2,1-b][1,3,4]thiadiazol-2-yloxy)ethyl)piperidine-1-carboxylate (0.015 g, 32.50%) as yellow semi solid.

MS: 464.9[M$^+$+1].

Step 3: Synthesis of ethyl 4-(1-(6-(2-fluoro-4-(methylsulfonyl)phenyl)imidazo[2,1-b][1,3,4]thiadiazol-2-yloxy)ethyl)piperidine-1-carboxylate

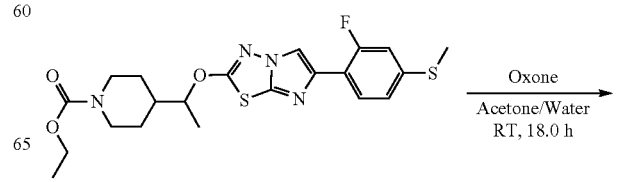

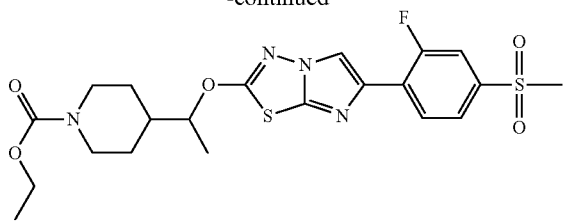

To a stirred soln. of compound ethyl 4-(1-(6-(2-fluoro-4-(methylthio)phenyl)imidazo[2,1-b][1,3,4]thiadiazol-2-yloxy)ethyl)piperidine-1-carboxylate (0.015 g, 0.03 mmol) in Acetone (4.0 ml), Oxone (0.02 g, 0.06 mmol) in Water (0.8 ml) was added and reaction continued at RT for 18.0 h. Progress of reaction was monitored by TLC. On completion acetone was evaporated from reaction mixture and residue was quenched with water, compound was extracted with ethyl acetate. The organic layer was concentrated under reduced pressure to give crude desired compound. Purification of the compound was done by silica gel (100-200 mesh) column chromatography using 15% Acetone in hexane that was concentrated to get compound ethyl 4-(1-(6-(2-fluoro-4-(methylsulfonyl)phenyl)imidazo[2,1-b][1,3,4]thiadiazol-2-yloxy)ethyl)piperidine-1-carboxylate (0.008 g, 49.90%) off white solid.

MS: 496.8[M⁺+1].

Example 37: 1-(3-isopropyl-1,2,4-oxadiazol-5-yl)-N-methyl-N-(3-(6-(methylsulfonyl)pyridin-3-yl)-1,2,4-thiadiazol-5-yl)piperidin-4-amine [1127]

Step 1: Synthesis of 1-(3-isopropyl-1,2,4-oxadiazol-5-yl)-N-methyl-N-(3-(6-(methylsulfonyl)pyridin-3-yl)-1,2,4-thiadiazol-5-yl)piperidin-4-amine

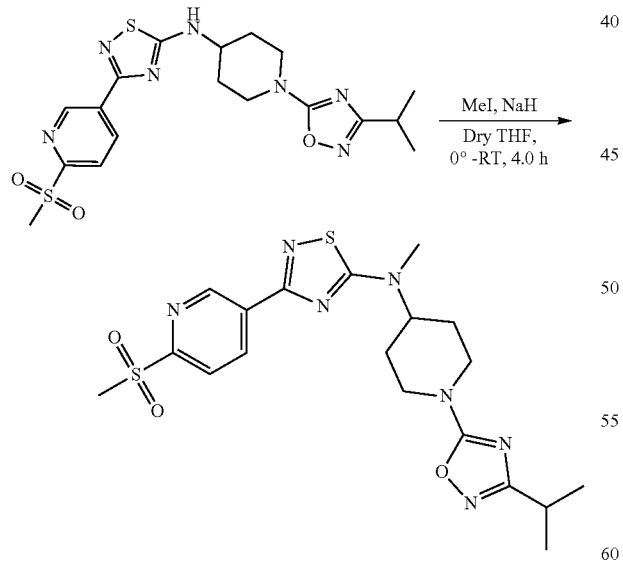

To a stirred soln. of 1-(3-isopropyl-1,2,4-oxadiazol-5-yl)-N-(3-(6-(methylsulfonyl)pyridin-3-yl)-1,2,4-thiadiazol-5-yl)piperidin-4-amine (0.01 g, 0.02 mmol) in Dry THF (3.0 ml), sodium hydride (0.002 gm, 0.03 mmol) at 0° C. and reaction allowed to run at 0° C. for 10.0 min. then methyl iodide (0.004 gm, 0.02 mmol) was added to reaction mixture and reaction continued at RT for next 4.0 h. Reaction was monitored by TLC. On completion reaction mixture was quenched with ice cold water and compound was extracted with ethyl acetate. The organic layer was washed with water, brine, dried over sodium sulphate and concentrated under reduced pressure to give to give crude desired product. Purification of the compound was done by silica gel (100-200 mess) column chromatography using 35% EtOAc in hexane that was concentrated to get compound 1-(3-isopropyl-1,2,4-oxadiazol-5-yl)-N-methyl-N-(3-(6-(methylsulfonyl)pyridin-3-yl)-1,2,4-thiadiazol-5-yl)piperidin-4-amine (0.008 g, 77.59%) as off white sticky.

MS: 463.9 [M⁺+1].

Example 38: In Vitro Cyclic AMP Assay cAMP measurements were done using Cisbio dynamic 2 HTRF kit according to the manufacturer's protocol. Briefly, CHO-hGPR119 cells were plated at a cell density of 5000 cells/well/5p into a white small volume 384 well plate. The final concentrations of IBMX and DMSO used were 1 mM and 0.5% respectively. Cells were treated with various concentrations of the test compound for 60 min at room temperature. Cells were lysed by buffer containing Anti-cAMP antibody and d2-cAMP reagents and incubated for 1 hour at room temperature. HTRF was measured at 337 nm excitation and emission wavelengths of 665 nm and 620 nm on a microplate reader (Flurostar, BMG Labtech). Graphpad prism software was utilized for EC50 determinations.

Results: The results of the compounds were represented in terms of % induction at 1 μM and EC50 and the same is represented at Table 1 herein below.

| Compound | Induction | EC50 |
| --- | --- | --- |
| 1001 | NA | |
| 1002 | NA | |
| 1003 | 3 | |
| 1004 | 6 | |
| 1005 | 2 | |
| 1006 | 9 | |
| 1007 | -8 | |
| 1008 | NA | |
| 1009 | NA | |
| 1010 | 2 | |
| 1011 | 2 | |
| 1012 | 22 | |
| 1013 | NA | |
| 1014 | NA | |
| 1015 | 3 | |
| 1016 | 54 | |
| 1017 | 39 | |
| 1018 | 20 | |
| 1019 | 11 | |
| 1020 | 1 | |
| 1021 | NA | |
| 1022 | 16 | |
| 1023 | 0 | |
| 1024 | 38 | |
| 1025 | 11 | |
| 1026 | NA | |
| 1027 | 41 | |
| 1028 | NA | |
| 1029 | 9 | |
| 1030 | 26 | |
| 1031 | 1 | |
| 1032 | 41 | |
| 1033 | 2 | |
| 1034 | 53 | |
| 1035 | 21 | |
| 1036 | 24 | |
| 1037 | NA | |
| 1038 | 6 | |

-continued

| Compound | Induction | EC50 |
|---|---|---|
| 1039 | 11 | |
| 1040 | 4 | |
| 1041 | NA | |
| 1042 | 2 | |
| 1043 | NA | |
| 1044 | 71 | |
| 1045 | 22 | |
| 1046 | 26 | |
| 1047 | 51 | |
| 1048 | 56 | |
| 1049 | 55 | |
| 1050 | 68 | |
| 1051 | 7 | |
| 1052 | 12 | |
| 1053 | 49 | |
| 1054 | 16 | |
| 1055 | 76 | |
| 1056 | 73 | |
| 1057 | 82 | |
| 1058 | 73 | A+ |
| 1059 | 68 | A++ |
| 1060 | 65 | A+ |
| 1061 | 79 | |
| 1062 | 78 | A+ |
| 1063 | 61 | |
| 1064 | 75 | A++ |
| 1065 | 62 | A |
| 1066 | 72 | A+ |
| 1067 | 55 | A++ |
| 1068 | 59 | B |
| 1069 | 65 | A+ |
| 1070 | 55 | B |
| 1071 | 75 | A++ |
| 1072 | 72 | A++ |
| 1073 | 33 | |
| 1074 | 44 | |
| 1075 | 64 | |
| 1076 | 15 | |
| 1077 | 33 | |
| 1078 | 54 | |
| 1079 | 87 | |
| 1080 | 74 | |
| 1081 | 66 | A++ |
| 1082 | 80 | A |
| 1083 | 77 | |
| 1084 | 72 | |
| 1085 | 74 | A++ |
| 1086 | 87 | A++ |
| 1087 | 75 | A |
| 1088 | 73 | A++ |
| 1089 | 72 | A |
| 1090 | 76 | A++ |
| 1091 | 33 | |
| 1092 | 25 | |
| 1093 | 75 | A |
| 1094 | 68 | |
| 1095 | 8 | |
| 1096 | 32 | |
| 1097 | NA | |
| 1098 | 68 | |
| 1099 | 63 | |
| 1100 | 78 | A++ |
| 1101 | 84 | |
| 1102 | 84 | A+ |
| 1103 | 9 | |
| 1104 | 46 | |
| 1105 | 30 | |
| 1106 | 62 | |
| 1107 | 67 | |
| 1108 | 70 | A++ |
| 1109 | 55 | |
| 1110 | 71 | |
| 1111 | 63 | |
| 1112 | 71 | |
| 1113 | 68 | A+ |
| 1114 | 4 | |
| 1115 | 14 | |
| 1116 | 36 | |
| 1117 | 2 | |
| 1118 | NA | |
| 1119 | 7 | |
| 1120 | 15 | |
| 1121 | NA | |
| 1122 | NA | |
| 1123 | 18 | |
| 1124 | 6 | |
| 1125 | NA | |
| 1126 | 7 | |
| 1127 | 4 | |

Example 39: Anti-Diabetic Effect of Compounds of the Invention in an In-Vitro Model of Pancreatic Beta Cells (HIT-T15)

Cell Culture:

HIT-T15 cells were grown in Ham's F12K medium with 2 mM 1-glutamine containing 2.5% horse serum and 10% fetal bovine serum. Cells were grown in minimal glucose concentration for insulin secretion studies. Studies were performed with cell passage numbers between 65 to 72.

cAMP Assay:

HIT-T15 cells were plated at a cell density of 5000 cells/well/5 µl into a white small volume 384 well plate. The final concentrations of IBMX and DMSO used were 1 mM and 0.5% respectively. Cells were treated with various concentrations of the test compound for 60 min at room temperature. Cells were lysed by buffer containing Anti-cAMP antibody and d2-cAMP reagents and incubated for 1 hour at room temperature. HTRF was measured at 337 nm excitation and emission wavelengths of 665 nm and 620 nm on a microplate reader (Flurostar, BMG Labtech). GraphPad prism 6 software was utilized for EC50 determinations.

Representative compounds of the invention were found to increase cAMP at an EC50 of less than 10 µM. Compounds showing an EC50 of less than 1 µM in the cAMP assay may be preferred.

Insulin Secretion Assay:

HIT-T15 cells were utilised for assessment of potentiation of glucose stimulated insulin secretion (GSIS) by test compounds. Cells were seeded at a cell density of 50,000 cells per well in 96 well plate. After 48 hours, cells were washed with Krebs-Ringer Bicarbonate buffer (KRB) and incubated with buffer containing 0.2 mM glucose for 30 minutes. After incubating cells twice in KRB buffer containing 0.2 mM glucose, cells were exposed to 11 mM glucose and test compounds at 10 µM and 1 µM for 1 hour. Supernatants were collected for measurement of insulin secreted from the cells. Insulin was measured using Cisbio insulin test kit following manufacturer's instructions, with a standard curve of known insulin concentrations. For each well, insulin levels are corrected by subtraction of the basal secretion level from the preincubation in the absence of glucose. Data is analysed using GraphPad prism 6 software. Representative compounds of the invention were studied for their insulin potentiation capacity and showed increase in insulin secretion at an EC50 of less than 10 µM, however the compounds showing increase in insulin secretion at an EC50 of less than 1 µM may be preferred.

Example 40: Glucagon-Like Peptide-1 (GLP-1) Secretion

To study the effect of GPR119 agonists on secretion of GLP-1 in C57BL/6 mice, animals were grouped based on basal glucose levels and fasted for 16 hours. Animals were dosed orally with vehicle or test compound at 10 mpk (n=20). After 30 minutes of compound dosing, ten animals were sacrificed from each group and blood was collected by cardiac puncture method. To the remaining 10 animals in each group, glucose, 3 g/kg, was administered. After ten minutes of glucose administration, animals were sacrificed by C02 asphyxiation method and blood was collected by cardiac puncture method. To avoid degradation of active GLP-1 in blood, DPP-IV inhibitor was added to the blood collection tubes. Plasma active GLP-1 levels were measured by using Merck Millipore ELISA kit. Statistical comparisons of the data were performed by one-way analysis of variance (ANOVA), followed by Bonferroni's test.

Results:

Compounds of the present invention showed significant increase in active GLP-1 secretion. Compounds which showed active GLP-1 secretion greater than ~1 fold with respect to vehicle may be preferred.

Example 41: Oral Glucose Tolerance Test

Male C57BL/6 mice (8-10 weeks) were grouped based on basal glucose levels and animals were fasted for 16 hours. Glucose level of each animal was estimated in blood collected from tail vein before animals were dosed orally with 0.5% Tween 80 and 0.5% NaCMC (vehicle control) and compounds at 3 and 10 mpk (n=5). After 30 minutes of compound dosing, blood glucose was again estimated and 2 g/kg/10 ml (20%) of Glucose solution was administered orally to all the animals. Blood glucose was estimated at 15, 30, 60, 90 and 120 minutes time points after glucose administration. Accu-Check active blood glucose meter was utilised for estimation of blood from tail vein.

Results:

Glucose reduction observed in animals treated with compounds of present invention is represented in terms of % AUC reduction. A greater glucose reduction in oral glucose tolerance test indicates the compound's efficacy in this rodent species. The compounds 1059, 1067, 1071, 1072, 1081, 1086, 1087, 1088, 1090, 1100, 1101,1108 and 1109 showed significant dose dependent glucose reduction at both 3 mpk and 10 mpk respectively.

Example 42: Oral Glucose Tolerance Test in Spranue-Dawley Rats

Male SD rats (8-10 weeks) were grouped based on basal glucose levels and animals were fasted for 16 hours. Glucose level of each animal was estimated in blood collected from tail vein before animals were dosed orally swith 0.5% Tween 80 and 0.5% NaCMC (vehicle control) and compounds at 3 and 10 mpk (n=5). After 30 minutes of compound dosing, blood glucose was again estimated and 2 g/kg/10 ml (20%) of Glucose solution was administered orally to all the animals. Blood glucose was estimated at 15, 30, 60, 90 and 120 minutes time points after glucose administration. Accu-Check active blood glucose meter was utilised for estimation of blood from tail vein.

Results:

Glucose reduction observed in animals treated with GPR119 agonists is represented in terms of % AUC reduction. A greater glucose reduction in oral glucose tolerance test indicates the compound's efficacy in this rodent species. The compounds 1059, 1067, 1071, 1072, 1086, 1087, 1090, 1091, 1101, 1108 and 1109 showed significant dose dependent glucose reduction at both 3 mpk and 10 mpk respectively.

We claim:

1. A process of preparing a compound of formula (5):

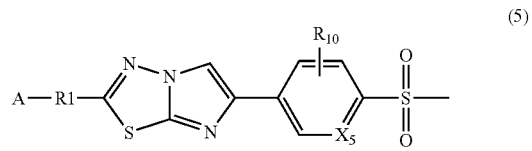

wherein the process comprises the steps of:
(a) synthesizing a compound of formula (4) from a compound of formula (3a);

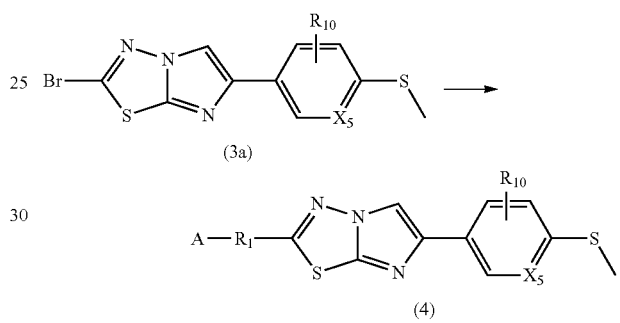

(b) oxidation of the compound (4) resulting from step (a) to form the compound of formula (5);

wherein A is selected from

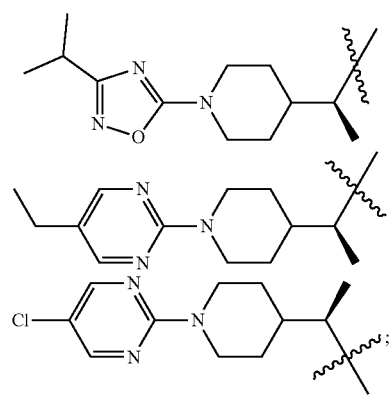

$R_1$ is selected from the group consisting of —O, $C_{1-6}$ alkyl, $C_{1-6}$ alkoxy, —$(CH_2)n$, amino, —CO, —CONH, —NH(Alkyl), —N(Alkyl)$_2$, —NH-aralkyl, —$CH_2O$, —$OCH(CH_3)$, $COOR_3$, —$CONR_3R_4$ or $NR_3COR_4$;

$R_3$ and $R_4$ are independently selected from the group consisting of hydrogen, or $C_{1-6}$ straight chain or branched chain alkyl which may be further substituted with halogen or $C_{1-6}$ alkyl;

X₅ is CH, N, O or S;

R₁₀ is H, OH, halogen, $C_{1-6}$ alkyl, $C_{1-6}$ alkoxy, —(CH₂)n, amino, —CO, —CONH, —NH(Alkyl), —N(Alkyl)₂, —NH-aralkyl or —OCH(CH₃);

n is 0, 1, 2 or 3.

2. The process of claim 1, wherein the compound of formula (3a) is prepared by reacting a compound of formula (1a) with a compound of formula 2a;

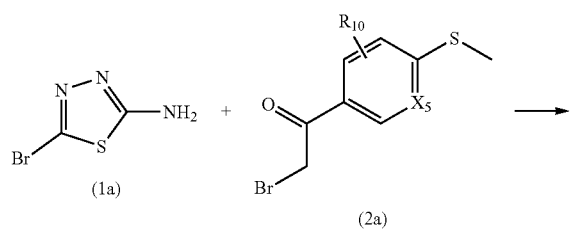

3. The process of claim 1, wherein the conversion in step (a) is carried out in the presence of a base and a solvent.

4. The process of claim 1, wherein the oxidation in step (b) is carried out in the presence of an oxidizing agent and a solvent.

-continued

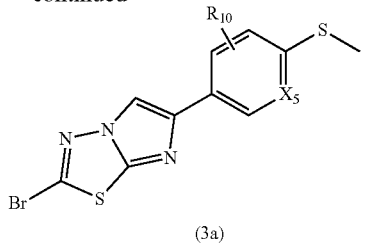

wherein X₅ is CH, N, O or S;
R₁₀ is H, OH, halogen, $C_{1-6}$ alkyl, $C_{1-6}$ alkoxy, —(CH₂)n, amino, —CO, —CONH, —NH(Alkyl), —N(Alkyl)₂, —NH-aralkyl or —OCH(CH₃);

n is 0, 1, 2 or 3.

5. A process of preparing 2-((S)-1-(1-(5-ethylpyrimidin-2-yl)piperidin-4-yl)ethoxy)-6-(2-fluoro-4-(methylsulfonyl)phenyl)imidazo[2,1-b][1,3,4]thiadiazole (1086) represented by the following structural formula:

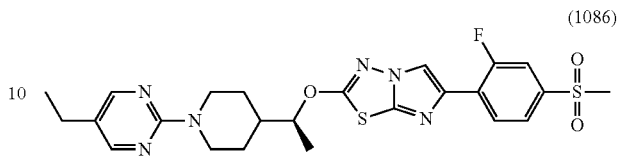

wherein said process comprises the steps of:
i. reacting 2-chloro-6-(2-fluoro-4-(methylthio)phenyl)imidazo[2,1-b][1,3,4]thiadiazole (41) with (S)-1-(1-(5-propylpyrimidin-2-yl) piperidin-4-yl) ethanol (53) to give 2-((S)-1-(1-(5-ethylpyrimidin-2-yl)piperidin-4-yl) ethoxy)-6-(2-fluoro-4-(methylthio)phenyl) imidazo[2,1-b][1,3,4]thiadiazole (54)

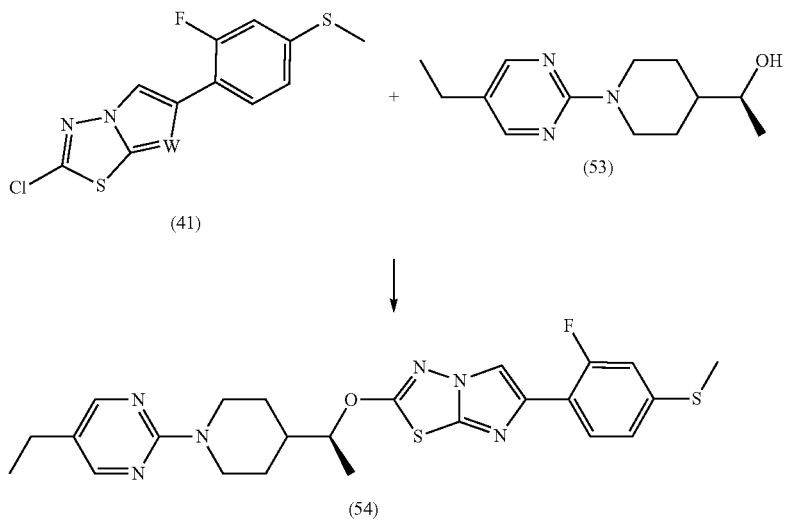

ii. oxidation of the compound 54 to the 2-((S)-1-(1-(5-ethylpyrimidin-2-yl)piperidin-4-yl) ethoxy)-6-(2-fluoro-4-(methylsulfonyl)phenyl)imidazo[2,1-b][1,3,4]thiadiazole (1086).

6. The process of claim 5, wherein the 2-chloro-6-(2-fluoro-4-(methylthio)phenyl) imidazo[2,1-b][1,3,4]thiadiazole (41) is prepared by a process comprising:
i. preparing 1-(2-fluoro-4-(methylthio) phenyl) ethanone (37) from (3-fluorophenyl)(methyl)sulfane (36);

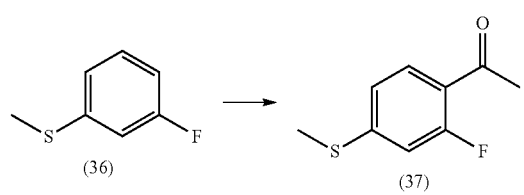

ii. converting the 1-(2-fluoro-4-(methylthio) phenyl) ethanone (37) to 2-bromo-1-(2-fluoro-4-(methylthio) phenyl) ethanone (38);

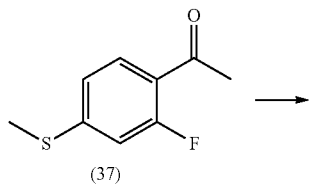

(37)

7. The process of claim 5, wherein (S)-1-(1-(5-propylpyrimidin-2-yl) piperidin-4-yl) ethanol (53) is prepared by a process comprising:

i. synthesis of 1-(piperidin-4-yl) ethanol hydrochloride (48) from piperidine-4-carboxylic acid (42);

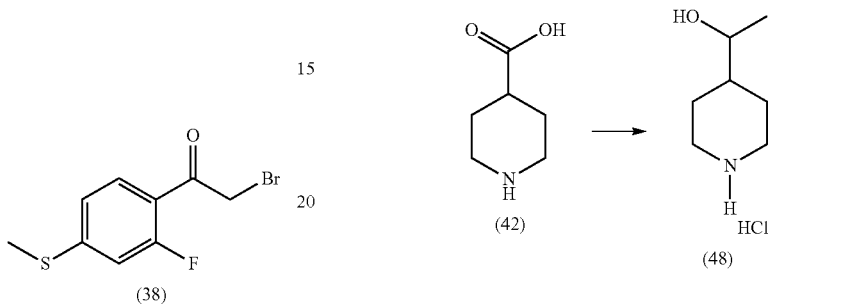

iii. preparing 5-chloro-1, 3, 4-thiadiazol-2-amine (40) from 1,3,4-thiadiazol-2-amine (39);

ii. synthesis of 1-(1-(5-ethylpyrimidin-2-yl) piperidin-4-yl) ethanol (50) from 1-(piperidin-4-yl) ethanol hydrochloride (48);

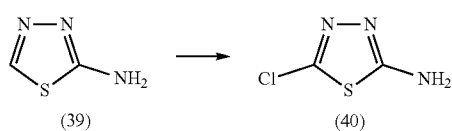 [SMILES: Nc1nncs1 ; Nc1nnc(Cl)s1]

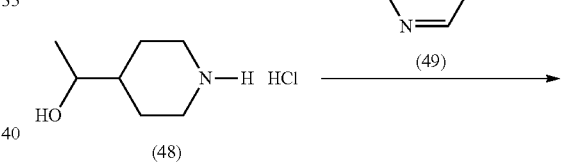

iv. reacting the 5-chloro-1, 3, 4-thiadiazol-2-amine (40) with the 2-bromo-1-(2-fluoro-4-(methylthio) phenyl) ethanone (38) to result in the compound 41:

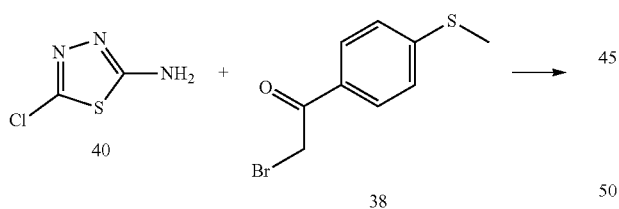

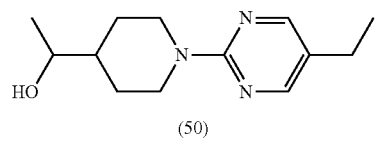

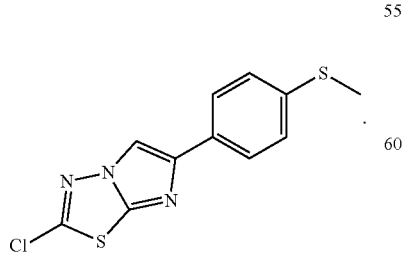

iii. resolution of the racemic mixture of 1-(1-(5-ethylpyrimidin-2-yl) piperidin-4-yl) ethanol (50) obtained in step (g) to (S)-1-(1-(5-propylpyrimidin-2-yl) piperidin-4-yl) ethanol (53)

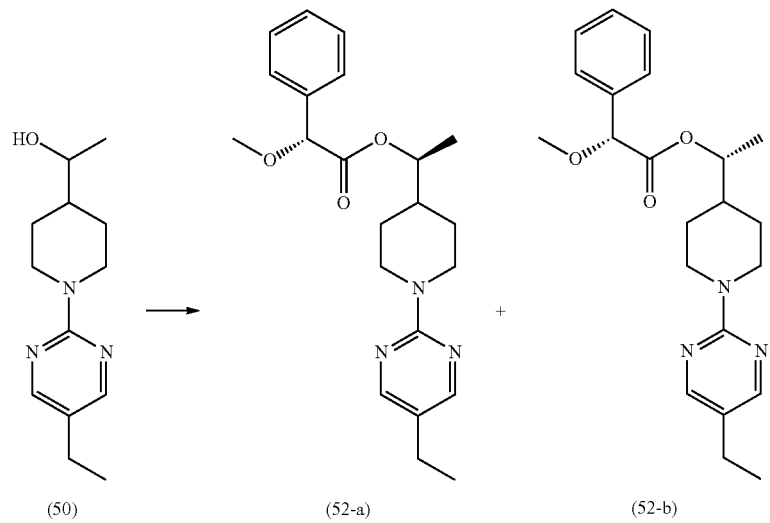
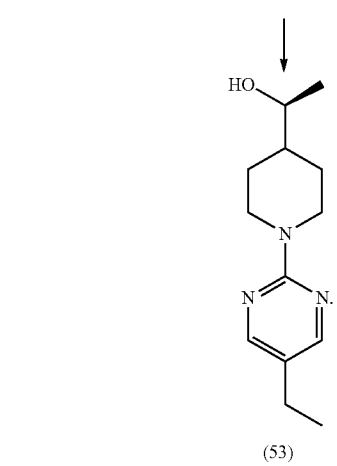
* * * * *